United States Patent [19]
Brown et al.

[11] Patent Number: 5,962,314
[45] Date of Patent: *Oct. 5, 1999

[54] CALCIUM RECEPTOR-ACTIVE MOLECULES

[75] Inventors: Edward M. Brown, Milton; Steven C. Hebert, Wellesley, both of Mass.; James E. Garrett, Jr., Salt Lake City, Utah

[73] Assignees: NPS Pharmaceuticals, Inc., Salt Lake City, Utah; Brigham and Women's Hospital, Boston, Mass.

[ * ] Notice: This patent is subject to a terminal disclaimer.

[21] Appl. No.: 08/943,986

[22] Filed: Oct. 3, 1997

Related U.S. Application Data

[63] Continuation of application No. 08/484,565, Jun. 7, 1995, Pat. No. 5,763,569, which is a continuation-in-part of application No. 08/353,784, Dec. 8, 1994, which is a continuation-in-part of application No. PCT/US94/12117, Oct. 21, 1994, application No. 08/292,827, Aug. 19, 1994, abandoned, application No. 08/141,248, Oct. 22, 1993, abandoned, and application No. 08/009,389, Feb. 23, 1993, abandoned.

[51] Int. Cl.[6] ............ C12N 15/63; C12N 15/11; C12N 15/12; C07K 7/00
[52] U.S. Cl. .............. 435/320.1; 435/325; 435/243; 435/252.3; 536/23.1; 536/23.4; 536/23.5; 536/24.31; 530/300; 530/326; 530/350
[58] Field of Search ............... 435/69.1, 252.3, 435/320.1, 325, 243; 536/23.1, 23.4, 23.5, 24.31; 530/300, 326, 350

[56] References Cited

U.S. PATENT DOCUMENTS

| | | |
|---|---|---|
| 3,262,977 | 7/1966 | Harsanyi et al. . |
| 3,842,067 | 10/1974 | Sarantakis . |
| 3,862,925 | 1/1975 | Sarantakis . |
| 3,972,859 | 8/1976 | Fujino et al. . |
| 4,000,197 | 12/1976 | Barfknecht et al. . |
| 4,105,602 | 8/1978 | Colescott et al. . |
| 4,391,826 | 7/1983 | Mills et al. . |
| 4,587,253 | 5/1986 | Halczenko et al. . |
| 4,600,494 | 7/1986 | Baldwin et al. . |
| 4,675,321 | 6/1987 | Baldwin et al. . |
| 4,677,101 | 6/1987 | Claremon et al. . |
| 4,728,660 | 3/1988 | Haynes et al. . |
| 4,808,718 | 2/1989 | Hartman et al. . |
| 4,839,369 | 6/1989 | Youssefyeh et al. . |
| 4,922,378 | 5/1990 | Kelly et al. . |
| 4,925,664 | 5/1990 | Jackson et al. . |
| 4,925,873 | 5/1990 | Friedhoff et al. . |
| 4,945,050 | 7/1990 | Sanford et al. . |
| 4,967,003 | 10/1990 | Rentzea et al. . |
| 4,987,071 | 1/1991 | Cech et al. . |
| 4,988,730 | 1/1991 | Korbonits et al. . |
| 5,011,834 | 4/1991 | Weber et al. . |
| 5,021,599 | 6/1991 | Beer et al. . |
| 5,030,576 | 7/1991 | Dull et al. . |
| 5,034,514 | 7/1991 | Nitecki et al. . |
| 5,045,466 | 9/1991 | Morrison . |
| 5,053,337 | 10/1991 | Weinshank et al. . |
| 5,064,657 | 11/1991 | Jackson et al. . |
| 5,082,837 | 1/1992 | Palfreyman . |
| 5,688,938 | 11/1997 | Brown et al. ............ 536/23.5 |

FOREIGN PATENT DOCUMENTS

| | | |
|---|---|---|
| 621300 | 12/1962 | Belgium . |
| 0005848 | 2/1979 | European Pat. Off. . |
| 0009702 | 9/1979 | European Pat. Off. . |
| 0007204 | 1/1980 | European Pat. Off. . |
| 0015505 | 9/1980 | European Pat. Off. . |
| 0023385 | 2/1981 | European Pat. Off. . |
| 0101069 | 8/1983 | European Pat. Off. . |
| 0092787 | 11/1983 | European Pat. Off. . |
| 0200101 | 12/1986 | European Pat. Off. . |
| 0253327 | 1/1988 | European Pat. Off. . |
| 0270376 | 7/1988 | European Pat. Off. . |
| 0289287 | 11/1988 | European Pat. Off. . |
| 0309100 | 3/1989 | European Pat. Off. . |
| 0384740 | 8/1990 | European Pat. Off. . |
| 0395357 | 10/1990 | European Pat. Off. . |
| 0408284 | 1/1991 | European Pat. Off. . |
| 0224163 | 10/1991 | European Pat. Off. . |
| 0508307 | 10/1992 | European Pat. Off. . |
| 0443606 | 5/1995 | European Pat. Off. . |
| 1231690 | 12/1967 | Germany . |
| 2541184 | 4/1976 | Germany . |
| 2113089 | 11/1982 | United Kingdom . |
| 2213818 | 8/1989 | United Kingdom . |
| 8204052 | 11/1982 | WIPO . |
| 8906135 | 7/1989 | WIPO . |
| 8909834 | 10/1989 | WIPO . |
| 9100853 | 1/1991 | WIPO . |
| 9109594 | 7/1991 | WIPO . |
| 9113077 | 9/1991 | WIPO . |
| 9214709 | 9/1992 | WIPO . |
| 9304373 | 4/1993 | WIPO . |
| 9418959 | 9/1994 | WIPO . |
| 9511221 | 4/1995 | WIPO . |
| 9518134 | 7/1995 | WIPO . |
| 9521815 | 8/1995 | WIPO . |

OTHER PUBLICATIONS

Ngo et al. (1994) In the Protein Folding Proble and Tertiary Structure Prediction Merz et al. (eds.) Birkhauss Beston pp. 433, 492–495.

(List continued on next page.)

*Primary Examiner*—John Ulm
*Assistant Examiner*—Christine Saoud
*Attorney, Agent, or Firm*—Lyon & Lyon LLP

[57] ABSTRACT

The present invention relates to the different roles inorganic ion receptors have in cellular and body processes. The present invention features: (1) molecules which can modulate one or more inorganic ion receptor activities, preferably the molecule can mimic or block an effect of an extracellular ion on a cell having an inorganic ion receptor, more preferably the extracellular ion is $Ca^{2+}$ and the effect is on a cell having a calcium receptor; (2) inorganic ion receptor proteins and fragments thereof, preferably calcium receptor proteins and fragments thereof; (3) nucleic acids encoding inorganic ion receptor proteins and fragments thereof, preferably calcium receptor proteins and fragments thereof; (4) antibodies and fragments thereof, targeted to inorganic ion receptor proteins, preferably calcium receptor protein; and (5) uses of such molecules, proteins, nucleic acids and antibodies.

36 Claims, 85 Drawing Sheets

OTHER PUBLICATIONS

Brom et al. 1993 Nature 366:575–580.

Garrett et al. (1995) J. Biol. Chem. 270.12919–12925.

Hebert et al. (1995) Cur. Op. Cell Biol. 7:484–492.

Abe et al., "Molecular Characterization of a Novel Metabotropic Glutamate Receptor mGluR5 Coupled to Inositol Phosphate/$Ca^{2+}$ Signal Transduction," *J. Biol. Chem.* 267:13361–13368 (1992).

Barney et al., "A Convenient Synthesis of Hindered Amines and α–Trifluoromethylamines from Ketones," *Tetrahedron Letters* 31:5547–5550 (1990).

Batra and Alenfall, "Effects of Diverse Categories of Drugs on Human Colon Tumour Cell Proliferation," *Anticancer Research* 11:1221–1224 (1991).

Becalski et al., "Catalytic asymmetric hydrogenation of imines. Use of rhodium(I)/phosphine comploexes and characterization of rhodium(I)/imine complexes," *Chemical Abstracts* 116:558 at Abstract No. 14742U (1992).

Bertz et al., "Asymmetric Induction with Amidocuprates," *J. Org. Chem.* 51:4953–4959 (1986).

Bringmann et al., "The Enantioselective Synthesis of Optically Active, Benzene Nucleus–Substituted 1–Phenylethylamines from the Corresponding Acetophenomes," *Leibigs Ann.Chem.* 5:795–805 (1990).

Bringmann et al., "Enantiomerically Pure N–Boc Protected β–Keto–γ–Amino Acid Esters from Simple Keto Precursors: A Novel, Stereocontrolled Approach to Statine Derivatives with Any Desired Configuration," *Synlet Letters* pp. 253–255 (1990).

Brinster et al., "Factors affecting the efficiency of introducing foreign DNA into mice by microinjecting eggs," *Proc. Natl. Acad. Sci. USA* 82:4438–4442 (1985).

Brown et al., "A Comparison of the Effects of Divalent and Trivalent Cations on Parathyroid Hormone Release, 3',5'–Cyclic–Adenosine Monophosphate Accumulation, and the Levels of Inositol Phosphates in Bovine Parathyroid Cells," *Endocrinology* 127:1064–1071 (1990).

Brown et al, "Cloning and characterization of an extracellular $Ca^{2+}$ sensing receptor from bovine parathryoid," *Nature* 366:575–580 (1993).

Brown, "Extracellular $Ca^{2+}$ Sensing, Regulation of Parathyroid Cell Function and Role of $Ca^{2+}$ and Other Ions as Extracelluar (First) Messengers," *Physiological Reviews* 71:371–411 (1991).

Brown et al., "High Extracellular $Ca^{2+}$ and $Mg^{2+}$ Stimulate Accumulation of Inositol Phosphates in Bovine Parathyroid Cells," *FEBS Letters* 218:113–118 (1987).

Brown et al., "Neomycin Mimics the Effects of High Extracellular Calcium Concentrations on Parathyroid Function in Dispersed Bovine Parathyroid Cells," *Endocrinology* 128:3047–3054 (1991).

Brown et al., "Polyarginine, Polylysine, and Protamine Mimic the Effects of High Extracellular Calcium Concentrations on Dispersed Bovine Parathyroid Cells," *Journal of Bone and Mineral Research* 6:1217–1225 (1991).

Buck and Axel, "A Novel Multigene Family May Encode Odorant Receptors: A Molecular Basis for Odor Recognition," *Cell* 65:175–187 (1991).

Capecchi, "Altering the Genome by Homologous Recombination," *Science* 244:1288–1292 (1989).

Capuano et al., "Characterization of the Human Calcium Receptor Gene," *Journal of Bone and Mineral Research* 9(1):S145 at abstract No. 98 (1994).

*Chemical Abstracts Formula Index*, vol. 110 p. 537F (1989).

*Chemical Abstracts Formula Index*, vol. 110 p. 1793F (1989).

Chen et al., "Divalent Cations Suppress 3',5'–Adenosine Monophosphate Accumulation by Stimulating a Pertussis Toxin–Sensitive Guanine Nucleotide–Binding Protein in Cultured Bovine Parathyroid Cells," *Endocrinology* 124(1):233–239 (1989).

Chen et al., "Effects of Fluoride on Parathyroid Hormone Secretion and Intracellular Second Messengers in Bovine Parathyroid Cells," *Journal of Bone and Mineral Research* 3(3):279–288 (1988).

Chen et al., "Injection of Bovine Parathyroid Poly(A)$^+$ RNA into Xenopus Oocytes Confers Sensitivity to High Extracellular Calcium," *Journal of Bone and Mineral Research* 9:293–300 (1994).

Chen and Brown, "The Diltiazem Analog TA–3090 Mimics the Actions of High Extracellular $Ca^{2+}$ on Parathyroid Function in Dispersed Bovine Parathyroid Cells," *Journal of Bone and Mineral Research* 5:581–587 (1990).

Clifton et al., "Arylethanolamines derived form salicylamide with alpha– and beta–adrenoceptor blocking activities. Preparation of labetalol, its enantiomers and related salicylamides," *J. Med. Chem.* 25:670–679 (1982).

Cooper et al., "Ch. 4—Receptors," *The Biochemical Basis of Neuropharmacology* 4th Edition, Cooper et al. eds., Oxford University Press, New York, pp. 61–76 (1982).

Danks, "Reaction of Hydride Transfer Reducing Agents with (1–Heterodiene) Tricarbonyliron(0) Complexes and the Synthesis of Saturated Amines and Alcohols," *Tetrahedron Letters* 35:4177–4178 (1994).

Davies and Ichihara, "Asymmetric Synthesis of R–β–Amino Butanoic Acid and S–62 –Tyrosine: Homochiral Lithium Amide Equivalents for Michael Additions to α,β–Unsaturated Esters," *Tetrahedron: Asymmetry* 2:183–186 (1991).

De Feo et al., "Natriuretic Peptide Receptors Regulate Endothelin Synthesis and Release From Parathyroid Cells," *Proc. Natl. Acad. Sci. USA* 88:6496–6500 (1991).

Dottavio–Martin and Ravel, "Radoilabeling of Proteins by Reductive Alkylation with [$^{14}$C]Formaldehyde and Sodium Cyanoborohydride," *Analytical Biochem.* 87:562–565 (1978).

Deulfer et al., "Synthesis of $^{14}$C–Dilevalol," *Journal of Labelled Compounds and Radiopharmaceuticals* 25(8):855–863 (1988).

Fergusen and Williams, "Cell–Surface Anchoring of Proteins Via Glycosylphosphatidylinositol Structures," *Ann. Rev. Biochem.* 57:285–320 (1988).

Fox et al., "A First Generation Calcimimetic Compound (NPS R–568) That Acts on the Parathyroid Cell Calcium Receptor: A Novel Therapeutic Approach for Hyperparathyroidism," *Journal of Bone and Mineral Research* 8(1):S181 at abstract No. 260 (1993).

Fox et al., "NPS R–568 Acts on Calcium Receptors to Inhibit Parathyroid Hormone and Stimulate Calcitonin Secretion: A Novel Therapeutic Approach for Hyperparathyroidisum," *J. American Society of Nephrology* 4:719 at abstract No. 120P (1993).

Fox et al., "NPS R–568 Inhibits Parathyroid Hormone Secretion and Stimulates Calcitonin Secretion in Hyperparathyroid Rats with Chronic Renal Failure," *J. American Society of Nephrology* 4:719 at abstract No. 69P (1993).

Fox et al., "Parathyroid Gland Calcium Receptor Gene Expression is Unaffected by Chronic Renal Failure or Low Dietary Calcium in Rats," *J. Am. Soc. Nephrology* 5:879 at abstract No. 90P (1994).

Fox et al., "Physiologically Relevant PTH Levels are Anabolic on Bone in Ovariectomized Rats," *Bone* 16(Supplement):194S at abstract No. 434 (1995).

Fox et al., "Prevention of Hypocalcemia Prolongs the Plasma Parathyroid Hormone and Calcitonin Responses to the Calcimimetic Compound NPS R–568 in Rats," *Journal of Bone and Mineral Research* 9(1):S409 at abstract No. C396 (1994).

Fuji et al., "Endothelin as an Autocrine Factor in the Regulation of Parathyroid Cells," *Proc. Natl. Acad. Sci. USA* 88:4235–4239 (1991).

Fuleihan et al., "Effects of the Lectin Concanavalin–A on the Regulation of Second Messengers and Parathyroid Hormone Release by Extracellular $Ca^{2+}$ in Bovine Parathyroid Cells," *Endocrinology* 128:2931–2936 (1991).

Fuleihan and Brown, "Effect on the Lectin Concanavalin–A on Calcium–Regulated Adenosine 3',5'–Monophosphate Accumulation in Bovine Parathyroid Cells," *Endocrinology* 126:1996–2002 (1990).

Garrett et al., "Cloning and Expression of a G–Protein––Coupled Calcium Receptor From a Human Parathyroid Adenoma," *Journal of Bone and Mineral Research* 8(Supplement 1):S148 at abstract No. 125 (1993).

Garrett et al., "Expression of the Parathyroid Calcium Receptor Gene in C–Cells," *Journal of Bone and Mineral Research* 9(1):S409 at abstract No. C398 (1994).

Goldberger and Anfinsen, "The Reversible Masking of Amino Groups in Ribonuclease and Its Possible Usefulness in the Synthesis of the Protein," *Biochemistry* vol. 1, Neurath et al. editors, Mack Printing Company, Easton, PA, pp. 401–405 (1962).

Gross and Witkop, "Selective Cleavage of the Methionyl Peptide Bonds in Ribonuclease with Cyanogen Bromide," *J. Amer. Chem. Soc.* 83:1510–1511 (1961).

Hammer et al., "Spontaneous Inflammatory Disease in Transgenic Rats Expressing HLA–B27 and Human $\beta_2$m: An Animal Model of HLA–B27–Associated Human Disorders," *Cell* 63:1099–1112 (1990).

Hammerland et al., "Mechanism of Action of the Calcimimetic Compounds NPS R–467 and NPS R–568 in Xenopus Oocytes Expressing a Bovine Parathyroid Cell Calcium Receptor," *Journal of Bone and Mineral Research* 8(Supplement 1):S133 at abstract No. 65 (1993).

Harootunian et al., "Effects of Calcitonin and Extracellular Calcium on Cytosolic Levels of Cyclic AMP and $Ca^{2+}$ in Rabbit Osteoclasts," *Journal of Bone and Mineral Research* 9(1):S246 at abstract No. B66 (1994).

Hashimoto et al., "Highly Diastereoselective Addition of Organometallic Reagents to Chiral Imines Derived from 1–(2–Methoxphenyl)ethylamine," *Synlett Letters* pp. 961–962 (1995).

Hawkins et al., "The Effects of High Extracellular $Ca^{2+}$ and $Mg^{2+}$ Concentrations on the Levels of Inositol 1,3,4,5–Tetrakisphosphate in Bovine Parathyroid Cells," *Endocrinology* 124:838–844 (1989).

Heath et al., "Inhibition of Human Parathyroid Hormone Secretion In Vivo by NPS R–568, a Calcimimetic Drug that Targets the Parathyroid Cell–Surface Calcium Receptor," *Bone* 16(Supplement):85S at abstract No. 23 (1995).

Hediger, "High Resolution Preparative Gel Electrophoresis of DNA Fragments and Plasmid DNA Using a Continuous Elution Apparatus," *Analytical Biochem.* 159:280–286 (1986).

Hensgens et al., *Nucleic Acids Research* 12:7327–7343 (1984).

Höltje and Maurhofer, "Conformational Analysis on Calcium Channel Active Diphenylalkylamines, Diphenylbutylpiperidines, Phenylalkylamines, and Perhexiline," *Quant. Struct.–Act. Relat.* 8:259–265 (1989).

Houamed et al., *Science* 252:1318–1321 (1991).

Houdebine and Chourrout, "Transgenesis in Fish," *Experientia* 47:891–897 (1991).

Hung et al., "Coupling of the Porcine Calcitonin Receptor to Cytosolic $Ca^{2+}$ and cAMP Levels in Xenopus Oocytes," *Journal of Bone and Mineral Research* 9(1):S410 at abstract No. C400 (1994).

Hutchison et al., "Mutagenesis at a Specific Position in a DNA Sequence," *J. Biol. Chem.* 253:6551–6560 (1978).

Jansen et al, "Immunotoxins: Hybrid Molecules Combining High Specificity and Potent Cytotoxicity," *Immunological Rev.* 62:185–216 (1982).

Jasys et al., "The Total Synthesis of Argiotoxins 636, 659 and 673," *Tetrahedron Letters* 29:6223–6226 (1988).

Joyner et al., "Production of a mutation in mouse En–2 gene by homologous recombination in embryonic stem cells," *Nature* 338:153–156 (1989).

Juaristi et al., "Use of N,N'–Dimethylpropyleneurea (DMPU) as Solvent in the Efficient Preparation of Enantiomerically Pure Secondary Amines," *Synthesis* pp. 1243–1246 (1993).

Katz et al., "Structure–Function Relationships for the Effects of Various Aminoglycoside Antibotics on Dispersed Bovine Parathyroid Cells," *Endocrinology* 131:903–910 (1992).

Kifor et al., "Phorbol Esters Modulate the High $Ca^{2+}$ – Stimulated Accumulation of Inositol Phosphates in Bovine Parathyroid Cells," *Journal of Bone and Mineral Research* 5(10):1003–1011 (1990).

Kifor and Brown, "Relationship between Diacylglycerol Levels and Extracellular $Ca^{2+}$ in Dispersed Bovine Parathyroid Cells," *Endocrinology* 123:2723–2729 (1988).

Killen and Lindstrom, "Specific Killing of Lymphocytes that Cause Experimental Autoimmune Myasthenia Gravis by Ricin Toxin–Acetylcholine Receptor Conjugates," *J. of Immunology* 133:2549–2553 (1984).

Kim et al., "Studies on the Structural Requirements for the Activity of the Skeletal Muscle Dihydropyridine Receptor/ Slow $Ca^{2+}$ Channel," *J. Biol. Chem.* 265:11858–11863 (1990).

Koenig et al., "Polyamines Mediate Androgenic Stimulation of Clacum Fluxes and Membrane Transport in Rat Heart Myocytes," *Circulation Research* 64:415–426 (1989).

Komeyoshi and Kudo, "Optically active amines and their manufacture, intermediates and uses," *Chemical Abstracts* 121:1060 at Abstract No. 230462Y (1994).

Larsson et al., "Paradoxical effects of K$^+$ and D–600 on parathyroid hormone secretion and cytoplasmic $Ca^{2+}$ in normal bovine and pathological human parathyroid cells," *Biochimica et Biophysica Acta* 847:263–269 (1985).

Lensink and De Vries, "Diastereoselective hydrogenation and kinetic resolution of imines using rhodium/diphosphine catalyzed hydrogenation," *Tetrahedron: Asymmetry* 4:215–222 (1993).

Lensink and de Vries, "Improving Enantioselectivity by Using a Mono–Sulphonated Diphosphine as Ligand for Homogenous Imine Hydrogenation," *Tetrahedron:Assymetry* 3(2)235–238 (1992).

Leszkovszky et al., "The Parmacology of Diphenylalkyl Derivatives," *Acta Physiologica Academiae Scientiarum Hungaricae Tomus* 29:283–297 (1966).

Levine, *Pharmacology: Drug Actions and Reactions*, Little Brown and Company, Inc. pp. 192–196 (1990).

Lindley, "A New Synthetic Substrate for Trypsin and its Application to the Determination of the Amino–acid Sequence of Proteins," *Nature* 178:647–648 (1956).

Lopez–Barneo and Armstrong, "Depolarizing Response of Rat Parathyroid Cells to Divalent Cations," *J. Gen. Physiol.* 82:269–294 (1983).

Majewski and MacKinnon, "Enantioselective deprotonation of protected 4–hydroxycyclohexanones," *Can. J. Chem.* 72:1699–1704 (1994).

Mattson et al., "An Improved Method for Reductive Alkylation of Amines Using Titanium(IV) Isopropoxide and Sodium Cyanoborohydride," *J. Org. Chem.* 55:2552–2554 (1990).

Merck Index, 11th Edition, Monograph No. 8699, pp. 420, 1379 (1989).

Merck Index, 11th Edition, Monograph No. 3916, p. 623 (1989).

Merrifield, "Solid Phase Peptide Synthesis. I. The Synthesis of a Tetrapeptide," *J. Amer. Chem. Society* 85:2149–2154 (1963).

Mikami et al., "Primary Structure and functional expression of the cardiac dihydropyridine–sensitive calcium channel," *Nature* 340:230–233 (1989).

Mithal et al., "Highly Purified Sheep C–Cells Express an Extracelluar $Ca^{2+}$ Receptor Similar to that Present in Parathyroid," *Journal of Bone and Mineral Research* 9(1):S282 at abstract No. B209 (1994).

Muff et al., "Regulation of Hormone Secretion and Cytosolic $Ca^{2+}$ by Extracellular $Ca^{2+}$ in Parathyroid Cells and C–Cell: Role of Voltage–Sensitive $Ca^{2+}$ Channels," *Archives of Biochemistry and Biophysics* 265:128–135 (1988).

Nason et al., "Synthesis of Neurotoxic Nephlla Spider Venoms: NSTX–3 and JSTX–3," *Tetrahedron Letters* 30:2337–2340 (1989).

Nelson et al., "Detection of Acridinium Esters by Chemiluminescence," in *Nonisotopic DNA Probe Techniques*, Kricka editor, Academic Press, Inc., San Diego, pp. 275–310 (1992)7.

Nemeth, "$Ca^{2+}$ Receptor–Dependent Regulation of Cellular Functions," *NIPS* 10:1–5 (1995) Check 1–15.

Nemeth and Scarpa, "Cystolic $Ca^{2+}$ and the regulation of secretion in parathyroid cells," *FEBS Letters* 203(1):15–19 (1986).

Nemeth, "Evidence for the Presence of a Novel $Ca^{2+}$–Binding Protein ($Ca^{2+}$ Receptor) on the Surface of Parathyroid Cells," *Calcium–Binding Proteins in Health and Disease*, Norman et al. editors, Academic Press, Inc., San Diego, pp. 36–38 (1987).

Nemeth and Scarpa, "Rapid Mobilization of Cellular $Ca^{2+}$ in Bovine Parathyroid Cells Evoked by Extracellular Divalent Cations—Evidence for a Cell Surface Calcium Receptor," *J. Biol. Chem.* 262(11):5188–5196 (1987).

Nemeth and Scarpa, "Receptor–Dependent Mobilization of Cellular $Ca^{2+}$ and the Regulation of Hormone Secretion in Parathyroid Cells," *Calcium Regulation and Bone Metabolism: Basic and Clinical Aspects* 9:167–171 (1987).

Nemeth, "Regulation of cystolic calcium by extracellular divalent cations in C–cells and parathyroid cells," *Cell Calcium* 11:323–327 (1990).

Nemeth et al., "Screening of compounds with potential action against calcium receptors and their use in therapy of disorders of calcium metabolism," *Chemical Abstracts* 122(1):P1057y (1995).

Nemeth and Scarpa, "Spermine Evokes the Rapid Mobilization of Cellular $Ca^{2+}$ in Parathyroid Cells," in *Calcium–Binding Proteins in Health and Disease*, Norman et al. editors, Academic Press, Inc., San Diego, pp. 33–35 (1987).

Nemeth and Carafoli, "The role of extracellular calcium in the regulation of intracellular calcium and cell function," *Cell Calcium* 11:319–321 (1990).

Opie, "Calcium Channel Antogonists Part V: Second–Generation Agents," *Cardiovascular Drugs and Therapy* 2:191–203 (1988).

Parker et al., "Targeted gene walking polymerase chain reaction," *Nucleic Acids Research* 19:3055–3060 (1991).

Pilch and Czech, "Ch. 10—Affinity Cross–Linking of Peptide Hormones and Their Receptors," in *Membranes, Detergents, and Receptor Solubilization*, Venter et al. editors, Alan R. Liss, Inc., New York, pp. 161–175 (1984).

Pollak et al., *Cell* 75:1297–1303 (1993).

Pursel et al., "Genetic Engineering of Livestock," *Science* 244:1281–1288 (1989).

Racke et al., "Functional expression of the parathyroid cell calcium receptor in Xenopus oocytes," *FEBS Letters* 333(1, 2):132–136 (1993).

Racke et al., "Functional Expression of the Parathyroid Cell Calcium Recptor in Xenopus Oocytes," *Journal of Bone and Mineral Research* Supplement 1, 6:S118 at abtract No. 141 (1991).

Rogers et al., "Calcium Receptor Expression in the Parathryoid Glands of Vitamin D–Deficient Rats is not Regulated by Plasma Caclium and 1,25(OH)$_2$D$_3$," *Journal of Bone and Mineral Research* 9(1):S409 at abstract No. C392 (1994).

Rogers et al., "Localization of Calcium Receptor mRNA in Rat Thyroid and Parathyroid Glands Using In Situ Hybridization Histochemistry," *Journal of Bone and Mineral Research* 9(1):S409 at abstract No. C390 (1994).

Rogers et al., "The Calcimimetic Compound NPS467 Reduces Plasma Calcium in a Dose–Dependent and Stero–Specific Manner," *Journal of Bone and Mineral Research* 8(Supplement 1):S180 at abstract No. 254 (1993).

Schäfer et al., "Polyamine Toxins from Spiders and Wasps," *The Alkaloids* 45:1–125 (1994).

Scheets et al., *Plant Science* 57:141–150 (1988).

Seely et al., "The Calcium Channel Blocker Diltiazem Lowers Serum Parathyroid Hormone Levels in Vivo and in Vitro," *Journal of Clinical Endocrinology and Metabolism* 68(6):1007–1012 (1989).

Shoback and Chen, "Injection of Poly (A)$^+$ RNA from Bovine Parathyroid Tissue into Xenopus Oocytes Confers Sensitivity to Extracellular Calcium," *Journal of Bone and Mineral Research* 6(Supplement 1):S135 at abstract No. 207 (1991).

Simons et al., "Gene Transfer into Sheep," *Bio/Technology* 6:179–183 (1988).

Steffey and Nemeth, "Extracellular Calcium–Sensing Mechanisms on Osteoclasts and Parathyroid Cells are Pharmacologically Distinct," *Journal of Bone and Mineral Research* 8(Supplement 11):S384 at at abstract No. 1071 (1993).

Steffey et al., "Calcimimetics: Structually and Mechanistically Novel Compounds that Inhibit Hormone Secretion From Parathyroid Cells," *Journal of Bone and Mineral Research* 8(Supplement 1):S175 ab abstract No. 236 (1993).

Triggle et al., "$Ca^{2+}$ Channel Ligands: Structure–Function Relationships of the 1,4–Dihydropyridines," *Medicinal Research Reviews* 9(2):123–180 (1989).

Van Niel and Pandit, "NADH Models XXI. Steroselective Reduction of Chiral Imines with Hantzsch Ester," *Tetrahedron* 41:6065–6011 (1985).

Wang and Bäckvall, "Ruthenium–catalysed Transfer Hydrogenation of Imines by Propan–2–ol," *J. Chem. Soc. Commun.* pp. 980–982 (1992).

Witkop, "Nonenzymatic Methods for the Preferential and Selective Cleavage and Modificaiton of Proteins," in *Advances in Protein Chemistry*, Anfinsen et al. editors, Academic Press, Inc., New York, 16:221–321 (1961).

Zaidi, "'Calcium Receptors' on Eukaryotic Cells with Special Reference to the Osteoclast," *Bioscience Reports* 10:493–507 (1990).

Zaidi et al., "Intracellular calcium in the control of osteoclast function. II. Paradoxical elevation of cytosolic free calcium by verapamil," *Biochemical and Biophysical Research Communications* 167:807–812 (1990).

FIG. 1a.
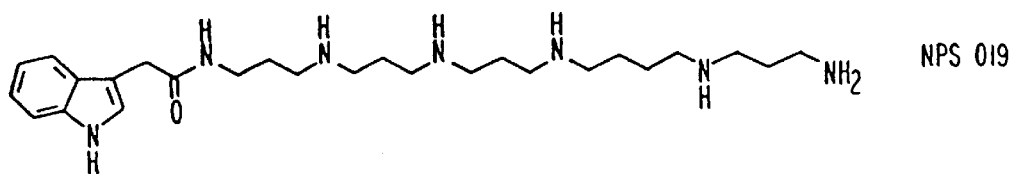
NPS 019
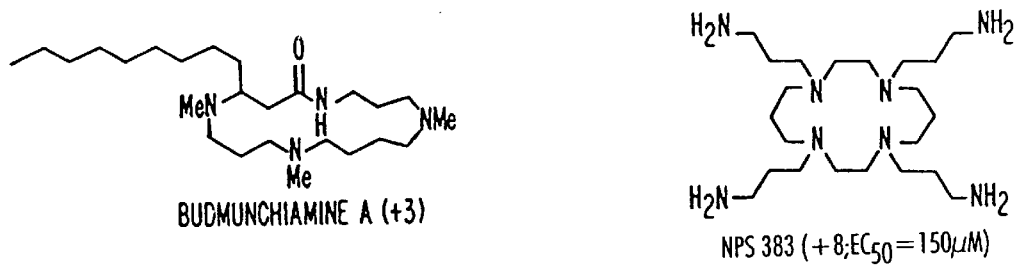
BUDMUNCHIAMINE A (+3)
NPS 383 (+8;EC$_{50}$=150µM)
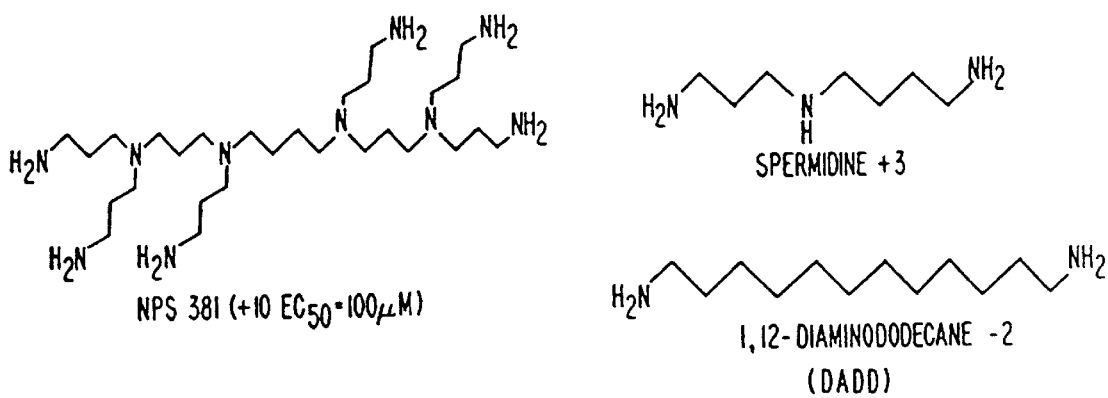
NPS 381 (+10 EC$_{50}$=100µM)
SPERMIDINE +3
1,12-DIAMINODODECANE -2
(DADD)
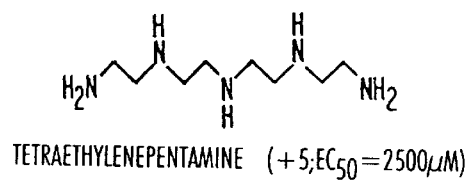
TETRAETHYLENEPENTAMINE (+5;EC$_{50}$=2500µM)
TRIETHYLENETETRAMINE (+4;EC$_{50}$=8000µM)
PENTAETHYLENEHEXAMINE (+6;EC$_{50}$=500µM)
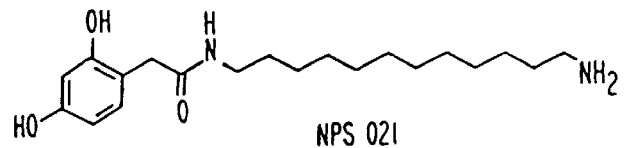
NPS 021

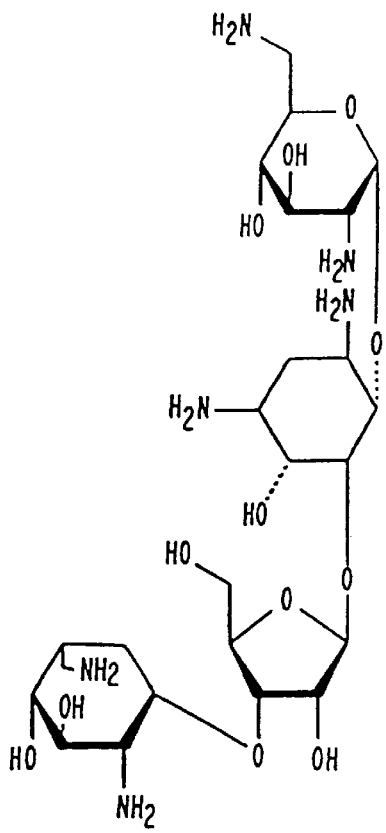
Neomycin B (+6)
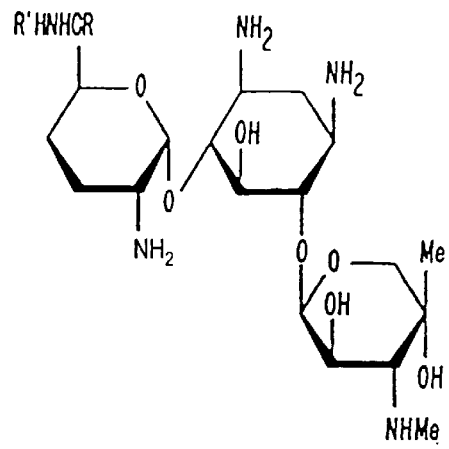
Gentamicin (Complex +5)
C1  R = R' = Me
C2  R = Me; R' = H
C1a R = R' = H
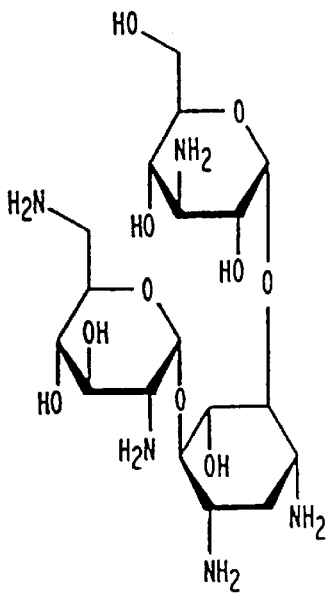
Bekanamycin (+5)
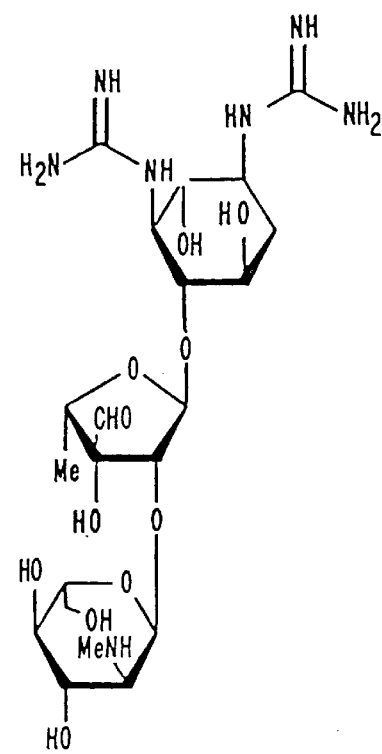
Streptomycin (+3)
FIG. 1b.

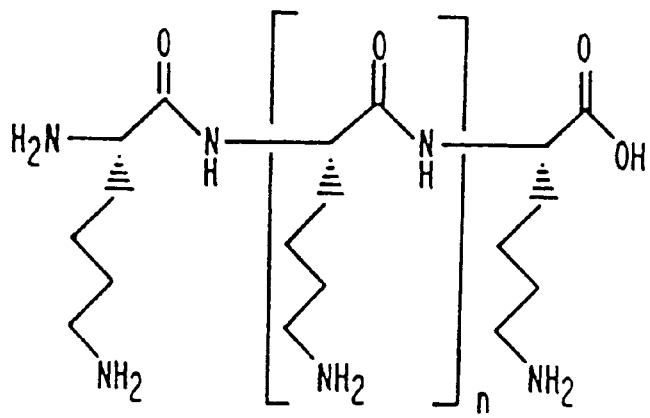
poly-Lys (27 kD) n=210  +210
poly-Lys (14 kD) n=110  +110
poly-Lys (38 kD) n=55   +55
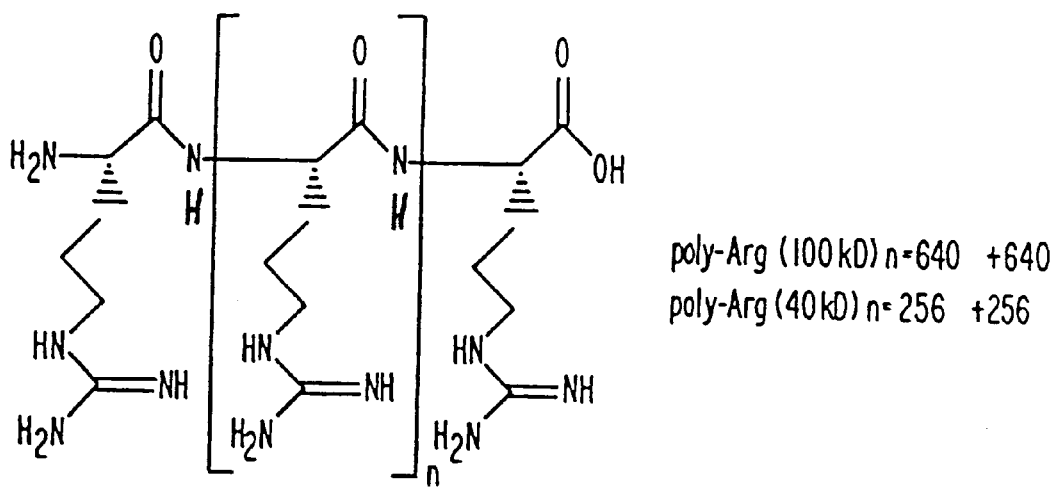
poly-Arg (100 kD) n=640  +640
poly-Arg (40 kD) n=256   +256
PROTAMINE  +21
H$_2$N-Pro-Arg-Arg-Arg-Arg-Ser-Ser-Ser-Arg-Pro-Val-Arg-Arg-Arg-Arg-
    Pro-Arg-Val-Ser-Arg-Arg-Arg-Arg-Arg-Arg-Gly-Gly-Arg-Arg-Arg-Arg-OH
*FIG. 1C.*

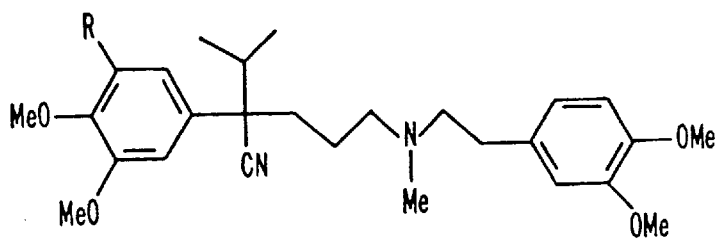
VERAPAMIL R=H +1
D-600 R=OMe +1
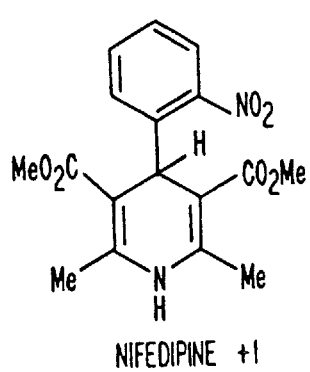
NIFEDIPINE +1
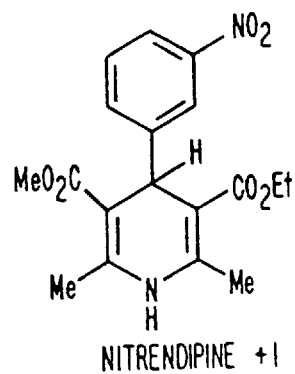
NITRENDIPINE +1
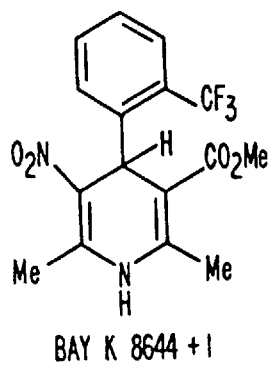
BAY K 8644 +1
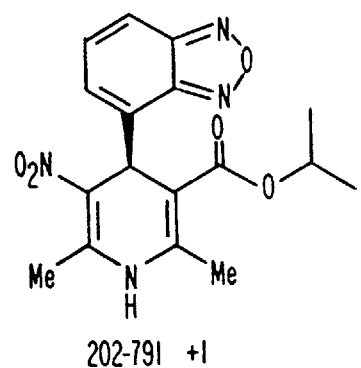
202-791 +1
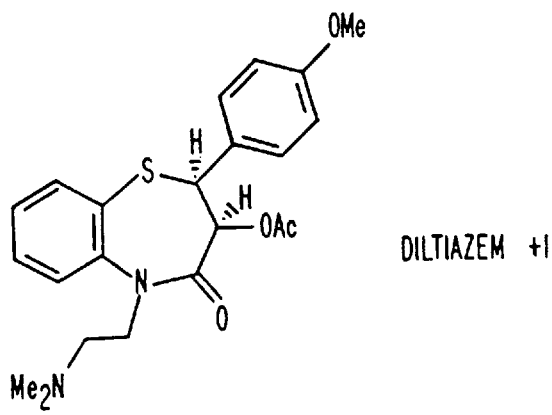
DILTIAZEM +1
FIG. 1d.

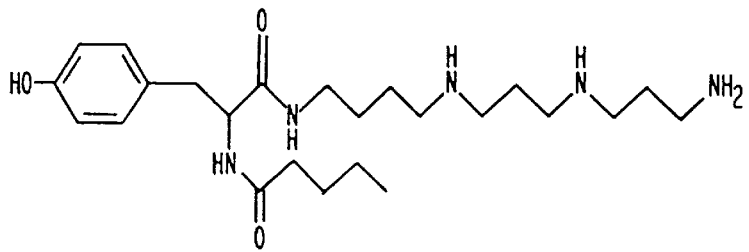
PHILANTHOTOXIN 433 +3
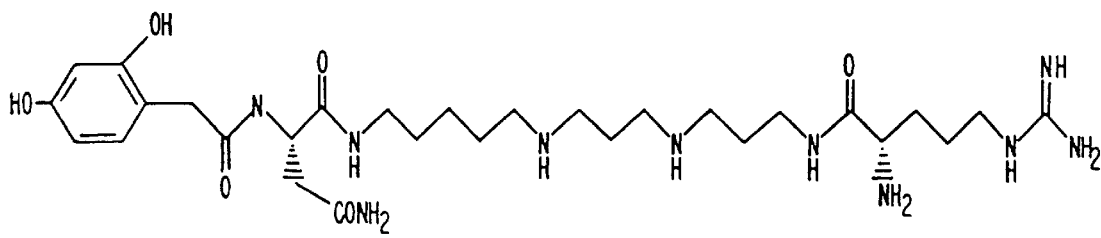
ARGIOTOXIN 636 +4
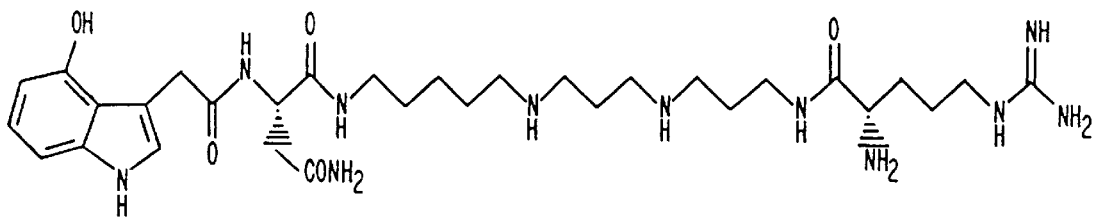
ARGIOTOXIN 659 +4
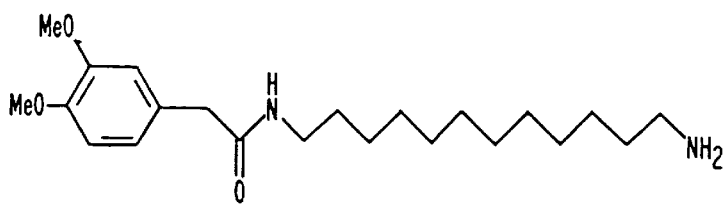
NPS 384
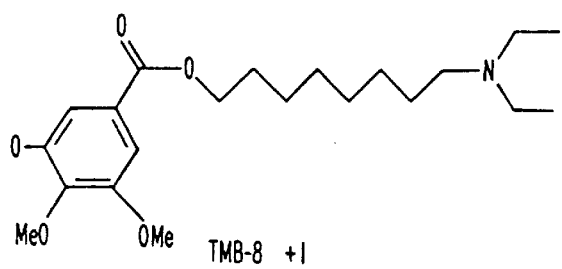
TMB-8 +1
FIG. 1e.

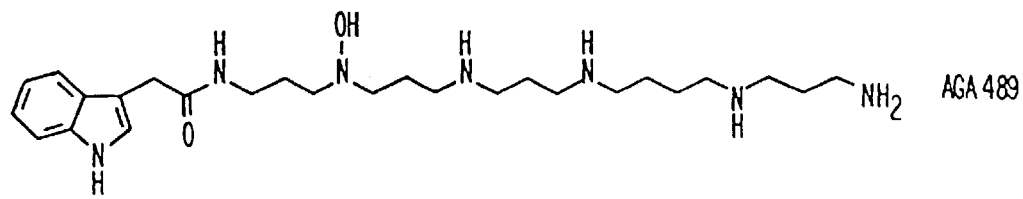 AGA 489
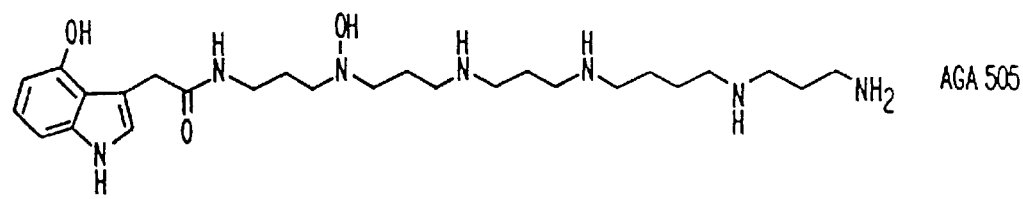 AGA 505
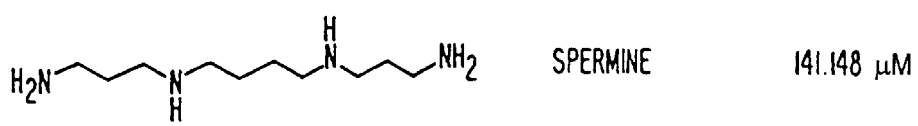 SPERMINE 141.148 μM
 HEXACYCLEN 20.9 μM
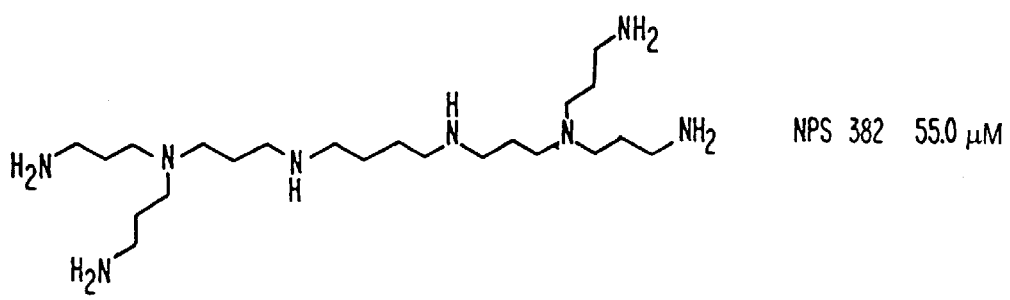 NPS 382 55.0 μM
FIG. 1f.

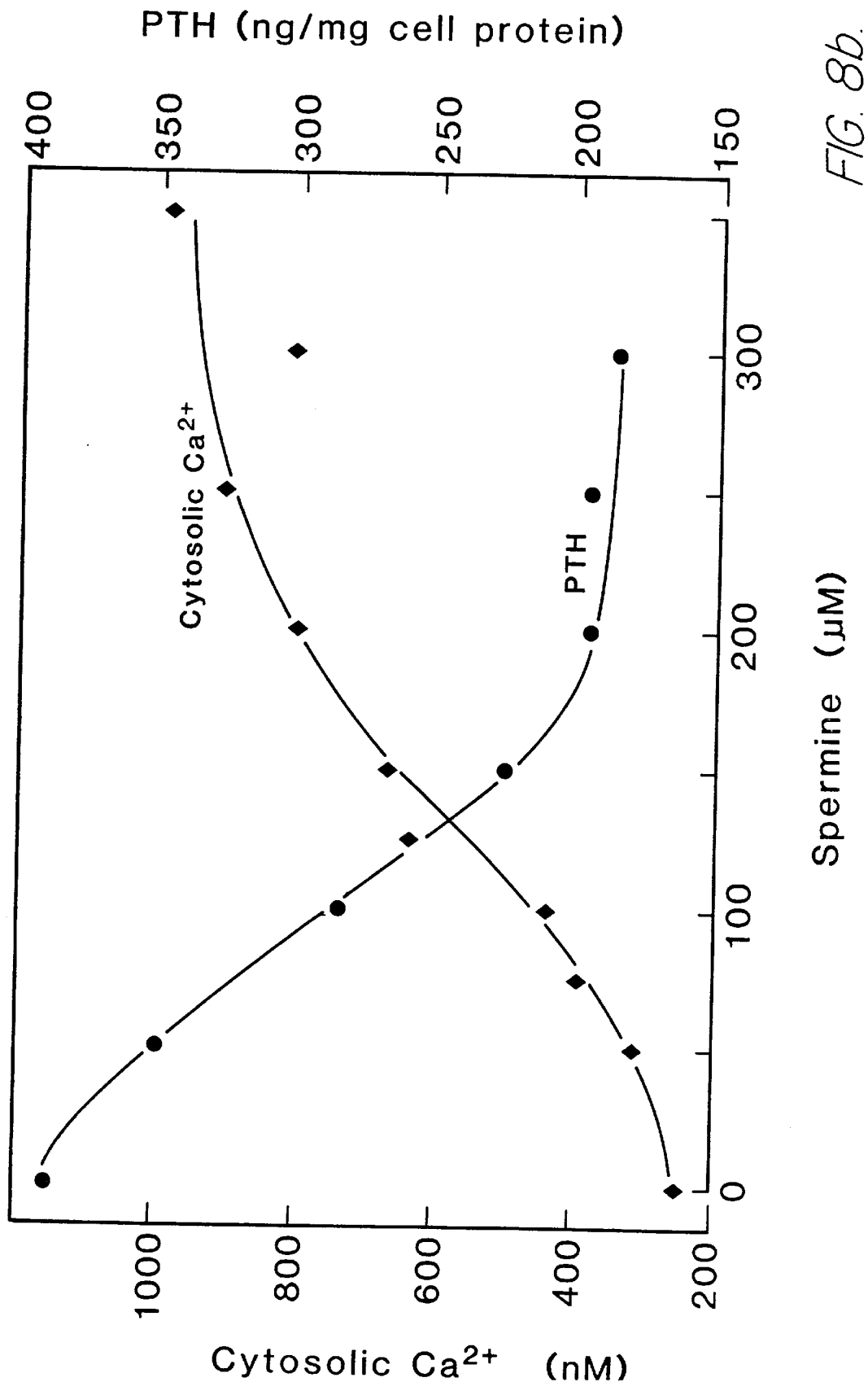

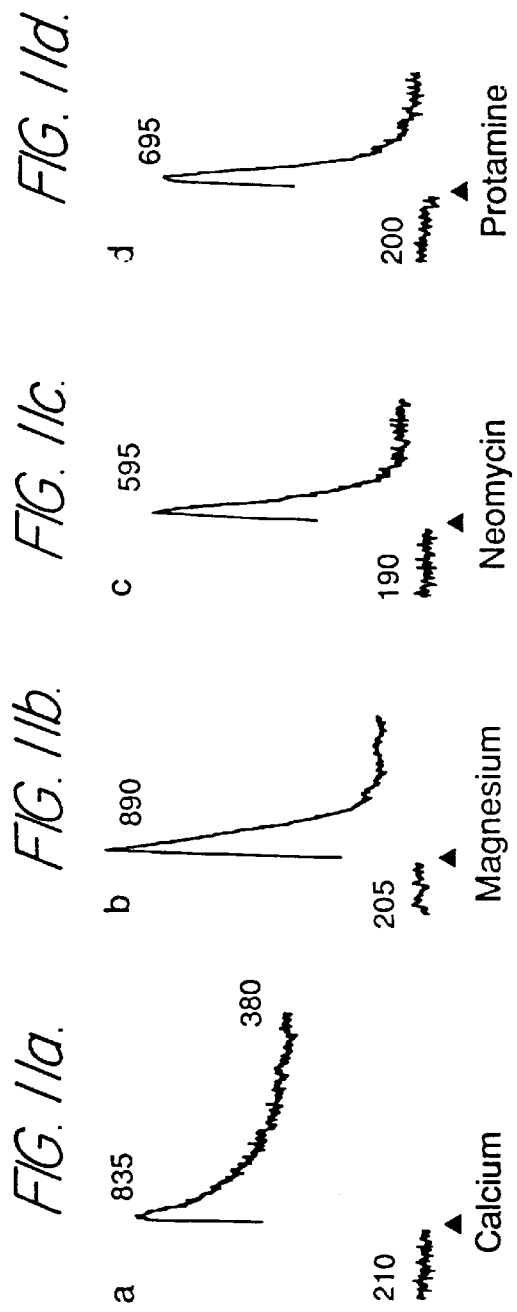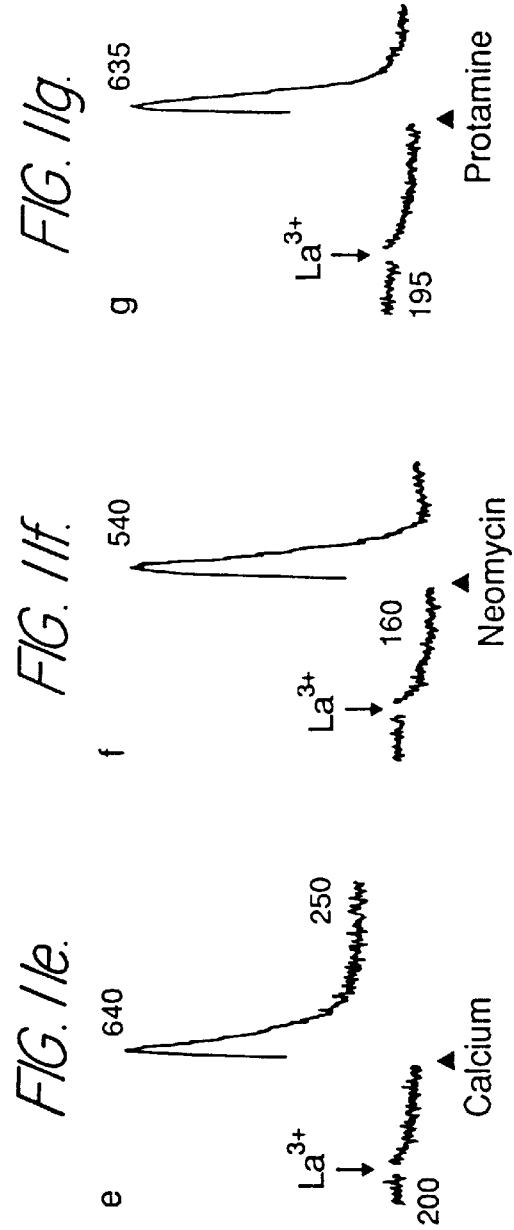

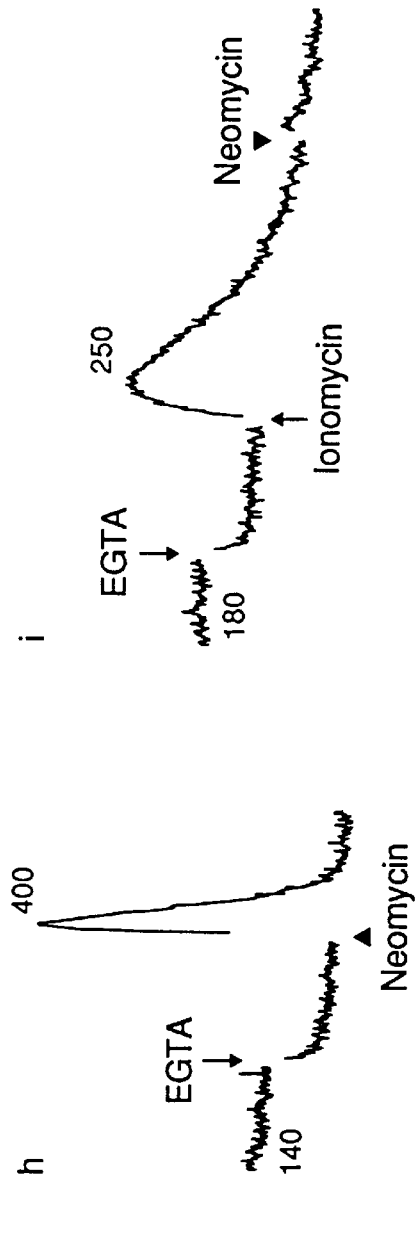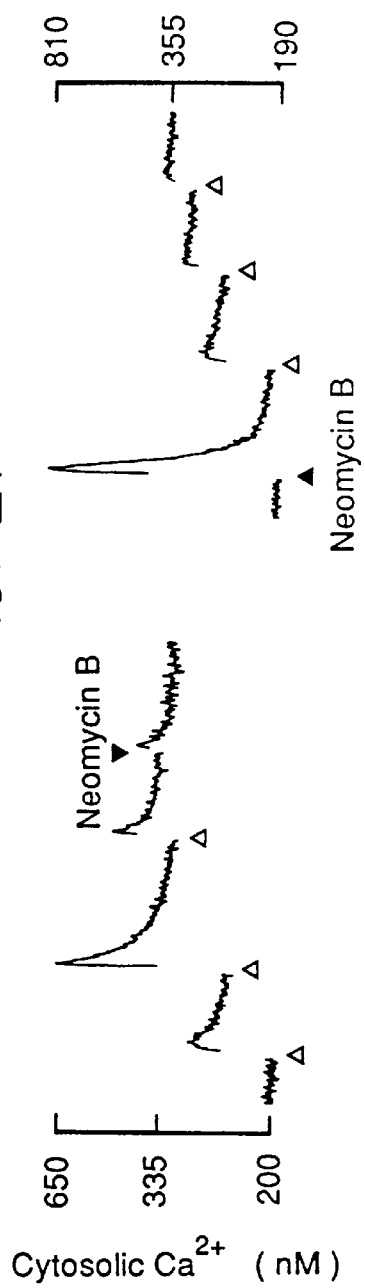

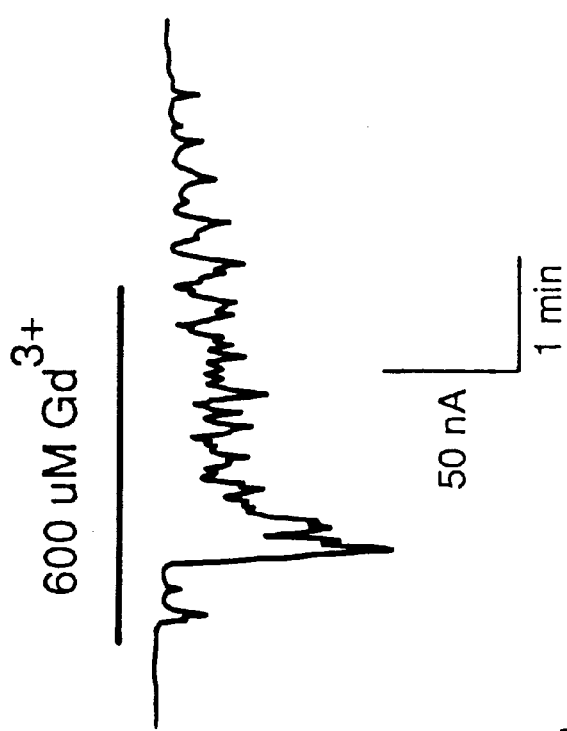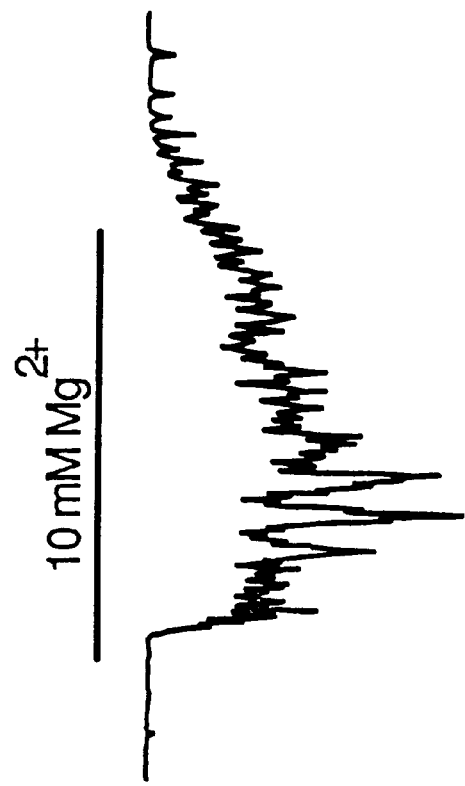

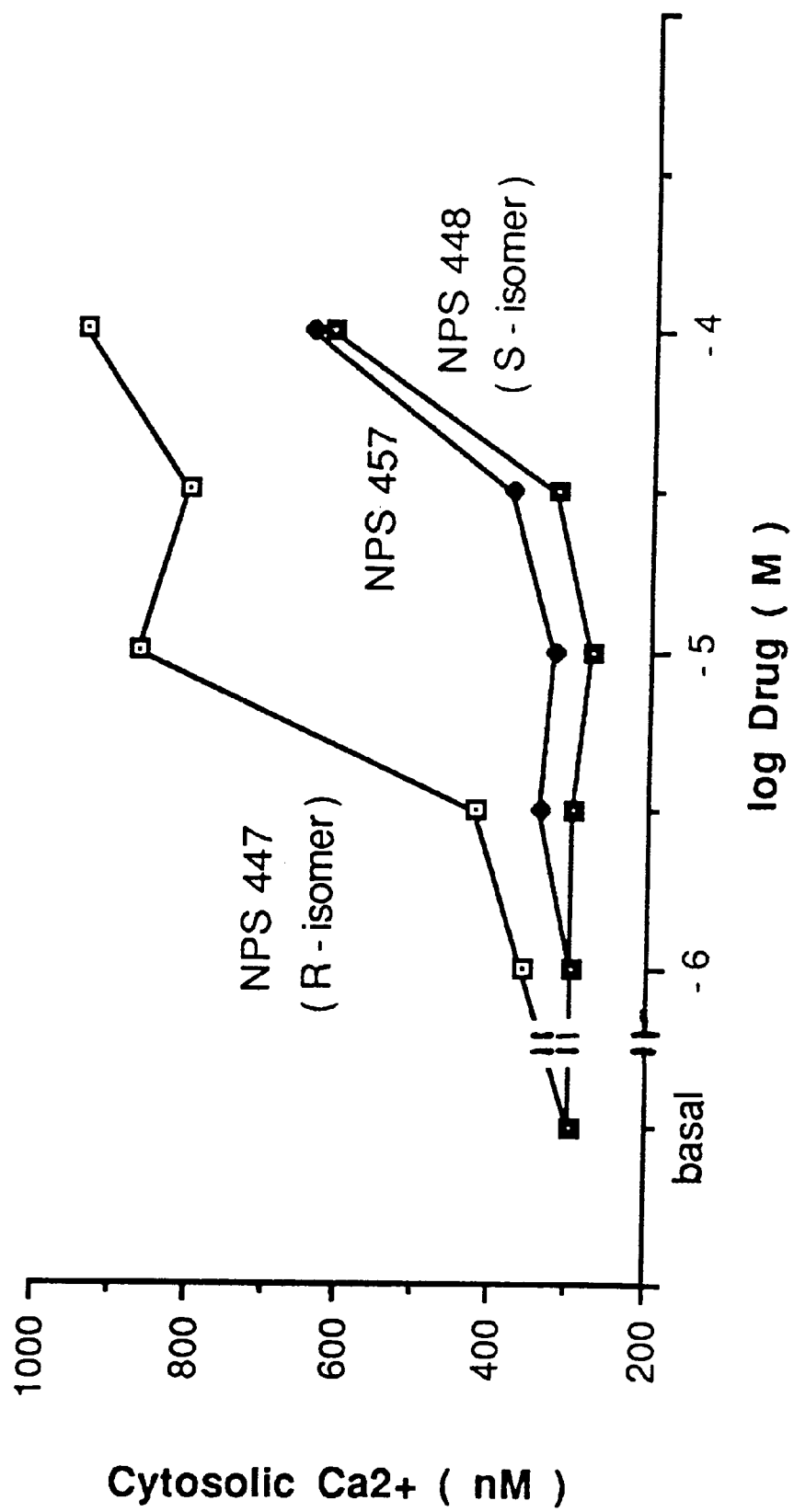

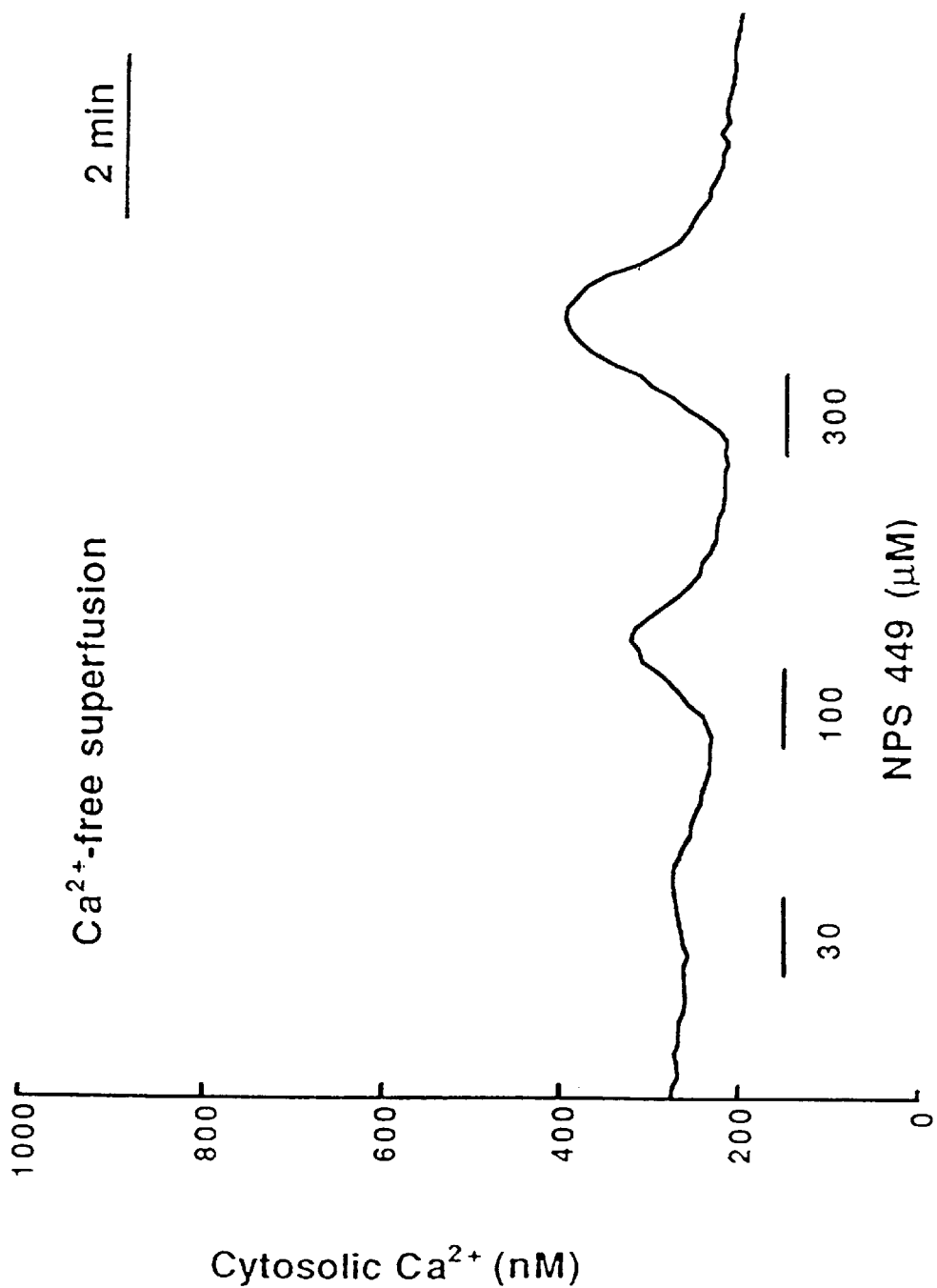
FIG. 3/b.

BoPCaRI cDNA RESTRICTION MAP

```
          10        20        30        40        50        60        70
 12345678901234567890123456789012345678901234567890123456789012345678901 2345
 CGGAAAAAAAAAAAAAAGTTCCCCACTCTAGTACAGAGAAGGTTGGCAGAGTCGTAAGCCCCCAACCTCTTAAACT    75

TCTCTGCATCTCCAAGGAGAAGGAGGGAAGAGGGGTTCTTTCCGACCTGAGGAGCTGGATCTGGGGTCCGAGAAC   150

CCCAAGGTAGCACCGGAAAGAACAGCACAGGAGGCGAGAGCGTGGCCGGTGGCCGGGAGAACCAGACCCGACGCG   225

CGGTCCTCGGCGCCGGGGTCCCGGGGACTCAGCTCAGCACGACTGGGAAGCCGAAAGTACTACACACGGTCTCTG   300

CATGATGTGACTTCTGAAGACTCAAGAGCCACCCACTTCACTAGTCTGCAATGGAGAAGGCAGAAATGGAAAGTC   375

AAACCCCACGGTTCCATTCTATTAATTCTGTAGACATGTGCCCCCACTGCAGGGAGTGAGTCGCACCAAGGGGGA   450

AAGTCCTCAGGGGCCCCCAGACCACCAGCGCTTGAGTCCCTCTTCCTGGAGAGAAAGCAGAACTATGGCACTTTA   525
                                                                MetAlaLeuTy
 TAGCTGCTGTTGGATCCTCTTGGCTTTTTCTACCTGGTGCACTTCCGCCTATGGGCCTGACCAGCGAGCCCAAAA   600
 rSerCysCysTrpIleLeuLeuAlaPheSerThrTrpCysThrSerAlaTyrGlyProAspGlnArgAlaGlnLy

GAAAGGGGACATTATCCTCGGGGGGCTCTTTCCTATTCATTTTGGGGTTGCAGTGAAAGATCAGGATCTAAAGTC   675
 sLysGlyAspIleIleLeuGlyGlyLeuPheProIleHisPheGlyValAlaValLysAspGlnAspLeuLysSe

GAGGCCGGAGTCCGTGGAGTGTATCAGGTATAATTTCCGAGGATTTCGCTGGTTACAAGCTATGATATTTGCCAT   750
 rArgProGluSerValGluCysIleArgTyrAsnPheArgGlyPheArgTrpLeuGlnAlaMetIlePheAlaIl

AGAGGAAATAAACAGCAGTCCAGCCCTTCTTCCCAACATGACCCTGGGATACAGGATATTCGACACTTGTAACAC   825
 eGluGluIleAsnSerSerProAlaLeuLeuProAsnMetThrLeuGlyTyrArgIlePheAspThrCysAsnTh

CGTCTCTAAAGCCTTGGAGGCCACCCTGAGTTTTGTGGCCCAGAACAAAATTGACTCTTTGAACCTTGATGAGTT   900
 rValSerLysAlaLeuGluAlaThrLeuSerPheValAlaGlnAsnLysIleAspSerLeuAsnLeuAspGluPh

CTGCAACTGCTCAGAGCACATCCCCTCTACCATCGCAGTGGTGGGAGCTACTGGCTCGGGCATCTCCACAGCAGT   975
 eCysAsnCysSerGluHisIleProSerThrIleAlaValValGlyAlaThrGlySerGlyIleSerThrAlaVa

GGCCAACCTGCTGGGGCTCTTCTACATCCCCCAGGTCAGCTATGCCTCCTCCAGCAGACTCCTCAGCAACAAGAA  1050
 lAlaAsnLeuLeuGlyLeuPheTyrIleProGlnValSerTyrAlaSerSerSerArgLeuLeuSerAsnLysAs

TCAATTCAAGTCCTTCCTCCGCACCATACCCAATGATGAACACCAGGCCACGGCCATGGCTGACATCATCGAGTA  1125
 nGlnPheLysSerPheLeuArgThrIleProAsnAspGluHisGlnAlaThrAlaMetAlaAspIleIleGluTy

CTTCCGCTGGAACTGGGTGGGCACAATTGCAGCTGACGATGACTATGGCCGGCCAGGGATCGAGAAGTTTCGAGA  1200
 rPheArgTrpAsnTrpValGlyThrIleAlaAlaAspAspAspTyrGlyArgProGlyIleGluLysPheArgGl

GGAAGCTGAGGAGAGGGACATCTGCATCGACTTCAGCGAGCTCATCTCCCAATACTCTGATGAGGAAAAGATCCA  1275
 uGluAlaGluGluArgAspIleCysIleAspPheSerGluLeuIleSerGlnTyrSerAspGluGluLysIleGl

GCAGGTGGTGGAGGTGATCCAGAATTCCACCGCCAAAGTCATTGTCGTCTTCTCCAGCGGCCCAGACCTGGAACC  1350
 nGlnValValGluValIleGlnAsnSerThrAlaLysValIleValValPheSerSerGlyProAspLeuGluPr
```

FIG. 47a.

```
         10        20        30        40        50        60        70
123456789012345678901234567890123456789012345678901234567890123456789012345
CCTCATCAAAGAGATCGTCCGGCGCAATATCACAGGCAGGATCTGGCTGGCCAGCGAGGCCTGGGCCAGCTCTTC    1425
oLeuIleLysGluIleValArgArgAsnIleThrGlyArgIleTrpLeuAlaSerGluAlaTrpAlaSerSerSe

CCTGATTGCTATGCCCGAGTATTTCCATGTGGTCGGAGGCACCATTGGGTTTGGTTTGAAAGCTGGGCAGATCCC    1500
rLeuIleAlaMetProGluTyrPheHisValValGlyGlyThrIleGlyPheGlyLeuLysAlaGlyGlnIlePr

AGGCTTCCGGGAATTCCTGCAGAAAGTCCACCCCAGGAAGTCTGTCCACAATGGTTTTGCCAAGGAGTTTTGGGA    1575
oGlyPheArgGluPheLeuGlnLysValHisProArgLysSerValHisAsnGlyPheAlaLysGluPheTrpGl

AGAAACATTTAACTGCCACCTGCAAGAGGGTGCTAAAGGCCCATTACCGGTGGACACCTTCCTGAGAGGTCACGA    1650
uGluThrPheAsnCysHisLeuGlnGluGlyAlaLysGlyProLeuProValAspThrPheLeuArgGlyHisGl

AGAAGGAGGTGCCAGGTTAAGCAACAGTCCCACTGCCTTCCGACCTCTGTGCACTGGGGAGGAGAACATCAGCAG    1725
uGluGlyGlyAlaArgLeuSerAsnSerProThrAlaPheArgProLeuCysThrGlyGluGluAsnIleSerSe

TGTCGAGACTCCTTACATGGATTATACACATTTACGGATATCCTACAACGTCTACTTAGCCGTCTACTCCATTGC    1800
rValGluThrProTyrMetAspTyrThrHisLeuArgIleSerTyrAsnValTyrLeuAlaValTyrSerIleAl

TCATGCCCTACAAGATATATACACCTGCATACCTGGGAGAGGGCTCTTCACCAACGGTTCCTGCGCAGATATCAA    1875
aHisAlaLeuGlnAspIleTyrThrCysIleProGlyArgGlyLeuPheThrAsnGlySerCysAlaAspIleLy

GAAGGTTGAAGCTTGGCAGGTCCTGAAACACCTGCGGCACCTAAATTTTACCAGCAATATGGGGGAGCAAGTAAC    1950
sLysValGluAlaTrpGlnValLeuLysHisLeuArgHisLeuAsnPheThrSerAsnMetGlyGluGlnValTh

TTTCGATGAATGTGGAGACCTGGCAGGGAACTATTCCATCATCAACTGGCACCTCTCCCCAGAGGACGGCTCCAT    2025
rPheAspGluCysGlyAspLeuAlaGlyAsnTyrSerIleIleAsnTrpHisLeuSerProGluAspGlySerIl

AGTGTTTAAGGAAGTTGGATATTACAATGTCTATGCCAAGAAAGGAGAGAGACTCTTCATCAATGATGAAAAAAT    2100
eValPheLysGluValGlyTyrTyrAsnValTyrAlaLysLysGlyGluArgLeuPheIleAsnAspGluLysIl

TCTGTGGAGTGGATTCTCAAGGGAGGTGCCTTTCTCCAACTGCAGTCGAGACTGCCTGGCAGGGACCAGGAAAGG    2175
eLeuTrpSerGlyPheSerArgGluValProPheSerAsnCysSerArgAspCysLeuAlaGlyThrArgLysGl

AATCATTGAGGGGGAGCCCACCTGCTGCTTTGAGTGTGTGGAATGTCCTGATGGGGAGTACAGCGACGAGACAGA    2250
yIleIleGluGlyGluProThrCysCysPheGluCysValGluCysProAspGlyGluTyrSerAspGluThrAs

TGCAAGTGCCTGTGATAAGTGCCCTGATGACTTCTGGTCCAATGAGAACCACACTTCCTGCATCGCCAAGGAGAT    2325
pAlaSerAlaCysAspLysCysProAspAspPheTrpSerAsnGluAsnHisThrSerCysIleAlaLysGluIl

CGAGTTTCTGTCGTGGACCGAGCCCTTCGGGATCGCACTCACGCTCTTTGCTGTGCTGGGCATTTTCCTCACAGC    2400
eGluPheLeuSerTrpThrGluProPheGlyIleAlaLeuThrLeuPheAlaValLeuGlyIlePheLeuThrAl

CTTCGTGCTGGGCGTCTTCATCAAGTTCCGCAACACGCCCATCGTCAAGGCCACCAACCGGGAGCTCTCCTATCT    2475
aPheValLeuGlyValPheIleLysPheArgAsnThrProIleValLysAlaThrAsnArgGluLeuSerTyrLe

CCTTCTCTTCTCCCTGCTCTGCTGCTTCTCCAGCTCCCTGTTCTTCATCGGGGAGCCCCAGGACTGGACGTGCCG    2550
uLeuLeuPheSerLeuLeuCysCysPheSerSerSerLeuPhePheIleGlyGluProGlnAspTrpThrCysAr

CCTGCGCCAGCCGGCCTTTGGCATCAGCTTCGTGCTCTGCATCTCGTGCATCCTGGTGAAAACCAATCGGGTCCT    2625
gLeuArgGlnProAlaPheGlyIleSerPheValLeuCysIleSerCysIleLeuValLysThrAsnArgValLe

CCTGGTGTTTGAGGCCAAGATTCCCACCAGCTTCCACCGGAAGTGGTGGGGCTCAACCTGCAGTTCCTGCTGGT    2700
uLeuValPheGluAlaLysIleProThrSerPheHisArgLysTrpTrpGlyLeuAsnLeuGlnPheLeuLeuVa
```

FIG. 47b.

```
          10        20        30        40        50        60        70
 12345678901234567890123456789012345678901234567890123456789012345678901234 5
 CTTCCTCTGCACCTTCATGCAGATTGTCATCTGTGCCATTTGGCTCAATACAGCGCCCCCCTCGAGCTACCGCAA   2775
 lPheLeuCysThrPheMetGlnIleValIleCysAlaIleTrpLeuAsnThrAlaProProSerSerTyrArgAs

CCACGAGCTGGAGGACGAGATCATCTTCATCACCTGCCACGAGGGCTCGCTCATGGCGCTGGGCTTCCTGATCGG   2850
 nHisGluLeuGluAspGluIleIlePheIleThrCysHisGluGlySerLeuMetAlaLeuGlyPheLeuIleGl

CTACACCTGCTTGCTGGCCGCCATCTGCTTCTTCTTCGCCTTCAAGTCCCGGAAGCTGCCAGAGAACTTCAATGA   2925
 yTyrThrCysLeuLeuAlaAlaIleCysPhePhePheAlaPheLysSerArgLysLeuProGluAsnPheAsnGl

AGCCAAGTTCATCACCTTCAGCATGCTCATCTTCTTCATCGTCTGGATCTCTTTCATCCCCGCCTACGCCAGCAC   3000
 uAlaLysPheIleThrPheSerMetLeuIlePhePheIleValTrpIleSerPheIleProAlaTyrAlaSerTh

TTACGGCAAGTTCGTCTCTGCCGTGGAGGTGATCGCCATCCTGGCGGCCAGCTTTGGCTTGCTGGCCTGTATCTT   3075
 rTyrGlyLysPheValSerAlaValGluValIleAlaIleLeuAlaAlaSerPheGlyLeuLeuAlaCysIlePh

CTTCAACAAGGTCTACATCATCCTCTTCAAGCCTTCCCGGAACACCATCGAGGAGGTGCGCTGCAGCACCGCGGC   3150
 ePheAsnLysValTyrIleIleLeuPheLysProSerArgAsnThrIleGluGluValArgCysSerThrAlaAl

ACACGCCTTCAAGGTGGCCGCCCGAGCCACGCTGCGCCGCAGCAACGTCTCCCGCCAGCGGTCCAGCAGCCTAGG   3225
 aHisAlaPheLysValAlaAlaArgAlaThrLeuArgArgSerAsnValSerArgGlnArgSerSerSerLeuGl

GGGCTCCACGGGATCCACCCCCTCCTCCTCCATCAGCAGCAAGAGCAACAGCGAGGACCCGTTCCCTCAGCAGCA   3300
 yGlySerThrGlySerThrProSerSerSerIleSerSerLysSerAsnSerGluAspProPheProGlnGlnGl

GCCGAAGAGGCAGAAGCAGCCGCAGCCGCTGGCCCTGAGCCCGCACAACGCGCAGCAGCCACAGCCGCGGCCACC   3375
 nProLysArgGlnLysGlnProGlnProLeuAlaLeuSerProHisAsnAlaGlnGlnProGlnProArgProPr

CTCGACCCCACAGCCGCAGCCACAGTCGCAGCAGCCGCCCCGATGCAAGCAGAAGGTCATCTTCGGCAGCGGCAC   3450
 oSerThrProGlnProGlnProGlnSerGlnGlnProProArgCysLysGlnLysValIlePheGlySerGlyTh

CGTCACCTTCTCGCTGAGCTTTGACGAGCCTCAGAAGACCGCCGTGGCTCACAGGAATTCCACGCACCAGACCTC   3525
 rValThrPheSerLeuSerPheAspGluProGlnLysThrAlaValAlaHisArgAsnSerThrHisGlnThrSe

CCTGGAGGCCCAGAAAAACAATGACGCCCTGACCAAACACCAGGCGTTGCTCCCGCTGCAGTGCGGAGAGACGGA   3600
 rLeuGluAlaGlnLysAsnAsnAspAlaLeuThrLysHisGlnAlaLeuLeuProLeuGlnCysGlyGluThrAs

CTCAGAATTGACCTCCCAGGAGACAGGCCTGCAGGGCCCTGTGGGTGAGGACCACCAGCTAGAGATGGAGGACCC   3675
 pSerGluLeuThrSerGlnGluThrGlyLeuGlnGlyProValGlyGluAspHisGlnLeuGluMetGluAspPr

CGAAGAGATGTCCCCGGCACTTGTAGTGTCTAATTCCCGGAGCTTTGTCATCAGTGGCGGAGGCAGCACTGTTAC   3750
 oGluGluMetSerProAlaLeuValValSerAsnSerArgSerPheValIleSerGlyGlyGlySerThrValTh

GGAAAACATGCTGCGTTCTTAAAAGGGAAGGAGAAAGCCAGTTCAGGGGGAATCCAGGCAGTTTCCCCGGGATGA   3825
 rGluAsnMetLeuArgSer

CCTTCTCCAAAGGGATGAGGAACTGCCCCCCCACCCCCACCCCCTTCCTCCAGGAAGGAGGGATAAGACCCACCA   3900

AATGCTTGGAACTTAGTTGCACTGCTATAAACGACAGTGAATGAAATAATGTCCCCCTTAAAATTAAAAAGAGGG   3975

GAGCGGTGTGCTTCTGTGGTTAGGTTTATCAGAGTGCTGAGATCCCTATAGTCAGGTTCGCCTTTCCTATCCCTG   4050
```

FIG. 47c.

```
          10        20        30        40        50        60        70
 12345678901234567890123456789012345678901234567890123456789012345678901234 5
 CTTCCATTCTCCTCTTCTGTTCTATCCCATCCAACAGTCCAGAGATAAAACCATGGCTTTAAGATACCCACCTAT   4125

TCCCCCTAGGGTCTTATTTGTTGTTTTTGTTGCTGTTGTTTTGGTTTGATTTTTGTTTTAATGTTGAAACGTCT     4200

GCCCTGAACTTTGCAGACAGCCTGGTCCAAAAACAAACCTGTGCAGAGTGACAGGACCTCCTATGGGCACCACTA    4275

GAGTTGAGTGCGAAAGACAGAATGTCGCCAGCGCTGCCCAACACCTTGACAGTGGGAAGAACTTGAAATGTCCAG    4350

AGCTGTAAGATGAATGTGTCCCCTCCTATTTATGAAAAATGTTAAATATGTGGTTTCCTACTTGCTGCTGCTGTC    4425

ACGTGACATGGAGAAGGTTAGCATCCATCCTCCAGCAGTATGTCTGATCTTGTCCAGAGTGTGATGGTGATGCCA    4500

CGTTTAGATTCCAATATCTCAGGAATCACCTCAGCCTGCATGAATCCAATGAGCTGTATCTGTAATTAATATTGT    4575

CATATGTAGCTTTATCCTTAAGAAAATGTGTTTGTTTTAATAGTCCGTGGAAAATATAAGCTGGAAAAAATGTCC   4650

CAGTCTGGTTGATATAAGGCAGTATTATTGAGTCCCGTTTTCTTTGCCCGCCCCACCACCCACACCCCAATGAGC   4725

TAAGCCCTAAATGAGCCCTTTCAGGGCCCAGGGATCCAGAAGCTCCCTCTTTCTCCACCCCAAACGCTTCCTGAA   4800

GTCAGATCCATGCCTTTCCCTGTGAAGAATAAGCTCCCAGTCTCTGACCTCCTACCAGTTTCTGGGGTAAGAACA   4875

CGTGGTTCCAAGAGAGCTCTCATGGGATATTACTCTTGGCACCCCCAATGCCATACTTAGGTTCCCTCCAGCAG    4950

TGGGATCTGCCCATGGGTAGTTACAAGATTGAACGTTGAATGGCATACTGCTGAACAGTCAGTTCTGGAGCTAGA   5025

GAGGCCTGGGGTCAAGTGCTGGGTTTGTCACTCACAAGTTGGGTGACCACAGGCAGGGAACCTTGACCTCACTCA   5100

GCCCCAGCTTCTTTGTGTCTAAAATGGAGGTAATAATCATCCTTTTCCCGCAGAGCTCTTATGTGGGTTAAATGA   5175

GATAAATGTATGTAAAGTATTTTAGCATGGTGCCTAGCCCATAGTAAGCACGCAATAAATATTAGTTAATATTAA   5250

AAAAAAAAAAAAAAAAAAAAAAAA                                                     5275
```

FIG. 47d.

```
           10        20        30        40        50        60        70
  12345678901234567890123456789012345678901234567890123456789012345678901234 5
  GCTGCTGTGGCCGGACCCGAAGGCGGGCGCCGGGAGCGCAGCGAGCCAGACGCGCCTCTCCAAGACCGTGACCTT           75

GGCATAGGGAGCGGGGCTGCGCGCAGTCCTGAGATCAGACCAGAGCTCATCCTCGTGGAGACCCACGGCCGAGGG         150

GCCGGAGCTGCCTCTGTGCGAGGGAGCCCTGGCCGCGGCGCAGAAGGCATCACAGGAGGCCTCTGCATGATGTGG         225

CTTCCAAAGACTCAAGGACCACCCACATTACAAGTCTGGATTGAGGAAGGCAGAAATGGAGATTCAAACACCACG         300

TCTTCTATTATTTTATTAATCAATCTGTAGACATGTGTCCCCACTGCAGGGAGTGAACTGCTCCAAGGGAGAAAC         375

TTCTGGGAGCCTCCAAACTCCTAGCTGTCTCATCCCTTGCCCTGGAGAGACGGCAGAACCATGGCATTTTATAGC         450
                                                                 MetAlaPheTyrSer

TGCTGCTGGGTCCTCTTGGCACTCACCTGGCACACCTCTGCCTACGGGCCAGACCAGCGAGCCCAAAAGAAGGGG         525
  CysCysTrpValLeuLeuAlaLeuThrTrpHisThrSerAlaTyrGlyProAspGlnArgAlaGlnLysLysGly

GACATTATCCTTGGGGGGCTCTTTCCTATTCATTTTGGAGTAGCAGCTAAAGATCAAGATCTCAAATCAAGGCCG         600
  AspIleIleLeuGlyGlyLeuPheProIleHisPheGlyValAlaAlaLysAspGlnAspLeuLysSerArgPro

GAGTCTGTGGAATGTATCAGGTATAATTTCCGTGGGTTTCGCTGGTTACAGGCTATGATATTTGCCATAGAGGAG         675
  GluSerValGluCysIleArgTyrAsnPheArgGlyPheArgTrpLeuGlnAlaMetIlePheAlaIleGluGlu

ATAAACAGCAGCCCAGCCCTTCTTCCCAACTTGACGCTGGGATACAGGATATTTGACACTTGCAACACCGTTTCT         750
  IleAsnSerSerProAlaLeuLeuProAsnLeuThrLeuGlyTyrArgIlePheAspThrCysAsnThrValSer

AAGGCCTTGGAAGCCACCCTGAGTTTTGTTGCTCAAAACAAAATTGATTCTTTGAACCTTGATGAGTTCTGCAAC         825
  LysAlaLeuGluAlaThrLeuSerPheValAlaGlnAsnLysIleAspSerLeuAsnLeuAspGluPheCysAsn

TGCTCAGAGCACATTCCCTCTACGATTGCTGTGGTGGGAGCAACTGGCTCAGGCGTCTCCACGGCAGTGGCAAAT         900
  CysSerGluHisIleProSerThrIleAlaValValGlyAlaThrGlySerGlyValSerThrAlaValAlaAsn

CTGCTGGGGCTCTTCTACATTCCCCAGGTCAGTTATGCCTCCTCCAGCAGACTCCTCAGCAACAAGAATCAATTC         975
  LeuLeuGlyLeuPheTyrIleProGlnValSerTyrAlaSerSerSerArgLeuLeuSerAsnLysAsnGlnPhe

AAGTCTTTCCTCCGAACCATCCCCAATGATGAGCACCAGGCCACTGCCATGGCAGACATCATCGAGTATTTCCGC        1050
  LysSerPheLeuArgThrIleProAsnAspGluHisGlnAlaThrAlaMetAlaAspIleIleGluTyrPheArg

TGGAACTGGGTGGGCACAATTGCAGCTGATGACGACTATGGGCGGCCGGGGATTGAGAAATTCCGAGAGGAAGCT        1125
  TrpAsnTrpValGlyThrIleAlaAlaAspAspAspTyrGlyArgProGlyIleGluLysPheArgGluGluAla

GAGGAAAGGGATATCTGCATCGACTTCAGTGAACTCATCTCCCAGTACTCTGATGAGGAAGAGATCCAGCATGTG        1200
  GluGluArgAspIleCysIleAspPheSerGluLeuIleSerGlnTyrSerAspGluGluGluIleGlnHisVal

GTAGAGGTGATTCAAAATTCCACGGCCAAAGTCATCGTGGTTTTCTCCAGTGGCCCAGATCTTGAGCCCCTCATC        1275
  ValGluValIleGlnAsnSerThrAlaLysValIleValValPheSerSerGlyProAspLeuGluProLeuIle

AAGGAGATTGTCCGGCGCAATATCACGGGCAAGATCTGGCTGGCCAGCGAGGCCTGGGCCAGCTCCTCCCTGATC        1350
  LysGluIleValArgArgAsnIleThrGlyLysIleTrpLeuAlaSerGluAlaTrpAlaSerSerSerLeuIle
```

*FIG. 48a.*

```
           10        20        30        40        50        60        70
  12345678901234567890123456789012345678901234567890123456789012345678901234 5
  GCCATGCCTCAGTACTTCCACGTGGTTGGCGGCACCATTGGATTCGCTCTGAAGGCTGGGCAGATCCCAGGCTTC    1425
  AlaMetProGlnTyrPheHisValValGlyGlyThrIleGlyPheAlaLeuLysAlaGlyGlnIleProGlyPhe

CGGGAATTCCTGAAGAAGGTCCATCCCAGGAAGTCTGTCCACAATGGTTTTGCCAAGGAGTTTTGGGAAGAAACA    1500
  ArgGluPheLeuLysLysValHisProArgLysSerValHisAsnGlyPheAlaLysGluPheTrpGluGluThr

TTTAACTGCCACCTCCAAGAAGGTGCAAAAGGACCTTTACCTGTGGACACCTTTCTGAGAGGTCACGAAGAAAGT    1575
  PheAsnCysHisLeuGlnGluGlyAlaLysGlyProLeuProValAspThrPheLeuArgGlyHisGluGluSer

GGCGACAGGTTTAGCAACAGCTCGACAGCCTTCCGACCCCTCTGTACAGGGGATGAGAACATCAGCAGTGTCGAG    1650
  GlyAspArgPheSerAsnSerSerThrAlaPheArgProLeuCysThrGlyAspGluAsnIleSerSerValGlu

ACCCCTTACATAGATTACACGCATTTACGGATATCCTACAATGTGTACTTAGCAGTCTACTCCATTGCCCACGCC    1725
  ThrProTyrIleAspTyrThrHisLeuArgIleSerTyrAsnValTyrLeuAlaValTyrSerIleAlaHisAla

TTGCAAGATATATATACCTGCTTACCTGGGAGAGGGCTCTTCACCAATGGCTCCTGTGCAGACATCAAGAAAGTT    1800
  LeuGlnAspIleTyrThrCysLeuProGlyArgGlyLeuPheThrAsnGlySerCysAlaAspIleLysLysVal

GAGGCGTGGCAGGTCCTGAAGCACCTACGGCATCTAAACTTTACAAACAATATGGGGGAGCAGGTGACCTTTGAT    1875
  GluAlaTrpGlnValLeuLysHisLeuArgHisLeuAsnPheThrAsnAsnMetGlyGluGlnValThrPheAsp

GAGTGTGGTGACCTGGTGGGGAACTATTCCATCATCAACTGGCACCTCTCCCCAGAGGATGGCTCCATCGTGTTT    1950
  GluCysGlyAspLeuValGlyAsnTyrSerIleIleAsnTrpHisLeuSerProGluAspGlySerIleValPhe

AAGGAAGTCGGGTATTACAACGTCTATGCCAAGAAGGGAGAAAGACTCTTCATCAACGAGGAGAAAATCCTGTGG    2025
  LysGluValGlyTyrTyrAsnValTyrAlaLysLysGlyGluArgLeuPheIleAsnGluGluLysIleLeuTrp

AGTGGGTTCTCCAGGGAGCCACTCACCTTTGTGCTGTCTGTCCTCCAGGTGCCCTTCTCCAACTGCAGCCGAGAC    2100
  SerGlyPheSerArgGluProLeuThrPheValLeuSerValLeuGlnValProPheSerAsnCysSerArgAsp

TGCCTGGCAGGGACCAGGAAAGGGATCATTGAGGGGGAGCCCACCTGCTGCTTTGAGTGTGTGGAGTGTCCTGAT    2175
  CysLeuAlaGlyThrArgLysGlyIleIleGluGlyGluProThrCysCysPheGluCysValGluCysProAsp

GGGGAGTATAGTGATGAGACAGATGCCAGTGCCTGTAACAAGTGCCCAGATGACTTCTGGTCCAATGAGAACCAC    2250
  GlyGluTyrSerAspGluThrAspAlaSerAlaCysAsnLysCysProAspAspPheTrpSerAsnGluAsnHis

ACCTCCTGCATTGCCAAGGAGATCGAGTTTCTGTCGTGGACGGAGCCCTTTGGGATCGCACTCACCCTCTTTGCC    2325
  ThrSerCysIleAlaLysGluIleGluPheLeuSerTrpThrGluProPheGlyIleAlaLeuThrLeuPheAla

GTGCTGGGCATTTTCCTGACAGCCTTTGTGCTGGGTGTGTTTATCAAGTTCCGCAACACACCCATTGTCAAGGCC    2400
  ValLeuGlyIlePheLeuThrAlaPheValLeuGlyValPheIleLysPheArgAsnThrProIleValLysAla

ACCAACCGAGAGCTCTCCTACCTCCTCCTCTTCTCCCTGCTCTGCTGCTTCTCCAGCTCCCTGTTCTTCATCGGG    2475
  ThrAsnArgGluLeuSerTyrLeuLeuLeuPheSerLeuLeuCysCysPheSerSerSerLeuPhePheIleGly

GAGCCCCAGGACTGGACGTGCCGCCTGCGCCAGCCGGCCTTTGGCATCAGCTTCGTGCTCTGCATCTCATGCATC    2550
  GluProGlnAspTrpThrCysArgLeuArgGlnProAlaPheGlyIleSerPheValLeuCysIleSerCysIle

CTGGTGAAAACCAACCGTGTCCTCCTGGTGTTTGAGGCCAAGATCCCCACCAGCTTCCACCGCAAGTGGTGGGGG    2625
  LeuValLysThrAsnArgValLeuLeuValPheGluAlaLysIleProThrSerPheHisArgLysTrpTrpGly

CTCAACCTGCAGTTCCTGCTGGTTTTCCTCTGCACCTTCATGCAGATTGTCATCTGTGTGATCTGGCTCTACACC    2700
  LeuAsnLeuGlnPheLeuLeuValPheLeuCysThrPheMetGlnIleValIleCysValIleTrpLeuTyrThr
```

GCGCCCCCCTCAAGCTACCGCAACCAGGAGCTGGAGGATGAGATCATCTTCATCACGTGCCACGAGGGCTCCCTC                2775
AlaProProSerSerTyrArgAsnGlnGluLeuGluAspGluIleIlePheIleThrCysHisGluGlySerLeu

ATGGCCCTGGGCTTCCTGATCGGCTACACCTGCCTGCTGGCTGCCATCTGCTTCTTCTTTGCCTTCAAGTCCCGG                2850
MetAlaLeuGlyPheLeuIleGlyTyrThrCysLeuLeuAlaAlaIleCysPhePhePheAlaPheLysSerArg

AAGCTGCCGGAGAACTTCAATGAAGCCAAGTTCATCACCTTCAGCATGCTCATCTTCTTCATCGTCTGGATCTCC                2925
LysLeuProGluAsnPheAsnGluAlaLysPheIleThrPheSerMetLeuIlePhePheIleValTrpIleSer

TTCATTCCAGCCTATGCCAGCACCTATGGCAAGTTTGTCTCTGCCGTAGAGGTGATTGCCATCCTGGCAGCCAGC                3000
PheIleProAlaTyrAlaSerThrTyrGlyLysPheValSerAlaValGluValIleAlaIleLeuAlaAlaSer

TTTGGCTTGCTGGCGTGCATCTTCTTCAACAAGATCTACATCATTCTCTTCAAGCCATCCCGCAACACCATCGAG                3075
PheGlyLeuLeuAlaCysIlePhePheAsnLysIleTyrIleIleLeuPheLysProSerArgAsnThrIleGlu

GAGGTGCGTTGCAGCACCGCAGCTCACGCTTTCAAGGTGGCTGCCCGGGCCACGCTGCGCCGCAGCAACGTCTCC                3150
GluValArgCysSerThrAlaAlaHisAlaPheLysValAlaAlaArgAlaThrLeuArgArgSerAsnValSer

CGCAAGCGGTCCAGCAGCCTTGGAGGCTCCACGGGATCCACCCCCTCCTCCTCCATCAGCAGCAAGAGCAACAGC                3225
ArgLysArgSerSerSerLeuGlyGlySerThrGlySerThrProSerSerSerIleSerSerLysSerAsnSer

GAAGACCCATTCCCACGGCCCGAGAGGCAGAAGCAGCAGCAGCCGCTGGCCCTAACCCAGCAAGAGCAGCAGCAG                3300
GluAspProPheProArgProGluArgGlnLysGlnGlnGlnProLeuAlaLeuThrGlnGlnGluGlnGlnGln

CAGCCCCTGACCCTCCCACAGCAGCAACGATCTCAGCAGCAGCCCAGATGCAAGCAGAAGGTCATCTTTGGCAGC                3375
GlnProLeuThrLeuProGlnGlnGlnArgSerGlnGlnGlnProArgCysLysGlnLysValIlePheGlySer

GGCACGGTCACCTTCTCACTGAGCTTTGATGAGCCTCAGAAGAACGCCATGGCCCACAGGAATTCTACGCACCAG                3450
GlyThrValThrPheSerLeuSerPheAspGluProGlnLysAsnAlaMetAlaHisArgAsnSerThrHisGln

AACTCCCTGGAGGCCCAGAAAAGCAGCGATACGCTGACCCGACACCAGCCATTACTCCCGCTGCAGTGCGGGGAA                3525
AsnSerLeuGluAlaGlnLysSerSerAspThrLeuThrArgHisGlnProLeuLeuProLeuGlnCysGlyGlu

ACGGACTTAGATCTGACCGTCCAGGAAACAGGTCTGCAAGGACCTGTGGGTGGAGACCAGCGGCCAGAGGTGGAG                3600
ThrAspLeuAspLeuThrValGlnGluThrGlyLeuGlnGlyProValGlyGlyAspGlnArgProGluValGlu

GACCCTGAAGAGTTGTCCCCAGCACTTGTAGTGTCCAGTTCACAGAGCTTTGTCATCAGTGGTGGAGGCAGCACT                3675
AspProGluGluLeuSerProAlaLeuValValSerSerSerGlnSerPheValIleSerGlyGlyGlySerThr

GTTACAGAAAACGTAGTGAATTCATAAAATGGAAGGAGAAGACTGGGCTAGGGAGAATGCAGAGAGGTTTCTTGG                3750
ValThrGluAsnValValAsnSer

GGTCCCAGGGATGAGGAATCGCCCCAGACTCCTTTCCTCTGAGGAAGAAGGGATAATAGACACATCAAATGCCCC                3825

GAATTTAGTCACACCATCTTAAATGACAGTGAATTGACCCATGTTCCCTTTAAAATTAAAAAAAAGAAGAGCCTT                3900

GTGTTTCTGTGGTTGCATTTGTCAAAGCATTGAGATCTCCACGGTCAGATTTGCTGTTCACCCACATCTAATGTC                3975

TCTTCCTCTGTTCTATCCCACCCAACAGCTCAGAGATGAAACTATGGCTTTAAACTACCCTCCAGAGTGTGCAGA                4050
```

FIG. 48c.

```
         10        20        30        40        50        60        70
12345678901234567890123456789012345678901234567890123456789012345678901234 5
CTGATGGGACATCAAATTTCCCACCACTAGAGCTGAGAGTCTGAAAGACAGAATGTCACCAGTCCTGCCCAATGC    4125

CTTGACAACAGACTGAATTTTAAATGTTCACAACATAAGGAGAATGTATCTCCTCCTATTTATGAAACCATATG    4200

ATATTTTGTCTCCTACCTGCTGCTGCTATTATGTAACATCCAGAAGGTTTGCACCCCTCCTATACCATATGTCTG   4275

GTTCTGTCCAGGACATGATACTGATGCCATGTTTAGATTCCAGGATCACAAGAATCACCTCAAATTGTTAGGAAG   4350

GGACTGCATAAACCAATGAGCTGTATCTGTAATTAATATTCCTATATGTAGCTTTATCCTTAGGAAAATGCTTCT   4425

GTTGTAATAGTCCATGGACAATATAAACTGAAAAATGTCAGTCTGGTTTATATAAGGCAGTATTATTGAGCTCTA   4500

TTTCCCCACCCCACTATCCTCACTCCCATAAGCTAAGCCTTATGTGAGCCCCTTCAGGGACTCAAGGGTCCAGAA   4575

GTCCCTCCCATCTCTACCCCAAAGAATTCCTGAAGCCAGATCCACCCTATCCCTGTACAGAGTAAGTTCTCAATT   4650

ATTGGCCTGCTAATAGCTGCTAGGGTAGGAAAGCGTGGTTCCAAGAAAGATCCACCCTCAAATGTCGGAGCTATG   4725

TTCCCTCCAGCAGTGGTATTAATACTGCCGGTCACCCAGGCTCTGGAGCCAGAGAGACAGACCGGGGTTCAAGCC   4800

ATGGCTTCGTCATTTGCAAGCTGAGTGACTGTAGGCAGGGAACCTTAACCTCTCTAAGCCACAGCTTCTTCATCT   4875

TTAAAATAAGGATAATAATCATTCCTTCCCCTCAGAGCTCTTATGTGGATTAAACGAGATAATGTATATAAAGTA   4950

CTTTAGCCTGGTACCTAGCACACAATAAGCATTCAATAAATATTAGTTAATATTAT                      5006
```

FIG. 48d.

```
               10        20        30        40        50        60        70
      1234567890123456789012345678901234567890123456789012345678901234567890123 45
      CAACAGGCACCTGGCTGCAGCCAGGAAGGACCGCACGCCCTTTCGCGCAGGAGAGTGGAAGGAGGGAGCTGTTTG      75

CCAGCACCGAGGTCTTGCGGCACAGGCAACGCTTGACCTGAGTCTTGCAGAATGAAAGGCATCACAGGAGGCCTC     150

TGCATGATGTGGCTTCCAAAGACTCAAGGACCACCCACATTACAAGTCTGGATTGAGGAAGGCAGAAATGGAGAT     225

TCAAACACCACGTCTTCTATTATTTTATTAATCAATCTGTAGACATGTGTCCCCACTGCAGGGAGTGAACTGCTC     300

CAAGGGAGAAACTTCTGGGAGCCTCCAAACTCCTAGCTGTCTCATCCCTTGCCCTGGAGAGACGGCAGAACCATG     375
                                                                             Met

GCATTTTATAGCTGCTGCTGGGTCCTCTTGGCACTCACCTGGCACACCTCTGCCTACGGGCCAGACCAGCGAGCC     450
      AlaPheTyrSerCysCysTrpValLeuLeuAlaLeuThrTrpHisThrSerAlaTyrGlyProAspGlnArgAla

CAAAAGAAGGGGGACATTATCCTTGGGGGGCTCTTTCCTATTCATTTTGGAGTAGCAGCTAAAGATCAAGATCTC     525
      GlnLysLysGlyAspIleIleLeuGlyGlyLeuPheProIleHisPheGlyValAlaAlaLysAspGlnAspLeu

AAATCAAGGCCGGAGTCTGTGGAATGTATCAGGTATAATTTCCGTGGGTTTCGCTGGTTACAGGCTATGATATTT     600
      LysSerArgProGluSerValGluCysIleArgTyrAsnPheArgGlyPheArgTrpLeuGlnAlaMetIlePhe

GCCATAGAGGAGATAAACAGCAGCCCAGCCCTTCTTCCCAACTTGACGCTGGGATACAGGATATTTGACACTTGC     675
      AlaIleGluGluIleAsnSerSerProAlaLeuLeuProAsnLeuThrLeuGlyTyrArgIlePheAspThrCys

AACACCGTTTCTAAGGCCTTGGAAGCCACCCTGAGTTTTGTTGCTCAAAACAAAATTGATTCTTTGAACCTTGAT     750
      AsnThrValSerLysAlaLeuGluAlaThrLeuSerPheValAlaGlnAsnLysIleAspSerLeuAsnLeuAsp

GAGTTCTGCAACTGCTCAGAGCACATTCCCTCTACGATTGCTGTGGTGGGAGCAACTGGCTCAGGCGTCTCCACG     825
      GluPheCysAsnCysSerGluHisIleProSerThrIleAlaValValGlyAlaThrGlySerGlyValSerThr

GCAGTGGCAAATCTGCTGGGGCTCTTCTACATTCCCCAGGTCAGTTATGCCTCCTCCAGCAGACTCCTCAGCAAC     900
      AlaValAlaAsnLeuLeuGlyLeuPheTyrIleProGlnValSerTyrAlaSerSerSerArgLeuLeuSerAsn

AAGAATCAATTCAAGTCTTTCCTCCGAACCATCCCCAATGATGAGCACCAGGCCACTGCCATGGCAGACATCATC     975
      LysAsnGlnPheLysSerPheLeuArgThrIleProAsnAspGluHisGlnAlaThrAlaMetAlaAspIleIle

GAGTATTTCCGCTGGAACTGGGTGGGCACAATTGCAGCTGATGACGACTATGGGCGGCCGGGGATTGAGAAATTC    1050
      GluTyrPheArgTrpAsnTrpValGlyThrIleAlaAlaAspAspAspTyrGlyArgProGlyIleGluLysPhe

CGAGAGGAAGCTGAGGAAAGGGATATCTGCATCGACTTCAGTGAACTCATCTCCCAGTACTCTGATGAGGAAGAG    1125
      ArgGluGluAlaGluGluArgAspIleCysIleAspPheSerGluLeuIleSerGlnTyrSerAspGluGluGlu

ATCCAGCATGTGGTAGAGGTGATTCAAAATTCCACGGCCAAAGTCATCGTGGTTTTCTCCAGTGGCCCAGATCTT    1200
      IleGlnHisValValGluValIleGlnAsnSerThrAlaLysValIleValValPheSerSerGlyProAspLeu

GAGCCCCTCATCAAGGAGATTGTCCGGCGCAATATCACGGGCAAGATCTGGCTGGCCAGCGAGGCCTGGGCCAGC    1275
      GluProLeuIleLysGluIleValArgArgAsnIleThrGlyLysIleTrpLeuAlaSerGluAlaTrpAlaSer

TCCTCCCTGATCGCCATGCCTCAGTACTTCCACGTGGTTGGCGGCACCATTGGATTCGCTCTGAAGGCTGGGCAG    1350
      SerSerLeuIleAlaMetProGlnTyrPheHisValValGlyGlyThrIleGlyPheAlaLeuLysAlaGlyGln
```

FIG. 49a.

```
         10        20        30        40        50        60        70
123456789012345678901234567890123456789012345678901234567890123456789012345
ATCCCAGGCTTCCGGGAATTCCTGAAGAAGGTCCATCCCAGGAAGTCTGTCCACAATGGTTTTGCCAAGGAGTTT   1425
IleProGlyPheArgGluPheLeuLysLysValHisProArgLysSerValHisAsnGlyPheAlaLysGluPhe

TGGGAAGAAACATTTAACTGCCACCTCCAAGAAGGTGCAAAAGGACCTTTACCTGTGGACACCTTTCTGAGAGGT   1500
TrpGluGluThrPheAsnCysHisLeuGlnGluGlyAlaLysGlyProLeuProValAspThrPheLeuArgGly

CACGAAGAAAGTGGCGACAGGTTTAGCAACAGCTCGACAGCCTTCCGACCCCTCTGTACAGGGGATGAGAACATC   1575
HisGluGluSerGlyAspArgPheSerAsnSerSerThrAlaPheArgProLeuCysThrGlyAspGluAsnIle

AGCAGTGTCGAGACCCCTTACATAGATTACACGCATTTACGGATATCCTACAATGTGTACTTAGCAGTCTACTCC   1650
SerSerValGluThrProTyrIleAspTyrThrHisLeuArgIleSerTyrAsnValTyrLeuAlaValTyrSer

ATTGCCCACGCCTTGCAAGATATATATACCTGCTTACCTGGGAGAGGGCTCTTCACCAATGGCTCCTGTGCAGAC   1725
IleAlaHisAlaLeuGlnAspIleTyrThrCysLeuProGlyArgGlyLeuPheThrAsnGlySerCysAlaAsp

ATCAAGAAAGTTGAGGCGTGGCAGGTCCTGAAGCACCTACGGCATCTAAACTTTACAAACAATATGGGGGAGCAG   1800
IleLysLysValGluAlaTrpGlnValLeuLysHisLeuArgHisLeuAsnPheThrAsnAsnMetGlyGluGln

GTGACCTTTGATGAGTGTGGTGACCTGGTGGGGAACTATTCCATCATCAACTGGCACCTCTCCCCAGAGGATGGC   1875
ValThrPheAspGluCysGlyAspLeuValGlyAsnTyrSerIleIleAsnTrpHisLeuSerProGluAspGly

TCCATCGTGTTTAAGGAAGTCGGGTATTACAACGTCTATGCCAAGAAGGGAGAAAGACTCTTCATCAACGAGGAG   1950
SerIleValPheLysGluValGlyTyrTyrAsnValTyrAlaLysLysGlyGluArgLeuPheIleAsnGluGlu

AAAATCCTGTGGAGTGGGTTCTCCAGGGAGGTGCCCTTCTCCAACTGCAGCCGAGACTGCCTGGCAGGGACCAGG   2025
LysIleLeuTrpSerGlyPheSerArgGluValProPheSerAsnCysSerArgAspCysLeuAlaGlyThrArg

AAAGGGATCATTGAGGGGGAGCCCACCTGCTGCTTTGAGTGTGTGGAGTGTCCTGATGGGGAGTATAGTGATGAG   2100
LysGlyIleIleGluGlyGluProThrCysCysPheGluCysValGluCysProAspGlyGluTyrSerAspGlu

ACAGATGCCAGTGCCTGTAACAAGTGCCCAGATGACTTCTGGTCCAATGAGAACCACACCTCCTGCATTGCCAAG   2175
ThrAspAlaSerAlaCysAsnLysCysProAspAspPheTrpSerAsnGluAsnHisThrSerCysIleAlaLys

GAGATCGAGTTTCTGTCGTGGACGGAGCCCTTTGGGATCGCACTCACCCTCTTTGCCGTGCTGGGCATTTTCCTG   2250
GluIleGluPheLeuSerTrpThrGluProPheGlyIleAlaLeuThrLeuPheAlaValLeuGlyIlePheLeu

ACAGCCTTTGTGCTGGGTGTGTTTATCAAGTTCCGCAACACACCCATTGTCAAGGCCACCAACCGAGAGCTCTCC   2325
ThrAlaPheValLeuGlyValPheIleLysPheArgAsnThrProIleValLysAlaThrAsnArgGluLeuSer

TACCTCCTCCTCTTCTCCCTGCTCTGCTGCTTCTCCAGCTCCCTGTTCTTCATCGGGGAGCCCCAGGACTGGACG   2400
TyrLeuLeuLeuPheSerLeuLeuCysCysPheSerSerSerLeuPhePheIleGlyGluProGlnAspTrpThr

TGCCGCCTGCGCCAGCCGGCCTTTGGCATCAGCTTCGTGCTCTGCATCTCATGCATCCTGGTGAAAACCAACCGT   2475
CysArgLeuArgGlnProAlaPheGlyIleSerPheValLeuCysIleSerCysIleLeuValLysThrAsnArg

GTCCTCCTGGTGTTTGAGGCCAAGATCCCCACCAGCTTCCACCGCAAGTGGTGGGGGCTCAACCTGCAGTTCCTG   2550
ValLeuLeuValPheGluAlaLysIleProThrSerPheHisArgLysTrpTrpGlyLeuAsnLeuGlnPheLeu

CTGGTTTTCCTCTGCACCTTCATGCAGATTGTCATCTGTGTGATCTGGCTCTACACCGCGCCCCCCTCAAGCTAC   2625
LeuValPheLeuCysThrPheMetGlnIleValIleCysValIleTrpLeuTyrThrAlaProProSerSerTyr

CGCAACCAGGAGCTGGAGGATGAGATCATCTTCATCACGTGCCACGAGGGCTCCCTCATGGCCCTGGGCTTCCTG   2700
ArgAsnGlnGluLeuGluAspGluIleIlePheIleThrCysHisGluGlySerLeuMetAlaLeuGlyPheLeu
```

FIG. 49b.

```
                10        20        30        40        50        60        70
       12345678901234567890123456789012345678901234567890123456789012345678901234 5
       ATCGGCTACACCTGCCTGCTGGCTGCCATCTGCTTCTTCTTTGCCTTCAAGTCCCGGAAGCTGCCGGAGAACTTC        2775
       IleGlyTyrThrCysLeuLeuAlaAlaIleCysPhePhePheAlaPheLysSerArgLysLeuProGluAsnPhe

AATGAAGCCAAGTTCATCACCTTCAGCATGCTCATCTTCTTCATCGTCTGGATCTCCTTCATTCCAGCCTATGCC        2850
       AsnGluAlaLysPheIleThrPheSerMetLeuIlePhePheIleValTrpIleSerPheIleProAlaTyrAla

AGCACCTATGGCAAGTTTGTCTCTGCCGTAGAGGTGATTGCCATCCTGGCAGCCAGCTTTGGCTTGCTGGCGTGC        2925
       SerThrTyrGlyLysPheValSerAlaValGluValIleAlaIleLeuAlaAlaSerPheGlyLeuLeuAlaCys

ATCTTCTTCAACAAGATCTACATCATTCTCTTCAAGCCATCCCGCAACACCATCGAGGAGGTGCGTTGCAGCACC        3000
       IlePhePheAsnLysIleTyrIleIleLeuPheLysProSerArgAsnThrIleGluGluValArgCysSerThr

GCAGCTCACGCTTTCAAGGTGGCTGCCCGGGCCACGCTGCGCCGCAGCAACGTCTCCCGCAAGCGGTCCAGCAGC        3075
       AlaAlaHisAlaPheLysValAlaAlaArgAlaThrLeuArgArgSerAsnValSerArgLysArgSerSerSer

CTTGGAGGCTCCACGGGATCCACCCCCTCCTCCTCCATCAGCAGCAAGAGCAACAGCGAAGACCCATTCCCACAG        3150
       LeuGlyGlySerThrGlySerThrProSerSerSerIleSerSerLysSerAsnSerGluAspProPheProGln

CCCGAGAGGCAGAAGCAGCAGCAGCCGCTGGCCCTAACCCAGCAAGAGCAGCAGCAGCAGCCCCTGACCCTCCCA        3225
       ProGluArgGlnLysGlnGlnGlnProLeuAlaLeuThrGlnGlnGluGlnGlnGlnGlnProLeuThrLeuPro

CAGCAGCAACGATCTCAGCAGCAGCCCAGATGCAAGCAGAAGGTCATCTTTGGCAGCGGCACGGTCACCTTCTCA        3300
       GlnGlnGlnArgSerGlnGlnGlnProArgCysLysGlnLysValIlePheGlySerGlyThrValThrPheSer

CTGAGCTTTGATGAGCCTCAGAAGAACGCCATGGCCCACGGGAATTCTACGCACCAGAACTCCCTGGAGGCCCAG        3375
       LeuSerPheAspGluProGlnLysAsnAlaMetAlaHisGlyAsnSerThrHisGlnAsnSerLeuGluAlaGln

AAAAGCAGCGATACGCTGACCCGACACCAGCCATTACTCCCGCTGCAGTGCGGGGAAACGGACTTAGATCTGACC        3450
       LysSerSerAspThrLeuThrArgHisGlnProLeuLeuProLeuGlnCysGlyGluThrAspLeuAspLeuThr

GTCCAGGAAACAGGTCTGCAAGGACCTGTGGGTGGAGACCAGCGGCCAGAGGTGGAGGACCCTGAAGAGTTGTCC        3525
       ValGlnGluThrGlyLeuGlnGlyProValGlyGlyAspGlnArgProGluValGluAspProGluGluLeuSer

CCAGCACTTGTAGTGTCCAGTTCACAGAGCTTTGTCATCAGTGGTGGAGGCAGCACTGTTACAGAAAACGTAGTG        3600
       ProAlaLeuValValSerSerSerGlnSerPheValIleSerGlyGlyGlySerThrValThrGluAsnValVal

AATTCATAAAATGGAAGGAGAAGACTGGGCTAGGGAGAATGCAGAGAGGTTTCTTGGGGTCCCAGGGATGAGGAA        3675
       AsnSer

TCGCCCCAGACTCCTTTCCTCTGAGGAAGAAGGGATAATAGACACATCAAATGCCCCGAATTTAGTCACACCATC        3750

TTAAATGACAGTGAATTGACCCATGTTCCCTTTAAAAAAAAAAAAAAAAAAAGCGGCCGC                        3809
```

FIG. 49c.

```
                  10        20        30        40        50        60        70
         123456789012345678901234567890123456789012345678901234567890123456789012345
         CGGGACTCTCCAGGCCGGCTCAGGCACCGGACTGTAGGTGTATTTGGAGGGATTTGGAGGCTGGAGACCCCAGGA      75

AGCACGCAGGCGGGAGCAGGCAAGGGGCGGAGCCCCGGGCCCGGCCAAGGTGGCCGTCAGAGGGTCTGCGGGGAG     150

GCAGTAGCTTGACCCAAGGCGACCAGGGAACTTCAGACGGTAGCACGCCACTCAAACAAATTAACTTGACATCGC     225

AAGCTGGGCGGGCTGGTACGACATCCTGACTTCAGCATCCAGCTGTTCCTGGGCAGACAGAGGGCCAACAGGTGT     300

TCCTGTGGAAGAAGCCAGGACAAGGACTCCAGAAAACATCTCGGGCAGCCTCTACATGATGTCACTTCTCAGGAC     375

TCGAGGACCAGCCACCCTACACCTCTACTACAGAGAAGGCAGAAATGGAGACCCAAAGGCCATCACTCCTGCTCT     450

GTCACTAACCACTCTGTAATCATGTCTCCCCACCAGAAGGTGTGAACCGCACCAGGGCCGTGGAGTTCTCGGGCT     525

CCCAATCCACTGACACCTTTACCTGTCCCCTGAAGAGAAGGCAACGCTATGGCATCGTACAGCTGCTGTTTGGCC     600
                                                        MetAlaSerTyrSerCysCysLeuAla

CTATTGGCTCTTGCCTGGCACTCCTCTGCCTATGGGCCTGACCAGCGAGCCCAAAAGAAGGGGGACATTATCCTA     675
         LeuLeuAlaLeuAlaTrpHisSerSerAlaTyrGlyProAspGlnArgAlaGlnLysLysGlyAspIleIleLeu

GGAGGTCTCTTTCCTATCCATTTTGGAGTAGCAGCCAAAGATCAAGATCTGAAGTCAAGACCAGAGTCTGTGGAG     750
         GlyGlyLeuPheProIleHisPheGlyValAlaAlaLysAspGlnAspLeuLysSerArgProGluSerValGlu

TGCATTAGGTATAACTTCCGTGGATTCCGATGGTTACAAGCCATGATATTCGCCATAGAGGAGATAAACAGCAGC     825
         CysIleArgTyrAsnPheArgGlyPheArgTrpLeuGlnAlaMetIlePheAlaIleGluGluIleAsnSerSer

CCCTCCCTTCTTCCCAACATGACACTGGGATATAGGATATTTGACACCTGTAACACCGTCTCCAAGGCGCTGGAA     900
         ProSerLeuLeuProAsnMetThrLeuGlyTyrArgIlePheAspThrCysAsnThrValSerLysAlaLeuGlu

GCCACCTTGAGTTTTGTTGCCCAGAACAAAATCGATTCTTTGAACCTGGACGAGTTCTGCAACTGCTCTGAGCAC     975
         AlaThrLeuSerPheValAlaGlnAsnLysIleAspSerLeuAsnLeuAspGluPheCysAsnCysSerGluHis

ATCCCTTCGACCATTGCCGTGGTGGGAGCCACCGGCTCCGGTGTCTCCACGGCGGTAGCCAACCTGCTGGGACTT    1050
         IleProSerThrIleAlaValValGlyAlaThrGlySerGlyValSerThrAlaValAlaAsnLeuLeuGlyLeu

TTCTACATCCCCCAGGTGAGCTACGCCTCCTCCAGCAGGCTCCTCAGCAATAAGAACCAGTACAAATCCTTCCTC    1125
         PheTyrIleProGlnValSerTyrAlaSerSerSerArgLeuLeuSerAsnLysAsnGlnTyrLysSerPheLeu

CGCACCATTCCCAATGACGAACACCAGGCAACCGCGATGGCCGACATCATCGAGTACTTCCGCTGGAACTGGGTG    1200
         ArgThrIleProAsnAspGluHisGlnAlaThrAlaMetAlaAspIleIleGluTyrPheArgTrpAsnTrpVal

GGCACAATTGCAGCTGATGACGACTATGGCAGACCTGGCATTGAGAAGTTCCGAGAGGAAGCCGAAGAGAGGGAT    1275
         GlyThrIleAlaAlaAspAspAspTyrGlyArgProGlyIleGluLysPheArgGluGluAlaGluGluArgAsp

ATCTGCATTGATTTTAGCGAGCTCATCTCCCAGTACTCTGACGAGGAAGAGATCCAGCAGGTGGTCGAAGTGATC    1350
         IleCysIleAspPheSerGluLeuIleSerGlnTyrSerAspGluGluGluIleGlnGlnValValGluValIle
```

FIG. 50a.

```
           10        20        30        40        50        60        70
  1234567890123456789012345678901234567890123456789012345678901234567890123456789012345
  CAAAACTCTACGGCCAAGGTCATTGTCGTTTTCTCCAGCGGCCCGGACCTAGAACCTCTCATCAAGGAGATTGTG           1425
  GlnAsnSerThrAlaLysValIleValValPheSerSerGlyProAspLeuGluProLeuIleLysGluIleVal

CGGCGTAACATCACAGGCAGGATCTGGCTGGCTAGCGAGGCCTGGGCCAGTTCCTCGCTGATTGCTATGCCTGAG           1500
  ArgArgAsnIleThrGlyArgIleTrpLeuAlaSerGluAlaTrpAlaSerSerSerLeuIleAlaMetProGlu

TATTTCCATGTAGTCGGGGGCACCATTGGGTTCGGTCTGAAGGCTGGGCAGATTCCAGGCTTCAGAGAATTCCTA           1575
  TyrPheHisValValGlyGlyThrIleGlyPheGlyLeuLysAlaGlyGlnIleProGlyPheArgGluPheLeu

CAGAAAGTTCATCCTAGGAAGTCTGTCCACAATGGTTTTGCCAAAGAGTTTTGGGAAGAAACTTTTAATTGCCAC           1650
  GlnLysValHisProArgLysSerValHisAsnGlyPheAlaLysGluPheTrpGluGluThrPheAsnCysHis

CTCCAAGAAGGCGCAAAAGGACCTTTACCTGTGGACACCTTCGTGAGAAGTCACGAAGAAGGTGGCAACAGGTTA           1725
  LeuGlnGluGlyAlaLysGlyProLeuProValAspThrPheValArgSerHisGluGluGlyGlyAsnArgLeu

CTCAATAGCTCTACTGCCTTCCGACCCCTCTGCACAGGGGATGAGAACATCAACAGTGTGGAGACCCCTTACATG           1800
  LeuAsnSerSerThrAlaPheArgProLeuCysThrGlyAspGluAsnIleAsnSerValGluThrProTyrMet

GATTACGAACATTTACGGATATCCTACAATGTGTACTTAGCCGTCTACTCCATTGCGCATGCCCTACAAGATATA           1875
  AspTyrGluHisLeuArgIleSerTyrAsnValTyrLeuAlaValTyrSerIleAlaHisAlaLeuGlnAspIle

TACACCTGCTTACCCGGAAGAGGGCTTTTCACCAACGGGTCCTGTGCAGACATCAAGAAGGTTGAGGCCTGGCAG           1950
  TyrThrCysLeuProGlyArgGlyLeuPheThrAsnGlySerCysAlaAspIleLysLysValGluAlaTrpGln

GTCTTGAAGCACCTACGGCACCTGAACTTCACCAACAACATGGGGGAGCAGGTGACCTTCGATGAGTGTGGTGAT           2025
  ValLeuLysHisLeuArgHisLeuAsnPheThrAsnAsnMetGlyGluGlnValThrPheAspGluCysGlyAsp

CTGGTGGGGAACTATTCTATCATCAACTGGCACCTCTCCCCAGAGGACGGCTCCATTGTGTTCAAGGAAGTTGGG           2100
  LeuValGlyAsnTyrSerIleIleAsnTrpHisLeuSerProGluAspGlySerIleValPheLysGluValGly

TACTACAATGTGTATGCCAAGAAGGGAGAAAGACTCTTCATCAATGAGGAGAAGATCTTGTGGAGTGGGTTCTCC           2175
  TyrTyrAsnValTyrAlaLysLysGlyGluArgLeuPheIleAsnGluGluLysIleLeuTrpSerGlyPheSer

AGAGAGGTGCCTTTCTCCAATTGCAGCCGGGACTGTCAGGCAGGGACCAGGAAGGGGATCATCGAGGGAGAGCCC           2250
  ArgGluValProPheSerAsnCysSerArgAspCysGlnAlaGlyThrArgLysGlyIleIleGluGlyGluPro

ACCTGCTGCTTTGAGTGTGTGGAGTGTCCTGATGGAGAGTACAGTGGAGAGACAGATGCGAGTGCCTGTGACAAG           2325
  ThrCysCysPheGluCysValGluCysProAspGlyGluTyrSerGlyGluThrAspAlaSerAlaCysAspLys

TGCCCGGATGACTTCTGGTCCAATGAGAACCACACTTCTTGCATTGCCAAGGAGATTGAGTTTCTGGCGTGGACC           2400
  CysProAspAspPheTrpSerAsnGluAsnHisThrSerCysIleAlaLysGluIleGluPheLeuAlaTrpThr

GAGCCCTTTGGAATCGCTCTCACTCTCTTTGCGGTGCTGGGCATTTTCCTGACCGCCTTTGTGCTGGGTGTCTTC           2475
  GluProPheGlyIleAlaLeuThrLeuPheAlaValLeuGlyIlePheLeuThrAlaPheValLeuGlyValPhe

ATCAAGTTCCGAAACACACCTATCGTCAAGGCCACCAACCGAGAACTGTCCTACCTCCTGCTCTTCTCCCTACTC           2550
  IleLysPheArgAsnThrProIleValLysAlaThrAsnArgGluLeuSerTyrLeuLeuLeuPheSerLeuLeu

TGCTGCTTCTCCAGCTCCTTGTTCTTCATTGGGGAGCCCCAGGACTGGACGTGCCGCCTGCGACAGCCTGCTTTC           2625
  CysCysPheSerSerSerLeuPhePheIleGlyGluProGlnAspTrpThrCysArgLeuArgGlnProAlaPhe

GGCATCAGCTTTGTGCTCTGTATCTCGTGCATCTTGGTGAAGACCAATCGCGTCCTCCTGGTATTTGAAGCCAAG           2700
  GlyIleSerPheValLeuCysIleSerCysIleLeuValLysThrAsnArgValLeuLeuValPheGluAlaLys
```

| | |
|---|---|
| ATACCCACCAGCTTCCACCGGAAGTGGTGGGGGCTCAACCTGCAGTTCCTGCTGGTTTTCCTCTGCACCTTCATG<br>IleProThrSerPheHisArgLysTrpTrpGlyLeuAsnLeuGlnPheLeuLeuValPheLeuCysThrPheMet | 2775 |
| CAGATCCTCATCTGCATCATCTGGCTCTACACGGCGCCCCCCTCTAGCTACCGCAACCATGAGCTGGAAGACGAA<br>GlnIleLeuIleCysIleIleTrpLeuTyrThrAlaProProSerSerTyrArgAsnHisGluLeuGluAspGlu | 2850 |
| ATCATCTTCATCACGTGCCATGAGGGCTCACTCATGGCACTTGGCTCCCTGATCGGCTATACCTGCCTGCTGGCT<br>IleIlePheIleThrCysHisGluGlySerLeuMetAlaLeuGlySerLeuIleGlyTyrThrCysLeuLeuAla | 2925 |
| GCCATCTGCTTCTTCTTTGCCTTCAAGTCCAGGAAGTTACCAGAGAACTTCAACGAAGCCAAGTTCATTACCTTC<br>AlaIleCysPhePhePheAlaPheLysSerArgLysLeuProGluAsnPheAsnGluAlaLysPheIleThrPhe | 3000 |
| AGCATGCTCATCTTCTTCATCGTCTGGATCTCCTTCATTCCAGCCTATGCCAGCACCTACGGCAAGTTTGTCTCT<br>SerMetLeuIlePhePheIleValTrpIleSerPheIleProAlaTyrAlaSerThrTyrGlyLysPheValSer | 3075 |
| GCCGTAGAGGTGATCGCCATTTTGGCAGCCAGCTTTGGCTTACTAGCCTGCATCTTCTTCAACAAGGTCTACATT<br>AlaValGluValIleAlaIleLeuAlaAlaSerPheGlyLeuLeuAlaCysIlePhePheAsnLysValTyrIle | 3150 |
| ATCCTCTTCAAGCCTTCCCGGAACACCATTGAGGAAGTCCGCTCCAGCACCGCAGCACATGCTTTCAAAGTAGCA<br>IleLeuPheLysProSerArgAsnThrIleGluGluValArgSerSerThrAlaAlaHisAlaPheLysValAla | 3225 |
| GCCCGCGCCACTCTACGCCGTCCCAACATCTCCCGGAAGCGGTCCAGCAGCCTTGGAGGCTCCACCGGCTCCATT<br>AlaArgAlaThrLeuArgArgProAsnIleSerArgLysArgSerSerSerLeuGlyGlySerThrGlySerIle | 3300 |
| CCCTCCTCCTCCATCAGCAGCAAAAGCAACAGCGAAGACCGGTTCCCGCAGCCAGAGAGGCAGAAGCAACAGCAA<br>ProSerSerSerIleSerSerLysSerAsnSerGluAspArgPheProGlnProGluArgGlnLysGlnGlnGln | 3375 |
| CCGCTGTCCCTGACCCAGCAAGAACAGCAGCAGCAGCCCCTGACCCTCCACCCACAGCAACAGCAGCAGCCACAG<br>ProLeuSerLeuThrGlnGlnGluGlnGlnGlnProLeuThrLeuHisProGlnGlnGlnGlnGlnProGln | 3450 |
| CAGCCGAGATGCAAACAGAAGGTCATCTTCGGCAGTGGTACGGTCACCTTCTCTCTGAGTTTTGACGAGCCTCAG<br>GlnProArgCysLysGlnLysValIlePheGlySerGlyThrValThrPheSerLeuSerPheAspGluProGln | 3525 |
| AAGAATGCCATGGCCCACAGGAACTCCATGCGTCAGAACTCCCTGGAGGCCCAGAGGAGCAACGACACCTTGGGC<br>LysAsnAlaMetAlaHisArgAsnSerMetArgGlnAsnSerLeuGluAlaGlnArgSerAsnAspThrLeuGly | 3600 |
| AGACACCAGGCCCTGCTTCCCCTACAGTGTGCAGATGCGGACTCAGAAATGACCATTCAGGAAACGGGCCTGCAA<br>ArgHisGlnAlaLeuLeuProLeuGlnCysAlaAspAlaAspSerGluMetThrIleGlnGluThrGlyLeuGln | 3675 |
| GGGCCCATGGTGGGGGACCACCAGCCAGAAATGGAAAGCTCAGATGAAATGTCCCCAGCGCTGGTCATGTCCACC<br>GlyProMetValGlyAspHisGlnProGluMetGluSerSerAspGluMetSerProAlaLeuValMetSerThr | 3750 |
| TCTCGGAGCTTCGTCATTAGTGGTGGAGGTAGCTCTGTGACGGAAAACGTATTACACTCCTAATGGAGGGAAAGG<br>SerArgSerPheValIleSerGlyGlyGlySerSerValThrGluAsnValLeuHisSer | 3825 |
| CTATCCAGTTGAGAGGTTTTTCTTAGAGCCCTGAGCAAAAGGATGGGTCCTTCCTTTCTTCCCAGGAAGCCAGGG | 3900 |
| AGAGTAGGTACGTCAAAGCCTGTACTCAGTTGCACTGCTTTGAATGACAGTGAACTGACTGGTGTGCTCTTTAGA | 3975 |
| GTTAAAAGAAGAGCCATGTTTTGGGGTCGTTTTCCAGAGCTCAGTATCACACCTGGGTTTGCTGAAGTCTTTTCC | 4050 |

FIG. 50c.

```
         10        20        30        40        50        60        70
123456789012345678901234567890123456789012345678901234567890123456789012345
TCTGCTCTATCCACCATCAGTTCAGAGACGAAAGCAAGGCTCTAAGCTACCCATCTGCTTCCCTCAAAAAAAAA  4125

AAAAAA  4131
```

FIG. 50d.

CALCIUM RECEPTOR-ACTIVE MOLECULES

RELATED APPLICATIONS

This is a continuation of Brown et al., U.S. Ser. No. 08/484,565, filed Jun. 7, 1995, now U.S. Pat. No. 5,763,569, which is a continuation-in-part of Nemeth et al., U.S. Ser. No. 08/353,784, filed Dec. 8, 1994, which is a continuation-in-part of Nemeth et al., PCT/US94/12117, filed Oct. 21, 1994, and a continuation-in-part of Nemeth et al., U.S. Ser. No. 08/292,827, filed Aug. 19, 1994, abandoned, and a continuation-in-part of Nemeth et al., U.S. Ser. No. 08/141,248, filed Oct. 22, 1993, abandoned, and a continuation-in-part of Nemeth et al., U.S. Ser. No. 08/009,389, filed Feb. 23, 1993, abandoned, the whole of each of these applications including the drawings are hereby incorporated herein by reference.

FIELD OF THE INVENTION

This invention relates to the design, development, composition and use of molecules able to modulate the activity of an inorganic ion receptor, preferably a calcium receptor. It also relates to a superfamily of receptors for inorganic ion (inorganic ion receptors) such as calcium receptors. The invention also relates to nucleic acids encoding such receptors, cells, tissues and animals containing such nucleic acids, antibodies to such receptors, assays utilizing such receptors, and methods relating to all of the foregoing.

BACKGROUND OF THE INVENTION

The following description provides a summary of information relevant to the present invention. It is not an admission that any of the information provided herein is prior art to the presently claimed invention, nor that any of the publications specifically or implicitly referenced are prior art to that invention.

Certain cells in the body respond not only to chemical signals, but also to ions such as extracellular calcium ions ($Ca^{2+}$). Changes in the concentration of extracellular $Ca^{2+}$ (referred to herein as "$[Ca^{2+}]$") alter the functional responses of these cells. One such specialized cell is the parathyroid cell which secretes parathyroid hormone (PTH). PTH is the principal endocrine factor regulating $Ca^{2+}$ homeostasis in the blood and extracellular fluids.

PTH, by acting on bone and kidney cells, increases the level of $Ca^{2+}$ in the blood. This increase in $[Ca^{2+}]$ then acts as a negative feedback signal, depressing PTH secretion. The reciprocal relationship between $[Ca^{2+}]$ and PTH secretion forms the essential mechanism maintaining bodily $Ca^{2+}$ homeostasis.

Extracellular $Ca^{2+}$ acts directly on parathyroid cells to regulate PTH secretion. The existence of a parathyroid cell surface protein which detects changes in $[Ca^{2+}]$ has been suggested. This protein acts as a receptor for extracellular $Ca^{2+}$ ("the calcium receptor"), and is suggested to detect changes in $[Ca^{2+}]$ and to initiate a functional cellular response, PTH secretion. For example, the role of calcium receptors and extracellular $Ca^{2+}$ in the regulation of intracellular $Ca^{2+}$ and cell function is reviewed in Nemeth et al., *Cell Calcium* 11: 319, 1990; the role of calcium 3 209/069 receptors in parafollicular and parathyroid cells is discussed in Nemeth, *Cell Calcium* 11: 323, 1990; and the role of calcium receptors on bone osteoclasts is discussed by Zaidi, *Bioscience Resorts* 10: 493, 1990.

Other cells in the body, specifically the osteoclast in bone, the juxtaglomerular, proximal tubule cells in the kidney, the keratinocyte in the epidermis, the parafollicular cell in the thyroid, intestinal cells, and the trophoblast in the placenta, have the capacity to sense changes in $[Ca^{2+}]$. It has been suggested that cell surface calcium receptors may also be present on these cells, imparting to them the ability to detect and to initiate or enable a response to changes in $[Ca^{2+}]$.

In parathyroid cells, osteoclasts, parafollicular cells (C-cells), keratinocytes, juxtaglomerular cells, trophoblasts, pancreatic beta cells and fat/adipose cells, an increase in $[Ca^{2+}]$ evokes an increase in intracellular free $Ca^{2+}$ concentration ("$[Ca^{2+}]_i$"). Such an increase may be caused by influx of extracellular $Ca^{2+}$ or by mobilization of $Ca^{2+}$ from intracellular organelles. Changes in $[Ca^{2+}]_i$ are readily monitored and quantitated using fluorimetric indicators such as fura-2 or indo-1 (Molecular Probes, Eugene, Oreg.). Measurement of $[Ca^{2+}]_i$ provides an assay to assess the ability of molecules to act as agonists or antagonists at the calcium receptor.

In parathyroid cells, increases in the concentration of extracellular $Ca^{2+}$ evoke rapid and transient increases in $[Ca^{2+}]_i$ which are followed by lower, yet sustained, increases in $[Ca^{2+}]_i$. The transient increases in $[Ca^{2+}]_i$ arise from the mobilization of intracellular $Ca^{2+}$, whereas the lower, sustained increases result from the influx of extracellular $Ca^{2+}$. The mobilization of intracellular $Ca^{2+}$ is accompanied by increased formation of inositol-1,4,5-triphosphate ($IP_3$) and diacylglycerol, two biochemical indicators which are associated with receptor-dependent mobilization of intracellular $Ca^{2+}$ in various other cells.

In addition to $Ca^{2+}$, various other di- and trivalent cations, such as $Mg^{2+}$, $Sr^{2+}$, $Ba^{2+}$, $La^{3+}$ and $Gd^{3+}$ also cause the mobilization of intracellular $Ca^{2+}$ in parathyroid cells. $Mg^2$ and $La^{3+}$ also increase the formation of $IP_3$. All of these inorganic cations depress the secretion of PTH. The postulated calcium receptor on the parathyroid cell is therefore promiscuous because it detects a variety of extracellular di- and trivalent cations.

The ability of various compounds to mimic extracellular $Ca^{2+}$ in vitro is discussed by Nemeth et al., (spermine and spermidine) in "Calcium-Binding Proteins in Health and Disease," 1987, Academic Press, pp. 33–35; Brown et al., (e.g., neomycin) *Endocrinology* 128: 3047, 1991; Chen et al., (diltiazem and its analog, TA-3090) *J. Bone and Mineral Res.* 5: 581, 1990; and Zaidi et al., (verapamil) *Biochem. Biophys. Res. Commun.* 167: 807, 1990.

Brown et al., *J. Bone Mineral Res.* 6: 11, 1991 discuss theories regarding the effects of $Ca^{2+}$ ions on parathyroid cells, and propose that the results may be explained by both a receptor-like mechanism and a receptor-independent mechanism as follows:

Polyvalent cations [e.g., divalent and trivalent cations] exert a variety of effects on parathyroid function, such as inhibition of parathyroid hormone (PTH) secretion and cAMP accumulation, stimulation of the accumulation of inositol phosphates, and elevation of the cytosolic calcium concentration. These actions are thought to be mediated through a "receptor-like" mechanism. The inhibition of agonist-stimulated cAMP accumulation by divalent and trivalent cations, for example, is blocked following preincubation with pertussis toxin. Thus, the putative polyvalent cation receptor may be coupled to inhibition of adenylate cyclase by the inhibitory guanine nucleotide regulatory (G) protein, $G_i$.

We recently showed that the polycationic antibiotic, neomycin, mimics the actions of di- and trivalent cations in several aspects of parathyroid function. To determine whether these actions were specific to this agent or represented a more generalized action of polycations, we tested the effects of the highly basic peptides, polyarginine and polylysine, as well as protamine on the same parameters in dispersed bovine parathyroid cells. The results demonstrate that the parathyroid cell responds to a variety of polycations as well as to polyvalent cations, potentially via similar biochemical pathways. These results are discussed in terms of the recently postulated, "receptor-independent" modulation of G proteins by polycations in other systems.

The $Ca^{2+}$ receptor has been presumed to be analogous to other G protein-coupled receptors [e.g., a glycoprotein], but recent studies with other cell types have raised the possibility that polycations can modulate cell function by alternative or additional mechanisms. In mast cells, for example, a variety of amphipathic cations, including mastoparan, a peptide from wasp venom, 48/80, a synthetic polycation, and polylysine, enhance secretion by a pertussis toxin-sensitive mechanism, suggesting the involvement of a G protein. No classic cell surface receptor has been identified that could mediate the actions of these diverse agents. Furthermore, these same compounds have been shown to activate directly purified G proteins in solution or in artificial phospholipid vesicles. On the basis of these observations, it has been proposed that amphipathic cations activate G proteins and, in turn, mast cell secretion by a "receptor-independent" mechanism.

Polycations have also been shown to interact strongly with acidic phospholipids. Polylysines of varying chain lengths (20–1000 amino acids) bind to artificial phospholipid vesicles with dissociation constants in the range of 0.5 nM to 1.5 $\mu$M. The binding affinity is directly related to the length of the polylysine chain, with polymers of 1000 amino acids having a $K_d$ of 0.5 nM, shorter polymers having higher Kd values, and lysine not interacting to a significant extent. This relationship between potency and chain length is similar to that observed for the effects of polylysine 10,200, polylysine 3800, and lysine on parathyroid function.

It is possible that the binding of polycations to biomembranes produces some of their biologic actions. The permeabilization of the plasma membrane induced in some cell types by a variety of pore-forming agents, including polycations, has been postulated to be mediated by their interaction with a phosphatidylserine-like structure. In addition, the "receptor-independent" activation of purified G proteins by amphipathic cations is potentiated when these proteins are incorporated into phospholipid vesicles.

Calcium ions, in the millimolar concentration range, also produce marked changes in membrane structure. In some cases, calcium can either antagonize or potentiate the interaction of polycations with membrane lipids. These considerations raise the possibility that the actions of both polyvalent cations and polycations on parathyroid cells could involve a receptor-independent mechanism not requiring the presence of a classic, cell surface, G protein-coupled receptor. Further studies, however, are required to elucidate the molecular basis for $Ca^{2+}$ sensing by this and other cell types. [Citations omitted.]

Shoback and Chen, *J. Bone Mineral Res.* 6 (Supplement 1) 1991, S135) and Racke et al., *J. Bone Mineral Res.* 6 (Supplement 1) 1991, S118) describe experiments which are said to indicate that a calcium receptor or $Ca^{2+}$ sensor is present in parathyroid cells. Messenger RNA isolated from such cells can be expressed in oocytes and caused to provide those oocytes with a phenotype which might be explained by the presence of a calcium receptor protein.

SUMMARY OF THE INVENTION

The present invention relates to the different roles inorganic ion receptors have in cellular and body processes. The present invention features: (1) molecules which can modulate one or more inorganic ion receptor activities, preferably the molecule can mimic or block an effect of an extracellular ion on a cell having an inorganic ion receptor, more preferably the extracellular ion is $Ca^{2+}$ and the effect is on a cell having a calcium receptor; (2) inorganic ion receptor proteins and fragments thereof, preferably calcium receptor proteins and fragments thereof; (3) nucleic acids encoding inorganic ion receptor proteins and fragments thereof, preferably calcium receptor proteins and fragments thereof; (4) antibodies and fragments thereof, targeted to inorganic ion receptor proteins, preferably calcium receptor protein; and (5) uses of such molecules, proteins, nucleic acids and antibodies.

The preferred use of the present invention is to treat diseases or disorders in a patient by modulating one or more inorganic ion receptor activities. Diseases or disorders which can be treated by modulating inorganic ion receptor activity include one or more of the following types: (1) those characterized by abnormal inorganic ion homeostasis; (2) those characterized by an abnormal amount of an extracellular or intracellular messenger whose production can be affected by inorganic ion receptor activity; (3) those characterized by an abnormal effect (e.g., a different effect in kind or magnitude) of an intracellular or extracellular messenger which can itself be ameliorated by inorganic ion receptor activity; and (4) other diseases or disorders in which modulation of inorganic ion receptor activity will exert a beneficial effect, for example, in diseases or disorders where the production of an intracellular or extracellular messenger stimulated by receptor activity compensates for an abnormal amount of a different messenger. Examples of extracellular messengers whose secretion and/or effect can be affected by modulating inorganic ion receptor activity include inorganic ions, hormones, neurotransmitters, growth factors, and chemokines. Examples of intracellular messengers include cAMP, cGMP, $IP_3$, and diacylglycerol.

Preferably, the compound modulates calcium receptor activity and is used in the treatment of diseases or disorders which can be affected by modulating one or more activities of a calcium receptor. Extracellular $Ca^{2+}$ is under tight homeostatic control and controls various processes such as blood clotting, nerve and muscle excitability, and proper bone formation. Calcium receptor proteins enable certain specialized cells to respond to changes in extracellular $Ca^{2+}$ concentration. For example, extracellular $Ca^{2+}$ inhibits the secretion of parathyroid hormone from parathyroid cells, inhibits bone resorption by osteoclasts, and stimulates secretion of calcitonin from C-cells.

Preferably, the disease or disorder is characterized by abnormal bone and mineral homeostasis, more preferably calcium homeostasis. Abnormal calcium homeostasis is characterized by one or more of the following activities: (1) an abnormal increase or decrease in serum calcium; (2) an abnormal increase or decrease in urinary excretion of calcium; (3) an abnormal increase or decrease in bone calcium levels, for example, as assessed by bone mineral density measurements; (4) an abnormal absorption of dietary calcium; (5) an abnormal increase or decrease in the production and/or release of messengers which affect serum calcium levels such as parathyroid hormone and calcitonin; and (6) an abnormal change in the response elicited by messengers which affect serum calcium levels. The abnormal increase or decrease in these different aspects of calcium homeostasis is relative to that occurring in the general population and is generally associated with a disease or disorder.

Diseases and disorders characterized by abnormal calcium homeostasis can be due to different cellular defects such as a defective calcium receptor activity or a defective intracellular protein acted on by a calcium receptor. For example, in parathyroid cells, the calcium receptor is coupled to the $G_i$ protein which in turn inhibits cyclic AMP production. Defects in $G_i$ protein can affect its ability to inhibit cyclic AMP production.

The inorganic ion receptor-modulating agents (e.g., molecules and compositions) can be used to treat patients. A "patient" refers to a mammal in which modulation of an inorganic ion receptor will have a beneficial effect. Patients in need of treatment involving modulation of inorganic ion receptors can be identified using standard techniques known to those in the medical profession. Preferably, a patient is a human having a disease or disorder characterized by one or more of the following: (1) abnormal inorganic ion homeostasis, more preferably abnormal calcium homeostasis; (2) an abnormal level of a messenger whose production or secretion is affected by inorganic ion receptor activity, more preferably affected by calcium receptor activity; and (3) an abnormal level or activity of a messenger whose function is affected by inorganic ion receptor activity, more preferably affected by calcium receptor activity.

Thus, a first aspect of the present invention features an inorganic ion receptor-modulating agent comprising a molecule which either evokes one or more inorganic ion receptor activities, or blocks one or more inorganic ion receptor activities. The agent has an $EC_{50}$ of less than or equal to 5 $\mu$M at its respective receptor and is not protamine. Preferably, the inorganic ion receptor is a calcium receptor and the molecule has an $EC_{50}$ of less than or equal to 5 $\mu$M at a calcium receptor and is not protamine.

Inorganic ion receptor activities are those processes brought about as a result of inorganic ion receptor activation. Such processes include the production of molecules which can act as intracellular or extracellular messengers.

Inorganic ion receptor-modulating agents include ionomimetics, ionolytics, calcimimetics, and calcilytics. Ionomimetics are molecules which bind to an inorganic ion receptor and mimics (i.e., evokes or potentiates) the effects of an inorganic ion at an inorganic ion receptor. Preferably, the molecule affects one or more calcium receptor activities. Calcimimetics are ionomimetics which affect one or more calcium receptor activities and bind to a calcium receptor.

Ionolytics are molecules which bind to an inorganic ion receptor and block (i.e., inhibits or diminishes) one or more activities caused by an inorganic ion on an inorganic ion receptor. Preferably, the molecule affects one or more calcium receptor activities. Calcilytics are ionolytics which inhibit one or more calcium receptor activities evoked by extracellular calcium and bind to a calcium receptor.

Ionomimetics and ionolytics may bind at the same receptor site as the native inorganic ion ligand binds or can bind at a different site (e.g., allosteric site). For example, NPS R-467 binding to a calcium receptor results in calcium receptor activity and, thus, NPS R-467 is classified as a calcimimetic. However, NPS R-467 binds to the calcium receptor at a different site (i.e., an allosteric site) than extracellular calcium.

The $EC_{50}$ is the concentration of agent which causes a half maximal mimicking effect. For example, the $EC_{50}$ for calcium receptor activities can be determined by assaying one or more of the activities of extracellular calcium at a calcium receptor. Examples of suitable assays for measuring $EC_{50}$ are described herein and include oocyte expression assays and measuring increases in intracellular calcium due to calcium receptor activity. Preferably, such assays measure the release or inhibition of a particular hormone associated with activity of a calcium receptor.

An inorganic ion receptor-modulating agent preferably selectively targets inorganic ion receptor activity in a particular cell. For example, selective targeting of a calcium receptor activity is achieved by an agent exerting a greater effect on a calcium receptor activity in one cell type than at another cell type for a given concentration of agent. Preferably, the differential effect is 10-fold or greater as measured in vivo or in vitro. More preferably, the differential effect is measured in vivo and the agent concentration is measured as the plasma concentration or extracellular fluid concentration and the measured effect is the production of extracellular messengers such as plasma calcitonin, parathyroid hormone, or plasma calcium. For example, in a preferred embodiment, the agent selectively targets PTH secretion over calcitonin secretion.

In one embodiment concerning the structure of the inorganic ion receptor-modulating agent, the molecule is positively charged at physiological pH, and is selected from the group consisting of branched or cyclic polyamines, positively charged polyamino acids, and arylalkylamines. Preferably, the branched polyamine has the formula $H_2N—(CH_2)_j—(NR_i—(CH_2)_j)_k—NH_2$ where k is an integer from 1 to 10, each j is the same or different and is an integer from 2 to 20, and each $R_i$ is the same or different and is selected from the group consisting of hydrogen and $—(CH_2)_j—NH_2$, where j is as defined above, and at least one $R_i$ is not hydrogen. Preferably, the inorganic ion receptor-modulating agent can modulate one or more calcium receptor activities.

In a preferred embodiment concerning the structure of inorganic ion receptor-modulating agents the arylalkylamine molecule has the formula:

STRUCTURE I

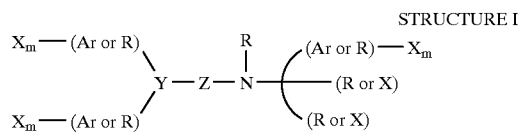

where each X independently is selected from the group consisting of H, $CH_3$, $CH_3O$, $CH_3CH_2O$, methylene dioxy, Br, Cl, F, I, $CF_3$, $CHF_2$, $CH_2F$, $CF_3O$, $CF_3CH_2O$, $CH_3S$, OH, $CH_2OH$, $CONH_2$, CN, $NO_2$, $CH_3CH_2$, propyl, isopropyl, butyl, isobutyl, t-butyl, and acetoxy;

Ar is a hydrophobic entity;

each R independently is selected from the group consisting of hydrogen, methyl, ethyl, propyl, isopropyl, allyl, butyl, isobutyl, t-butyl, cyclopentyl, cyclohexyl, cycloheptyl, cyclooctyl, indenyl, indanyl, dihydroindolyl, thiodihydroindolyl, and 2-, 3-, or 4-piperid(in)yl;

Y is selected from the group consisting of CH, nitrogen and an unsaturated carbon; and Z is selected from the group consisting of oxygen, nitrogen, sulfur,

STRUCTURE II

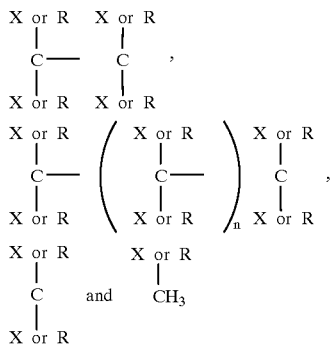

where each n is independently between 1 and 4 inclusive; and each m is independently between 0 and 5 inclusive.

A hydrophobic entity refers to a non-polar group or moiety such as an aromatic or a cycloaliphatic ring or ring system. Preferably, the hydrophobic entity is selected from the group consisting of phenyl, cyclohexyl, 2-, 3-, or 4-pyridyl, 1- or 2-naphthyl, α- or β-tetrahydronaphthyl, 1- or 2-quinolinyl, 2- or 3-indolyl, benzyl, and phenoxy.

More preferably, the inorganic ion receptor-modulating agent is a substituted R-phenylpropyl-α-phenethylamine, substituted R-benzyl-α-1-napthylethylamine analogues, and derivatives having the formula:

STRUCTURE III

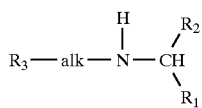

where alk is straight- or branched-chain alkylene of from 0 to 6 carbon atoms;

$R_1$ is lower alkyl of from 1 to 3 carbon atoms or lower haloalkyl of from 1 to 3 carbon atoms substituted with from 1 to 7 halogen atoms;

$R_2$ and $R_3$ are independently selected carbocyclic aryl or cycloalkyl groups, either monocyclic or bicyclic, having 5- to 7-membered rings optionally substituted with 1 to 5 substituents independently selected from lower alkyl of 1 to 3 carbon atoms, lower haloalkyl of 1 to 3 carbon atoms substituted with 1 to 7 halogen atoms, lower alkoxy of 1 to 3 carbon atoms, halogen, nitro, amino, alkylamino, amido, lower alkylamido of 1 to 3 carbon atoms, cyano, hydroxy, acyl of 2 to 4 carbon atoms, lower hydroxyalkyl of 1 to 3 carbon atoms or lower thioalkyl of 1 to 3 carbon atoms. Suitable carbocyclic aryl groups are groups having one or two rings, at least one of which has aromatic character and include carbocyclic aryl groups such as phenyl and bicyclic carbocyclic aryl groups such as naphthyl.

Preferred compounds include those where alk is n-propylene, methylene, or R-methyl methinyl. Also preferred are compounds where $R_1$ is R-methyl. Also preferred are those compounds where $R_2$ and $R_3$ are optionally substituted phenyl or naphthyl.

More preferred compounds are those where $R_2$ is mono-substituted phenyl, more preferably meta-substituted; or 1-naphthyl. More preferred $R_3$ groups are unsubstituted or monosubstituted phenyl, especially meta- or ortho-substituted, or 2-naphthyl. Preferred substituents for $R_2$ are halogen, haloalkyl, preferably trihalomethyl, alkoxy, preferably methoxy, and thioalkyl, preferably thiomethyl. Preferred substituents for $R_3$ are meta- or ortho-halogen, preferably chlorine, fluorine, or $CF_3$ and para- or ortho-alkoxy, preferably methoxy, and meta-lower alkyl, preferably methyl.

As is apparent from the above formula, preparation of the molecules may result in racemic mixtures containing individual stereoisomers. More preferred compounds are R-phenylpropyl-α-phenethylamine and R-benzyl-α-1-naphthylethylamine derivatives which are believed to exhibit enhanced activity in lowering serum ionized calcium.

More preferably, the molecule is a substituted R-phenylpropyl-α-phenethylamine derivative, or a substituted R-benzyl-α-phenethylamine derivative, having the structure:

STRUCTURE IV

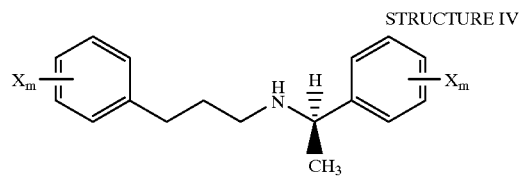

or

STRUCTURE V

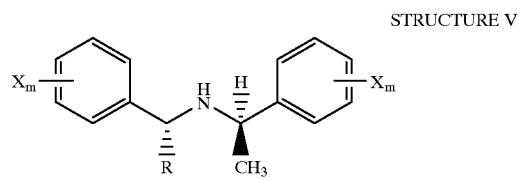

where each X is preferably independently selected from the group consisting of Cl, F, I, $CF_3$, $CH_3$, isopropyl, $CH_3O$, $CH_3S$, $CF_3O$, $CF_3CH_2O$, an aliphatic ring and an attached or fused, preferably fused aromatic ring. Preferably, the aromatic and aliphatic rings have 5 to 7 members. More preferably, the aromatic and aliphatic rings contain only carbon atoms (i.e., the ring is not a heterocyclic ring); and R is preferably H, $CH_3$, ethyl, or isopropyl.

In more preferred embodiments the molecule inhibits parathyroid hormone secretion from a parathyroid cell; inhibits bone resorption in vivo by an osteoclast; inhibits bone resorption in vitro by an osteoclast; stimulates calcitonin secretion in vitro or in vivo from a c-cell; or the molecule evokes the mobilization of intracellular $Ca^{2+}$ to cause an increase in $[Ca^{2+}]_i$.

Preferably, the molecule is either a calcimimetic or calcilytic having an $EC_{50}$ or $IC_{50}$ at a calcium receptor of less than or equal to 5 μM, and even more preferably less than or equal to 1 μM, 100 nmolar, 10 nmolar, or 1 nmolar. Such lower $EC_{50}$'s or $IC_{50}$'s are advantageous since they allow lower concentrations of molecules to be used in vivo or in vitro for therapy or diagnosis. The discovery of molecules with such low $EC_{50}$'s and $IC_{50}$'s enables the design and synthesis of additional molecules having similar or improved potency, effectiveness, and/or selectivity.

In another preferred embodiment, the molecule has an $EC_{50}$ or $IC_{50}$ less than or equal to 5 μM at one or more, but not all cells chosen from the group consisting of parathyroid cell, bone osteoclast, juxtaglomerular kidney cell, proximal tubule kidney cell, distal tubule kidney cell, central nervous system cell, peripheral nervous system cell, cell of the thick ascending limb of Henle's loop and/or collecting duct, keratinocyte in the epidermis, parafollicular cell in the thyroid (C-cell), intestinal cell, trophoblast in the placenta, platelet, vascular smooth muscle cell, cardiac atrial cell, gastrin-secreting cell, glucagon-secreting cell, kidney mesangial cell, mammary cell, beta cell, fat/adipose cell, immune cell, GI tract cell, skin cell, adrenal cell, pituitary cell, hypothalamic cell and cell of the subfornical organ.

More preferably, the cells are chosen from the group consisting of parathyroid cell, central nervous system cell, peripheral nervous system cell, cell of the thick ascending limb of Henle's loop and/or collecting duct in the kidney, parafollicular cell in the thyroid (C-cell), intestinal cell, GI tract cell, pituitary cell, hypothalamic cell and cell of the subfornical organ. This presence of a calcium receptor in this group of cells has been confirmed by physical data such as in situ hybridization and antibody staining.

Another aspect of the present invention features a calcium receptor-modulating agent comprising a molecule selected from the group consisting of: NPS R-467, NPS R-568, compound 1D, compound 3U, compound 3V, compound 4A, compound 4B, compound 4C, compound 4D, compound 4G, compound 4H, compound 4J, compound 4M, compound 4N, compound 4P, compound 4R/6V, compound 4S, compound 4T/4U, compound 4V, compound 4W, compound 4Y, compound 4Z/5A, compound 5B/5C, compound 5W/5Y, compound 6E, compound 6F, compound 6R, compound 6T, compound 6X, compound 7W, compound 7X, compound 8D, compound 8J, compound 8K, compound 8R, compound 8S, compound 8T, compound 8U, compound 8X, compound 8Z, compound 9C, compound 9D, compound 9R, compound 9S, compound 10F, compound 11D, compound 11X, compound 11Y, compound 12L, compound 12U, compound 12V, compound 12W, compound 12Y, compound 13Q, compound 13R, compound 13S, compound 13U, compound 13X, compound 14L, compound 14Q, compound 14U, compound 14V, compound 14Y, compound 15G, compound 16Q, compound 16R, compound 16T, compound 16V, compound 16W, compound 16X, compound 17M, compound 17O, compound 17P, compound 17R, compound 17W, compound 17X, compound 20F, compound 20I, compound 20J, compound 20R, compound 20S, compound 21D, compound 21F, compound 21G, compound 21O, compound 21P, compound 21Q, and compound 21R (see FIG. 36).

Another aspect of the present invention features a pharmaceutical composition made up of an inorganic ion receptor-modulating agent and a physiologically acceptable carrier. Such agents can be used to treat patients by modulating inorganic ion receptor activity.

Prior to this invention, applicant was unaware of any agent acting on the calcium receptor useful in the treatment of diseases caused by irregularity in operation or regulation of a calcium receptor or in diseases in an animal having normal calcium receptors, but which can be treated by modulating calcium activity.

A pharmacological agent or composition refers to an agent or composition in a form suitable for administration into a mammal, preferably a human. Considerations concerning forms suitable for administration are known in the art and include toxic effects, solubility, route of administration, and maintaining activity. For example, pharmacological agents or compositions injected into the blood stream should be soluble.

Pharmaceutical compositions can also be formulated as pharmaceutically acceptable salts (e.g., acid addition salts) and complexes thereof. The preparation of such salts can facilitate the pharmacological use of an agent by altering its physical characteristics without preventing it from exerting a physiological effect.

Another aspect of the present invention features a method for modulating inorganic ion receptor activity, preferably calcium receptor activity. The method involves the step of providing to a cell comprising an inorganic ion receptor an amount of an inorganic ion receptor-modulating molecule sufficient to either mimic one or more effects of an inorganic ion at the inorganic ion receptor, or block one or more effects of the inorganic ion at the inorganic ion receptor. The method can carried out in vitro or in vivo.

Preferably, the molecule is either a calcimimetic or a calcilytic which modulates one or more calcium receptor activity. Examples of calcium receptor-modulating molecules or agents are described herein. Additional calcium receptor-modulating agents can be obtained based on the present disclosure. More preferably, the method is carried out in vivo to treat a patient.

Another aspect the present invention features a method for treating a patient by modulating inorganic ion receptor activity. The method involves administering to the patient a therapeutically effective amount of an inorganic ion receptor-modulating agent.

In a preferred embodiment, the disease or disorder is treated by modulating calcium receptor activity by administering to the patient a therapeutically effective amount of a calcium receptor-modulating agent.

Preferably the disease or disorder is characterized by one or more of the following: (1) abnormal inorganic ion homeostasis, more preferably abnormal calcium homeostasis; (2) an abnormal level of a messenger whose production or secretion is affected by inorganic ion receptor activity, more preferably affected by calcium receptor activity; and (3) an abnormal level or activity of a messenger whose function is affected by inorganic ion receptor activity, more preferably affected by calcium receptor activity.

Diseases characterized by abnormal calcium homeostasis include hyperparathyroidism, osteoporosis and other bone and mineral-related disorders, and the like (as described, e.g., in standard medical text books, such as "Harrison's Principles of Internal Medicine"). Such diseases are treated using calcium receptor-modulating agents which mimic or block one or more of the effects of extracellular $Ca^{2+}$ on a calcium receptor and, thereby, directly or indirectly affect the levels of proteins or other molecules in the body of the patient.

By "therapeutically effective amount" is meant an amount of an agent which relieves to some extent one or more symptoms of the disease or disorder in the patient; or returns to normal either partially or completely one or more physiological or biochemical parameters associated with or causative of the disease.

In a preferred embodiment, the patient has a disease or disorder characterized by an abnormal level of one or more calcium receptor-regulated components and the molecule is active on a calcium receptor of a cell selected from the group consisting of: parathyroid cell, bone osteoclast, juxtaglomerular kidney cell, proximal tubule kidney cell, distal tubule kidney cell, central nervous system cell, peripheral nervous system cell, cell of the thick ascending limb of Henle's loop and/or collecting duct, keratinocyte in the epidermis, parafollicular cell in the thyroid (C-cell), intestinal cell, trophoblast in the placenta, platelet, vascular smooth muscle cell, cardiac atrial cell, gastrin-secreting cell, glucagon-secreting cell, kidney mesangial cell, mammary cell, beta cell, fat/adipose cell, immune cell, GI tract cell, skin cell, adrenal cell, pituitary cell, hypothalamic cell and cell of the subfornical organ.

More preferably, the cells are chosen from the group consisting of: parathyroid cell, central nervous system cell, peripheral nervous system cell, cell of the thick ascending limb of Henle's loop and/or collecting duct in the kidney, parafollicular cell in the thyroid (C-cell), intestinal cell, GI tract cell, pituitary cell, hypothalamic cell and cell of the subfornical organ.

In a preferred embodiment, the agent is a calcimimetic acting on a parathyroid cell calcium receptor and reduces the level of parathyroid hormone in the serum of the patient. More preferably, the level is reduced to a degree sufficient to cause a decrease in plasma $Ca^{2+}$. Most preferably, the parathyroid hormone level is reduced to that present in a normal individual.

In another preferred embodiment, the agent is a calcilytic acting on a parathyroid cell calcium receptor and increases the level of parathyroid hormone in the serum of the patient. More preferably, the level is increased to a degree sufficient to cause an increase in bone mineral density of a patient.

In another aspect, the invention features a method for diagnosing a disease or disorder in a patient characterized by an abnormal number of inorganic ion receptors, or an altered inorganic ion receptor. The method involves identifying the number and/or location and/or functional integrity of one or more inorganic ion receptor. The number and/or location and/or functional integrity is compared with that observed in patients characterized as normal or diseased as an indication of the presence of the disease or disorder.

Diagnoses can be carried out using inorganic ion receptor-binding agents. For example, calcium receptor-modulating agents binding to calcium receptors, and antibodies which bind to calcium receptors, can be used for diagnoses. Preferably, binding agents are labeled with a detectable moiety, such as a radioisotope or alkaline phosphatase.

An altered receptor has a different structure than the receptor has in normal individuals and is associated with a disease or disorder involving an inorganic ion receptor. Such alterations may affect receptor function, and can be detected by assaying for a structural difference between the altered and normal receptor. Binding agents which bind to an altered receptor, but not to a normal receptor, can be used to determine the presence of an altered receptor. Additionally, a binding agent which can bind to a normal receptor, but not to a particular altered receptor, can be used to determine the presence of the particular altered receptor.

Similarly, the number of receptors can be determined by using agents binding to the tested-for receptor. Such assays generally involve using a labeled binding agent and can be carried out using standard formats such as competitive, non-competitive, homogenous, and heterogenous assays.

In other preferred embodiments, the method is an immunoassay in which an antibody to a calcium receptor is used to identify the number and/or location and/or functional integrity of the calcium receptors; the assay involves providing a labeled calcimimetic or calcilytic molecule; the presence of a cancer, e.g., an ectopic tumor of the parathyroid, is tested for by measuring calcium receptor number or alteration; and conditions characterized by an above-normal number of osteoclasts in bone or an increased level of activity of osteoclasts in bone is tested for by measuring the number of calcium receptors.

In another aspect, the invention features a method for identifying a molecule useful as a therapeutic molecule to modulate inorganic ion receptor activity or as a diagnostic agent to diagnose patients suffering from a disease characterized by an abnormal inorganic ion activity. Preferably, the method is used to identify calcimimetics or calcilytics by screening potentially useful molecules for an ability to mimic or block an activity of extracellular $Ca^{2+}$ on a cell having a calcium receptor and determining whether the molecule has an $EC_{50}$ or $IC_{50}$ of less than or equal to 5 $\mu$M. More preferably, the molecule is tested for its ability to mimic or block an increase in $[Ca^{2+}]_i$ elicited by extracellular $Ca^{2+}$.

Identification of inorganic ion receptor-modulating agents is facilitated by using a high-throughput screening system. High-throughput screening allows a large number of molecules to be tested. For example, a large number of molecules can be tested individually using rapid automated techniques or in combination using a combinational library. Individual compounds able to modulate inorganic ion receptor activity present in a combinational library can be obtained by purifying and retesting fractions of the combinational library. Thus, thousands to millions of molecules can be screened in a single day.

Active molecules can be used as models to design additional molecules having equivalent or increased activity. Preferably, the identification method uses a recombinant inorganic ion receptor, more preferably a recombinant calcium receptor. Recombinant receptors can be introduced into different cells using a vector encoding the receptor.

Preferably, the activity of molecules in different cells is tested to identify a calcimimetic or calcilytic molecule which mimics or blocks one or more activities of $Ca^{2+}$ at a first type of calcium receptor, but not at a second type of calcium receptor.

Another aspect of the present invention features a purified nucleic acid containing at least 12 contiguous nucleotides of a nucleic acid sequence provided in SEQ. ID. NO. 1, SEQ. ID. NO. 2, SEQ. ID. NO. 3 or SEQ. ID. NO. 4. By "purified" in reference to nucleic acid is meant the nucleic acid is present in a form (i.e., its association with other molecules) other than found in nature. For example, purified receptor nucleic acid is separated from one or more nucleic acids which are present on the same chromosome. Preferably, the purified nucleic acid is separated from at least 90% of the other nucleic acids present on the same chromosome.

Another example of purified nucleic acid is recombinant nucleic acid. Preferably, recombinant nucleic acid contains nucleic acid encoding an inorganic ion receptor or receptor fragment cloned in an expression vector. An expression vector contains the necessary elements for expressing a cloned nucleic acid sequence to produce a polypeptides. An expression vector contains a promoter region (which directs the initiation of RNA transcription) as well as the DNA sequences which, when transcribed into RNA, will signal synthesis initiation.

Recombinant nucleic acid may contain nucleic acid encoding for an inorganic ion receptor, receptor fragment, or inorganic ion receptor derivative, under the control of its genomic regulatory elements, or under the control of exogenous regulatory elements including an exogenous promoter. By "exogenous" is meant a promoter that is not normally coupled in vivo transcriptionally to the coding sequence for the inorganic ion receptor. Preferably, the nucleic acid is provided as a substantially purified preparation representing at least 75%, more preferably 85%, most preferably 95% of the total nucleic acids present in the preparation.

Nucleic acid sequences provided in SEQ. ID. NO. 1, SEQ. ID. NO. 2, SEQ. ID. NO. 3, and SEQ. ID. NO. 4 each encode for a calcium receptor. Nucleic acid sequences encoding both full length calcium receptors, calcium receptor fragments, derivatives of full length calcium receptors, and derivatives of calcium receptor fragments are useful in the present invention.

Uses of nucleic acids encoding cloned receptors or receptor fragments include one or more the following: (1) producing receptor proteins which can be used, for example, for structure determination, to assay a molecule's activity on a receptor, and to obtain antibodies binding to the receptor; (2) being sequenced to determine a receptor's nucleotide sequence which can be used, for example, as a basis for comparison with other receptors to determine conserved regions, determine unique nucleotide sequences for normal and altered receptors, and to determine nucleotide sequences to be used as target sites for antisense nucleic acids, ribozymes, hybridization detection probes, or PCR amplification primers; (3) as hybridization detection probes to detect the presence of a native receptor and/or a related receptor in a sample; and (4) as PCR primers to generate particular nucleic acid sequence regions, for example to generate regions to be probed by hybridization detection probes.

Preferably, the nucleic acid contains at least 14, more preferably at least 20, more preferably at least 27, and most preferably at least 45, contiguous nucleic acids of a sequence provided in SEQ. ID. NO. 1, SEQ. ID. NO. 2, SEQ. ID. NO. 3, or SEQ. ID. NO. 4. Advantages of longer-length nucleic acid include producing longer-length protein fragments having the sequence of a calcium receptor which can be used, for example, to produce antibodies; increased nucleic acid probe specificity under higher stringent hybridization assay conditions; and more specificity for related inorganic ion receptor nucleic acid under lower stringency hybridization assay conditions.

Another aspect of the present invention features a purified nucleic acid encoding an inorganic ion receptor or fragment thereof. The nucleic acid encodes at least 6 contiguous amino acids provided in SEQ. ID. NO. 5, SEQ. ID. NO. 6, SEQ. ID. NO. 7 or SEQ. ID. NO. 8. Due to the degeneracy of the genetic code, different combinations of nucleotides can code for the same polypeptide. Thus, numerous inorganic ion receptors and receptor fragments having the same amino acid sequences can be encoded for by different nucleic acid sequences. In preferred embodiments, the nucleic acid encodes at least 12, at least 18, or at least 54 contiguous amino acids of SEQ. ID. NO. 5, SEQ. ID. NO. 6, SEQ. ID. NO. 7 or SEQ. ID. NO. 8.

Another aspect of the present invention features a purified nucleic acid having a nucleic acid sequence region of at least 12 contiguous nucleotides substantially complementary to a sequence region in SEQ. ID. NO. 1, SEQ. ID. NO. 2, SEQ. ID. NO. 3 or SEQ. ID. NO. 4. By "substantially complementary" is meant that the purified nucleic acid can hybridize to the complementary sequence region in nucleic acid encoded by SEQ. ID. NO. 1, SEQ. ID. NO. 2, SEQ. ID. NO. 3 or SEQ. ID. NO. 4 under stringent hybridizing conditions. Such nucleic acid sequences are particularly useful as hybridization detection probes to detect the presence of nucleic acid encoding a particular receptor. Under stringent hybridization conditions, only highly complementary nucleic acid sequences hybridize. Preferably, such conditions prevent hybridization of nucleic acids having 4 mismatches out of 20 contiguous nucleotides, more preferably 2 mismatches out of 20 contiguous nucleotides, most preferably one mismatch out of 20 contiguous nucleotides. In preferred embodiments, the nucleic acid is substantially complementary to at least 20, at least 27, or at least 45, contiguous nucleotides provided in SEQ. ID. NO. 1, SEQ. ID. NO. 2, SEQ. ID. NO. 3, or SEQ. ID. NO. 4.

Another aspect of the present invention features a purified polypeptide having at least 6 contiguous amino acids of an amino acid sequence provided in SEQ. ID. NO. 5, SEQ. ID. NO. 6, SEQ. ID. NO. 7 or SEQ. ID. NO. 8. By "purified" in reference to a polypeptide is meant that the polypeptide is in a form (i.e., its association with other molecules) distinct from naturally occurring polypeptide. Preferably, the polypeptide is provided as a substantially purified preparation representing at least 75%, more preferably 85%, most preferably 95% of the total protein in the preparation. In preferred embodiments, the purified polypeptide has at least 12, 18, or 54 contiguous amino acids of SEQ. ID. NO. 5, SEQ. ID. NO. 6, SEQ. ID. NO. 7 or SEQ. ID. NO. 8.

Preferred receptor fragments include those having functional receptor activity, a binding site, epitope for antibody recognition (typically at six amino acids), and/or a site which binds a calcimimetic or calcilytic. Other preferred receptor fragments include those having only an extracellular portion, a transmembrane portion, an intracellular portion, and/or a multiple transmembrane portion (e.g., seven transmembrane portion). Such receptor fragments have various uses such as being used to obtain antibodies to a particular region and being used to form chimeric receptors with fragments of other receptors to create a new receptor having unique properties.

The invention also features derivatives of full-length inorganic ion receptors and fragments thereof having the same, or substantially the same, activity as the full-length parent inorganic ion receptor or fragment. Such derivatives include amino acid addition(s), substitutions), and deletion (s) to the receptor which do not prevent the derivative receptor from carrying out one or more of the activities of the parent receptor.

Another aspect of the present invention features a recombinant cell or tissue. The recombinant cell or tissue is made up of a recombined nucleic acid sequence encoding at least 6 contiguous amino acids provided in SEQ. ID. NO. 5, SEQ. ID. NO. 6, SEQ. ID. NO. 7 or SEQ. ID. NO. 8 and a cell able to express the nucleic acid. Recombinant cells have various uses including acting as biological factories to produce polypeptides encoded for by the recombinant nucleic acid, and for producing cells containing a functioning calcium receptor. Cells containing a functioning calcium receptor can be used, for example, to screen for calcimimetics or calcilytics.

In preferred embodiments, the recombinant nucleic acid encodes a functioning calcium receptor, more preferably a human calcium receptor; the cell or tissue is selected from the group consisting of: parathyroid cell, bone osteoclast, juxtaglomerular kidney cell, proximal tubule kidney cell, distal tubule kidney cell, central nervous system cell, peripheral nervous system cell, cell of the thick ascending limb of Henle's loop and/or collecting duct, keratinocyte in the epidermis, parafollicular cell in the thyroid (C-cell), intestinal cell, trophoblast in the placenta, platelet, vascular smooth muscle cell, cardiac atrial cell, gastrin-secreting cell, glucagon-secreting cell, kidney mesangial cell, mammary cell, beta cell, fat/adipose cell, immune cell, GI tract cell, skin cell, adrenal cell, pituitary cell, hypothalamic cell and cell of the subfornical organ; and the recombinant nucleic acid encodes at least 12, 18 or 54 is contiguous amino acids of SEQ. ID. NO. 5, SEQ. ID. NO. 6, SEQ. ID. NO. 7 or SEQ. ID. NO. 8.

Another aspect of the present invention features a calcium receptor-binding agent able to bind a polypeptide having an amino acid sequence of SEQ. ID. NO. 5, SEQ. ID. NO. 6, SEQ. ID. NO. 7 or SEQ. ID. NO. 8. The binding agent is preferably a purified antibody which recognizes an epitope present on a polypeptide having an amino acid sequence of SEQ. ID. NO. 5, SEQ. ID. NO. 6, SEQ. ID. NO. 7 or SEQ. ID. NO. 8. Other binding agents include molecules which bind to the receptor, for example, calcimimetics and calcilytics binding to the calcium receptor.

By "purified" in reference to an antibody is meant that the antibody is in a form (i.e., its association with other molecules) distinct from naturally occurring antibody, such as in a purified form. Preferably, the antibody is provided as a purified preparation representing at least 1%, more preferably at least 50%, more preferably at least 85%, most preferably at least 95% of the total protein in the preparation.

Antibodies able to bind inorganic ion receptors have various uses such as being used as therapeutic agents to modulate calcium receptor activity; as diagnostic tools for determining calcium receptor number and/or location and/or functional integrity to diagnose a $Ca^{2+}$-related disease; and as research tools for studying receptor synthesis, structure, and function. For example, antibodies targeted to the calcium receptor are useful to elucidate which portion of the receptor a particular molecule such as the natural ligand, a calcimimetic, or calcilytic, binds.

In preferred embodiments, the binding agent binds to an extracellular region of a calcium receptor and the binding agent binds to a calcium receptor expressed in tissue or cells selected from the group consisting of: parathyroid cell, bone osteoclast, juxtaglomerular kidney cell, proximal tubule kidney cell, distal tubule kidney cell, central nervous system cell, peripheral nervous system cell, cell of the thick ascending limb of Henle's loop and/or collecting duct, keratinocyte in the epidermis, parafollicular cell in the thyroid (C-cell), intestinal cell, trophoblast in the placenta, platelet, vascular smooth muscle cell, cardiac atrial cell, gastrin-secreting cell, glucagon-secreting cell, kidney mesangial cell, mammary cell, beta cell, fat/adipose cell, immune cell, GI tract cell, skin cell, adrenal cell, pituitary cell, hypothalamic cell and cell of the subfornical organ. More preferably, the cells are chosen from the group consisting of parathyroid cell, central nervous system cell, peripheral nervous system cell, cell of the thick ascending limb of Henle's loop and/or collecting duct in the kidney, parafollicular cell in the thyroid (C-cell), intestinal cell, GI tract cell, pituitary cell, hypothalamic cell and cell of the subfornical organ.

In other preferred embodiments, the binding agent is coupled to a toxin. Binding agents coupled to a toxin can be used to deliver the toxin to a cell containing a particular receptor. For example, an antibody coupled to a toxin directed to a cancer cell characterized by an abnormal receptor can selectively kill the cancer cell.

In other aspects, the invention provides transgenic, non-human mammals containing a transgene encoding an inorganic ion receptor or a gene affecting the expression of an inorganic ion receptor and methods of creating a transgenic nonhuman mammal containing a transgene encoding an inorganic ion receptor. Preferably, these aspects use a calcium receptor.

Transgenic nonhuman mammals are particularly useful as an in vivo test system for studying the effects of introducing an inorganic ion receptor, preferably a calcium receptor; regulating the expression of an inorganic ion receptor, preferably a calcium receptor (i.e., through the introduction of additional genes, antisense nucleic acids, or ribozymes); and studying the effect of molecules which mimic or block the effect of inorganic ions on an inorganic ion receptor, preferably mimic or block the effect of calcium on a calcium receptor. In preferred embodiments, the transgene encodes a calcium receptor; alters the expression of a calcium receptor; inactivates the expression of the inorganic ion receptor, preferably a calcium receptor; and up-regulates or down-regulates the expression of the inorganic ion receptor, preferably a calcium receptor.

Another aspect of the present invention features a method for treating a patient by administering a therapeutically effective amount of nucleic acid encoding a functioning inorganic ion receptor. Preferably, nucleic acid encoding a functioning calcium receptor is administered to a patient having a disease or disorder characterized by one or more of the following: (1) abnormal calcium homeostasis; (2) an abnormal level of a messenger whose production or secretion is affected by calcium receptor activity; and (3) an abnormal level or activity of a messenger whose function is affected by calcium receptor activity. The nucleic acid can be administered using standard techniques such as through the use of retroviral vectors and liposomes.

Another aspect of the present invention features a method for treating a patient by administering a therapeutically effective amount of a nucleic acid which inhibits expression of an inorganic ion receptor. Preferably, the administered nucleic acid inhibits expression of a calcium receptor and the disease or disorder is characterized by one or more of the following: (1) abnormal calcium homeostasis; (2) an abnormal level of a messenger whose production or secretion is affected by calcium receptor activity; and (3) an abnormal level or activity of a messenger whose function is affected by calcium receptor activity.

Nucleic acids able to inhibit expression of an inorganic ion receptor include anti-sense oligonucleotides, ribozymes and nucleic acid able to combine through homologous recombination with an endogenous gene encoding the receptor. Target sites of inhibitory nucleic acid include promoters, other regulatory agents acting on promoters, mRNA, pre-processed mRNA, and genomic DNA. Administration can be carried out by providing a transgene encoding the agent or by any other suitable method depending upon the use to which the particular method is directed.

Another aspect of the present invention features a method for identifying an inorganic ion receptor-modulating agent. The method involves contacting a cell containing a recombinant nucleic acid encoding an inorganic ion receptor with the agent and detecting a change in inorganic ion receptor activity. Preferably, the method is used to identify a calcium receptor-modulating agent.

Thus, the present invention features agents and methods useful in the diagnosis and treatment of a variety diseases and disorders by targeting inorganic ion receptor activity. For example, molecules mimicking external calcium may be used to selectively depress secretion of parathyroid hormone from parathyroid cells, or depress bone resorption by osteoclasts, or stimulate secretion of calcitonin from C-cells. Such molecules can be used to treat diseases characterized by abnormal calcium homeostasis such as hyperparathyroidism and osteoporosis.

Other features and advantages of the invention will be apparent from the following description of the preferred embodiments thereof and from the claims.

BRIEF DESCRIPTION OF THE DRAWINGS

FIGS. 1a–1f depict representative molecules useful in the invention.

Figure 2:
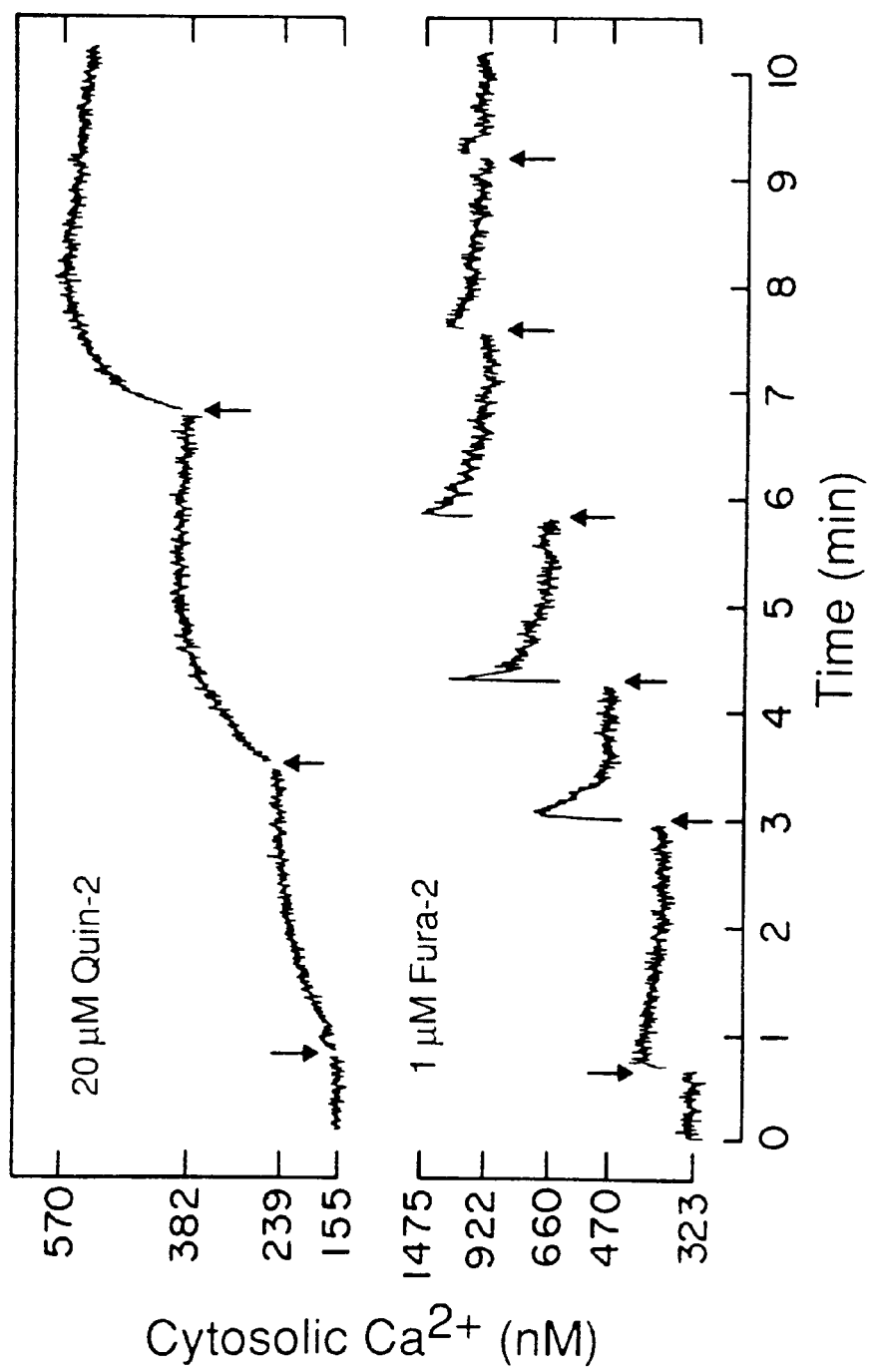
FIG. 2 is a graphical representation showing increases in $[Ca^{2+}]_i$ induced by extracellular $Ca^{2+}$ in quin-2- or fura-2- loaded bovine parathyroid cells. The initial [Ca$^{2+}$] was 0.5 mM (using CaCl$_2$) and, at each of the arrows, was increased in 0.5 mM increments.
Figure 3A:
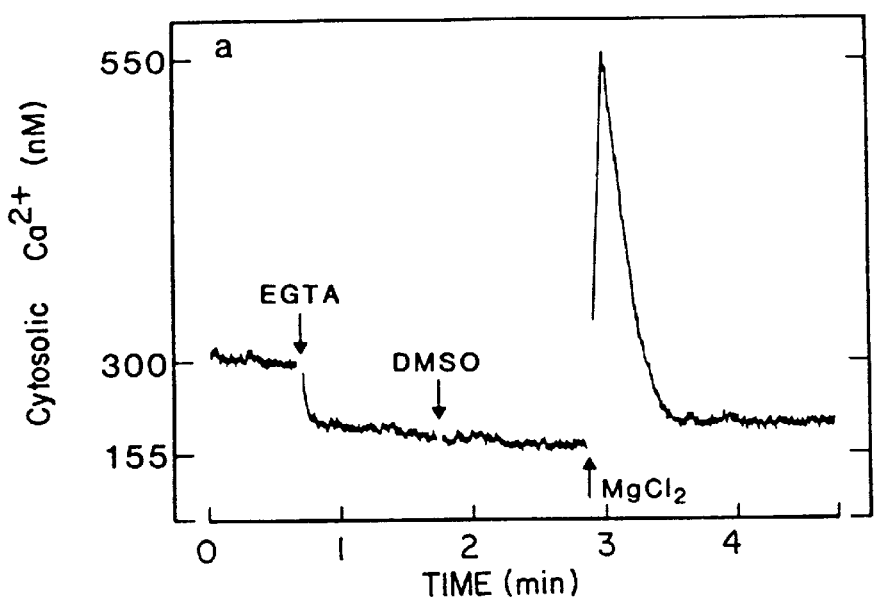
Figure 3B:
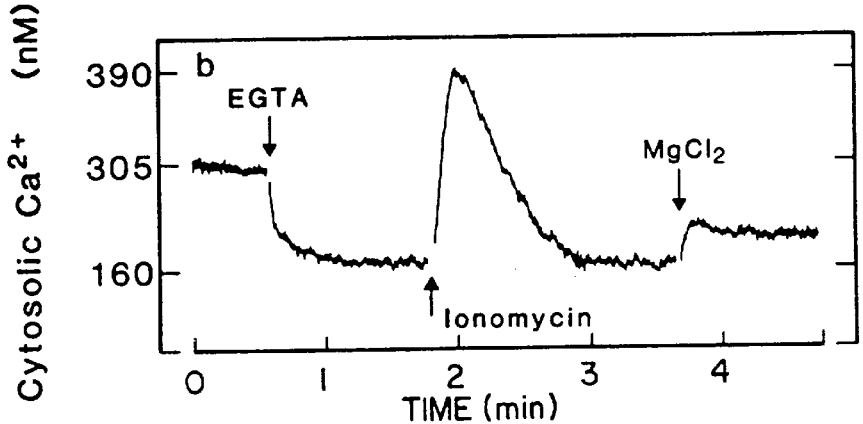
Figure 3C:
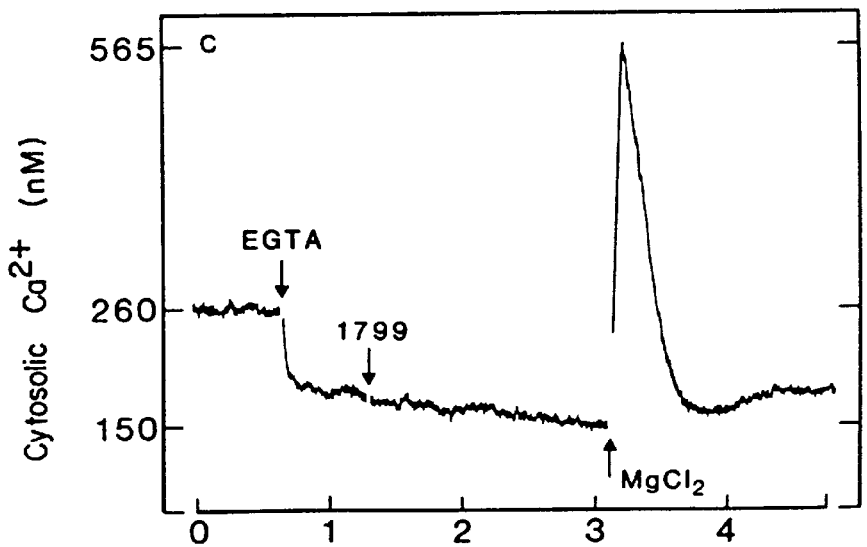

FIGS. 3a–3c are graphical representations showing mobilization of [Ca$^{2+}$]$_i$ in bovine parathyroid cells. The initial [Ca$^{2+}$] was 0.5 mM and was decreased to <1 μM by the addition of EGTA as indicated. (a) Extracellular Mg$^{2+}$ (8 mM final) elicits an increase in [Ca$^{2+}$]$_i$ in the absence of extracellular Ca$^{2+}$. (b) Pretreatment with ionomycin (1 μM) blocks the response to Mg$^{2+}$. (c) Pretreatment with 5 μM molecule 1799 (a mitochondrial uncoupler) is without effect on the response to Mg$^{2+}$.

Figure 4A:
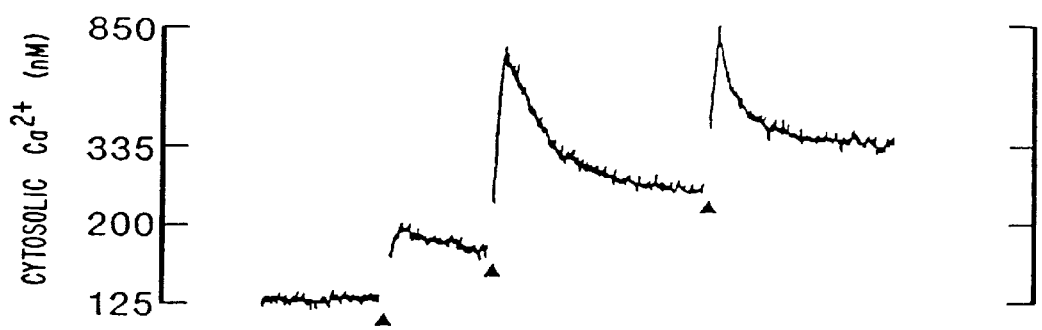
Figure 4B:
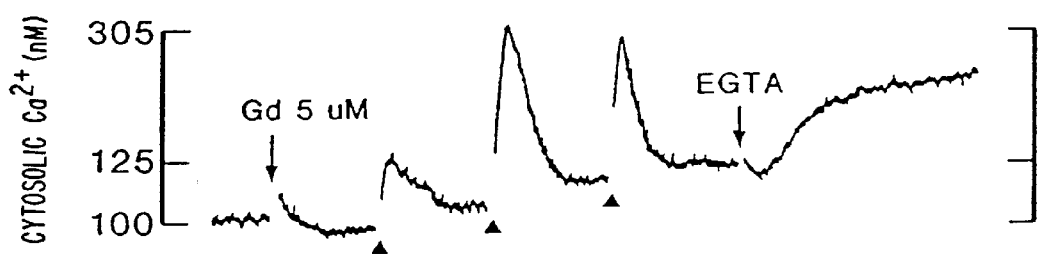
Figure 4C:
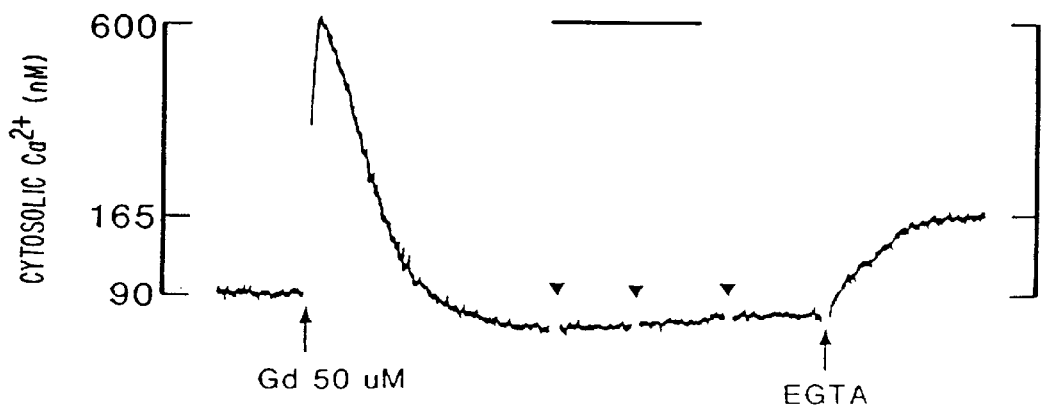

FIGS. 4a–4c are graphical representations showing preferential inhibitory effects of a low concentration of Gd$^{3+}$ on steady-state increases in [Ca$^{2+}$]$_i$ and that a high concentration of Gd$^{3+}$ elicits a transient increase in [Ca$^{2+}$]$_i$ in bovine parathyroid cells. Top panel: Control. Initial concentration of extracellular Ca$^{2+}$ was 0.5 mM and was increased by 0.5 mM at each of the arrowheads. Middle panel: Gd$^{3+}$ (5 μM) blocks steady-state, but not transient increases in [Ca$^{2+}$]$_i$ elicited by extracellular Ca$^{2+}$. Lower panel: Gd$^{3+}$ (50 μM) elicits a transient increase in [Ca$^{2+}$]$_i$ and abolishes both transient and sustained responses to extracellular Ca$^{2+}$. In the middle and lower panels, just enough EGTA was added to chelate preferentially Gd$^{3+}$: the block of Ca$^{2+}$ influx is removed and [Ca$^{2+}$]$_i$ rises promptly.

Figure 5C:
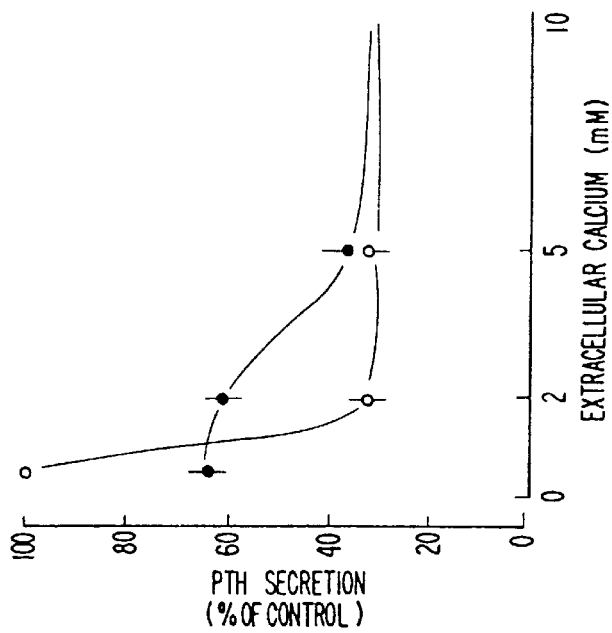
Figure 5B:
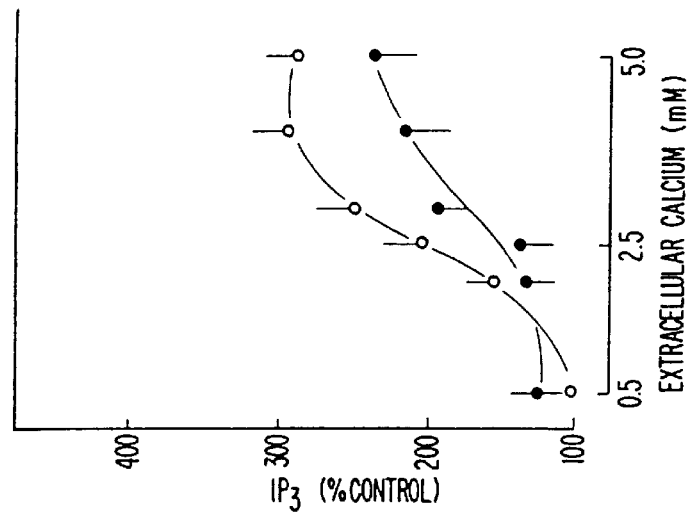
Figure 5A:
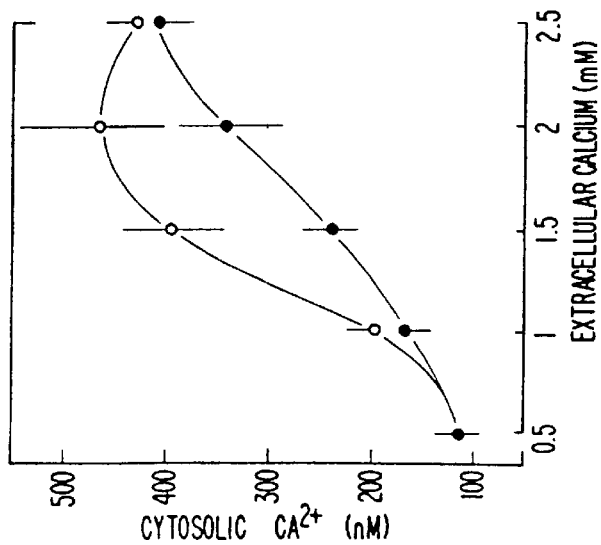

FIGS. 5a–5c are graphical representations showing that the effects of phorbol myristate acetate (PMA) on [Ca$^{2+}$]$_i$, IP$_3$ formation, and PTH secretion are overcome by increasing concentrations of extracellular Ca$^{2+}$ in bovine parathyroid cells. For each variable, there is a shift to the right in the concentration-response curve for extracellular Ca$^{2+}$. The concentration-response curves vary sigmoidally as [Ca$^{2+}$] increases linearly. The open circles refer to no PMA. The closed circles refer to 100 nM PMA.

Figure 6:
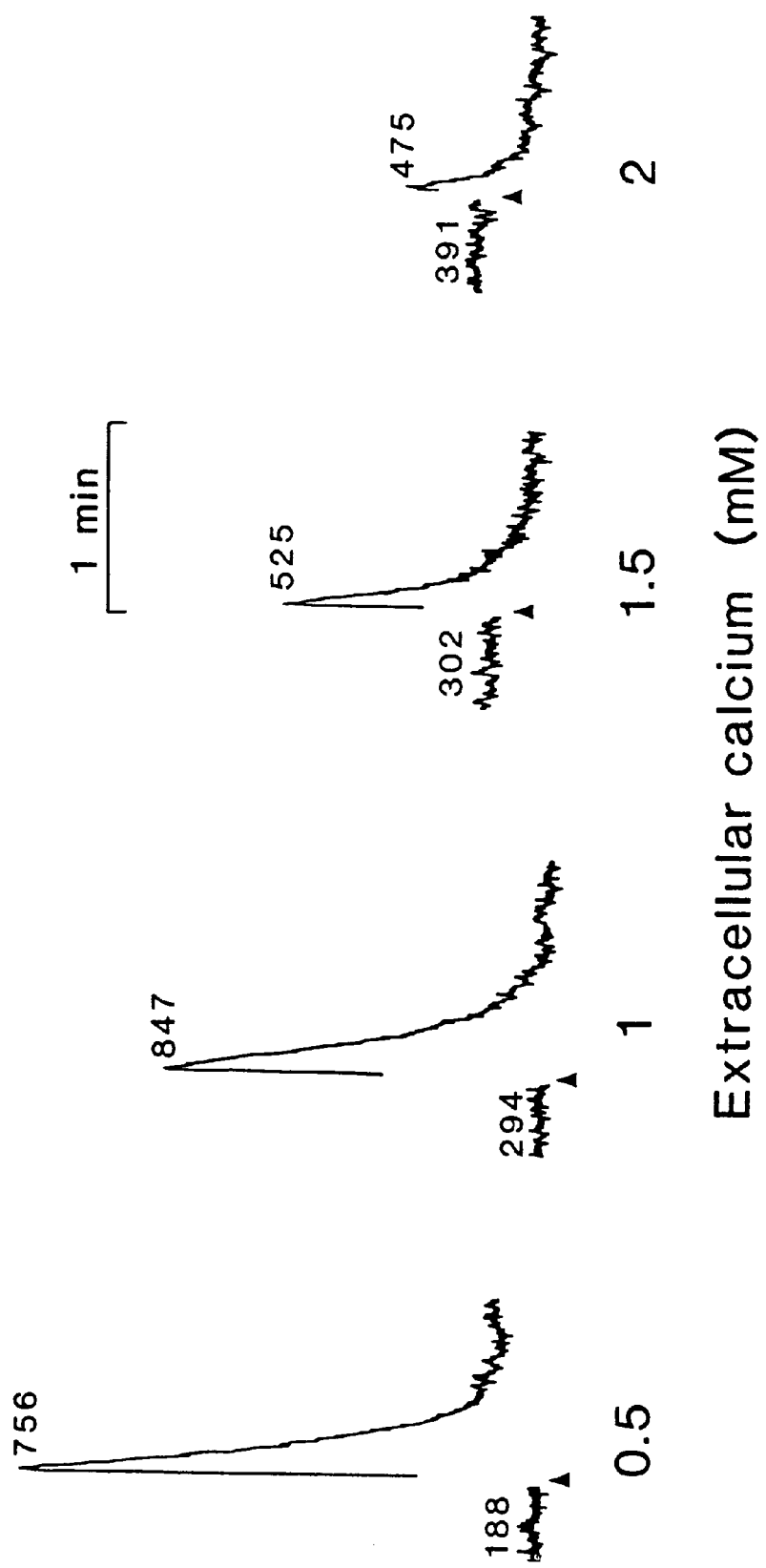

FIG. 6 is a graphical representation showing that increases in [Ca$^{2+}$]$_i$ elicited by spermine are progressively depressed by increasing [Ca$^{2+}$] in bovine parathyroid cells. Spermine (200 μM) was added at the time shown by arrowheads. In this and all subsequent figures, the numbers accompanying the traces are [Ca$^{2+}$]$_i$ in nM.

Figure 7:
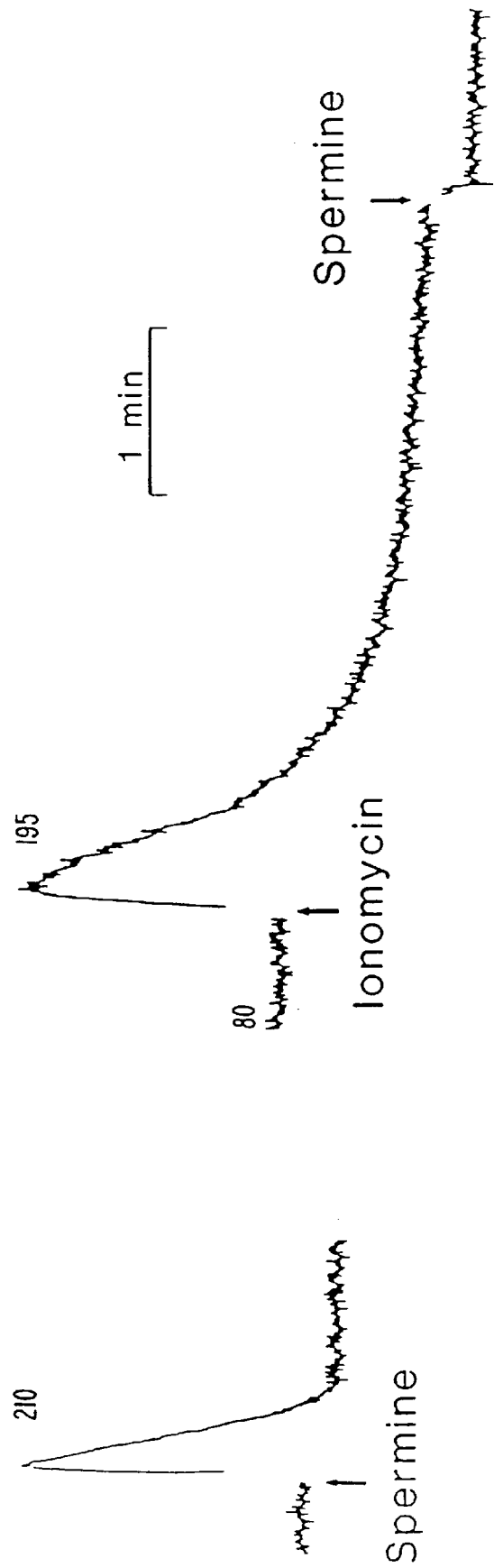

FIG. 7 is a graphical representation showing that spermine mobilizes intracellular Ca$^{2+}$ in bovine parathyroid cells. EGTA was added to reduce [Ca$^{2+}$] to <1 μM before the addition of spermine (200 μM) as indicated (left trace) Pretreatment with ionomycin (1 μM) blocks the response to spermine (right trace).

Figure 8A:
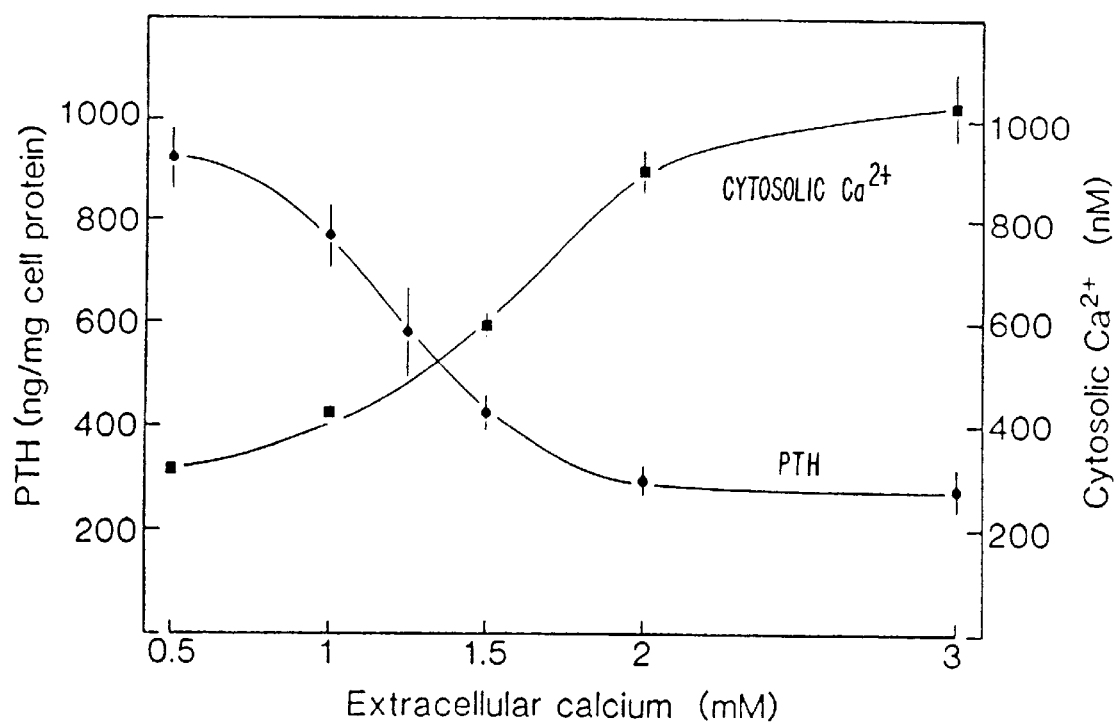

FIGS. 8a and 8b are graphical representations showing that spermine increases [Ca$^{2+}$]$_i$ and inhibits PTH secretion in bovine parathyroid cells similarly to extracellular Ca$^{2+}$. The data points for the spermine dose concentration-response curves are the means of two experiments.

Figure 9A:
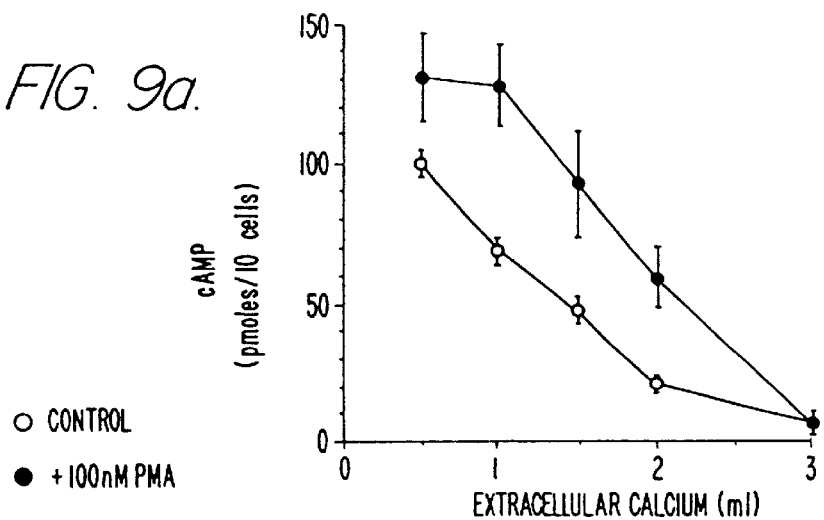
Figure 9B:
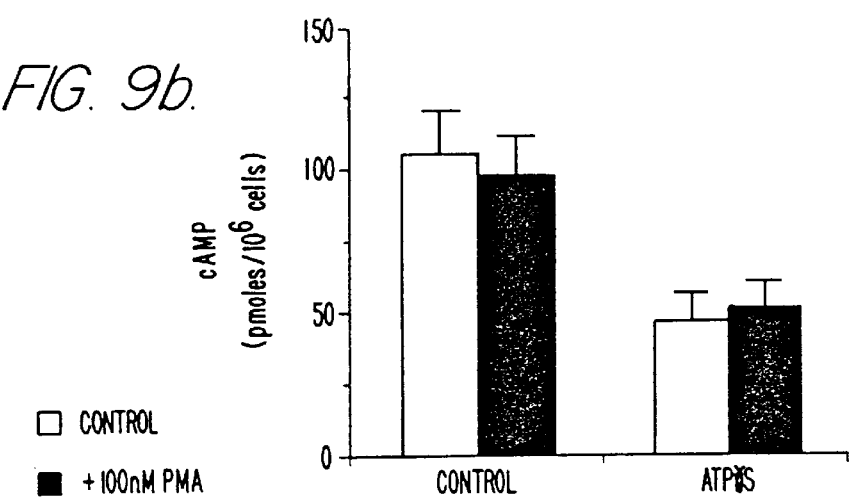
Figure 9C:
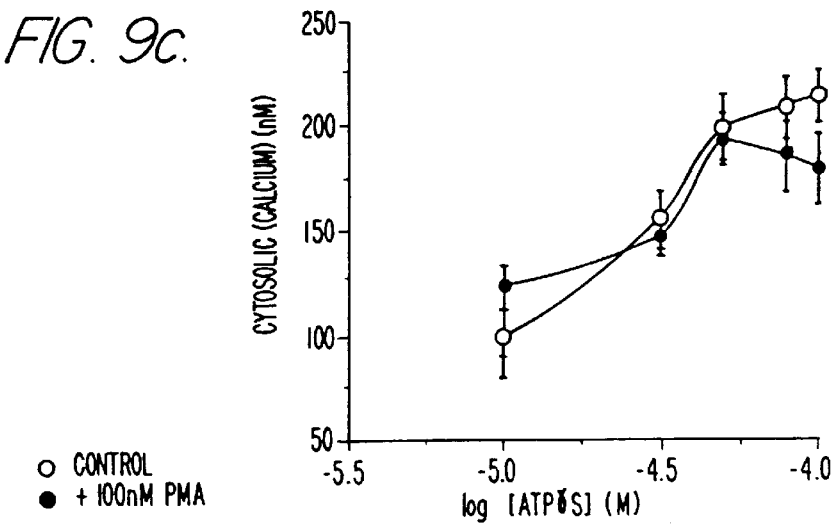

FIGS. 9a–9c are graphical representations showing the contrasting effects of PMA on responses to extracellular Ca$^{2+}$ and on responses to ATPγS in bovine parathyroid cells. Left panel: The concentration-response curve for extracellular Ca$^{2+}$-induced inhibition of cyclic μMP formation is shifted to the right by PMA (100 nM). Middle panel: PMA does not affect the ability of ATPγS to increase [Ca$^{2+}$]$_i$. The concentration-response curve to ATPγS shows classical sigmoidal behavior as a function of the log concentration, in contrast to extracellular divalent cations.

Figures 10A, 10B, 10C:
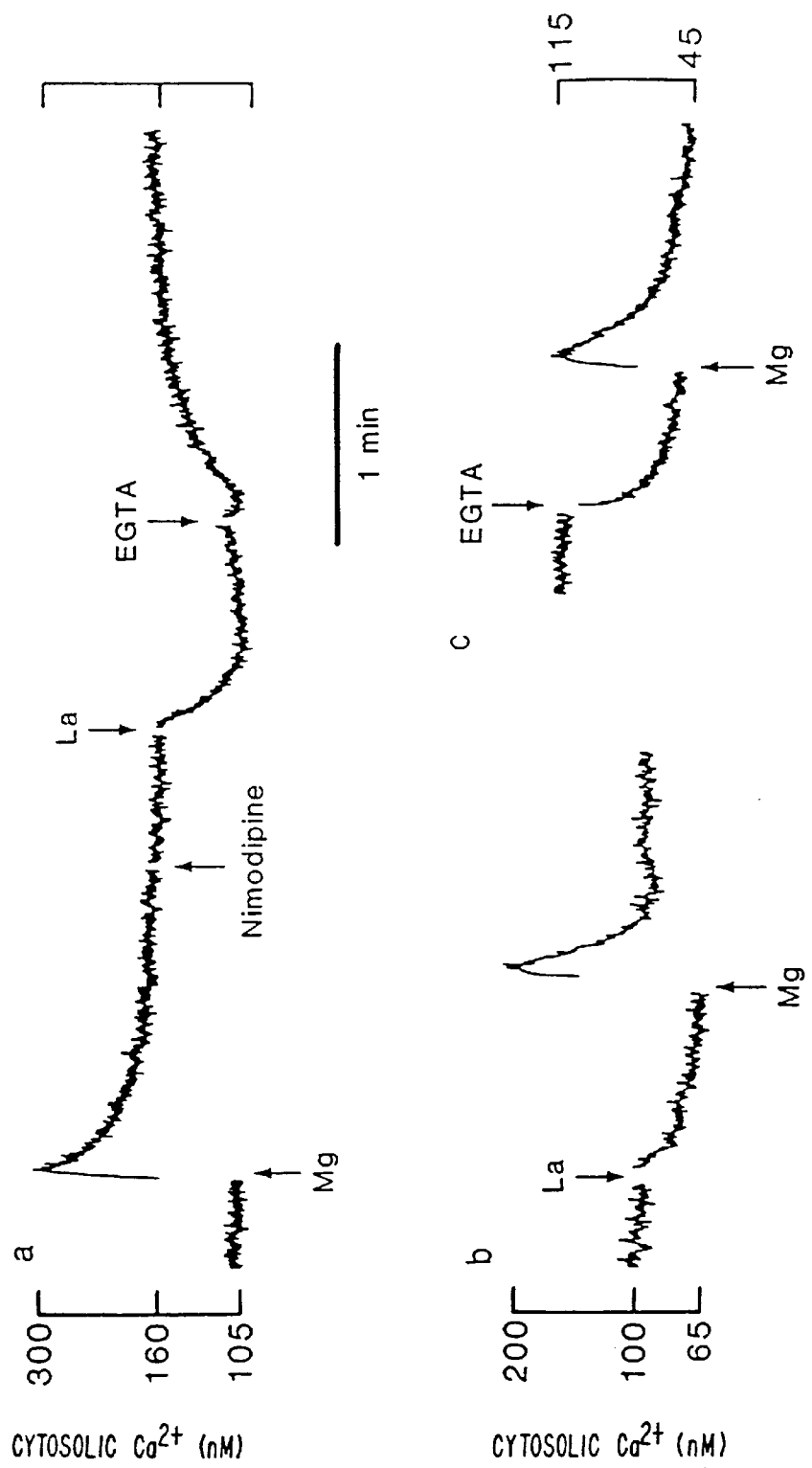

FIGS. 10a–10c are graphical representations showing mobilization of intracellular Ca$^{2+}$ in human parathyroid cells evoked by extracellular Mg$^{2+}$. Cells were obtained from an adenoma and bathed in buffer containing 0.5 mM extracellular Ca$^{2+}$. (a) Transient and sustained increases in [Ca$^{2+}$]$_i$ elicited by extracellular Mg$^{2+}$ (10 mM, final) shows that sustained increases are not affected by nimodipine (1 μM) but are depressed by La$^{3+}$ (1 μM) and return promptly when La$^{3+}$ is selectively chelated by a low concentration of EGTA (50 μM) (b) La$^{3+}$ (1 μM) blocks the sustained, but not the transient increase in [Ca$^{2+}$]$_i$ elicited by extracellular Mg$^{2+}$. (c) Cytosolic Ca$^{2+}$ transients elicited by extracellular Mg$^{2+}$ persist in the absence of extracellular Ca$^{2+}$.

FIGS. 11a–11i are graphical representations showing mobilization of intracellular Ca$^{2+}$ evoked by neomycin or protamine in bovine parathyroid cells. In all traces, the initial [Ca$^{2+}$] and [Mg$^{2+}$] was 0.5 and 1 mM, respectively. In traces (a) and (b), the Ca$^{2+}$ and Mg$^{2+}$ concentrations were increased to 2 and 8 mM, from 0.5 and 1 mM, respectively. In the other traces, (c) through (i) neomycin B (30 μM) or protamine (1 μg/ml) were added as indicated. La$^{3+}$ (1 μM), EGTA (1 mM), or ionomycin (100 nM) were added as indicated. Each trace is representative of the pattern seen in 5 or more trials using at least 3 different cell preparations. Bar=1 minute.

FIG. 12 is a graphical representation showing that neomycin B blocks transient, but does not block steady-state increases in [Ca$^{2+}$]$_i$ elicited by extracellular Ca$^{2+}$ in bovine parathyroid cells. Left control: [Ca$^{2+}$] was initially 0.5 mM and was increased in 0.5 mM increments at each of the open arrowheads before the addition of neomycin B (30 μM). Right: Neomycin B (30 μM) was added before [Ca$^{2+}$]. Bar=1 minute.

Figure 13A:
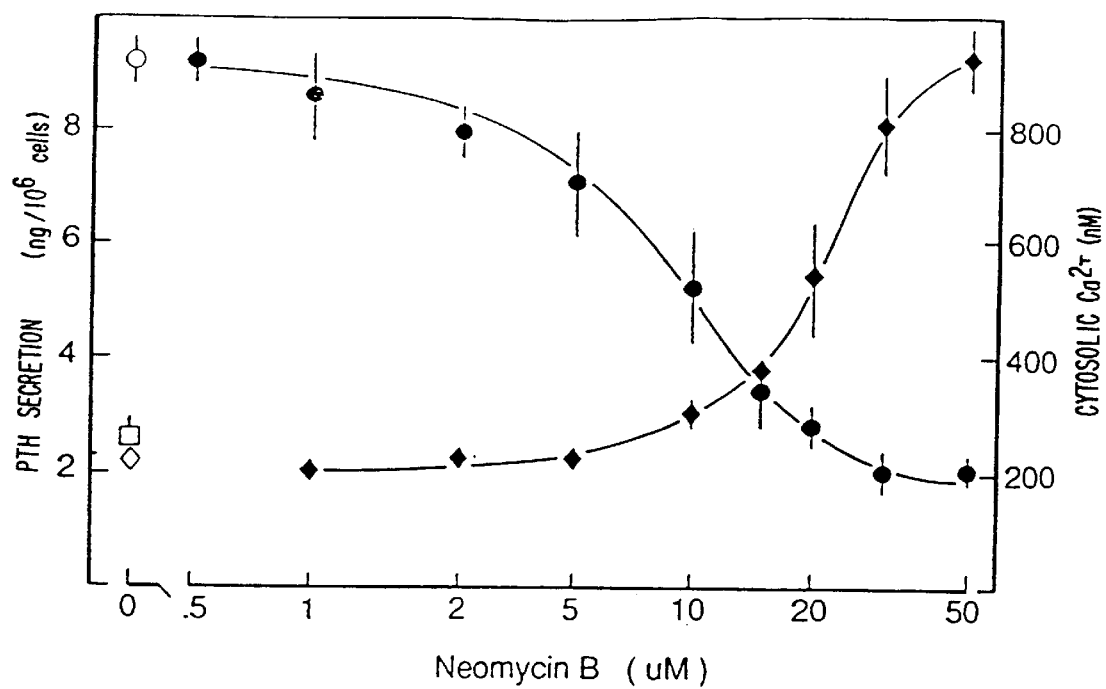
Figure 13B:
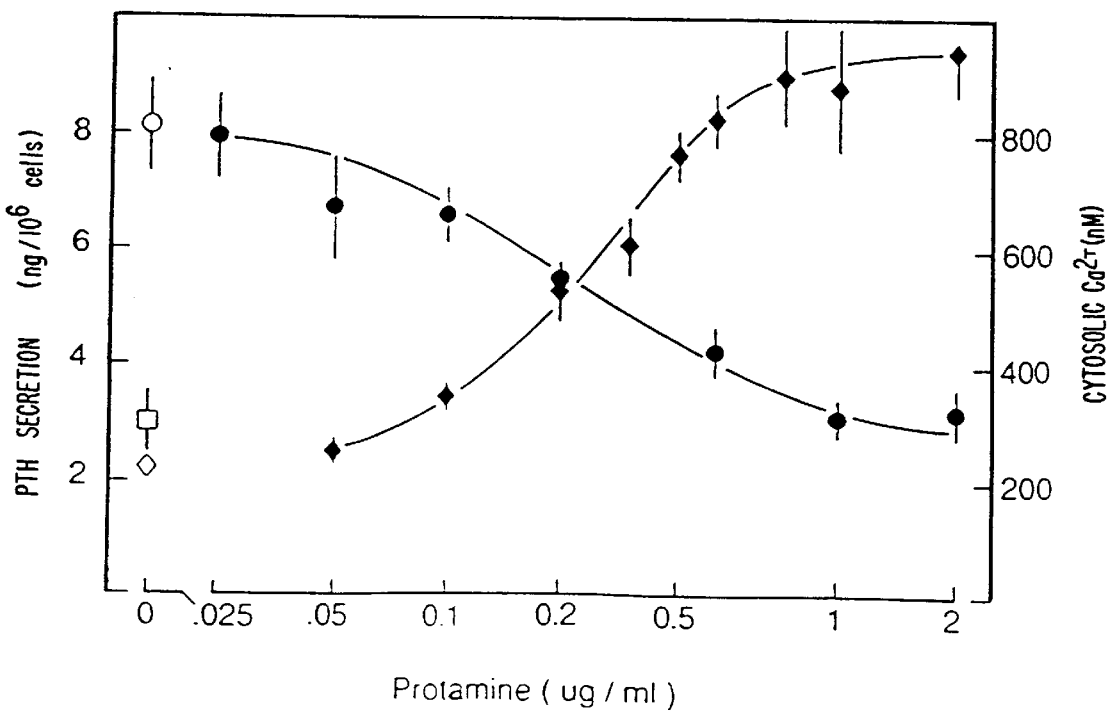

FIGS. 13a and 13b are graphical representations showing that neomycin B or protamine inhibit PTH secretion at concentrations which evoked increases in [Ca$^{2+}$]$_i$ in bovine parathyroid cells. Cells were incubated with the indicated concentrations of organic polycation for 30 minutes in the presence of 0.5 mM extracellular Ca$^{2+}$. Bovine cells were used in the experiments with protamine and human (adenoma) parathyroid cells were used in the experiments with neomycin B. Each point is the mean±SEM of 3 experiments. Circles refer to PTH levels in the presence of 0.5 mM extracellular Ca$^{2+}$ in the presence (closed circles) and absence (open circles) of neomycin B (FIG. 13a) or protamine (FIG. 13b). Diamonds refer to [Ca$^{2+}$]$_i$ levels in the presence of 0.5 mM extracellular Ca$^{2+}$ in the presence (closed diamonds) and absence (open diamond) of neomycin B (FIG. 13a) or protamine (FIG. 13b). The open square refers to PTH secretion in the presence of 2 mM extracellular Ca$^{2+}$.

Figure 14:
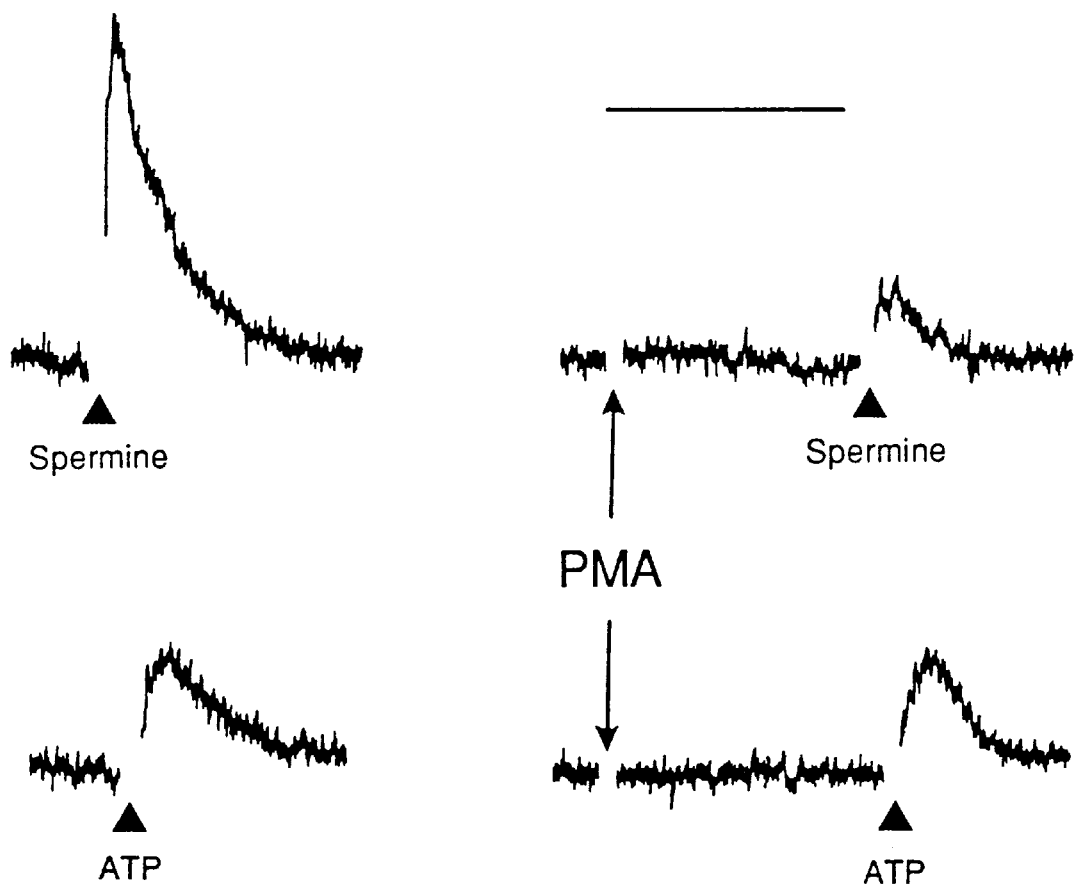

FIG. 14 is a graphical representation showing the preferential inhibitory effects of PMA on cytosolic Ca$^{2+}$ transients elicited by spermine in bovine parathyroid cells. Initial [Ca$^{2+}$] was 0.5 mM; PMA (100 nM), spermine (200 μM) or ATP (50 μM) were added as indicated. Bar=1 minute.

FIGS. 15a and 15b are graphical representations showing that PMA shifts to the right the concentration-response curves for extracellular Ca$^{2+}$—and neomycin B-induced increases in [Ca$^{2+}$]$_i$ in bovine parathyroid cells. Cells were either untreated (open circles) or pretreated with 100 nM PMA for 1 minute (closed circles) before increasing [Ca$^{2+}$] or before adding neomycin B as indicated. Each point is the mean±SEM of 3 to 5 experiments.

Figures 16A, 16B:
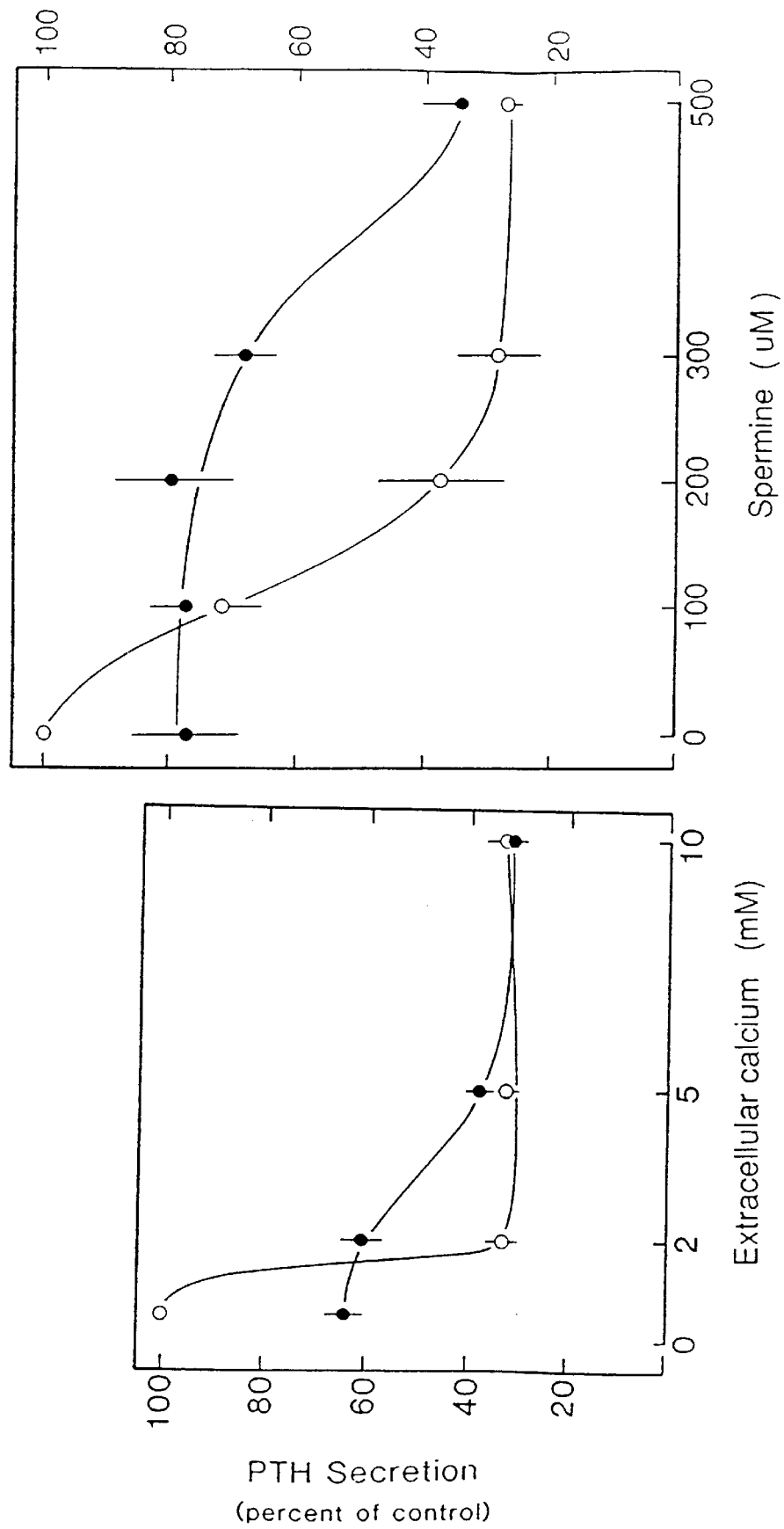

FIGS. 16a and 16b are graphical representations showing that PMA shifts to the right the concentration-response curves for extracellular Ca$^{2+}$—and spermine-induced inhibition of PTH secretion in bovine parathyroid cells. Cells were incubated with the indicated [Ca$^{2+}$] and spermine for 30 minutes in the presence (closed circles) or absence (open circles) of 100 nM PMA. Each point is the mean±SEM of 3 experiments.

Figure 17:
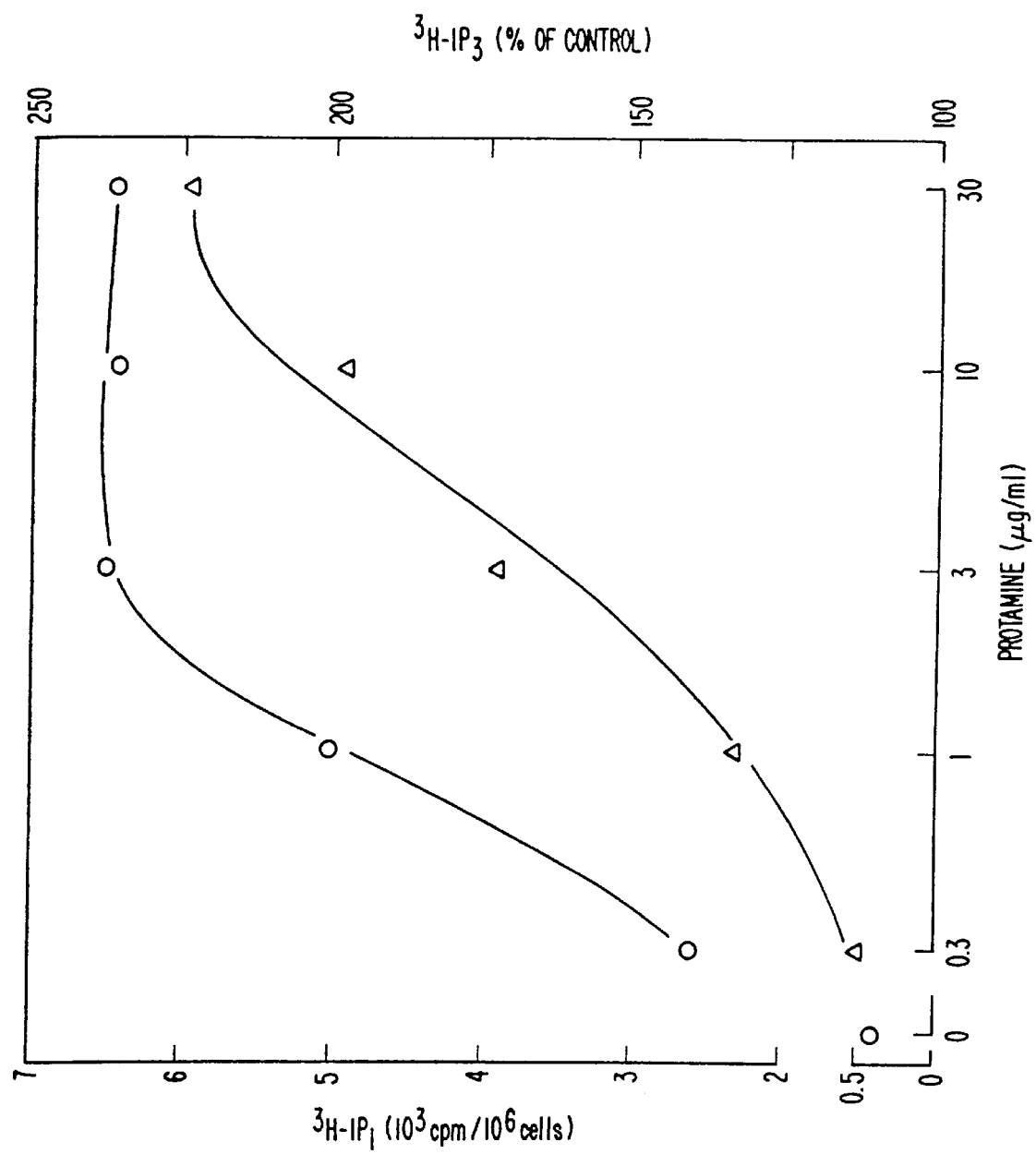

FIG. 17 is a graphical representation showing that protamine increases the formation of inositol phosphates in bovine parathyroid cells. Parathyroid cells were incubated overnight in culture media containing 4 $\mu$Ci/ml $^3$H-myo-inositol, washed, and incubated with the indicated concentration of protamine at 37° C. After 30 seconds, the reaction was terminated by the addition of $CHCl_3$:MeOH:HCl and $IP_1$ (circles) and $IP_3$ (triangles) separated by anion exchange chromatography. Each point is the mean of 2 experiments, each performed in triplicate.

Figure 18B:
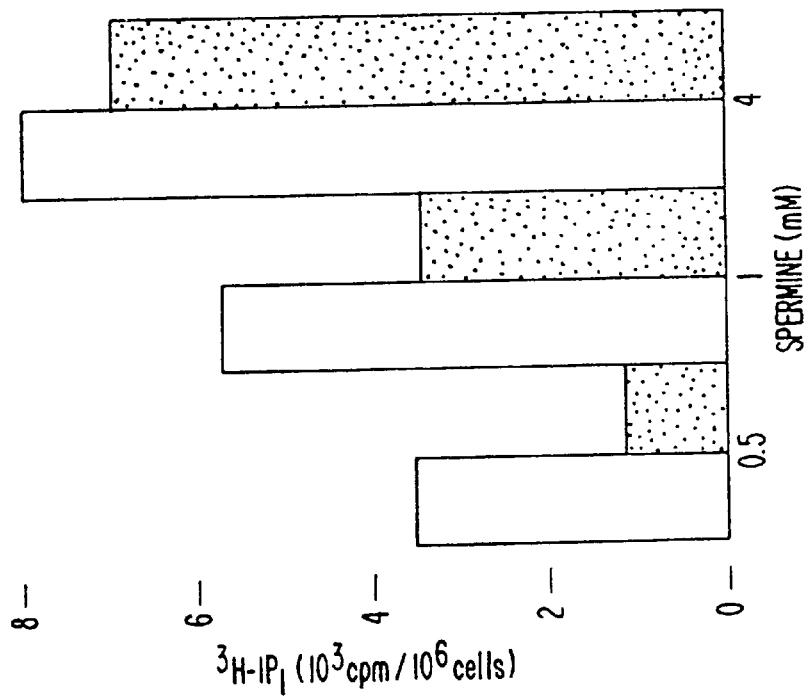
Figure 18A:
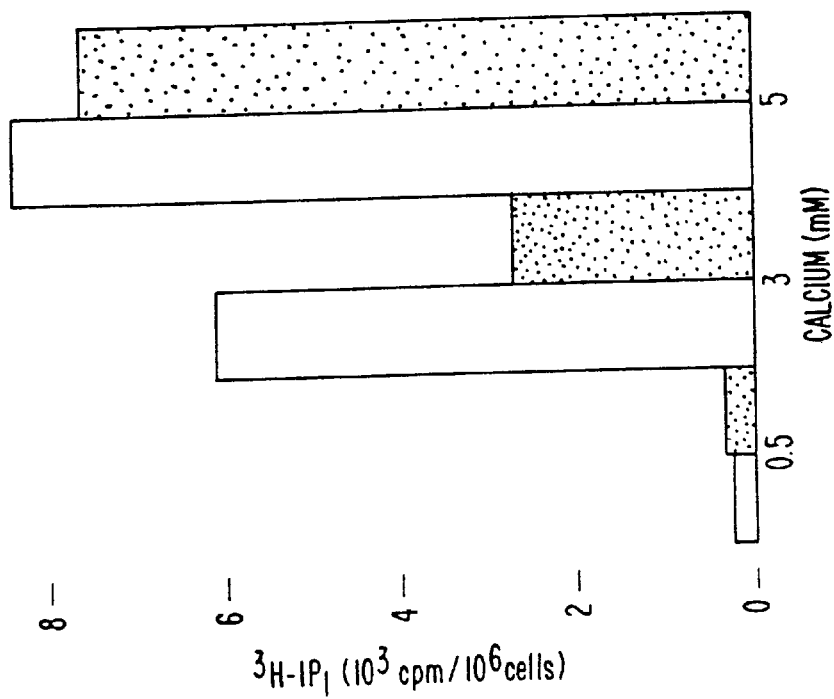

FIGS. 18a and 18b are graphical representations showing that PMA depresses the formation of $IP_1$ evoked by extracellular $Ca^{2+}$ or spermine in bovine parathyroid cells. $^3$H-Myo-indsitol-labeled cells were exposed to the indicated $[Ca^{2+}]_i$ or spermine for 30 seconds before terminating the reaction and determining $IP_1$ by anion exchange chromatography. Hatched columns: Cells were pretreated with PMA (100 nM) for 5 minutes before increasing $[Ca^{2+}]_i$ or adding spermine. Each value is the mean of 2 experiments, each performed in triplicate.

Figure 19:
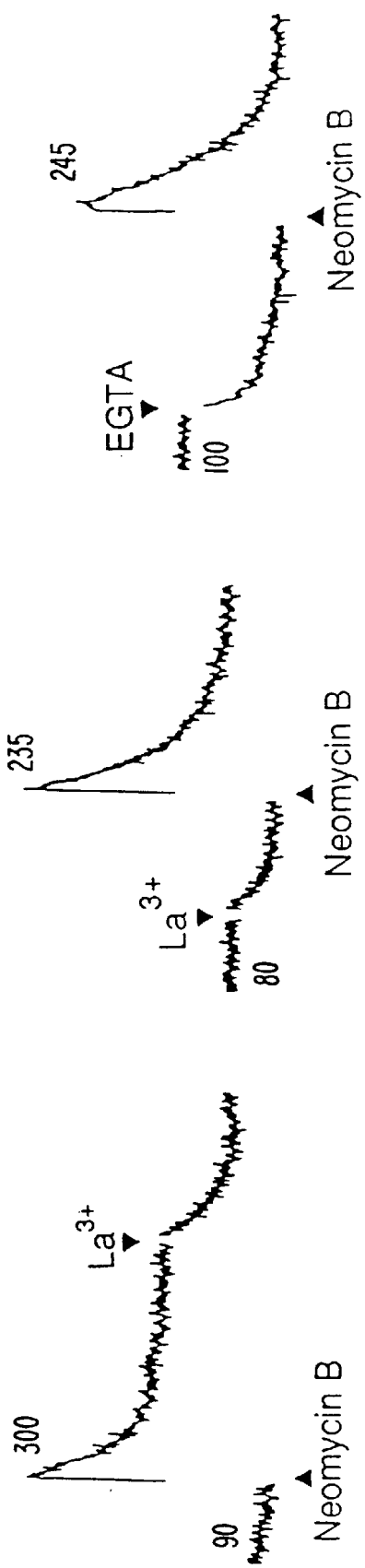

FIG. 19 is a graphical representation showing transient and sustained increases in $[Ca^{2+}]_i$ elicited by neomycin B in human (adenoma) parathyroid cells. Extracellular $Ca^{2+}$ was 0.5 mM. (a) The sustained increase in $[Ca^{2+}]_i$ elicited by neomycin B (10 $\mu$M) was depressed by $La^{3+}$ (1 $\mu$M). (b) The transient increase in $[Ca^{2+}]_i$ evoked by neomycin B (10 $\mu$M) was unaffected by $La^{3+}$ (1 $\mu$M). (c) Transient increases in $[Ca^{2+}]_i$ persisted in the absence of extracellular $Ca^{2+}$ (1 mM of EGTA and 10 $\mu$M of neomycin B).

Figure 20A:
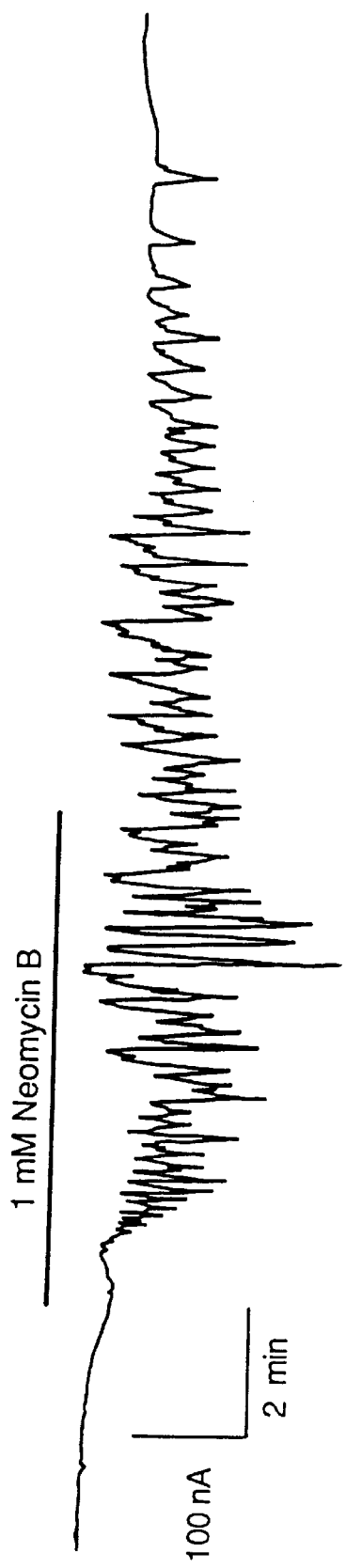
Figure 20B:
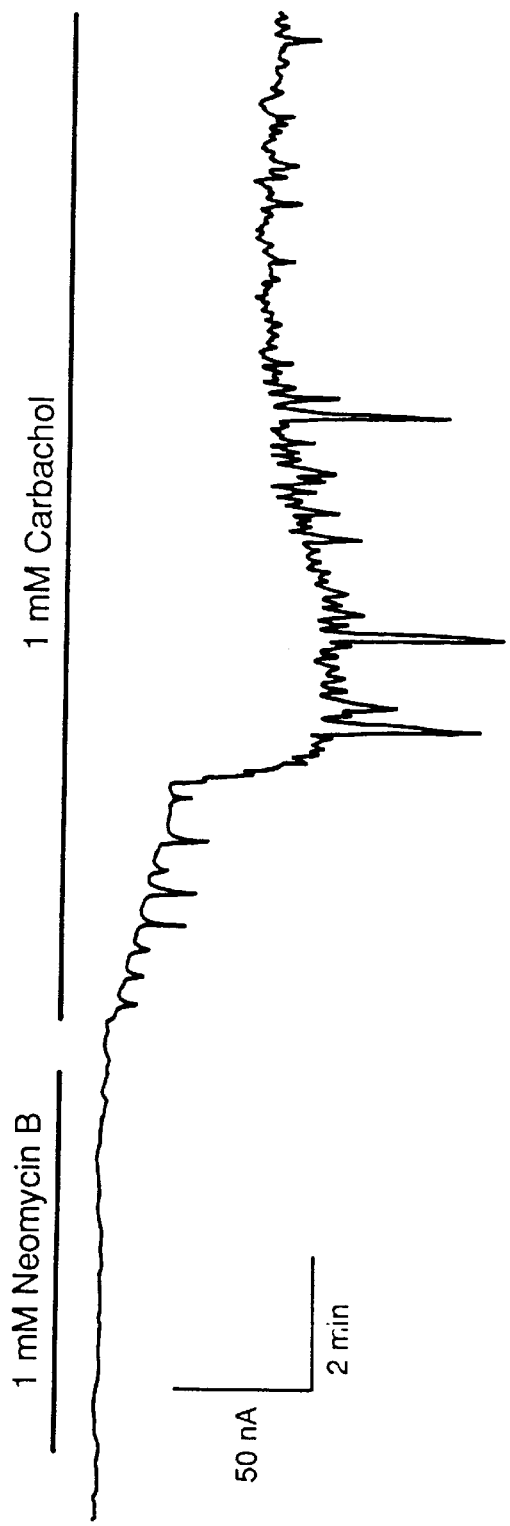

FIGS. 20a and 20b are graphical representations showing that neomycin B evokes oscillating increases in the $Cl^-$ current in Xenopus oocytes expressing the calcium receptor. Upper trace from an oocyte three days after injection with human (hyperplastic) parathyroid cell poly(A)$^+$-mRNA. Lower trace from an oocyte injected with water. Neomycin B failed to elicit a response in five water-injected oocytes and carbachol elicited a response in one, which is shown. In both traces, the holding potential was –76 mV.

Figure 21:
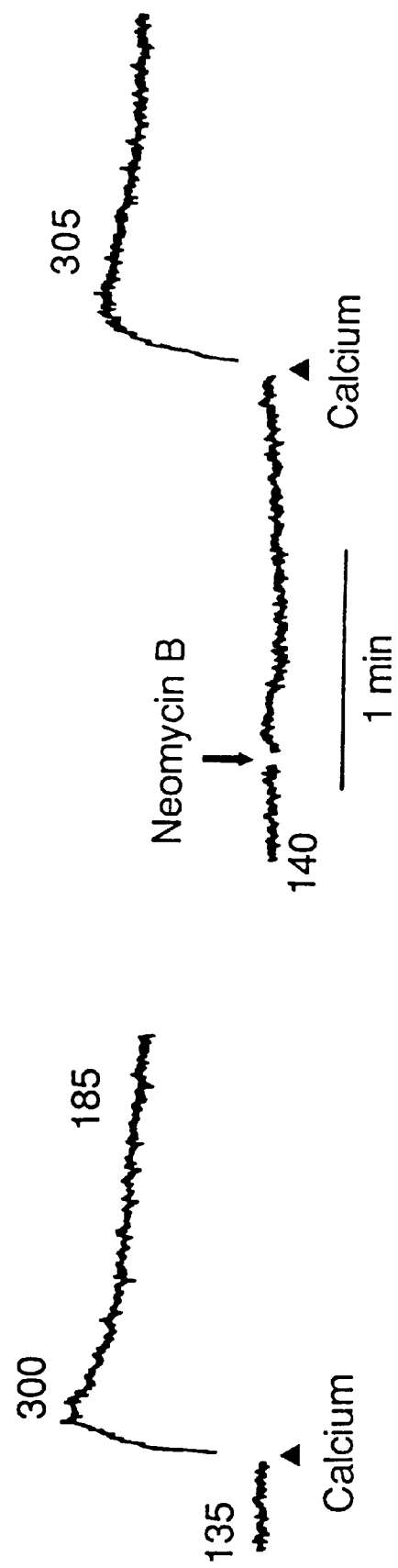

FIG. 21 is a graphical representation showing that neomycin B fails to affect basal or evoked increases in C-cells. Control, left trace: fura-2-loaded rMTC 6–23 cells were initially bathed in buffer containing 1 mM $Ca^{2+}$ before increasing $[Ca^{2+}]_i$ to 3 mM. Right trace: pretreatment with 5 mM neomycin B.

Figure 22:
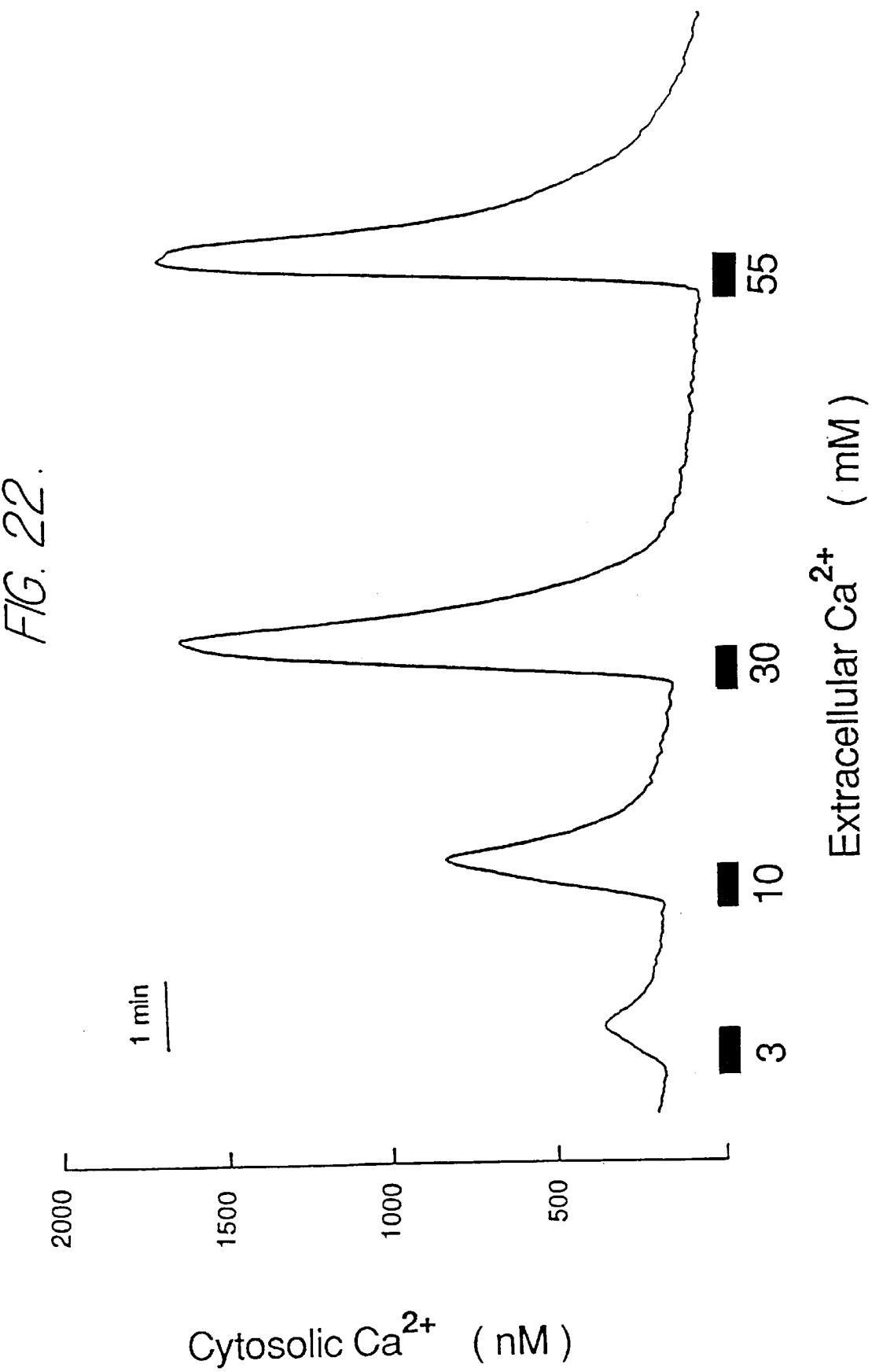

FIG. 22 is a graphical representation showing that extracellular $Ca^{2+}$ evokes increases in $[Ca^{2+}]_i$ in rat osteoclasts. Microfluorimetric recording in a single rat osteoclast loaded with indo-1 and superfused for the indicated times (bars) with buffer containing the indicated $[Ca^{2+}]$. Normal buffer, superfused between the bars, contained 1 mM $Ca^{2+}$.

Figure 23:
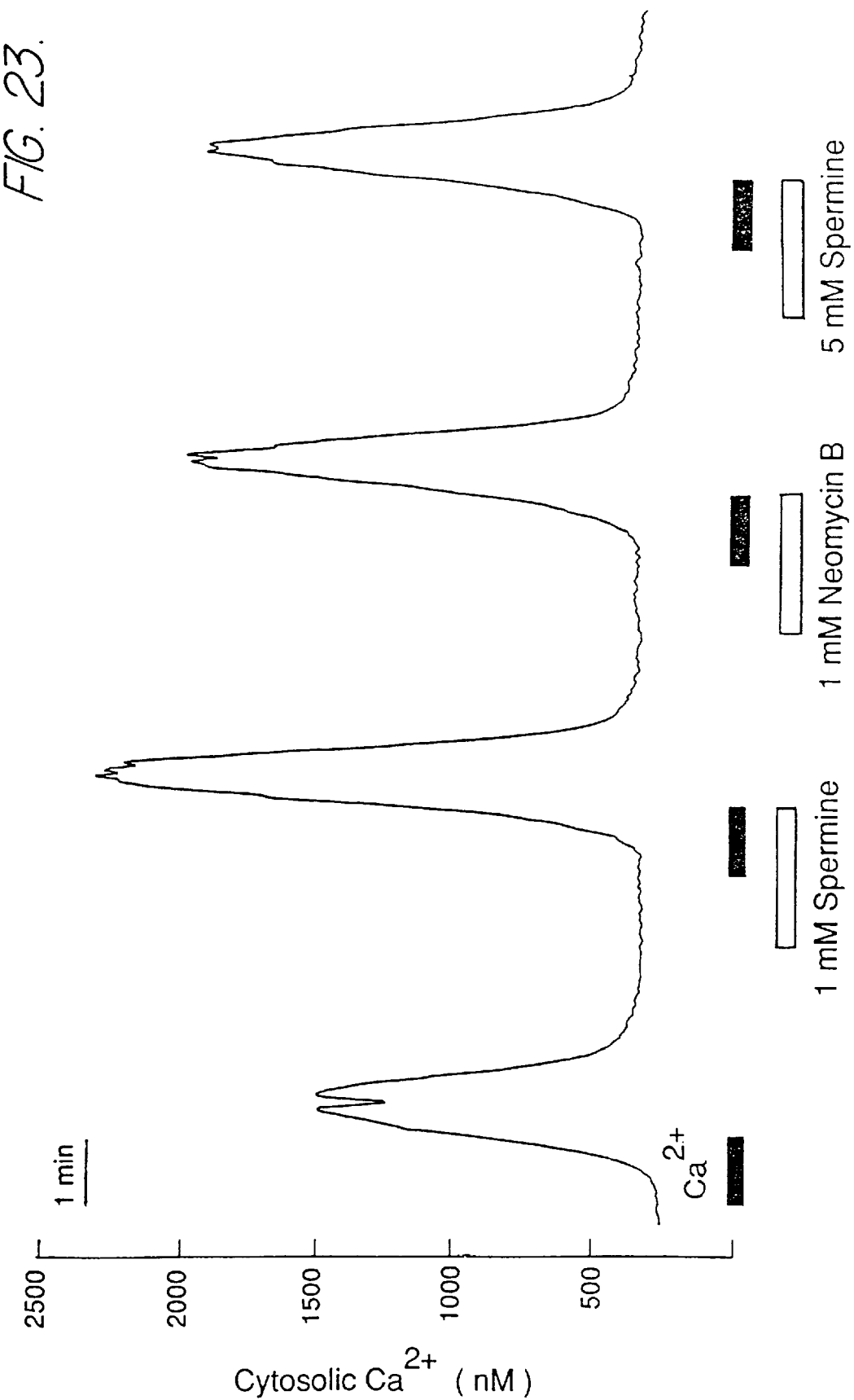

FIG. 23 is a graphical representation showing that spermine or neomycin B fail to evoke increases in $[Ca^{2+}]_i$ in rat osteoclasts. An indo-1-loaded osteoclast was superfused with the indicated concentration of spermine or neomycin B (open bars) alone or together with 20 mM $Ca^{2+}$ (solid bars).

Figure 24:
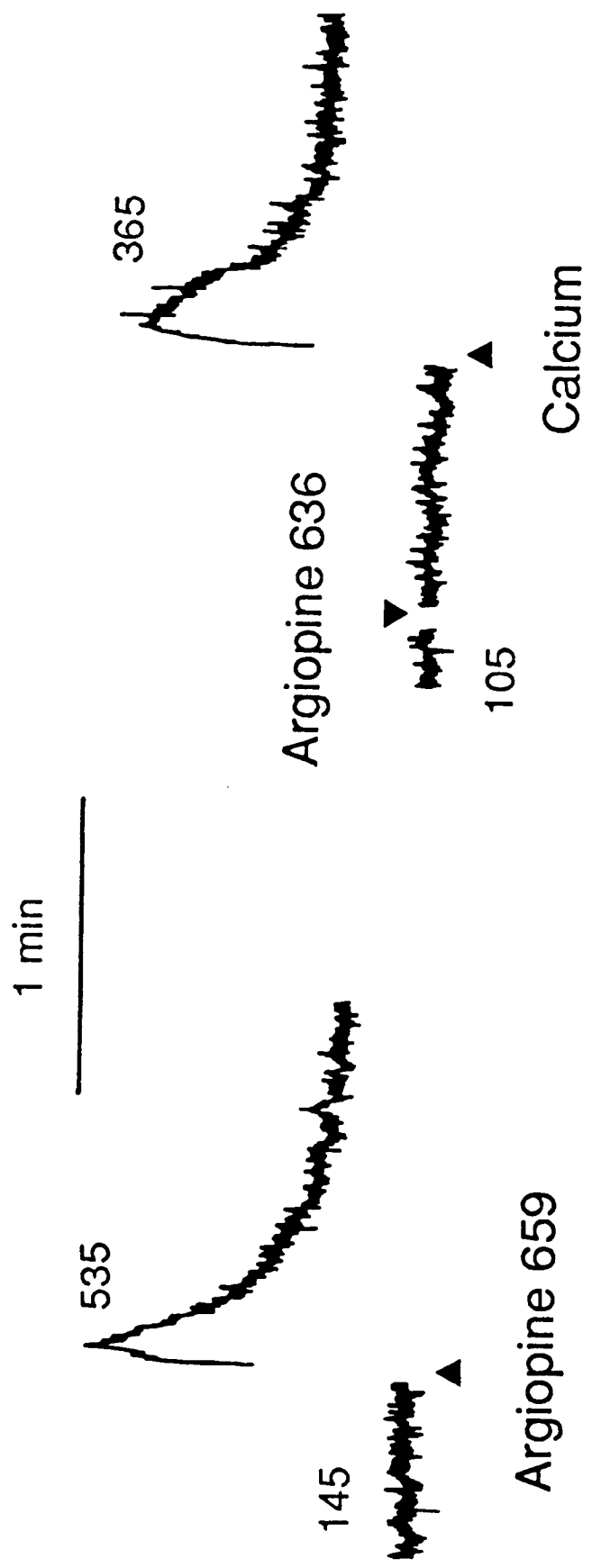

FIG. 24 is a graphical representation showing the differential effects of argiotoxin 659 and argiotoxin 636 on $[Ca^{2+}]_i$ in bovine parathyroid cells (structures shown in FIG. 1e). The initial $[Ca^{2+}]$ was 0.5 mM and was increased to 1.5 mM where indicated (right trace). Where indicated, argiotoxin 659 (300 $\mu$M) or argiotoxin 636 (400 $\mu$M) was added.

FIGS. 25a–25c are graphical representations showing that extracellular $Mg^{2+}$ or $Gd^{3+}$ evoke oscillatory increases in $Cl^-$ current in Xenopus oocytes injected with bovine parathyroid cell poly(A)$^+$-mRNA. In trace (a), the concentration of extracellular $Ca^{2+}$ was <1 $\mu$M and in traces (b) and (c) it was 0.7 mM. Trace (c) shows that extracellular $Mg^{2+}$ fails to elicit a response in an oocyte injected only with the mRNA for the substance K receptor, although superfusion with substance K evokes a response. Holding potential was –70 to –80 mV.

Figure 26:
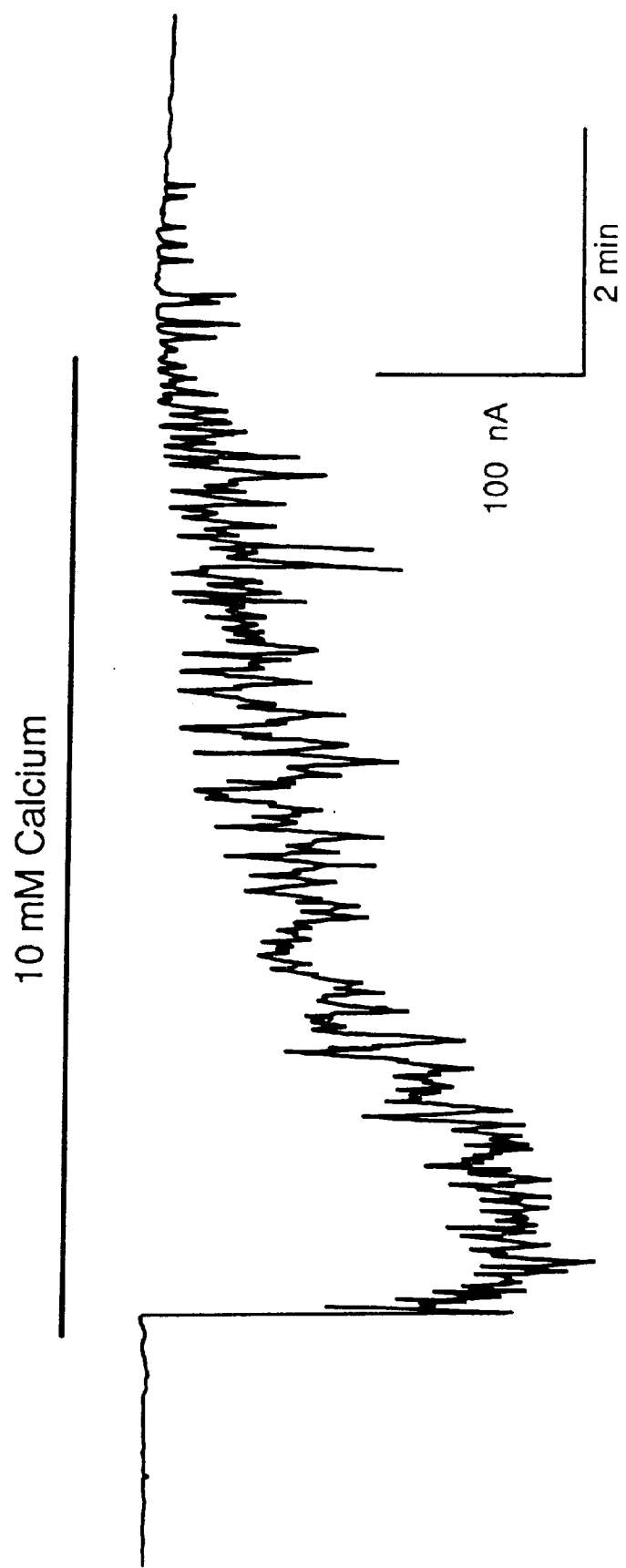

FIG. 26 is a graphical representation showing that extracellular $Ca^{2+}$ elicits oscillatory increases in $Cl^-$ current in Xenopus oocytes injected with human (hyperplastic) parathyroid tissue poly(A)$^+$-mRNA. The oocyte was tested for responsivity to extracellular $Ca^{2+}$ three days after injection of 50 ng poly(A)$^+$-mRNA. Holding potential was –80 mV.

Figure 27:

FIG. 27 is a graphical representation showing the mobilization of intracellular $Ca^{2+}$ in bovine parathyroid cells elicited by budmunchiamine. Budmunchiamine (300 $\mu$M, structure shown in FIG. 1a) was added where indicated.

Figure 28B:
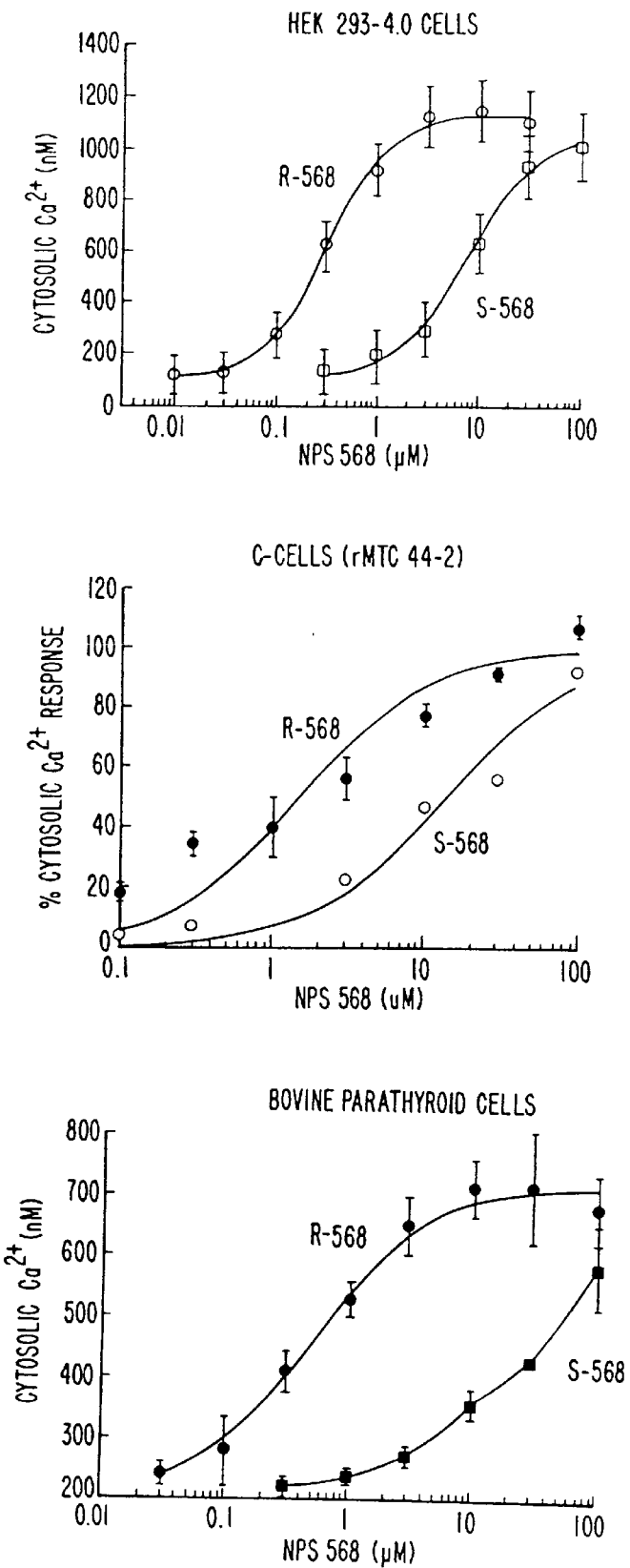

FIGS. 28a and 28b are graphical representations showing that the ability of molecules to mobilize intracellular $Ca^{2+}$ in cells expressing a calcium receptor is stereospecific. Different cells were tested for response to pure stereoisomers and racemic mixtures. HEK 293 cells stably transfected with a cDNA clone corresponding to pHuPCaR4.0 (top panel, FIG. 28b), the rat C-cell line 44-2 isolated from a medullary thyroid carcinoma (middle panel, FIG. 28b) and bovine parathyroid cells (FIG. 28a and bottom panel FIG. 28b) were loaded with fura-2 and suspended in buffer containing 1.0 mM (top and middle panels FIG. 28b) or 0.5 mM extracellular $Ca^{2+}$ (FIG. 28a and bottom panel FIG. 28b). Intracellular $Ca^{2+}$ was monitored using a fluorimeter. Each point on the graph represents the peak response (highest concentration of intracellular calcium achieved) to the addition of the indicated concentration of the indicated compound. In FIG. 28a, NPS 457 is a racemic mixture containing compound 1B (see FIG. 36a) and the corresponding S isomer; NPS 447 is R-fendiline; and NPS 448 is S-fendiline.

Figure 29:
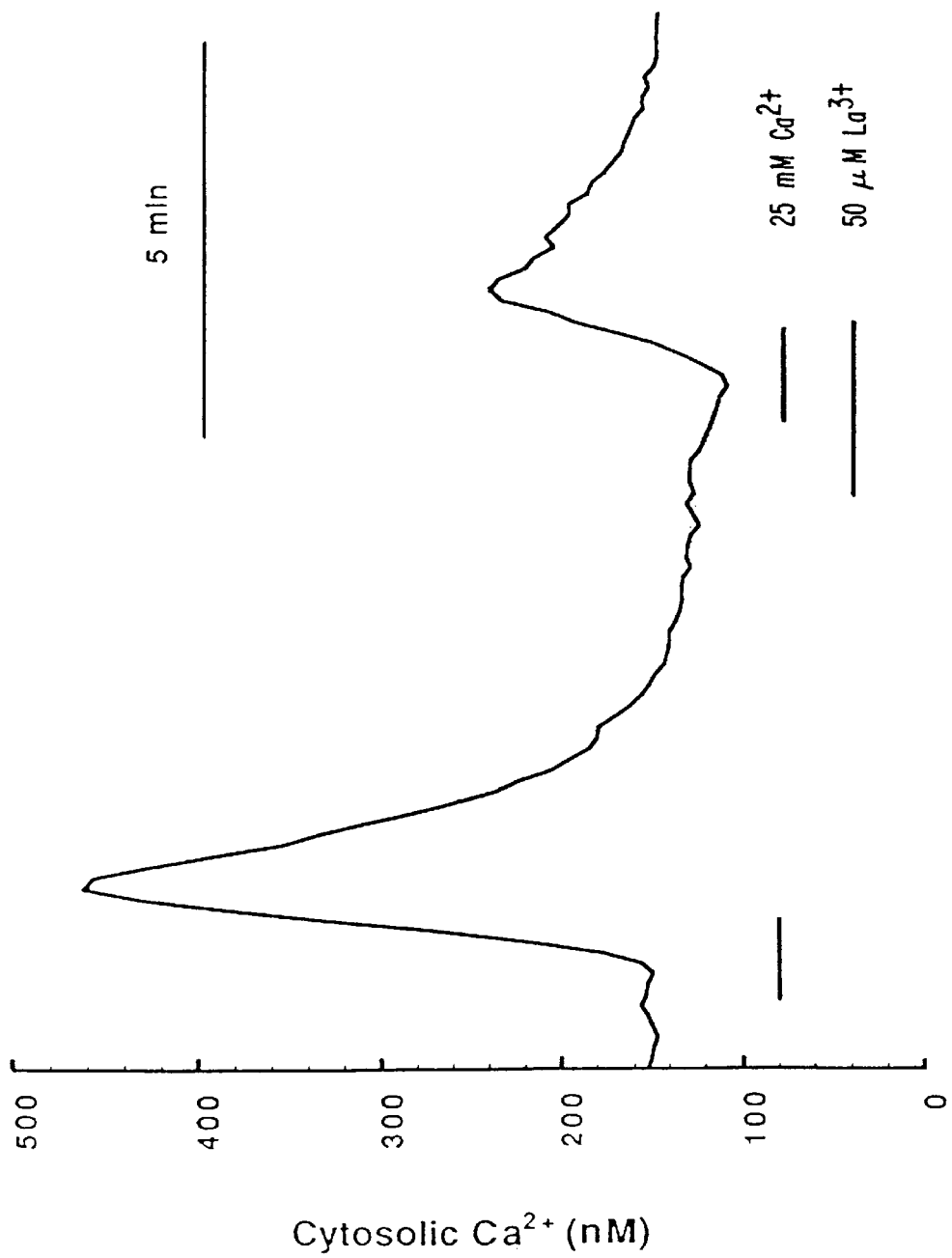

FIG. 29 is a graphical representation showing effects of $La^{3+}$ on $[Ca^{2+}]_i$ in osteoclasts. A representative trace from a single rat osteoclast loaded with indo-1 is shown. At low concentrations, $La^{3+}$ partially blocks increases in $[Ca^{2+}]_i$ elicited by extracellular $Ca^{2+}$.

Figure 30A:
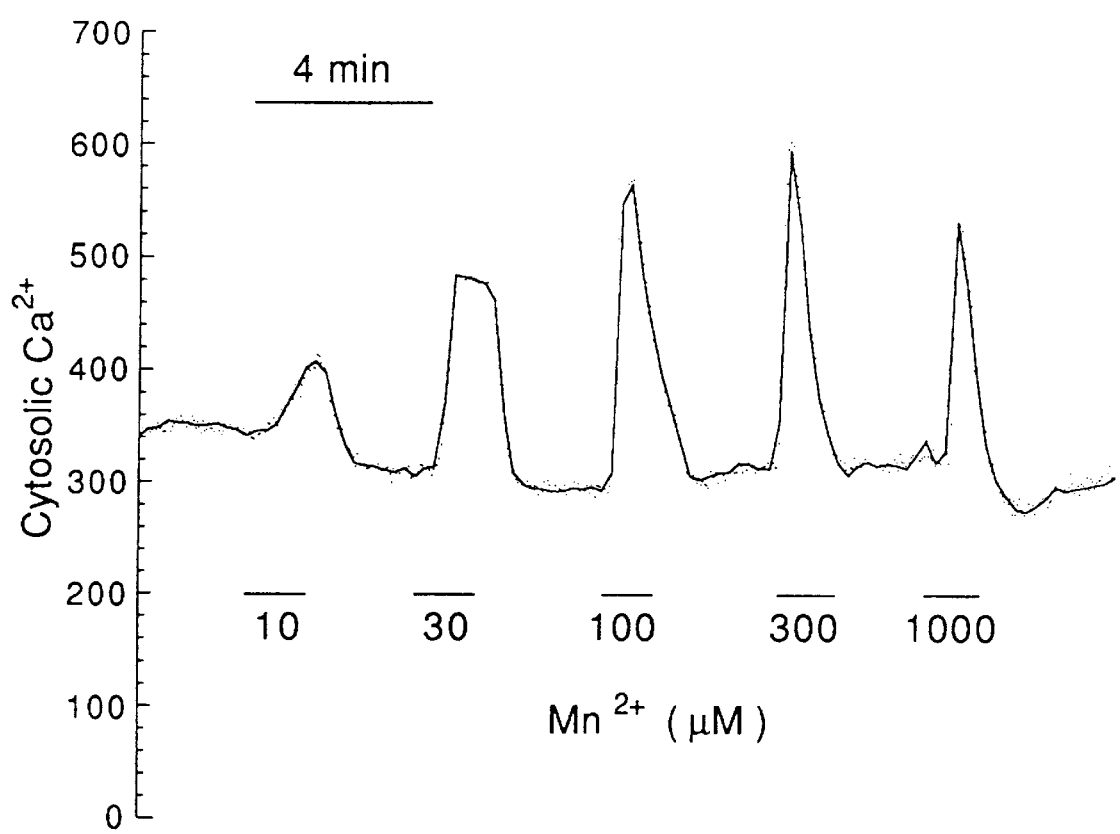
Figure 30B:
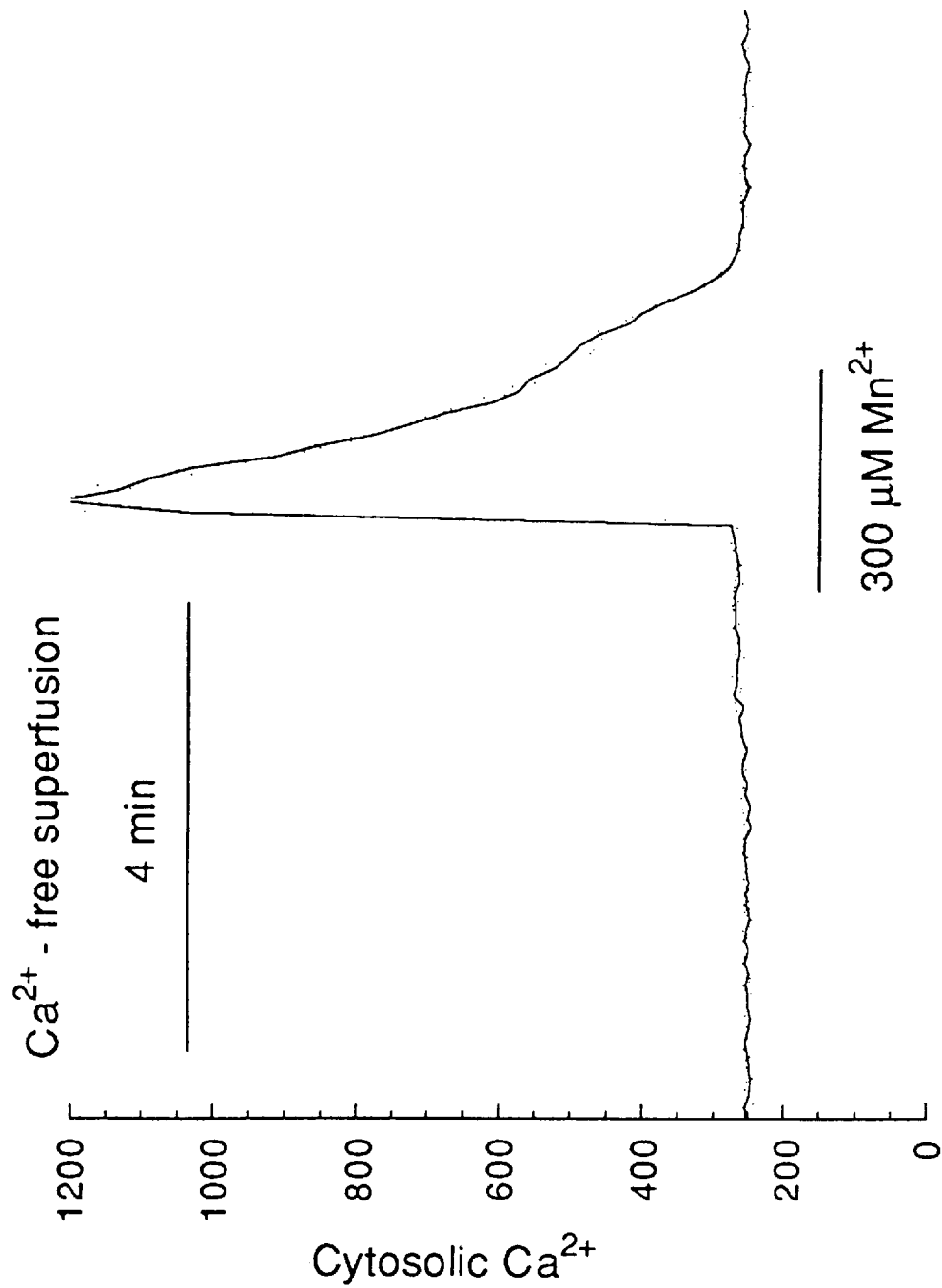

FIGS. 30a and 30b are graphical representations showing the mobilization of intracellular $Ca^{2+}$ elicited by extracellular $Mn^{2+}$ in rat osteoclasts. Extracellular $Mn^{2+}$ evokes concentration-dependent increases in $[Ca^{2+}]_i$ (FIG. 30a) that persist in the absence of extracellular $Ca^{2+}$ (FIG. 30b).

Figure 31A:
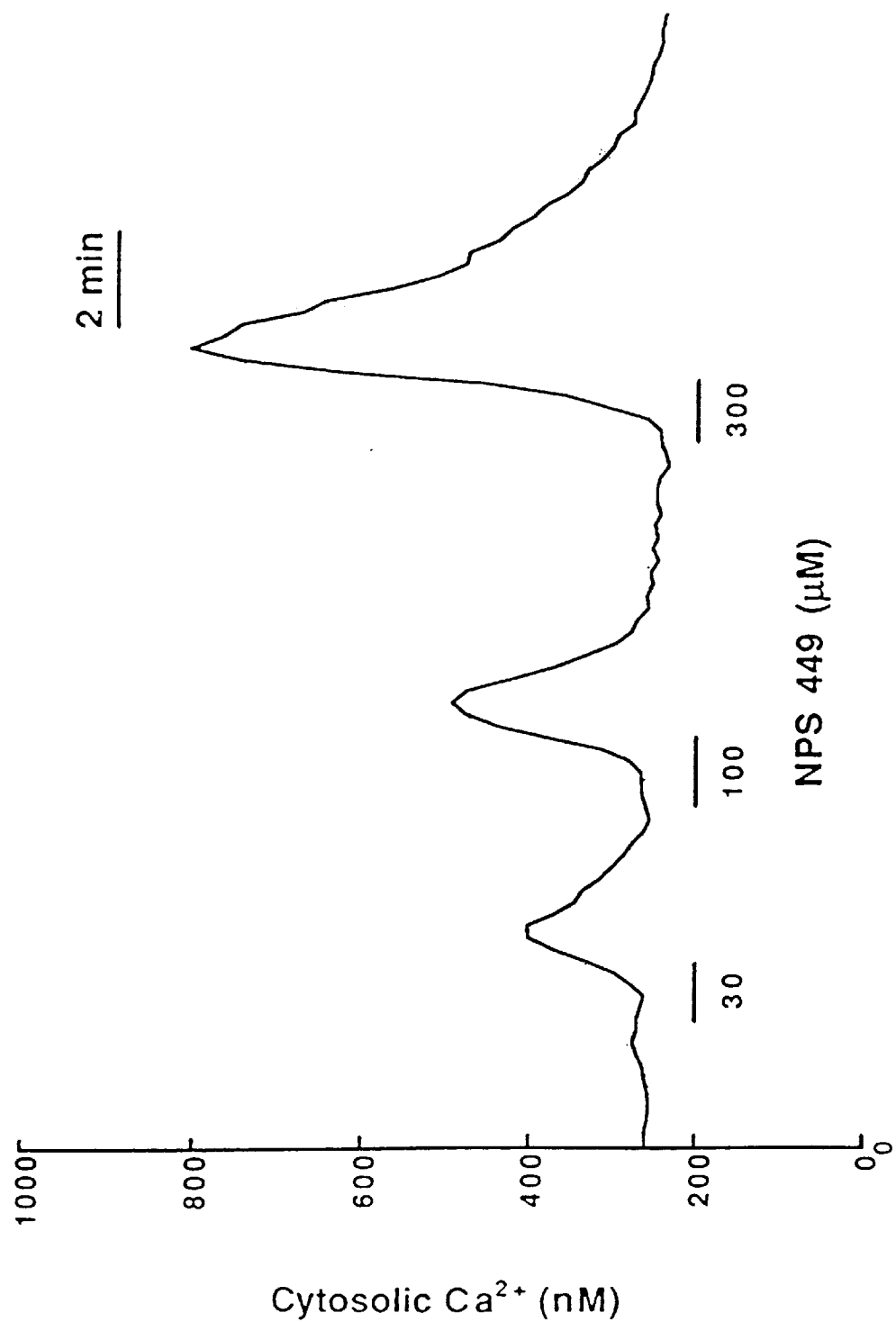

FIGS. 31a and 31b are graphical representations showing mobilization of $[Ca^{2+}]_i$ in rat osteoclasts elicited by prenylamine (shown in the figures as NPS 449). Isolated rat osteoclasts loaded with indo-1 were superfused with the indicated concentrations of prenylamine in the presence (FIG. 31a) or absence (FIG. 31b) of 1 mM extracellular $CaCl_2$.

Figure 32:
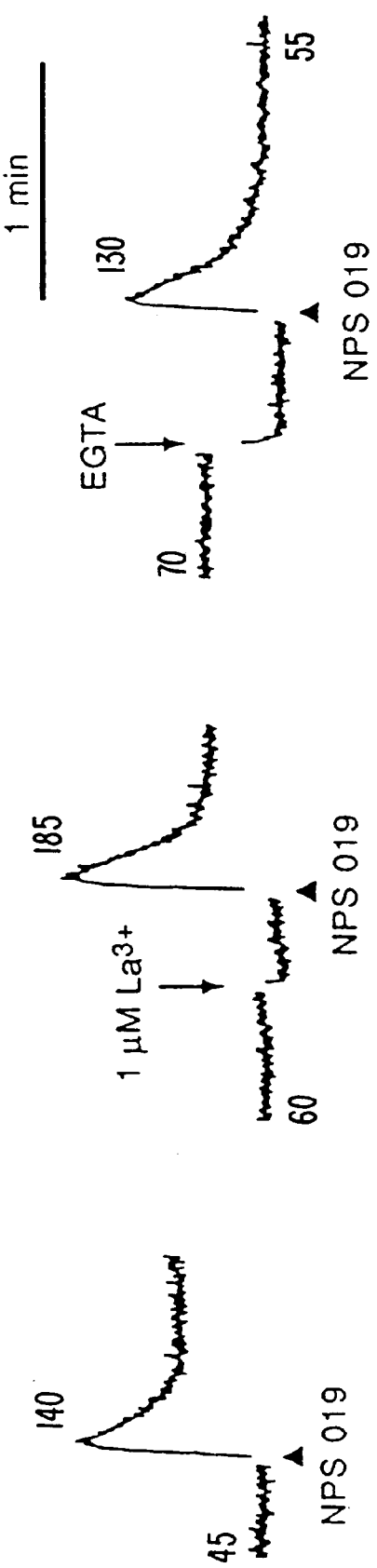

FIG. 32 is a graphical representation showing the mobilization of intracellular $Ca^{2+}$ in C-cells evoked by NPS 019 (see FIG. 1a). rMTC 6–23 cells were loaded with fura-2 and bathed in buffer containing 0.5 mM $[Ca^{2+}]$. Where indicated, NPS 019 was added to a final concentration of 10 $\mu$M. Representative traces show that the transient increase in $[Ca^{2+}]_i$ elicited by NPS 019 is refractory to inhibition by $La^{3+}$ (middle trace) and persists in the absence of extracellular $Ca^{2+}$ (right trace, 1 mM EGTA).

Figure 33:
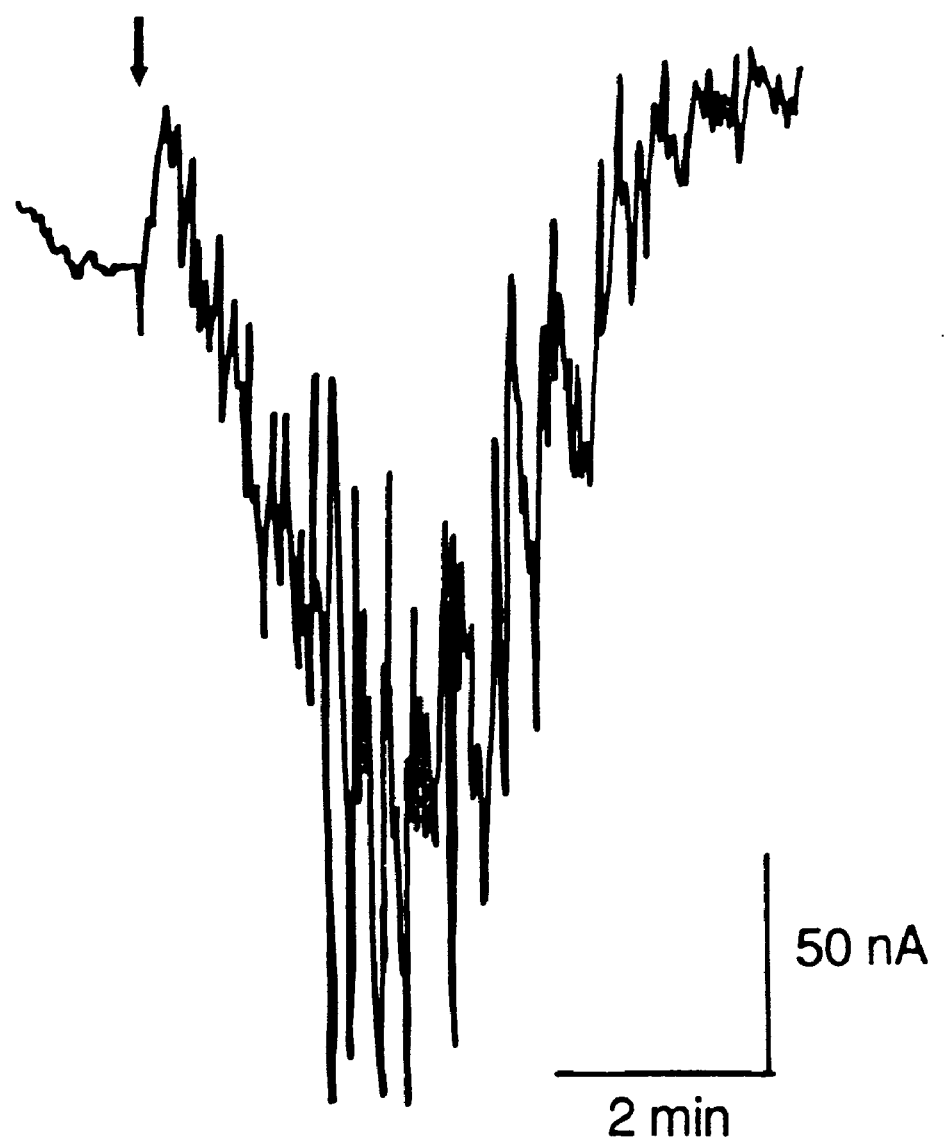

FIG. 33 is a graphical representation showing that fendiline (shown in the figure as NPS 456) evokes oscillatory increases in $Cl^-$ current in Xenopus oocytes which have been injected with 50 ng bovine parathyroid cell poly(A)$^+$-mRNA.

Figure 34:
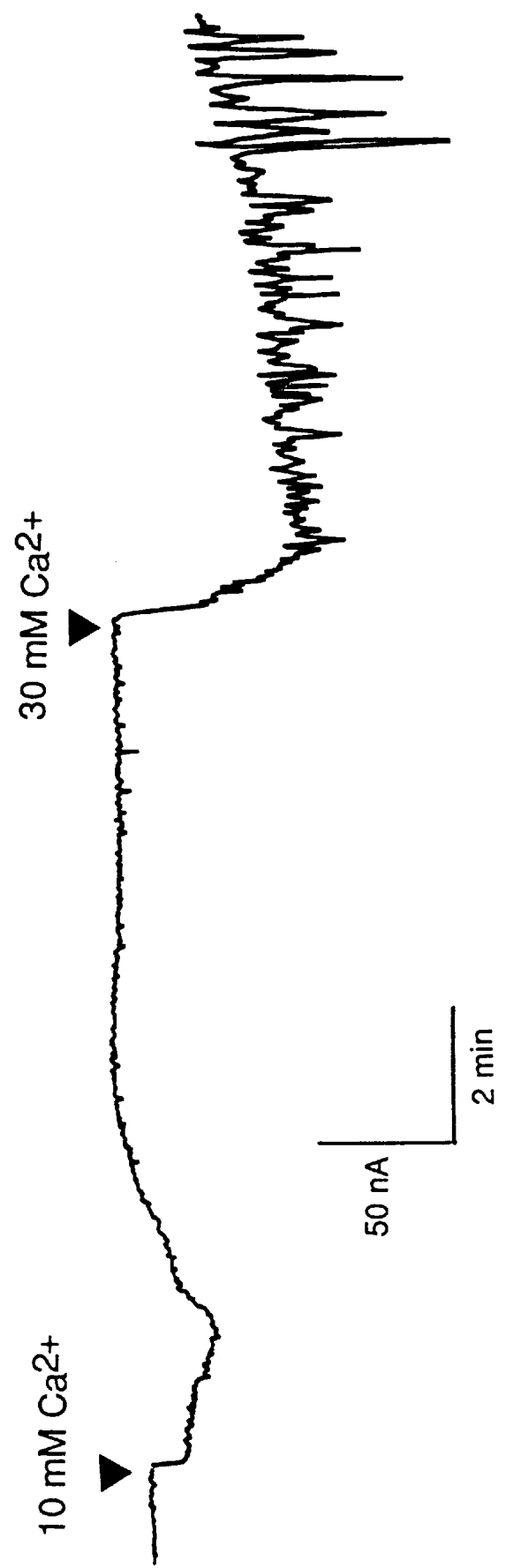

FIG. 34 is a graphical representation showing that extracellular $Ca^{2+}$ evokes oscillatory increases in $Cl^-$ current in

*Xenopus oocytes* which have been injected with human osteoclast mRNA. The oocyte was tested for responsivity to extracellular $Ca^{2+}$ three days after injection of 50 ng of total poly(A)$^+$-mRNA.

Figure 35:
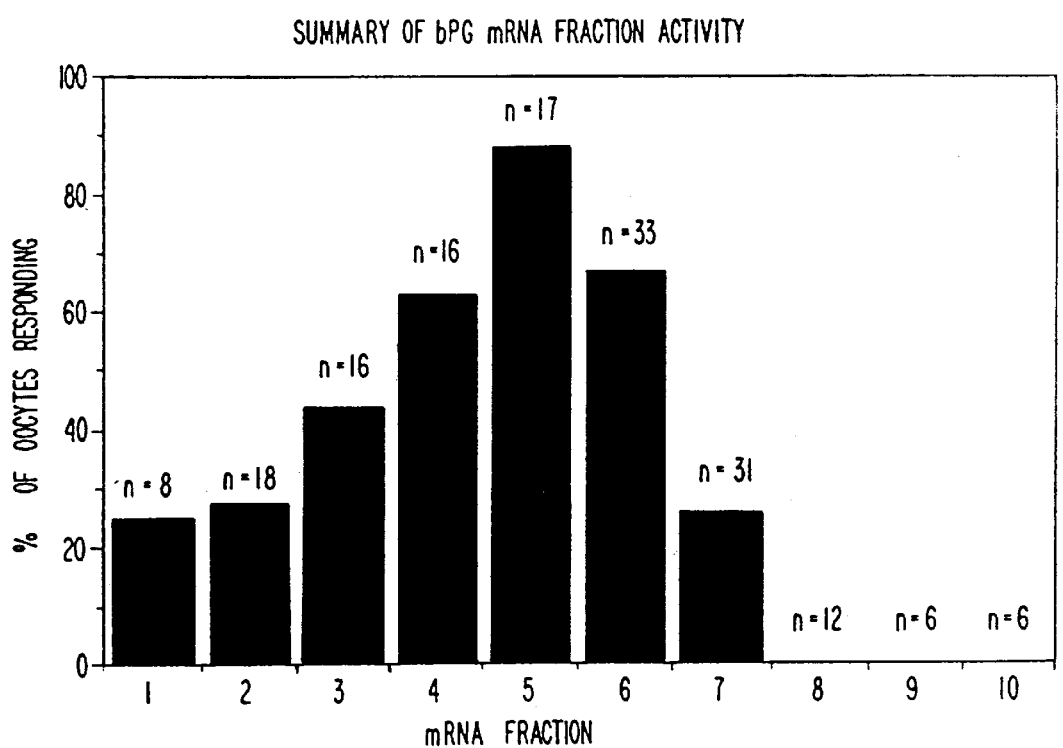

FIG. 35 is a graphical representation showing that the parathyroid cell calcium receptor is encoded by mRNA in a size range of 2.5–3.5 kb. Bovine parathyroid cell poly(A)$^+$-mRNA was size fractionated on glycerol gradients and pooled into ten fractions. Each fraction was injected (50 ng/fraction) separately into *Xenopus oocytes*. After three days, the oocytes were examined for their ability to respond to neomycin B (10 mM) with oscillatory increases in the Cl$^-$ current.

Figure 36A:
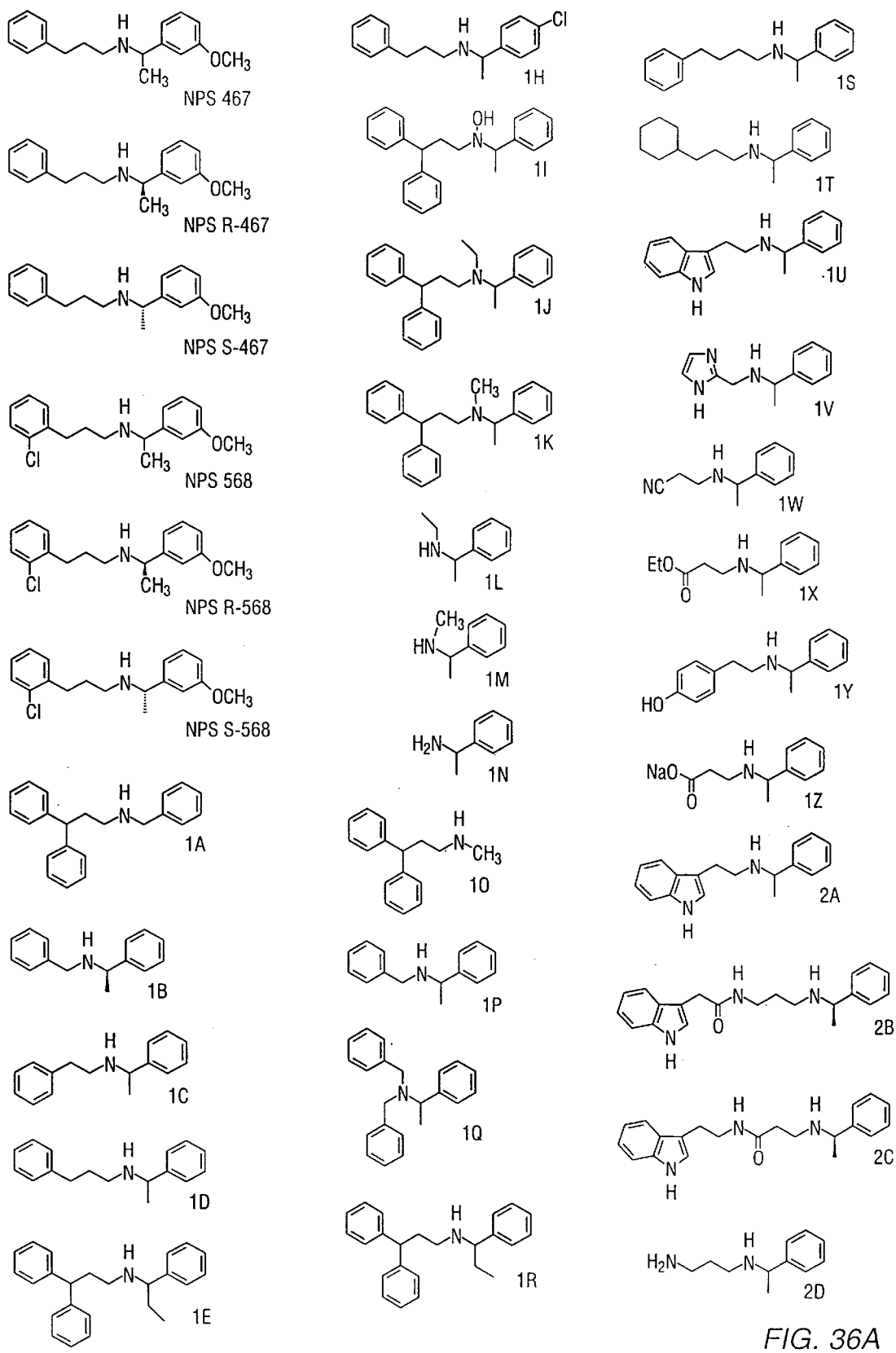
Figure 36B:
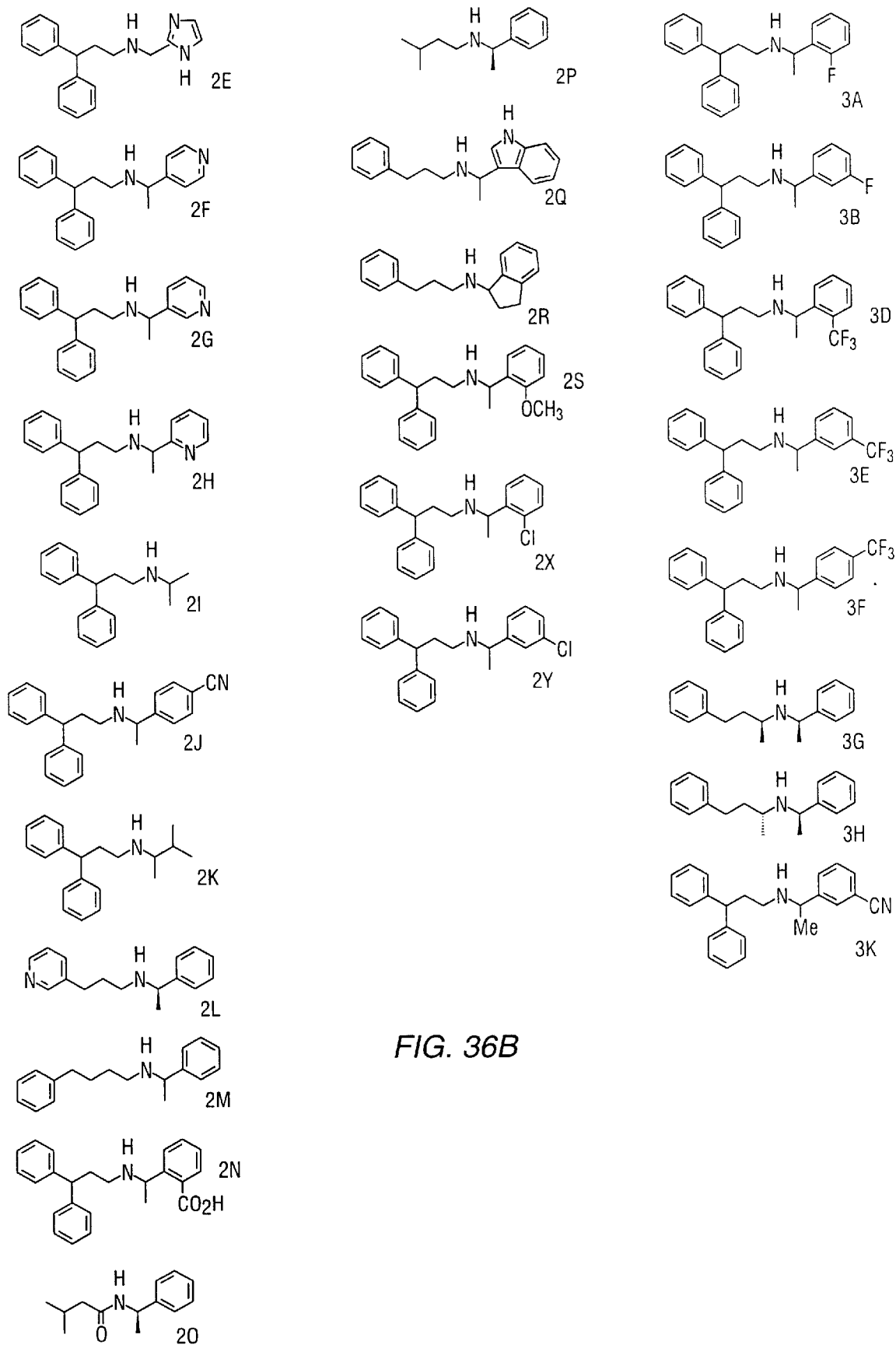
Figure 36C:
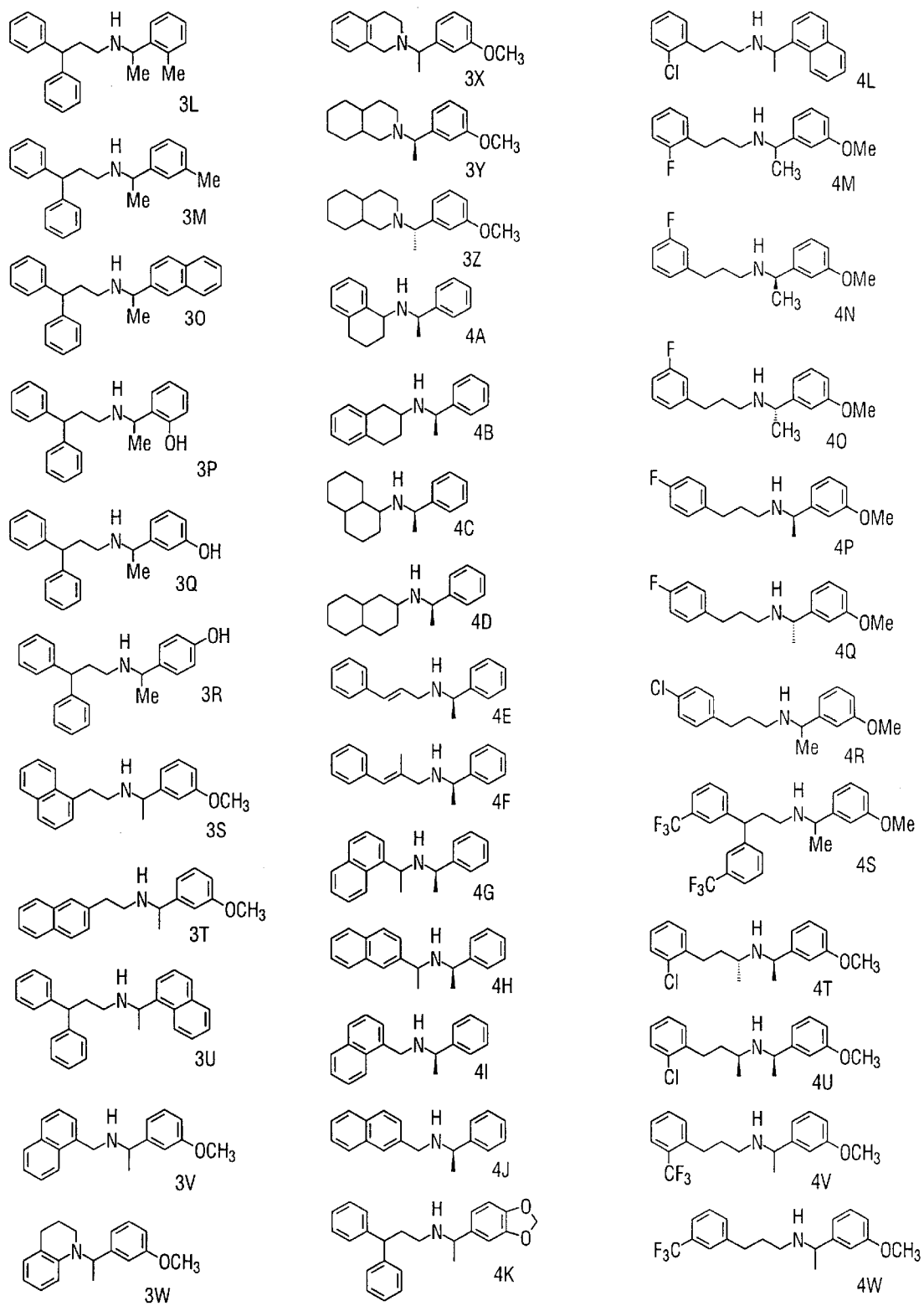
Figure 36D:
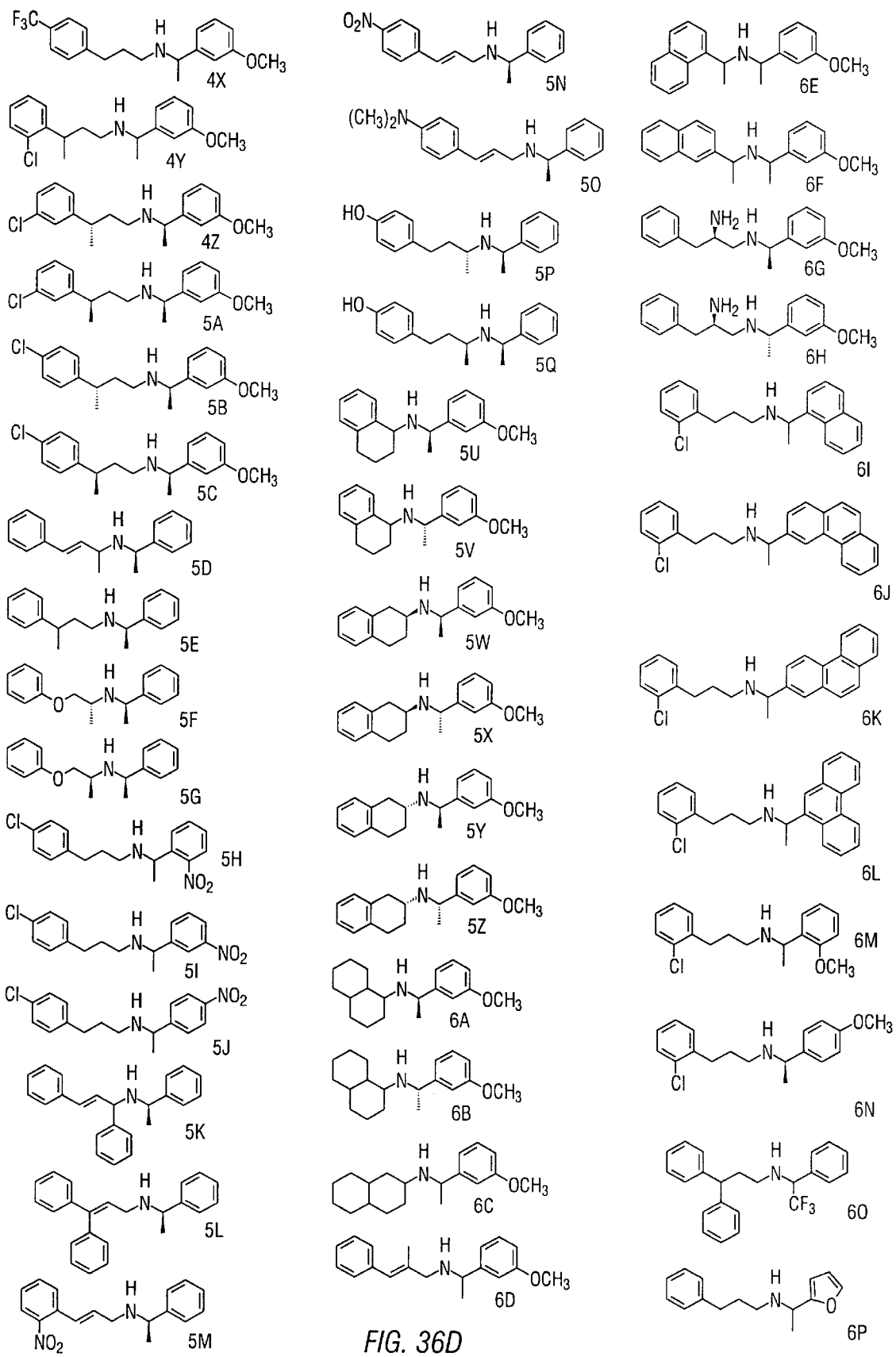
Figure 36E:
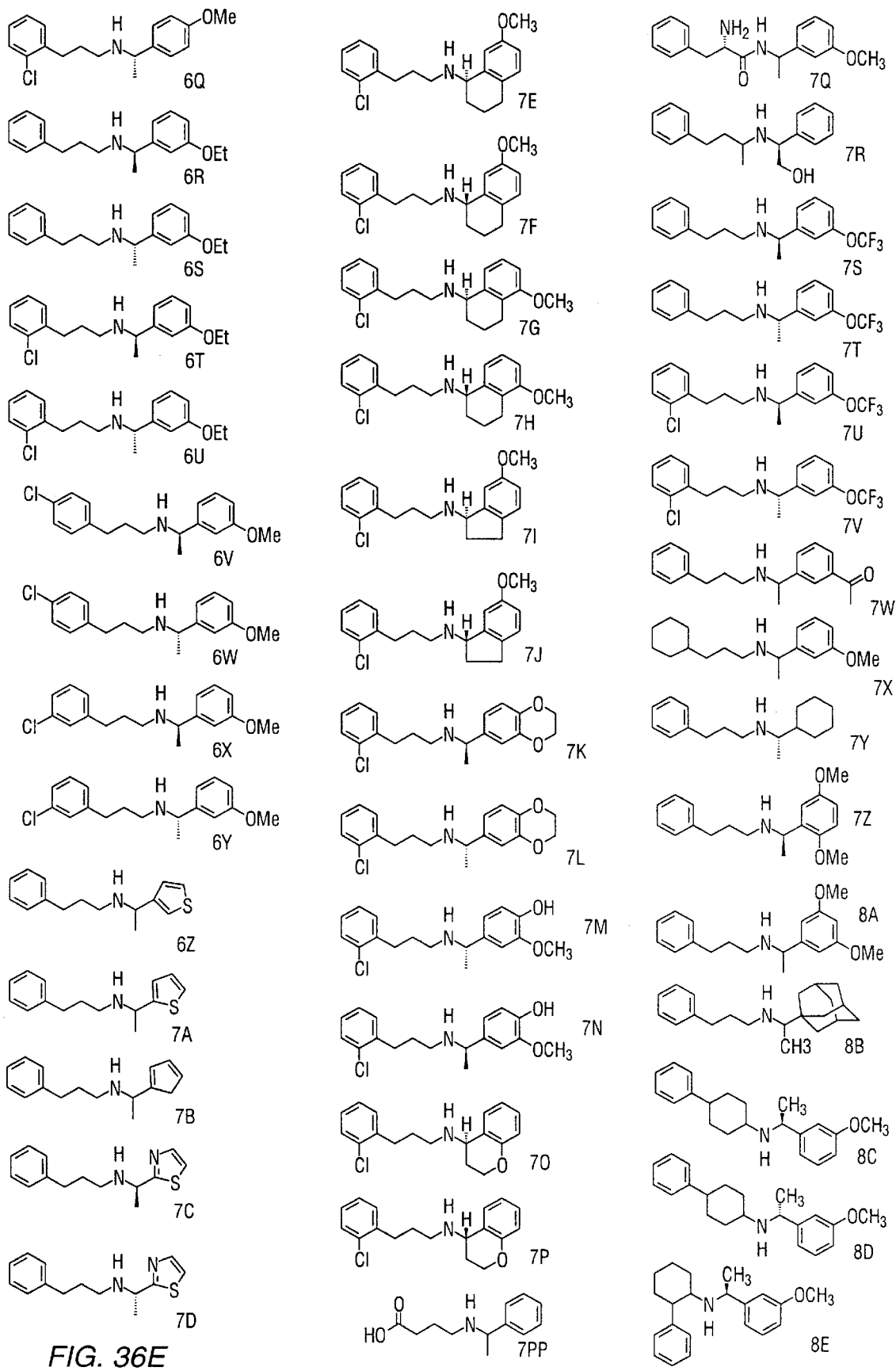
Figure 36F:
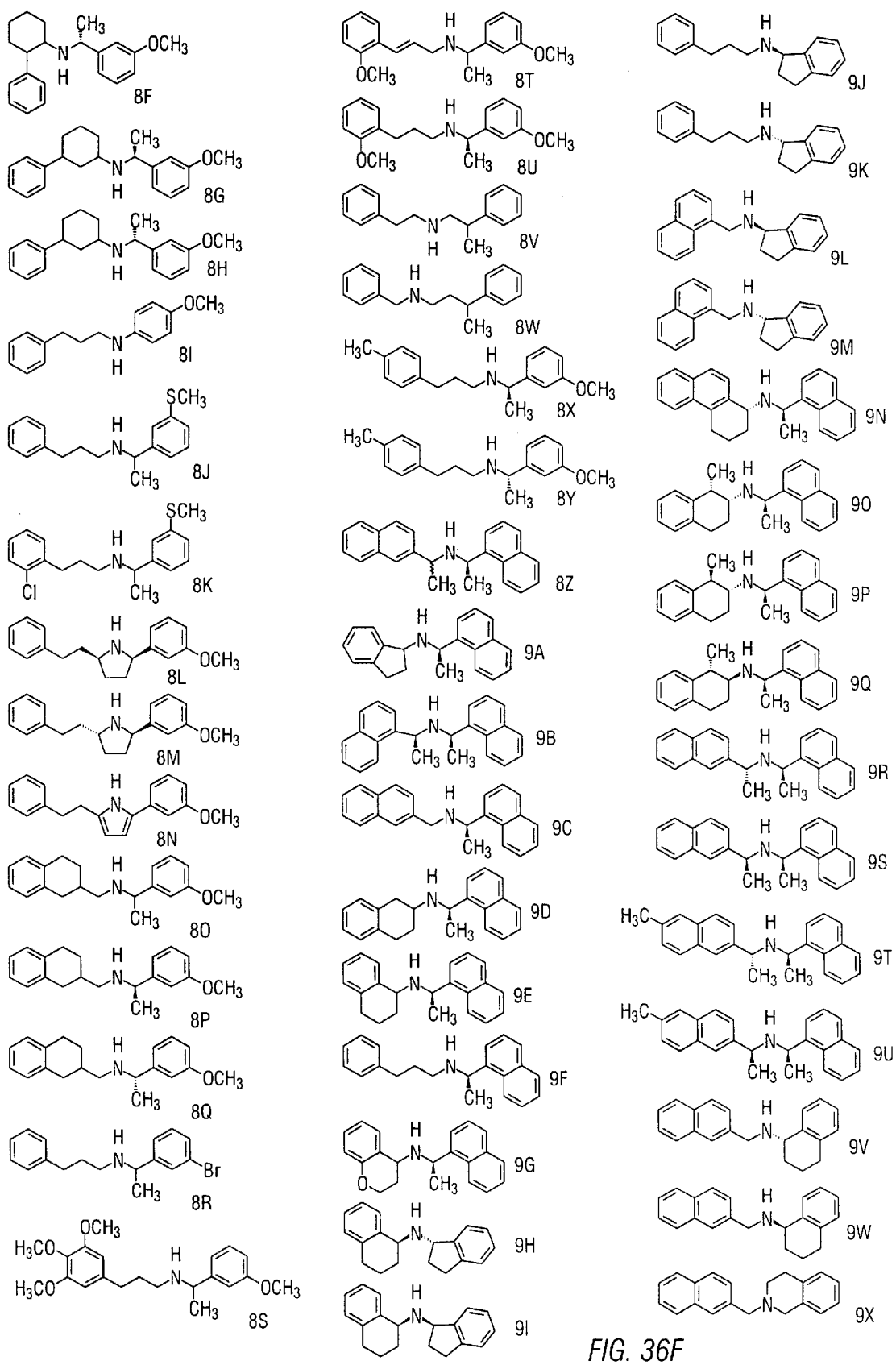
Figure 36G:
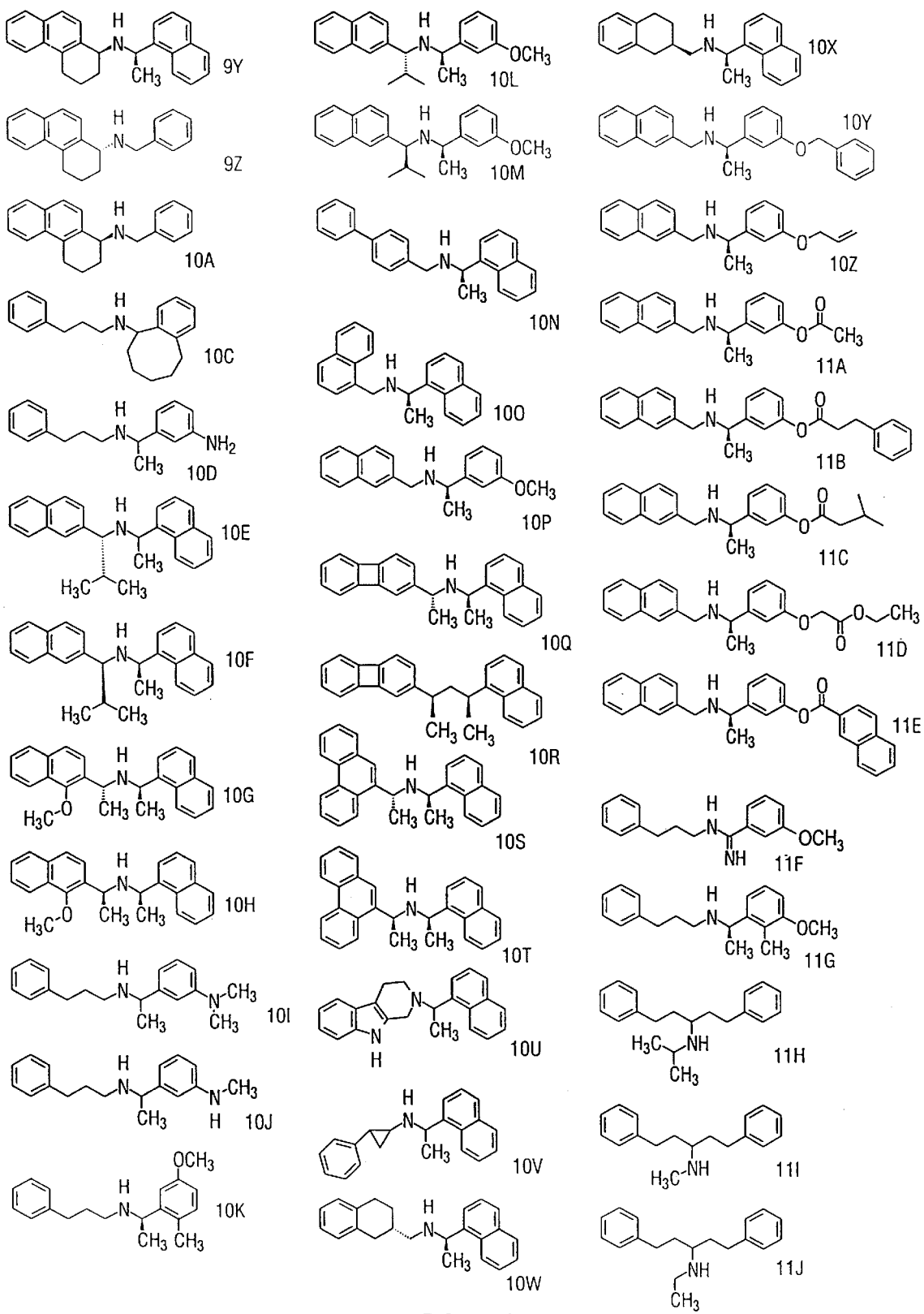
Figure 36H:
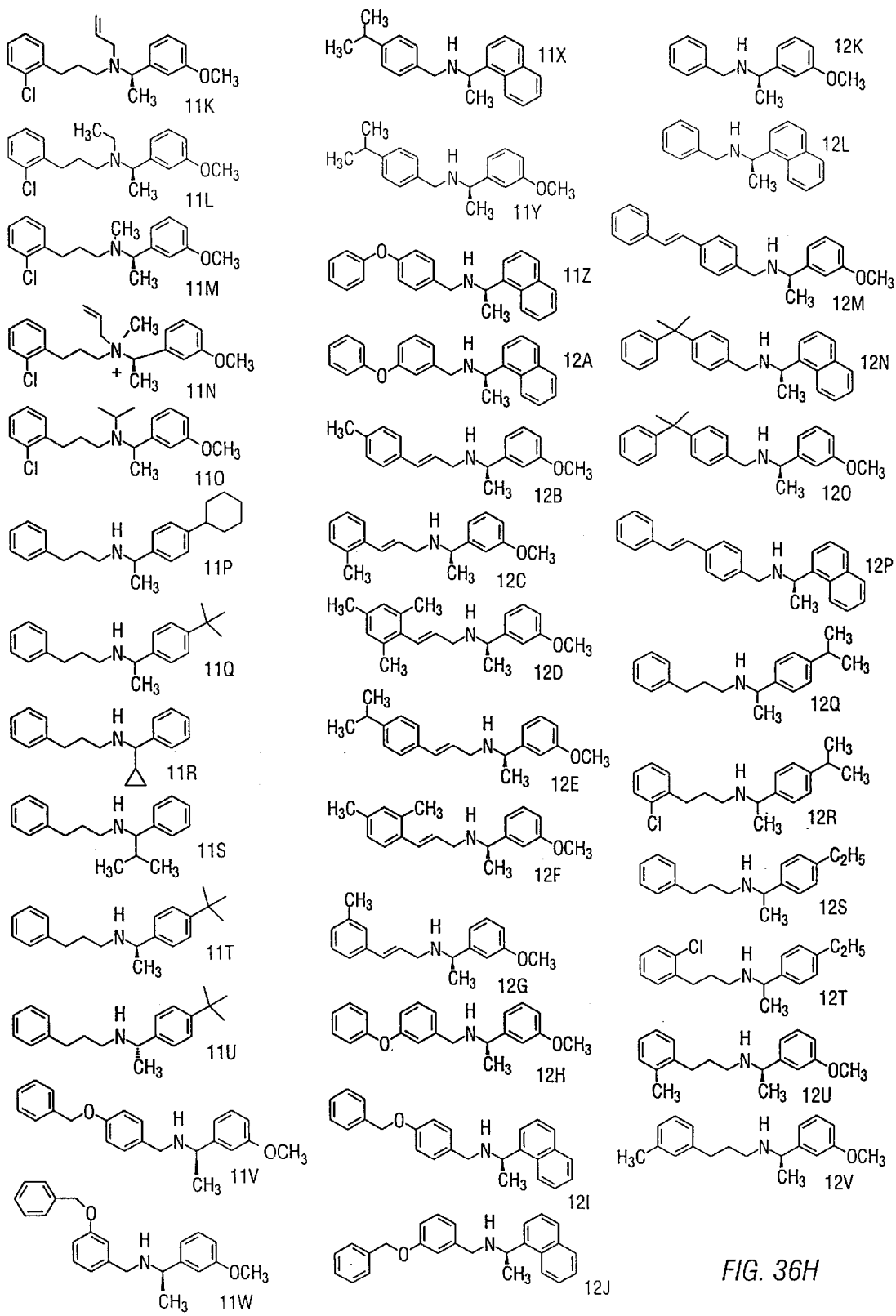
Figure 36I:
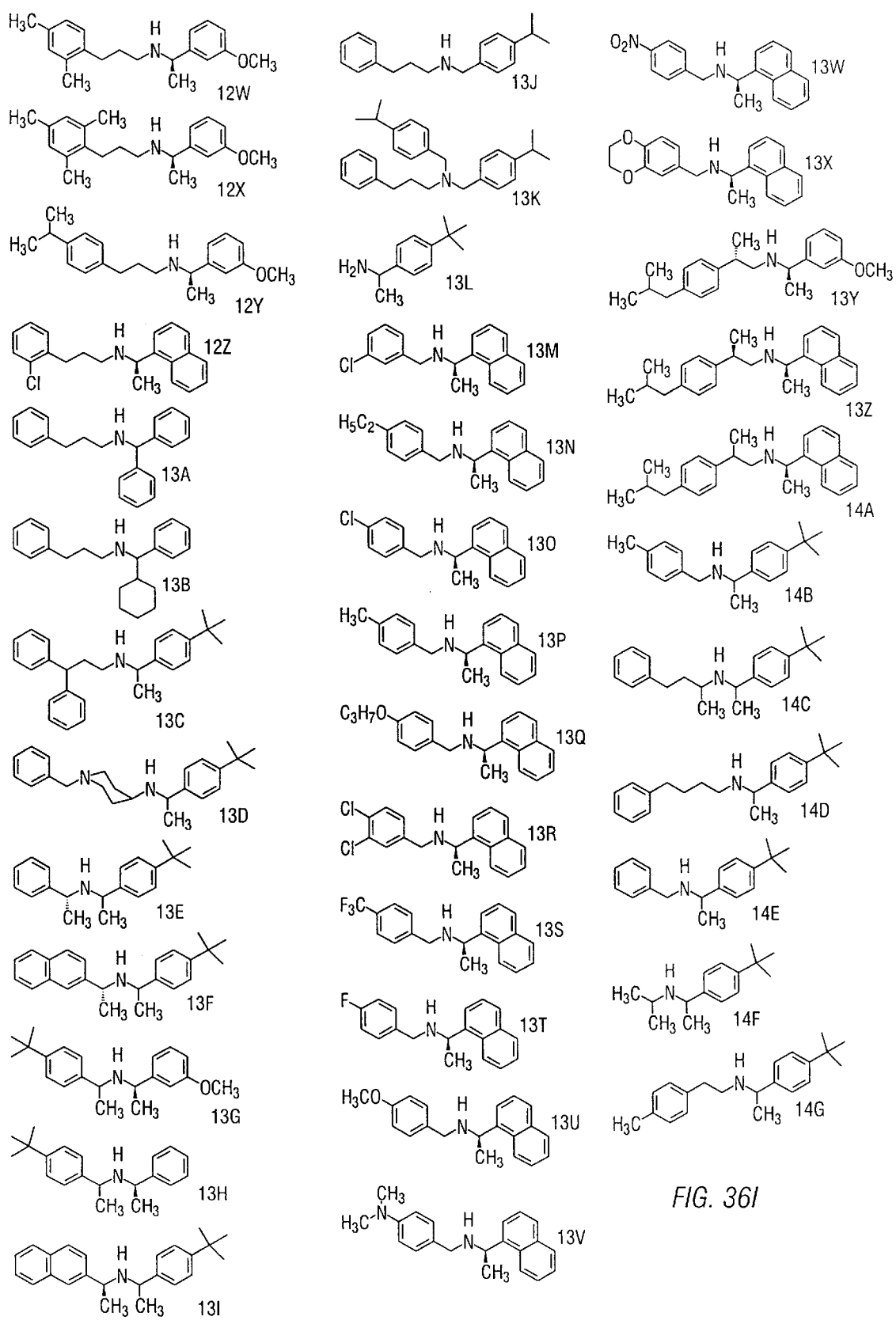
Figure 36J:
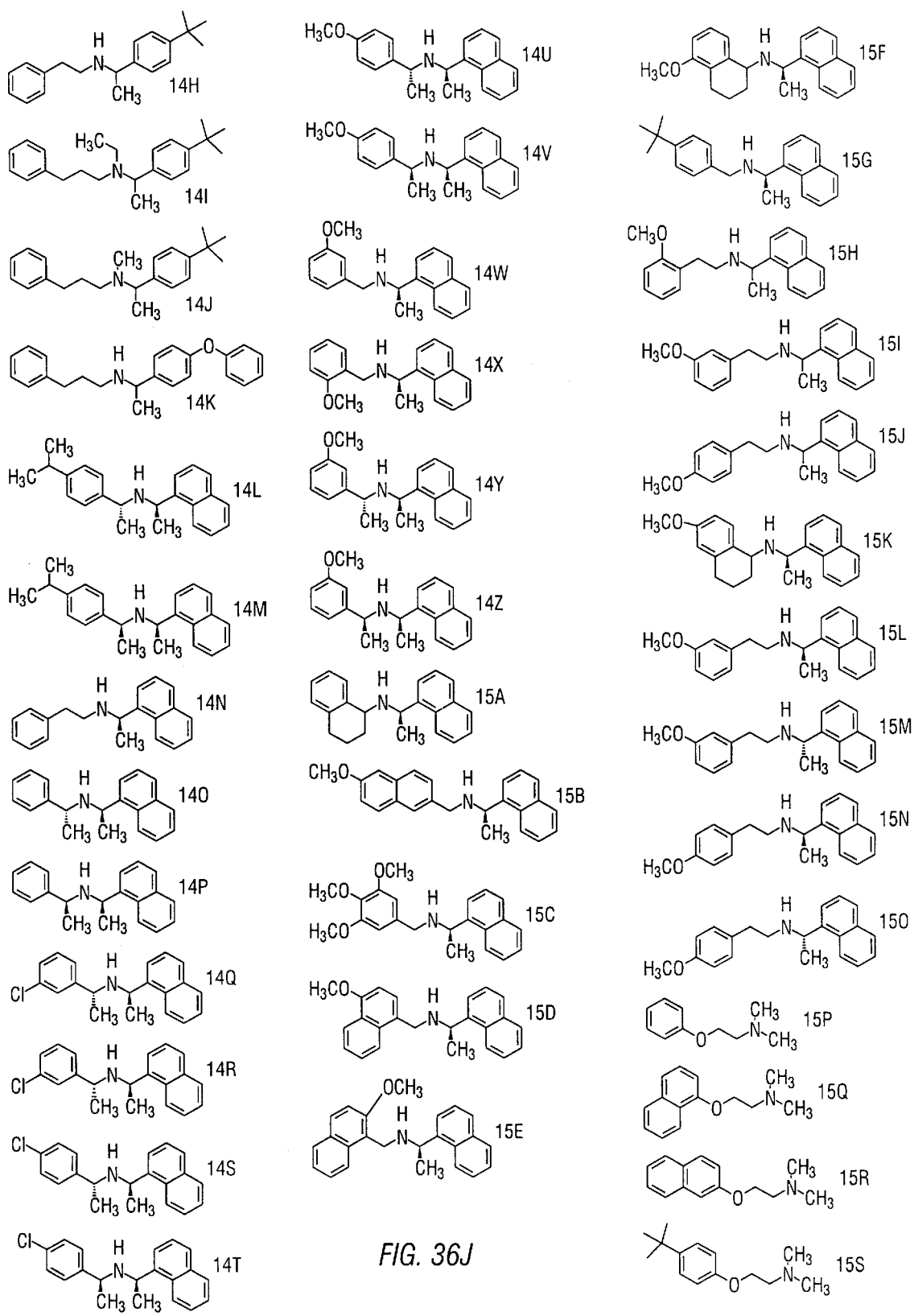
Figure 36K:
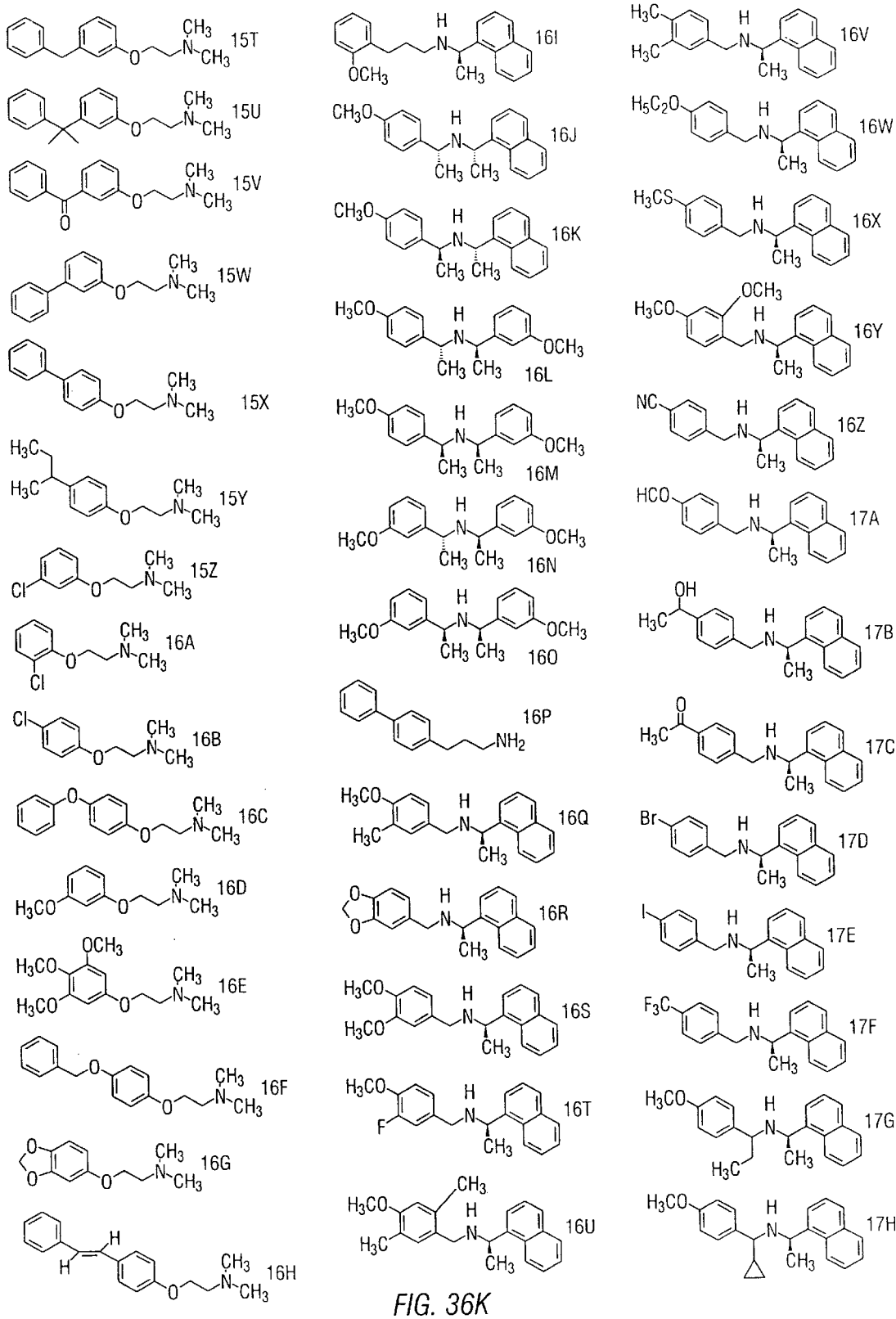
Figure 36L:
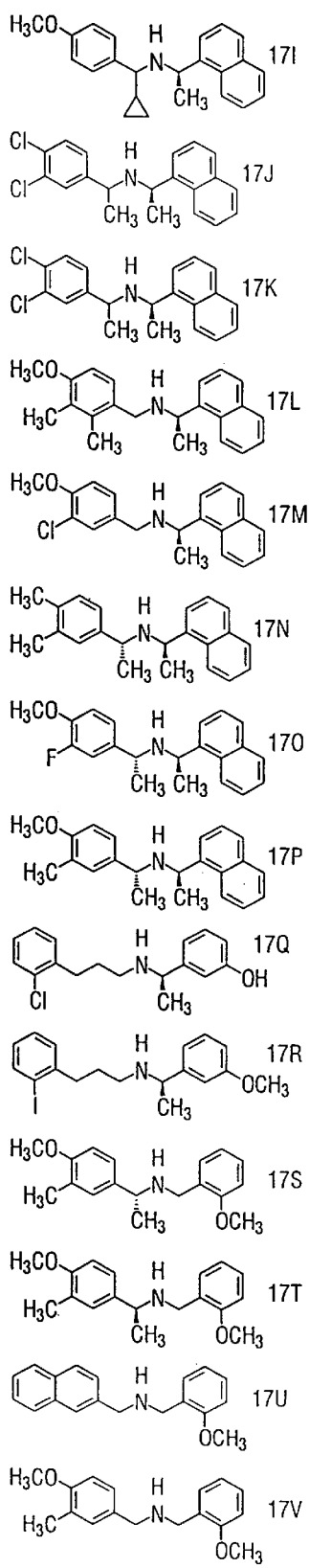
Figure 36M:
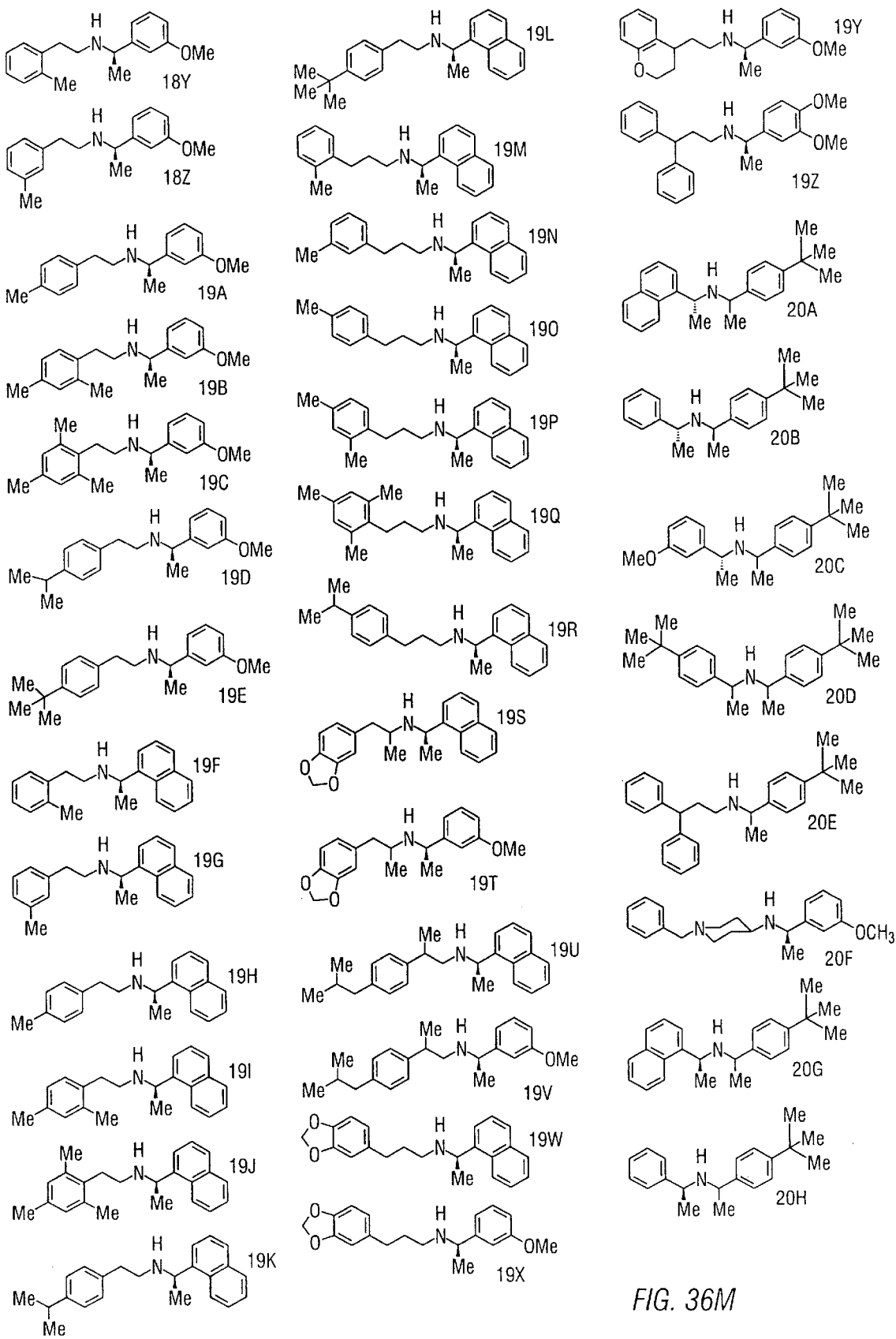
Figure 36N:
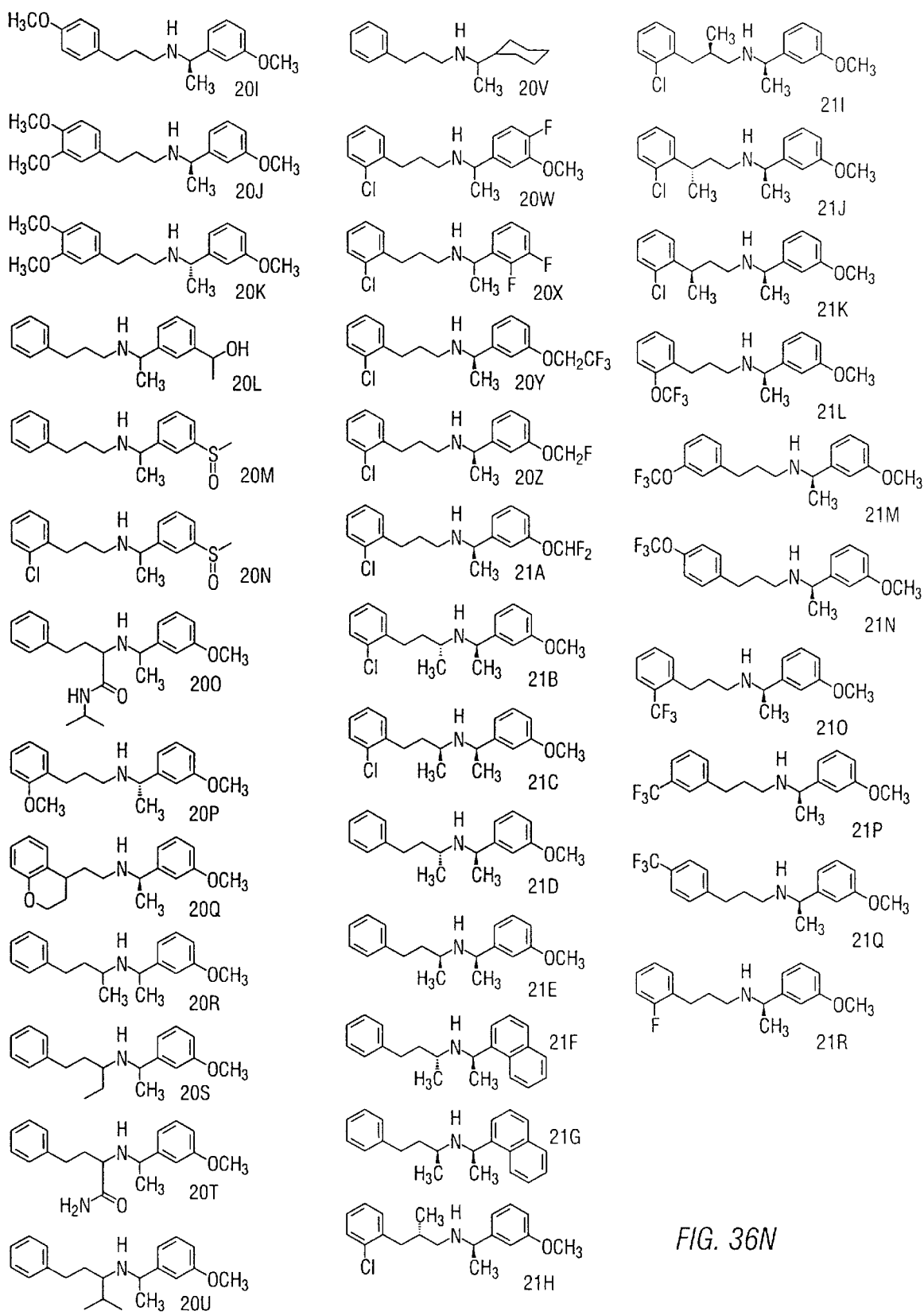

FIGS. 36a–36n shows the chemical structures of molecules based on the lead structure diphenylpropyl-α-phenethylamine (fendeline), illustrating a family of molecules which were synthesized and screened to find the useful molecules of the invention.

Figures 37A, 37B:
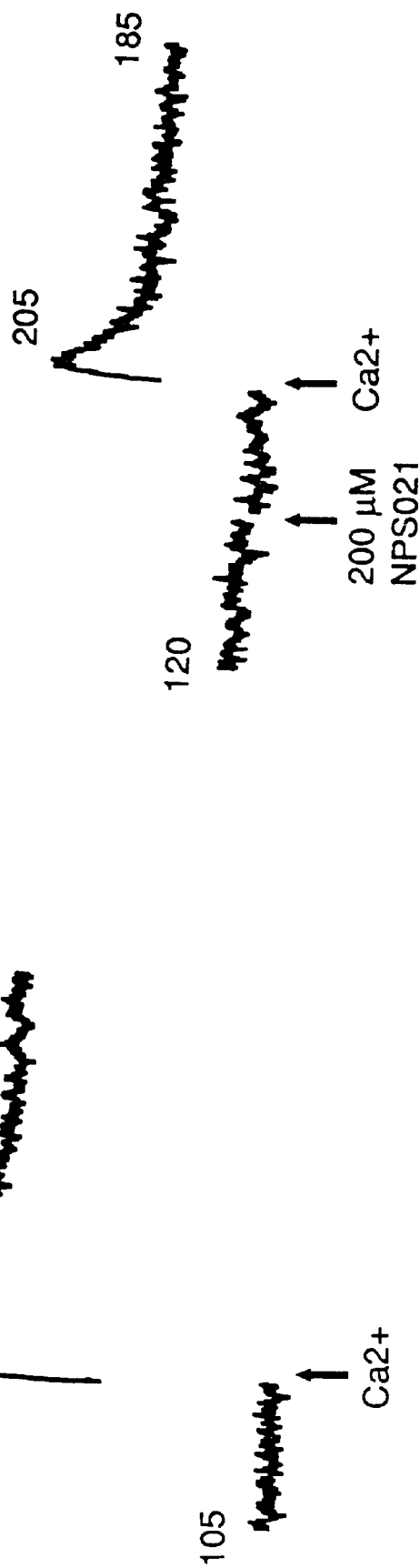

FIGS. 37a and 37b are graphical representations showing that NPS 021 is a calcilytic compound that blocks the effects of extracellular $Ca^{2+}$ on $[Ca^{2+}]_i$ in bovine parathyroid cells. Cells were initially bathed in buffer containing 0.5 mM $CaCl_2$ and, where indicated, the $[Ca^{2+}]$ was increased to a final of 2 mM (left trace). The addition of NPS 021 (200 $\mu$M) caused no change in $[Ca^{2+}]_i$, but inhibited the increase in $[Ca^{2+}]_i$ elicited by extracellular $Ca^{2+}$ (right trace).

Figure 38:
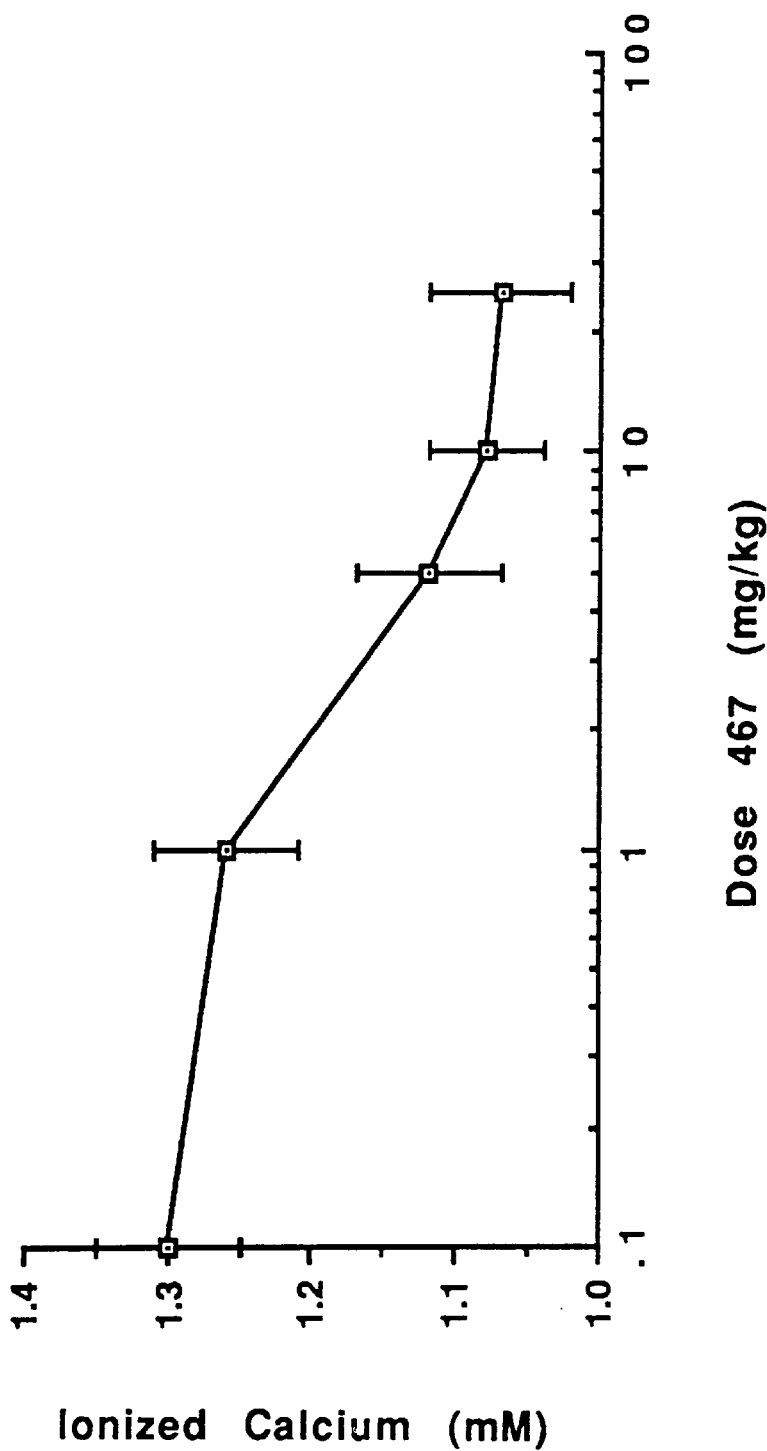

FIG. 38 is a graph showing the in vivo serum $Ca^{2+}$ response to NPS R,S-467 in a test animal (a rat). The dosage is provided as mg of drug per kg weight of the test animal.

Figure 39:
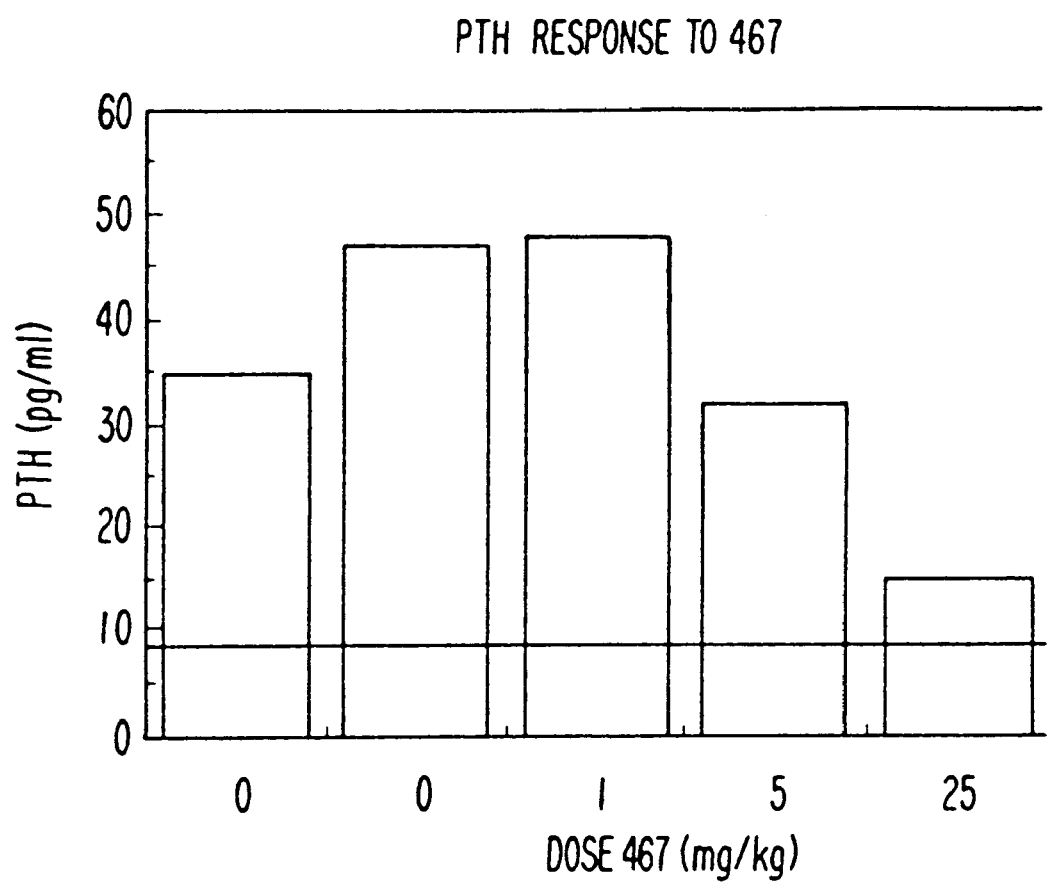

FIG. 39 is a graph showing the in vivo PTH response to NPS R,S-467 in a test animal (a rat). The dosage is provided as mg of drug per kg weight of the test animal.

Figure 40:
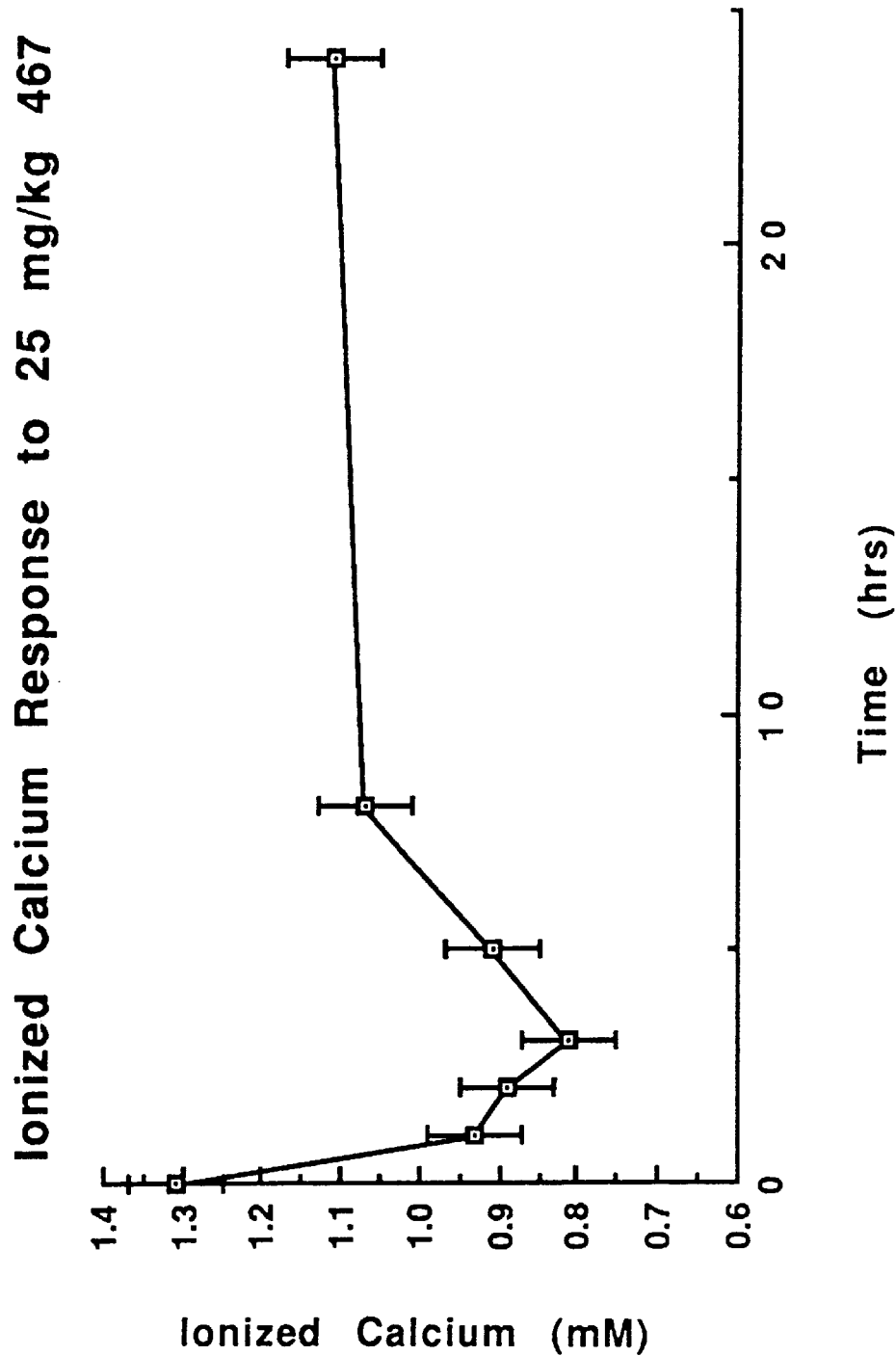

FIG. 40 is a graph showing in vivo serum $Ca^{2+}$ response over the course of 24 hours to 25 mg/kg NPS R,S-467 in a test animal (a rat). The dosage is provided as mg of drug per kg weight of the test animal.

Figure 41:
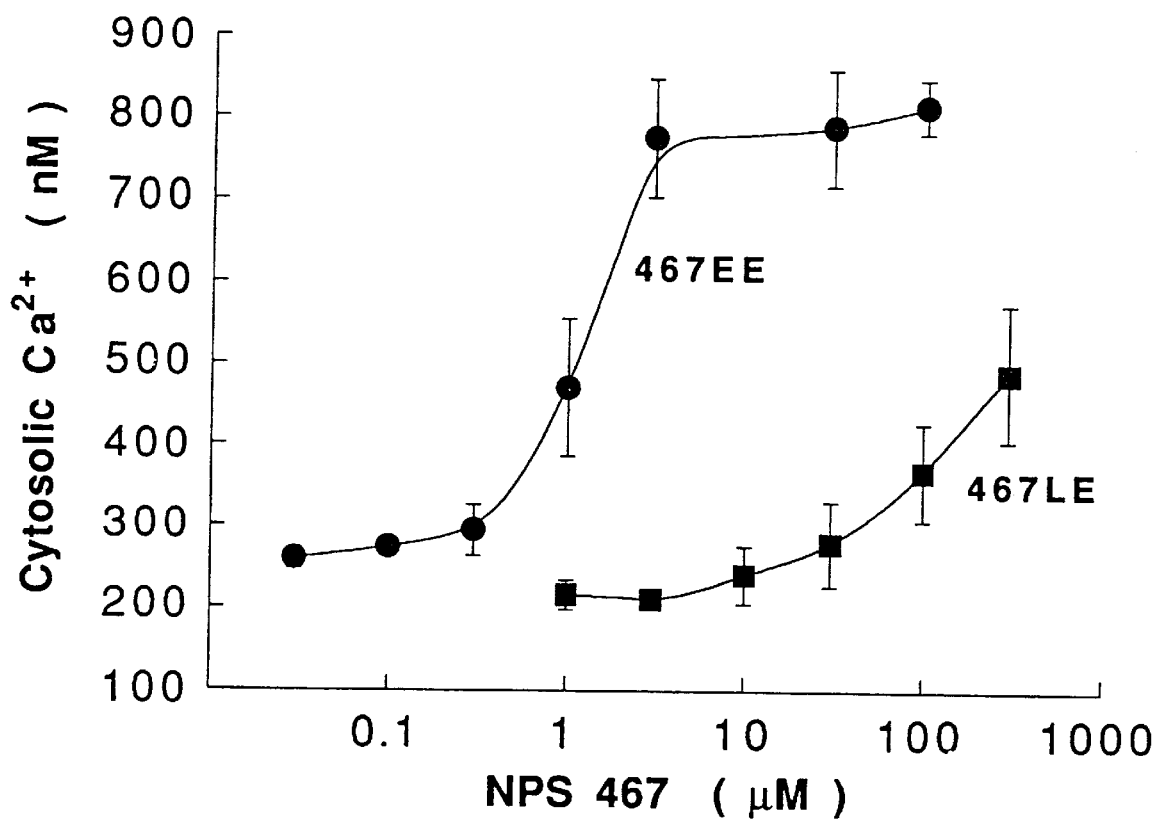

FIG. 41 is a graph showing the in vitro response of $[Ca^{2+}]_i$ in cultured bovine parathyroid cells to different enantiomers of NPS 467. EE refers to the R enantiomer. LE and to the S enantiomer.

Figure 42:
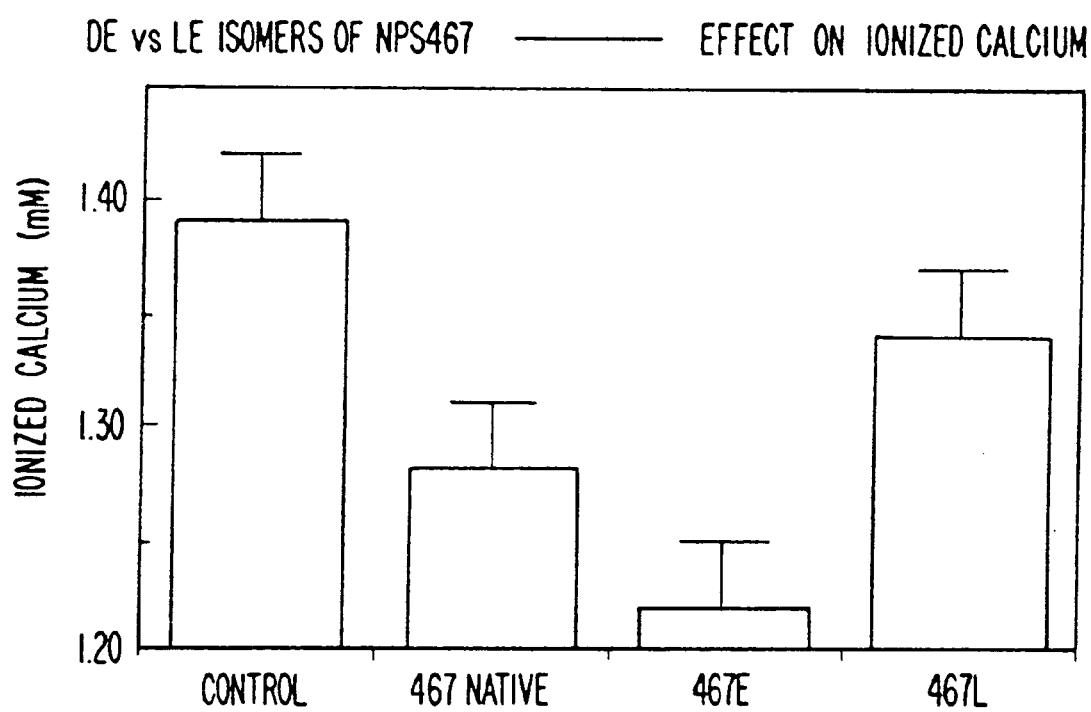

FIG. 42 is a graph showing the in vivo response of ionized serum $Ca^{2+}$ in rats to different enantiomers of NPS 467. DE and E refer to the R enantiomer. LE and L refer to the S enantiomer. Native refers to the racemic mixture.

Figure 43A:
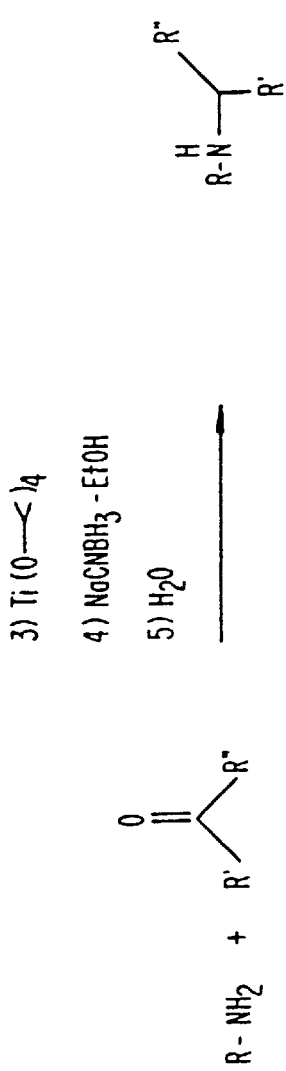
Figure 43B:
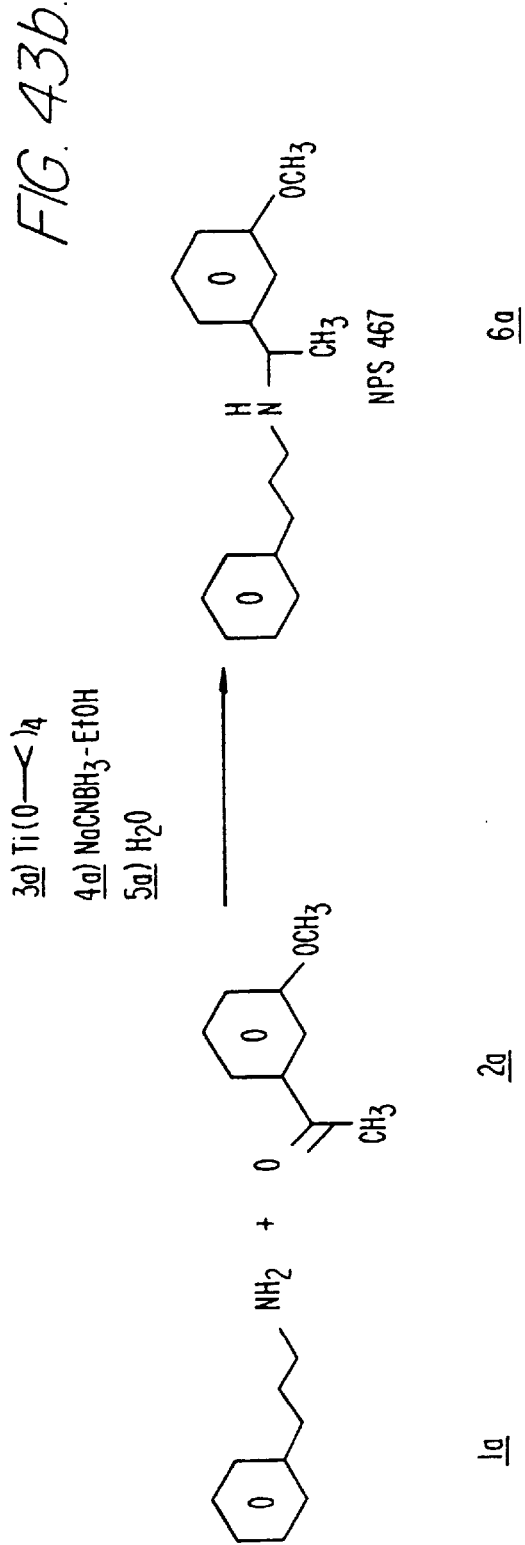

FIG. 43a depicts a reaction scheme for the preparation of fendiline or fendiline analogues or derivatives depicted in FIG. 36. FIG. 43b depicts a reaction scheme for the synthesis of NPS 467.

Figure 44:
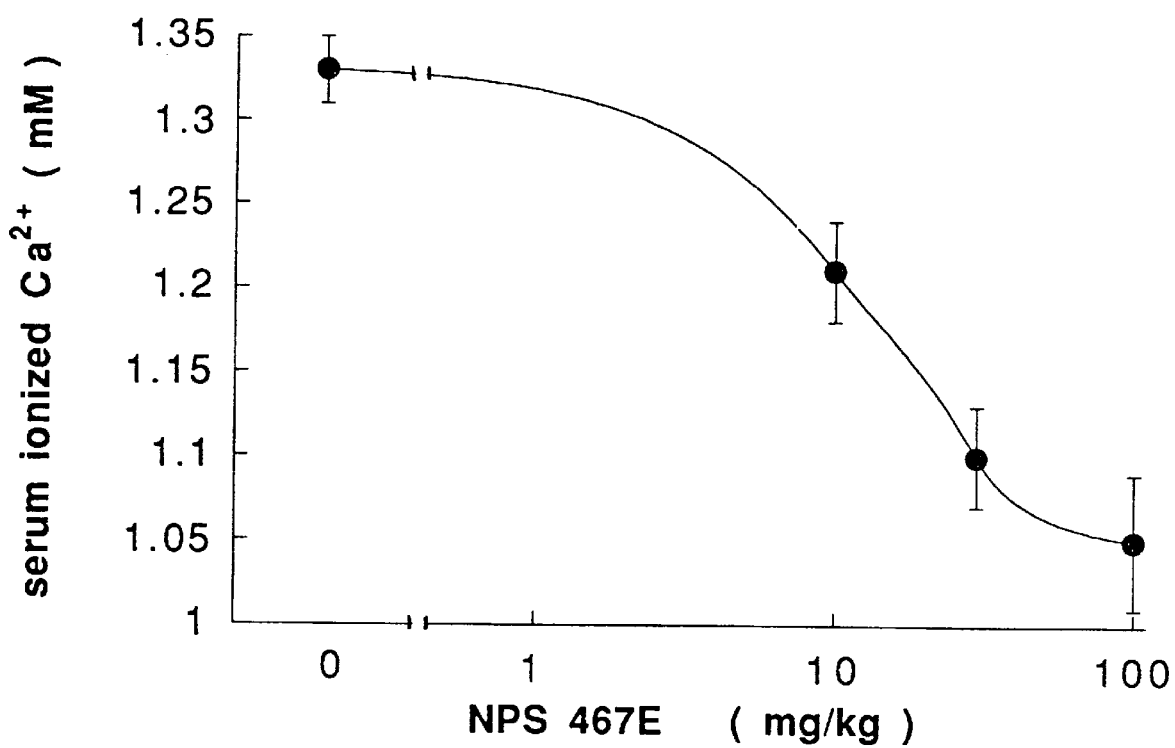

FIG. 44 depicts a dose-response curve showing that NPS R-467 (NPS-467E) lowers serum ionized calcium in rats when administered orally.

Figure 45:
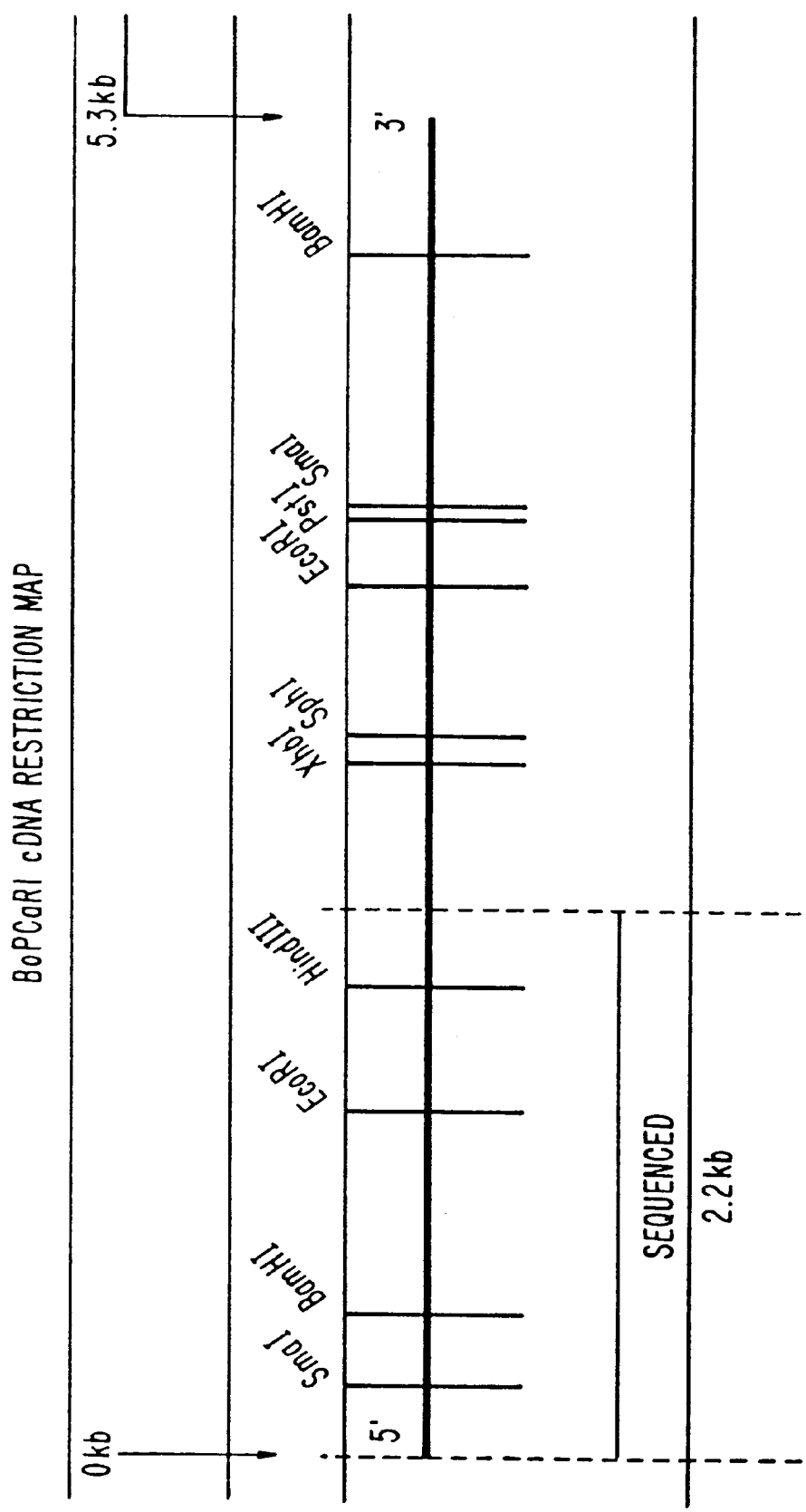

FIG. 45 is a restriction map of BoPCaR 1.

Figure 46:
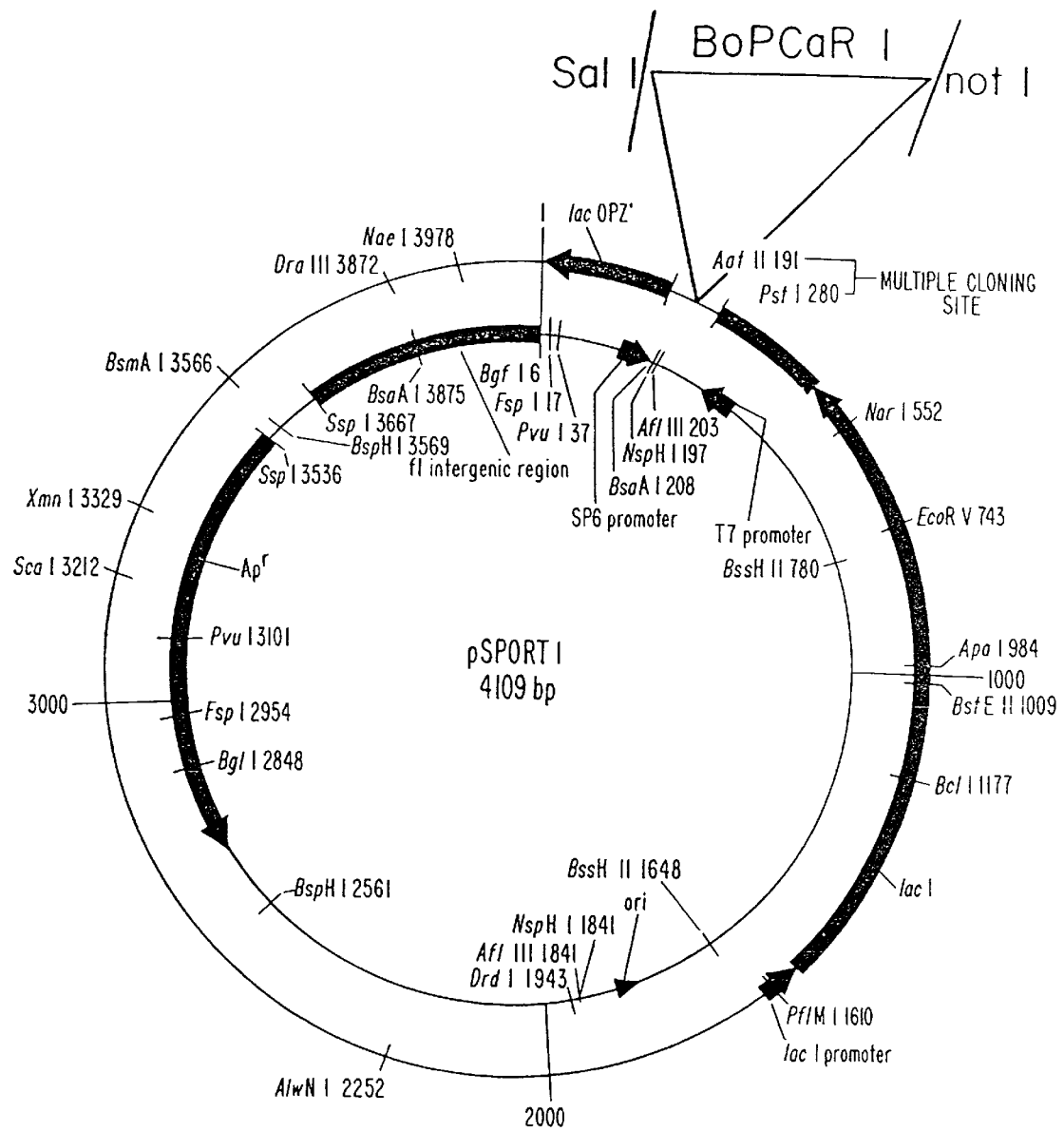

FIG. 46 is a restriction map of the plasmid containing BoPCaR 1, deposited with the ATCC under accession number 75416.

FIGS. 47a–d show the nucleotide sequence corresponding to the ~5 Kb fragment of BoPCaR 1 and the encoded-for amino acid sequence (SEQ. ID. NO. 1).

FIGS. 48a–48d show the nucleotide sequence corresponding to the ~5 Kb insert from pHuPCaR 5.2 and the encoded-for amino acid sequence (SEQ. ID. NO. 2).

FIGS. 49a–49c show the nucleotide sequence corresponding to the ~4 Kb insert from pHuCaR 4.0 and the encoded-for amino acid sequence (SEQ. ID. NO. 3).

FIGS. 50a–50c show the nucleotide sequence corresponding to the ~4 Kb insert of pRakCaR 3A and the encoded-for amino acid sequence (SEQ. ID. NO. 4).

Figure 51:
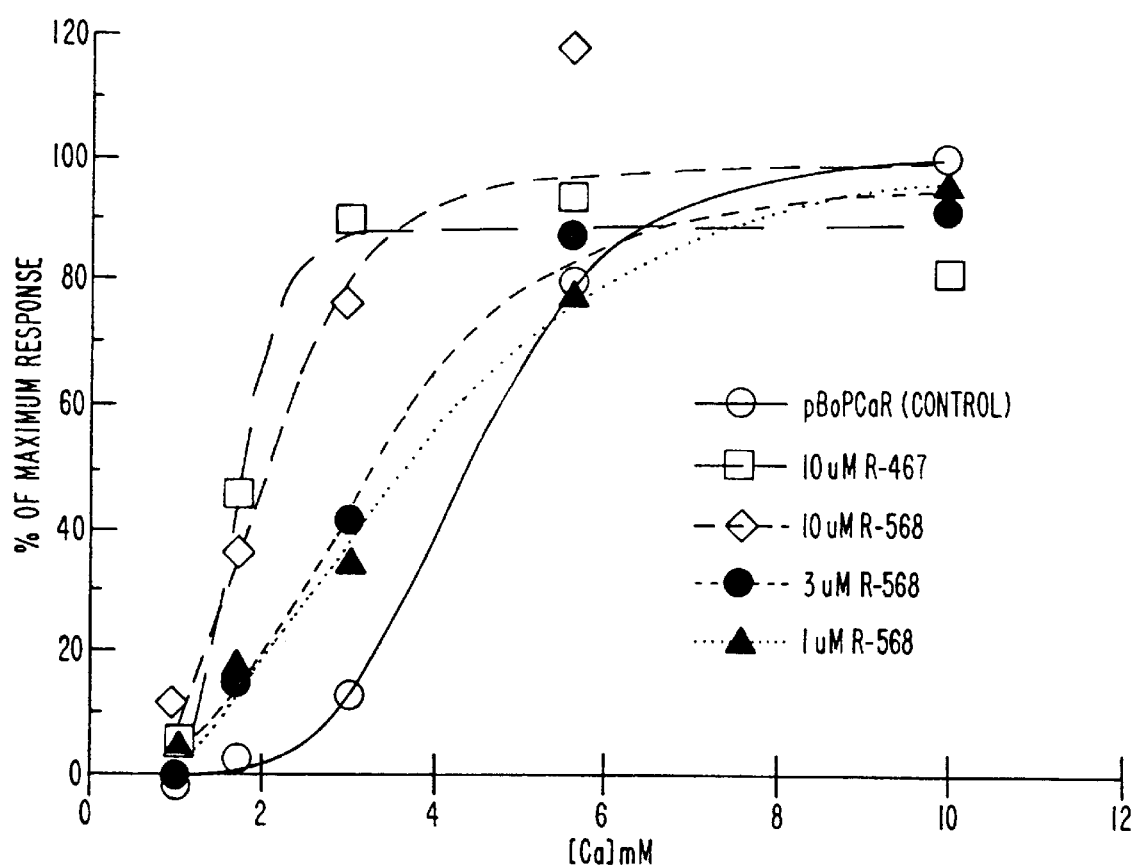

FIG. 51 depicts the ability of NPS R-467 and NPS R-568 to potentiate the response of a calcium receptor to submaximal concentrations of extracellular $Ca^{2+}$, and shift the extracellular $Ca^{2+}$ concentration-response curve to the left.

Figure 52:
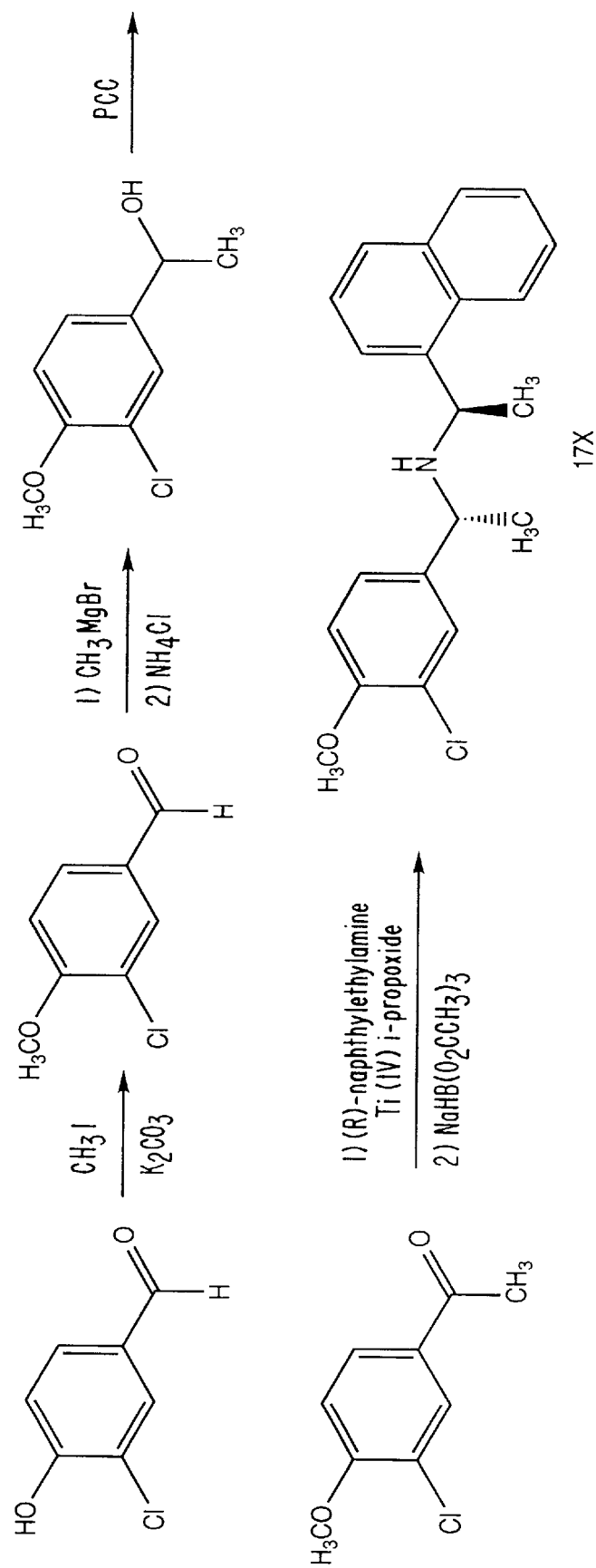

FIG. 52 depicts a reaction scheme for compound 17X.

DESCRIPTION OF THE PREFERRED EMBODIMENTS

The present invention features: (1) molecules which can modulate one or more inorganic ion receptor activities, preferably the molecule can mimic or block an effect of an extracellular ion on a cell having an inorganic ion receptor, more preferably the extracellular ion is $Ca^{2+}$ and the effect is on a cell having a calcium receptor; (2) inorganic ion receptor proteins and fragments thereof, preferably calcium receptor proteins and fragments thereof; (3) nucleic acids encoding inorganic ion receptor proteins and fragments thereof, preferably calcium receptor proteins and fragments thereof; (4) antibodies and fragments thereof, targeted to inorganic ion receptor proteins, preferably calcium receptor protein; and (5) uses of such molecules, proteins, nucleic acids and antibodies.

Applicant is the first to demonstrate a $Ca^{2+}$ receptor protein in parathyroid cells, and to pharmacologically differentiate such $Ca^{2+}$ receptors in other cells, such as C-cells and osteoclasts. Applicant is also the first to describe methods by which molecules active at these $Ca^{2+}$ receptors can be identified and used as lead molecules in the discovery, development, design, modification and/or construction of useful calcimimetics or calcilytics which are active at $Ca^{2+}$ receptors.

Publications concerned with the calcium activity, calcium receptor and/or calcium receptor modulating compounds include the following: Brown et al., *Nature* 366: 574, 1993; Nemeth et al., PCT/US93/01642, International Publication Number WO 94/18959; Nemeth et al., PCT/US92/07175, International Publication Number WO 93/04373; Shoback and Chen, *J. Bone Mineral Res.* 9: 293 (1994); and Racke et al., *FEBS Lett.* 333: 132, (1993). These publications are not admitted to be prior art to the claimed invention.

I. CALCIUM RECEPTOR-MODULATING AGENTS

Calcium receptor-modulating agents can mimic or block an effect of extracellular $Ca^{2+}$ on cell having a calcium receptor. Generic and specific structures of calcium receptor-modulating agents are provided in the Summary supra, and in FIGS. 1 and 36. Preferred calcium receptor-modulating agents are calcimimetics and calcilytics. The ability of molecules to-mimic or block an activity of $Ca^{2+}$ at calcium receptors can be determined using procedures described below. The same type of procedures can be used to measure the ability of a molecule to mimic or block an activity of other inorganic ions at their respective inorganic ion receptors by assaying for specific inorganic ion receptor activities. Examples of these procedures, and other examples provided herein, are not limiting, in the invention, but merely illustrate methods which are readily used or adapted by those of ordinary skill in the art.

A. Calcium Receptor

Calcium receptors are present on different cell types and can have different activities in different cell types. The pharmacological effects of the following cells, in response to calcium, is consistent with the presence of a calcium receptor: parathyroid cell, bone osteoclast, juxtaglomerular kidney cell, proximal tubule kidney cell, distal tubule kidney cell, central nervous system cell, peripheral nervous system cell, cell of the thick ascending limb of Henle's loop and/or collecting duct, keratinocyte in the epidermis, parafollicular cell in the thyroid (C-cell), intestinal cell, trophoblast in the placenta, platelet, vascular smooth muscle cell, cardiac atrial cell, gastrin-secreting cell, glucagon-secreting cell, kidney mesangial cell, mammary cell, beta cell, fat/adipose cell, immune cell, GI tract cell, skin cell, adrenal cell, pituitary cell, hypothalamic cell and cell of the subfornical organ. In addition, the presence of calcium receptors on parathyroid cell, central nervous system cell, peripheral nervous system cell, cell of the thick ascending limb of Henle's loop and/or collecting duct in the kidney, parafollicular cell in the thyroid (C-cell), intestinal cell, GI tract cell, pituitary cell, hypothalamic cell and cell of the subfornical organ, has been confirmed by physical data.

The calcium receptor on these cell types may be different. It is also possible that a cell can have more than one type of calcium receptor. Comparison of calcium receptor activities and amino acid sequences from different cells indicate that distinct calcium receptor types exist. For example, calcium receptors can respond to a variety of di- and trivalent cations. The parathyroid calcium receptor responds to calcium and $Gd^{3+}$, while osteoclasts respond to divalent cations such as calcium, but do not respond to $Gd^{3+}$. Thus, the parathyroid calcium receptor is pharmacologically distinct from the calcium receptor on the osteoclast.

On the other hand, the nucleic acid sequences encoding calcium receptors present in parathyroid cells and C-cells indicate that these receptors have a very similar amino acid structure. Nevertheless, calcimimetic compounds exhibit differential pharmacology and regulate different activities at parathyroid cells and C-cells. Thus, pharmacological properties of calcium receptors may vary significantly depending upon the cell type or organ in which they are expressed even though the calcium receptors may have similar or even identical structures.

Calcium receptors, in general, have a low affinity for extracellular $Ca^{2+}$ (apparent $K_d$ generally greater than about 0.5 mM). Calcium receptors may include a free or bound effector mechanism as defined by Cooper, Bloom and Roth, "The Biochemical Basis of Neuropharmacology", Ch. 4, and are thus distinct from intracellular calcium receptors, e.g., calmodulin and the troponins.

Calcium receptors respond to changes in extracellular calcium levels. The exact changes depend on the particular receptor and cell line containing the receptor. For example, the in vitro effect of calcium on the calcium receptor in a parathyroid cell includes the following:

1. An increase in internal calcium. The increase is due to the influx of external calcium and/or to mobilization of internal calcium. Characteristics of the increase in internal calcium include the following:
    (a) A rapid (time to peak <5 seconds) and transient increase in $[Ca^{2+}]_i$ that is refractory to inhibition by 1 μM $La^{3+}$ or 1 μM $Gd^{3+}$ and is abolished by pretreatment with ionomycin (in the absence of extracellular $Ca^{2+}$);
    (b) The increase is not inhibited by dihydropyridines;
    (c) The transient increase is abolished by pretreatment for 10 minutes with 10 mM sodium fluoride;
    (d) The transient increase is diminished by pretreatment with an activator of protein kinase C (PKC) such as phorbol myristate acetate (PMA), mezerein or (−)-indolactam V. The overall effect of the protein kinase C activator is to shift the concentration-response curve of calcium to the right without affecting the maximal response; and
    (e) Pretreatment with pertussis toxin (100 ng/ml for >4 hours) does not affect the increase.
2. A rapid (<30 seconds) increase in the formation of inositol-1,4,5-triphosphate or diacylglycerol. Pretreatment with pertussis toxin (100 ng/ml for >4 hours) does not affect this increase;
3. The inhibition of dopamine- and isoproterenol-stimulated cyclic μMP formation. This effect is blocked by pretreatment with pertussis toxin (100 ng/ml for >4 hours); and
4. The inhibition of PTH secretion. Pretreatment with pertussis toxin (100 ng/ml for >4 hours) does not affect the inhibition in PTH secretion.

Using techniques known in the art, the effect of calcium on other calcium receptors in different cells can be readily determined. Such effects may be similar in regard to the increase in internal calcium observed in parathyroid cells. However, the effect is expected to differ in other aspects, such as causing or inhibiting the release of a hormone other than parathyroid hormone.

B. Calcimimetics

The ability of molecules to mimic or block the activity of $Ca^{2+}$ at calcium receptors can be determined using the assays described in the present application. For example, calcimimetics possess one or more and preferably all of the following activities when tested on parathyroid cells in vitro:

1. The molecule causes a rapid (time to peak <5 seconds) and transient increase in $[Ca^{2+}]_i$ that is refractory to inhibition by 1 μM $La^{3+}$ or 1 μM $Gd^{3+}$. The increase in $[Ca^{2+}]_i$ persists in the absence of extracellular $Ca^{2+}$, but is abolished by pretreatment with ionomycin (in the absence of extracellular $Ca^{2+}$);
2. The molecule potentiates increases in $[Ca^{2+}]_i$ elicited by submaximal concentrations of extracellular $Ca^{2+}$;
3. The increase in $[Ca^{2+}]_i$ elicited by extracellular $Ca^{2+}$ is not inhibited by dihydropyridines;
4. The transient increase in $[Ca^{2+}]_i$ caused by the molecule is abolished by pretreatment for 10 minutes with 10 mM sodium fluoride;
5. The transient increase in $[Ca^{2+}]_i$ caused by the molecule is diminished by pretreatment with an activator of protein kinase C (PKC), such as phorbol myristate acetate (PMA), mezerein or (−)-indolactam V. The overall effect of the protein kinase C activator is to shift the concentration-response curve of the molecule to the right without affecting the maximal response;
6. The molecule causes a rapid (<30 seconds) increase in the formation of inositol-1,4,5-triphosphate and/or diacylglycerol;
7. The molecule inhibits dopamine- or isoproterenol-stimulated cyclic AMP formation;
8. The molecule inhibits PTH secretion;
9. Pretreatment with pertussis toxin (100 ng/ml for >4 hours) blocks the inhibitory effect of the molecule on cyclic AMP formation, but does not effect increases in $[Ca^{2+}]_i$, inositol-1,4,5-triphosphate, or diacylglycerol, nor decreases in PTH secretion;
10. The molecule elicits increases in $Cl^-$ current in Xenopus oocytes injected with poly(A)$^+$-enriched mRNA from bovine or human parathyroid cells, but is without effect in Xenopus oocytes injected with water, or liver mRNA; and 11. Similarly, using a cloned calcium receptor from a parathyroid cell, the molecule will elicit a response in *Xenopus oocytes* injected with the specific cDNA or mRNA encoding the receptor.

Parallel definitions of molecules mimicking $Ca^{2+}$ activity on other calcium-responsive cells, preferably at a calcium receptor, are evident from the examples provided herein. Preferably, the agent has one or more, more preferably all of the following activities: evokes a transient increase in internal calcium, having a duration of less that 30 seconds (preferably by mobilizing internal calcium); evokes a rapid increase in $[Ca^{2+}]_i$, occurring within thirty seconds; evokes a sustained increase (greater than thirty seconds) in $[Ca^{2+}]_i$ (preferably by causing an influx of external calcium); evokes an increase in inositol-1,4,5-triphosphate or diacylglycerol levels, preferably within less than 60 seconds; and inhibits dopamine- or isoproterenol-stimulated cyclic AMP formation.

The transient increase in $[Ca^{2+}]_i$ is preferably abolished by pretreatment of the cell for ten minutes with 10 mM sodium fluoride, or the transient increase is diminished by brief pretreatment (not more than ten minutes) of the cell with an activator,of protein kinase C, preferably, phorbol myristate acetate (PMA), mezerein or (–) indolactam V.

C. Calcilytics

The ability of a molecule to block or decrease the activity of extracellular calcium at a cell surface calcium receptor can be determined using standard techniques based on the present disclosure. For example, molecules which block or decrease the effect of extracellular calcium, when used in reference to a parathyroid cell, possess one or more, and preferably all of the following characteristics when tested on parathyroid cells in vitro:

1. The molecule blocks, either partially or completely, the ability of increased concentrations of extracellular $Ca^{2+}$ to:
   (a) increase $[Ca^{2+}]_i$,
   (b) mobilize intracellular $Ca^{2+}$,
   (c) increase the formation of inositol-1,4,5-triphosphate,
   (d) decrease dopamine- or isoproterenol-stimulated cyclic AMP formation, and
   (e) inhibit PTH secretion;
2. The molecule blocks increases in $Cl^-$ current in *Xenopus oocytes* injected with poly(A)$^+$-mRNA from bovine or human parathyroid cells elicited by extracellular $Ca^{2+}$ or calcimimetic compounds, but not in *Xenopus oocytes* injected with water or liver mRNA; and
3. Similarly, using a cloned calcium receptor from a parathyroid cell, the molecule will block a response in *Xenopus oocytes* injected with the specific cDNA, mRNA or cRNA encoding the calcium receptor, elicited by extracellular $Ca^{2+}$ or a calcimimetic compound.

Parallel definitions of molecules blocking $Ca^{2+}$ activity on other calcium responsive cells, preferably at a calcium receptor, are evident from the examples provided herein.

D. Designing Calcium Receptor-Modulating Agents

Generally, calcium receptor-modulating agents are identified by screening molecules which are modelled after a molecule shown to have a particular activity (i.e., a lead molecule). Derivative molecules are readily designed by standard procedures and tested using the procedures described herein.

Rational design of calcium receptor-modulating agents involves studying a molecule known to be calcimimetic or calcilytic and then modifying the structure of the known molecule. For example, polyamines are potentially calcimimetic since spermine mimics the action of $Ca^{2+}$ in several in vitro systems. Results show that spermine does indeed cause changes in $[Ca^{2+}]_i$ and PTH secretion reminiscent of those elicited by extracellular di- and trivalent cations (see below). Conversely, $Ga^{3+}$ antagonizes the effects of $Gd^{3+}$ on the bovine parathyroid calcium receptor(s). The experiments outlined below are therefore aimed at demonstrating that this phenomenology, obtained with spermine, involves the same mechanisms used by extracellular $Ca^{2+}$. To do this, the effects of spermine on a variety of physiological and biochemical parameters which characterize activation of the calcium receptor were assessed. Those molecules having similar types of effects, and preferably at a greater magnitude, are useful in this invention and can be discovered by selecting or making molecules having a structure similar to spermine. Once another useful molecule is discovered this selection process can be readily repeated. The same type of analysis can be preformed using different lead molecules shown to have desired activity.

For clarity, a specific series of screening protocols to identify molecules active at a parathyroid cell calcium receptor is described below. Equivalent assays can be used for molecules active at other calcium receptors or other inorganic ion receptors, or which otherwise mimic or antagonize cellular functions regulated by extracellular $[Ca^{2+}]$ at a calcium receptor. These assays exemplify the procedures which are useful to find molecules, including calcimimetic molecules, of this invention. Equivalent procedures can be used to find ionolytic molecules, including calcilytic molecules, by screening for those molecules most antagonistic to the actions of the ion, including extracellular $Ca^{2+}$. In vitro assays can be used to characterize the selectivity, saturability, and reversibility of these calcimimetics and calcilytics by standard techniques.

1. Screening Procedures

Various screening procedures can be carried out to assess the ability of a compound to act as a calcilytic or calcimimetic by measuring its ability to have one or more activities of a calcilytic or calcimimetic. In the case of parathyroid cells, such activities include the effects on intracellular calcium, inositol phosphates, cyclic AMP and PTH.

Measuring $[Ca^{2+}]_i$ with fura-2 provides a very rapid means of screening new organic molecules for activity. In a single afternoon, 10–15 compounds (or molecule types) can be examined and their ability to mobilize or inhibit mobilization of intracellular $Ca^{2+}$ can be assessed by a single experimenter. The sensitivity of observed increases in $[Ca^{2+}]_i$ to depression by PMA can also be assessed.

For example,. bovine parathyroid cells loaded with fura-2 are initially suspended in buffer containing 0.5 mM $CaCl_2$. A test substance is added to the cuvette in a small volume (5–15 µl) and changes in the fluorescence signal are measured. Cumulative increases in the concentration of the test substance are made in the cuvette until some predetermined concentration is achieved or no further changes in fluorescence are noted. If no changes in fluorescence are noted, the molecule is considered inactive and no further testing is performed.

In the initial studies, e.g., with polyamine-type molecules, molecules were tested at concentrations as high as 5 or 10 mM. As more potent molecules became known, the ceiling concentration was lowered. For example, newer molecules are tested at concentrations no greater than 500 µM. If no changes in fluorescence are noted at this concentration, the molecule can be considered inactive.

Molecules causing increases in $[Ca^{2+}]_i$ are subjected to additional testing. Two characteristics of a molecule which can be considered in screening a calcimimetic molecule are the mobilization of intracellular $Ca^{2+}$ and sensitivity to PKC activators. Molecules causing the mobilization of intracellular $Ca^{2+}$ in a PMA-sensitive manner have invariably been found to be calcimimetic molecules and to inhibit PTH secretion. Sensitivity to PKC activators is measured in cells where PKC has not undergone treatment resulting in persistent activation. Chronic pretreatment with low concentrations of PMA (about 30–100 nM treatment for about 24 hours) results in persistent activation of PKC and allows for the inhibition of PTH secretion by extracellular $Ca^{2+}$ without any accompanying increase in $[Ca]_i$.

A single preparation of cells can provide data on $[Ca^{2+}]_i$ cyclic AMP levels, $IP_3$ and PTH secretion. A typical procedure is to load cells with fura-2 and then divide the cell suspension in two; most of the cells are used for measurement of $[Ca^{2+}]_i$ and the remainder are incubated with molecules to assess their effects on cyclic AMP and PTH secretion. Because of the sensitivity of the radioimmunoassays for cyclic AMP and PTH, both variables can be determined in a single incubation tube containing 0.3 ml cell suspension (about 500,000 cells).

Measurements of inositol phosphates are a time-consuming aspect of the screening. However, ion-exchange columns eluted with chloride (rather than formate) provide a very rapid means of screening for $IP_3$ formation, since rotary evaporation (which takes around 30 hours) is not required. This method allows processing of nearly 100 samples in a single afternoon by a single experimenter. Those molecules that prove interesting, as assessed by measurements of $[Ca^{2+}]_i$, cyclic AMP, $IP_3$, and PTH, can be subjected to a more rigorous analysis by examining formation of various inositol phosphates and assessing their isomeric form by HPLC.

Additional testing can, if needed, be performed to confirm the ability of a molecule to act as a calcimimetic prior to its use to inhibit PTH in human cells or test animals. Typically, all the various tests for calcimimetic or calcilytic activity are not performed. Rather, if a molecule causes the mobilization of intracellular $Ca^{2+}$ in a PMA-sensitive manner, it is advanced to screening on human parathyroid cells. For example, measurements of $[Ca^{2+}]_i$ are performed to determine the $EC_{50}$, and to measure the ability of the molecule to inhibit PTH secretion in human parathyroid cells which have been obtained from patients undergoing surgery for primary or secondary hyperparathyroidism. The lower the $EC_{50}$ or $IC_{50}$, the more potent the molecule as a calcimimetic or calcilytic.

Calcimimetic and calcilytic molecules affecting PTH secretion are then preferably assessed for selectivity, for example, by also examining the effects of such compounds on $[Ca^{2+}]_i$ or calcitonin secretion in calcitonin-secreting C-cells such as the rat MTC 6–23 cells.

The following is illustrative of methods useful in these screening procedures. Examples of typical results for various test calcimimetic or calcilytic molecules are provided in FIGS. 2–34.

(a) Parathyroid Cell Preparation

This section describes procedures used to obtain and treat parathyroid cells from calves and humans. Parathyroid glands were obtained from freshly slaughtered calves (12–15 weeks old) at a local abattoir and transported to the laboratory in ice-cold parathyroid cell buffer (PCB) which contains (mM): NaCl, 126; KCl, 4; $MgCl_2$, 1; Na-HEPES, 20; pH 7.4; glucose, 5.6, and variable amounts of $CaCl_2$, e.g., 1.25 mM. Human parathyroid glands, were obtained from patients undergoing surgical removal of parathyroid tissue for primary or uremic hyperparathyroidism (uremic HPT), and were treated similarly to bovine tissue.

Glands were trimmed of excess fat and connective tissue and then minced with fine scissors into cubes approximately 2–3 mm on a side. Dissociated parathyroid cells were prepared by collagenase digestion and then purified by centrifugation in Percoll buffer. The resultant parathyroid cell preparation was essentially devoid of red blood cells, adipocytes, and capillary tissue as assessed by phase contrast microscopy and Sudan black B staining. Dissociated and purified parathyroid cells were present as small clusters containing 5 to 20 cells. Cellular viability, as indexed by exclusion of trypan blue or ethidium bromide, was routinely 95%.

Although cells can be used for experimental purposes at this point, physiological responses (e.g., suppressibility of PTH secretion and resting levels of $[Ca^{2+}]_i$) should be determined after culturing the cells overnight. Primary culture also has the advantage that cells can be labeled with isotopes to near isotopic equilibrium, as is necessary for studies involving measurements of inositol phosphate metabolism.

After purification on Percoll gradients, cells were washed several times in a 1:1 mixture of Ham's F12-Dulbecco's modified Eagle's medium (GIBCO) supplemented with 50 $\mu$g/ml streptomycin, 100 U/ml penicillin, 5 $\mu$g/ml gentamicin and $ITS^+$. $ITS^+$ is a premixed solution containing insulin, transferrin, selenium, and bovine serum albumin (BSA)—linolenic acid (Collaborative Research, Bedford, Mass.). The cells were then transferred to plastic flasks (75 or 150 $cm^2$; Falcon) and incubated overnight at 37° C. in a humid atmosphere of 5% $CO_2$. No serum is added to these overnight cultures, since its presence allows the cells to attach to the plastic, undergo proliferation, and dedifferentiate. Cells cultured under the above conditions were readily removed from the flasks by decanting, and show the same viability as freshly prepared cells.

(b) Measurement of Cytosolic $Ca^+$ in Parathyroid Cells

This section describes procedures used to measure cytosolic $Ca^{2+}$ in parathyroid cells. Purified parathyroid cells were resuspended in 1.25 mM $CaCl_2$-2% BSA-PCB containing 1 $\mu$M fura-2-acetoxymethylester and incubated at 37° C. for 20 minutes. The cells were then pelleted, resuspended in the same buffer, but lacking the ester, and incubated a further 15 minutes at 37° C. The cells were subsequently washed twice with PCB containing 0.5 mM $CaCl_2$ and 0.5% BSA and maintained at room temperature (about 20° C.). Immediately before use, the cells were diluted five-fold with prewarmed 0.5 mM $CaCl_2$-PCB to obtain a final BSA concentration of 0.1%. The concentration of cells in the cuvette used for fluorescence recording was $1-2 \times 10^6$/ml.

The fluorescence of indicator-loaded cells was measured at 37° C. in a spectrofluorimeter (Biomedical Instrumentation Group, University of Pennsylvania, Philadelphia, Pa.) equipped with a thermostated cuvette holder and magnetic stirrer using excitation and emission wavelengths of 340 and 510 nm, respectively. This fluorescence indicates the level of cytosolic $Ca^{2+}$. Fluorescence signals were calibrated using digitonin (50 $\mu$g/ml, final) to obtain maximum fluorescence ($F_{max}$), and EGTA (10 mM, pH 8.3, final) to obtain minimal fluorescence ($F_{min}$), and a dissociation constant of 224 nM. Leakage of dye is dependent on temperature and most occurs within the first 2 minutes after warming the cells in the cuvette. Dye leakage increases only very slowly thereafter. To correct the calibration for dye leakage, cells were placed in the cuvette and stirred at 37° C. for 2–3 minutes.

The cell suspension was then removed, the cells pelleted, and the supernatant returned to a clean cuvette. The supernatant was then treated with digitonin and EGTA to estimate dye leakage, which is typically 10–15% of the total $Ca^{2+}$-dependent fluorescent signal. This estimate was subtracted from the apparent $F_{min}$.

(c) Measurement of Cytosolic $Ca^{2+}$ in C-cells

This section describes procedures used to measure cytosolic $Ca^{2+}$ in cells. Neoplastic C-cells derived from a rat medullary thyroid carcinoma (rMTC 6–23) were obtained from American Type Culture Collection (ATCC No. 1607) and cultured as monolayers in Dulbecco's Modified Eagle's medium (DMEM) plus 15% horse serum in the absence of antibiotics. For measurements of $[Ca^{2+}]_i$, the cells were harvested with 0.02% EDTA/0.05% trypsin, washed twice with PCB containing 1.25 mM $CaCl_2$ and 0.5% BSA, and loaded with fura-2 as described in section I.D.2(b), supra. Measurements of $[Ca^{2+}]_i$ were performed as described above with appropriate corrections for dye leakage.

(d) Measurement of $[Ca^{2+}]_i$ in Rat Osteoclasts

This section describes techniques used to measure $[Ca^{2+}]_i$ in rat osteoclasts. Osteoclasts were obtained from 1–2 day old Sprague-Dawley rats using aseptic conditions. The rat pups were sacrificed by decapitation, the hind legs removed, and the femora rapidly freed of soft tissue and placed in prewarmed F-12/DMEM media (DMEM containing 10% fetal calf serum and antibiotics (penicillin-streptomycin-gentamicin; 100 U/ml-100 µg/ml-100 µg/ml)). The bones from two pups were cut lengthwise and placed in 1 ml culture medium. Bone cells were obtained by gentle trituration of the bone fragments with a plastic pipet and diluted with culture medium. The bone fragments were allowed to settle and equal portions (about 1 ml) of the medium transferred to a 6-well culture plate containing 25-mm glass coverslips. The cells were allowed to settle for 1 hour at 37° C. in a humidified 5% $CO_2$-air atmosphere. The coverslips were then washed 3 times with fresh media to remove nonadherent cells. Measurements of $[Ca^{2+}]_i$ in osteoclasts were performed within 6–8 hours of removing nonadherent cells.

Cells attached to the coverslip were loaded with indo-1 by incubation with 5 µM indo-1 acetoxymethylester/0.01% Pluronic F28 for 30 minutes at 37° C. in F-12/DMEM lacking serum and containing instead 0.5% BSA. The coverslips were subsequently washed and incubated an additional 15 minutes at 37° C. in F-12/DMEM lacking the acetoxyester before being transferred to a superfusion chamber mounted on the stage of a Nikon Diaphot inverted microscope equipped for microfluorimetry. Osteoclasts were easily identified by their large size and presence of multiple nuclei. The cells were superfused with buffer (typically PCB containing 0.1% BSA and 1 mM $Ca^{2+}$) at 1 ml/min with or without test substance. The fluorescence emitted by excitation at 340 nm was directed through the video port of the microscope onto a 440 nm dichroic mirror and fluorescence intensity at 495 and 405 nm collected by photomultiplier tubes. The outputs from the photomultiplier tubes were amplified, digitized, and stored in an 80386 PC. Ratios of fluorescence intensity were used to estimate $[Ca^{2+}]_i$.

(e) Measuring $[Ca^{2+}]_i$ in Oocytes

Additional studies used *Xenopus oocytes* injected with mRNA from bovine or human parathyroid cells and measured $Cl^-$ current as an indirect means of monitoring increases in $[Ca^{2+}]_i$. The following is an example of such studies used to test the effect of neomycin.

Oocytes were injected with poly(A)$^+$-enriched mRNA from human parathyroid tissue (hyperplastic glands from a case of secondary HPT). After 3 days, the oocytes were tested for their response to neomycin. Neomycin B evoked oscillatory increases in the $Cl^-$ current which ceased upon superfusion with drug-free saline (see FIG. 20). Responses to neomycin B were observed at concentrations between 100 µM and 10 mM.

To ensure that the response evoked by neomycin B was contingent upon injection of parathyroid mRNA, the effect of neomycin B on currents in water-injected oocytes was determined. In each of five oocytes examined, neomycin B (10 mM) failed to cause any change in the current.

About 40% of oocytes are known to respond to carbachol, an effect mediated by an endogenous muscarinic receptor. In five oocytes examined one showed inward currents in response to carbachol and this is shown in the lower trace of FIG. 20. Thus, in cells expressing a muscarinic receptor coupled to increases in $[Ca^{2+}]_i$ and $Cl^-$ current, neomycin B fails to evoke a response. This shows that the response to neomycin B depends on expression of a specific protein encoded by parathyroid cell mRNA. It strongly suggests that in intact cells, neomycin B acts directly on the calcium receptor to alter parathyroid cell function.

(f) Measurement of PTH Secretion

In most experiments, cells loaded with fura-2 were also used in studies of PTH secretion. Loading parathyroid cells with fura-2 does not change their PTH secretory response to extracellular $Ca^{2+}$.

PTH secretion was measured by first suspending cells in PCB containing 0.5 mM $CaCl_2$ and 0.1% BSA. Incubations were performed in plastic tubes (Falcon 2058) containing 0.3 ml of the cell suspension with or without small volumes of $CaCl_2$ and/or organic polycations. After incubation at 37° C. for various times (typically 30 minutes), the tubes were placed on ice and the cells pelleted at 2° C. Samples of the supernatant were brought to pH 4.5 with acetic acid and stored at −70° C. This protocol was used for both bovine and human parathyroid cells.

For bovine cells, the amount of PTH in sample supernatants was determined by a homologous radioimmunoassay using GW-1 antibody or its equivalent at a final dilution of 1/45,000. $^{125}$I-PTH (65-84; INCSTAR, Stillwater, Minn.) was used as tracer and fractions separated by dextran-activated charcoal. Counting of samples and data reduction were performed on a Packard Cobra 5005 gamma counter.

For human cells, a commercially available radioimmunoassay kit (INS-PTH; Nichols Institute, Los Angeles, Calif.) which recognizes intact and N-terminal human PTH was used because GW-1 antibody recognizes human PTH poorly.

(g) Measurement of cyclic AMP

This section describes measuring cyclic AMP levels. Cells were incubated as above for PTH secretion studies and at the end of the incubation, a 0.15-ml sample was taken and transferred to 0.85 ml of hot (70° C.) water and heated at this temperature for 5–10 minutes. The tubes were subsequently frozen and thawed several times and the cellular debris sedimented by centrifugation. Portions of the supernatant were acetylated and cyclic AMP concentrations determined by radioimmunoassay.

(h) Measurement of Inositol Phosphate Formation

This section describes procedures measuring inositol phosphate formation. Membrane phospholipids were labeled by incubating parathyroid cells with 4 µCi/ml $^3$H-myo-inositol for 20–24 hours. Cells were then washed and resuspended in PCB containing 0.5 mM $CaCl_2$ and 0.1% BSA. Incubations were performed in microfuge tubes in the absence or presence of various concentrations of organic polycation for different times. Reactions were terminated by the addition of 1 ml chloroform-methanol-12 N HCl (200:100:1; v/v/v). Aqueous phytic acid hydrolysate (200 μl; 25 μg phosphate/tube). The tubes were centrifuged and 600 μl of the aqueous phase was diluted into 10 ml water.

Inositol phosphates were separated by ion-exchange chromatography using AG1-X8 in either the chloride- or formate-form. When only $IP_3$ levels were to be determined, the chloride-form was used, whereas the formate form was used to resolve the major inositol phosphates ($IP_3$, $IP_2$, and $IP_1$). For determination of just $IP_3$, the diluted sample was applied to the chloride-form column and the column was washed with 10 ml 30 mM HCl followed by 6 ml 90 mM HCl and the $IP_3$ was eluted with 3 ml 500 mM HCl. The last eluate was diluted and counted. For determination of all major inositol phosphates, the diluted sample was applied to the formate-form column and $IP_1$, $IP_2$, and $IP_3$ eluted sequentially by increasing concentrations of formate buffer. The eluted samples from the formate columns were rotary evaporated, the residues brought up in cocktail, and counted.

The isomeric forms of $IP_3$ were evaluated by HPLC. The reactions were terminated by the addition of 1 ml 0.45 M perchloric acid and stored on ice for 10 minutes. Following centrifugation, the supernatant was adjusted to pH 7–8 with $NaHCO_3$. The extract was then applied to a Partisil SAX anion-exchange column and eluted with a linear gradient of ammonium formate. The various fractions were then desalted with Dowex followed by rotary evaporation prior to liquid scintillation counting in a Packard Tri-carb 1500 LSC.

For all inositol phosphate separation methods, appropriate controls using authentic standards were used to determine if organic polycations interfered with the separation. If so, the samples were treated with cation-exchange resin to remove the offending molecule prior to separation of inositol phosphates.

2. Use of Lead Molecules

By systematically measuring the ability of a lead molecule to mimic or antagonize the effect of extracellular $Ca^{2+}$, the importance of different functional groups for calcimimetics and calcilytics were identified. Of the molecules tested, some are suitable as drug candidates while others are not necessarily suitable as drug candidates. The suitability of a molecule as a drug candidate depends on factors such as efficacy and toxicity. Such factors can be evaluated using standard techniques. Thus, lead molecules can be used to demonstrate that the hypothesis underlying calcium receptor-based therapies is correct and to determine the structural features that enable the calcium receptor-modulating agents to act on the calcium receptor and, thereby, to obtain other molecules useful in this invention.

Examples of molecules useful as calcimimetics include branched or cyclic polyamines, positively charged polyamino acids, and arylalkylamines. In addition, other positively charged organic molecules, including naturally occurring molecules and their analogues, are useful calcimimetics. These naturally occurring molecules and their analogues preferably have positive charge-to-mass ratios that correlate with those ratios for the molecules exemplified herein. (Examples include material isolated from marine species, arthropod venoms, terrestrial plants and fermentation broths derived from bacteria and fungi.) It is contemplated that one group of preferred naturally occurring molecules and analogues useful as calcimimetics will have a ratio of positive charge: molecular weight (in daltons) from about 1:40 to 1:200, preferably from about 1:40 to 1:100.

FIG. 36 provides additional examples of molecules expected to act as either calcilytics or calcimimetics based upon their structure. In general these molecules were synthesized based on the lead molecule, fendiline, and tested to determine their respective $EC_{50}$ or $IC_{50}$ values. Studies of stereoisomers, such as NPS 447 (R-fendiline) and NPS 448 (S-fendiline), have revealed stereospecific effects of molecular structure. The most active compounds tested to date are designated NPS R-467, NPS R-568, compound 8J, compound 8U, compound 9R, compound 11X, compound 12U, compound 12V, compound 12Z, compound 14U, compound 17M, compound 17P and compound 17X (see Table 8, infra). These compounds all have $EC_{50}$ values of less than 5 μM at the parathyroid cell calcium receptor.

The examples described herein demonstrate the general design of molecules useful as ionomimetics and ionolytics, preferably, calcimimetics and calcilytics. The examples also describe screening procedures to obtain additional molecules, such as the screening of natural product libraries. Using these procedures, those of ordinary skill in the art can identify other useful ionomimetics and ionolytics, preferably calcimimetics and calcilytics.

(a) Functional Groups

This section describes useful functional groups for conferring increased mimetic or lytic activity and analytical procedures which can be used to identify different functional groups from lead molecules. Analysis of lead molecules have identified useful functional groups such as aromatic groups, stereospecificity (R-isomer) and preferred charge-to-molecule weight ratios. The described analytic steps and analogous analyses can be conducted on other lead molecules to obtain calcium receptor-modulating agents of increasing activity.

A factor examined earlier on was the charge-to-size ratio of a calcium receptor-modulating agent. Initial results of testing the correlation between net positive charge and potency in mobilizing intracellular $Ca^{2+}$ in parathyroid cells revealed that protamine (+21; $EC_{50}$=40 nM) was more effective than neomycin B (+6; $EC_{50}$=20 μM in human parathyroid cells and 40 μM in bovine parathyroid cells), which was more effective than spermine (+4; $EC_{50}$=150 μM).

These results raised the question of whether positive charge alone determines potency, or if there are other structural features contributing to activity on the calcium receptor. This was important to determine at the outset because of its impact on the view that the calcium receptor can be targeted with effective and specific therapeutic molecules. Thus, a variety of other organic polycations related to neomycin B and spermine were studied to determine the relationship between the net positive charge of a molecule and its potency to mobilize intracellular $Ca^{2+}$.

The first series of molecules studied were the aminoglycosides. The ability of these molecules to mobilize intracellular $Ca^{2+}$ was determined in bovine parathyroid cells. The rank order of potency for eliciting cytosolic $Ca^{2+}$ transients was neomycin B ($EC_{50}$=20 or 40 μM)>gentamicin (150 μM)>bekanamycin (200 μM)>streptomycin (600 μM). Kanamycin and lincomycin were without effect when tested at a concentration of 500 μM. The net positive charge on these aminoglycosides at pH 7.3 is neomycin B (+6) >gentamicin (+5)=bekanamycin (+5)>kanamycin (average +4.5)>streptomycin (+3)>lincomycin (+1). Thus, within the aminoglycoside series there is some correlation between net positive charge and calcium receptor-modulating activity. However, the correlation is not absolute as illustrated by kanamycin, which would be predicted to be more potent than streptomycin, having no activity.

Testing of various polyamines revealed additional and more marked discrepancies between net positive charge and potency. Three structural classes of polyamines were examined: (1) straight-chain, (2) branched-chain, and (3) cyclic. The structures of the polyamines tested are provided in FIG. 1. Amongst the straight-chain polyamines, spermine (+4; $EC_{50}$=150 μM) was more potent than pentaethylenehexamine (+6; $EC_{50}$=500 μM) and tetraethylenepentamine (+5; $EC_{50}$=2.5 mM), even though the latter molecules have a greater net positive charge.

Branched-chain polyamines having different numbers of secondary and primary amino groups and, thus, varying in net positive charge were synthesized and tested. Two of these molecules, NPS 381 and NPS 382, were examined for effects on $[Ca^{2+}]_i$ in bovine parathyroid cells. NPS 382 (+8; $EC_{50}$=50 μM) was about twice as potent as NPS 381 (+10; $EC_{50}$=100 μM) even though it contains two fewer positive charges.

A similar discrepancy between positive charge and potency was noted in experiments with cyclic polyamines. For example, hexacyclen (+6; $EC_{50}$=20 μM) was more potent than NPS 383 (+8; $EC_{50}$=150 μM). The results obtained with these polyamines show that positive charge is not the sole factor contributing to potency.

Additional studies provided insights into other structural features of molecules that impart activity on the parathyroid cell calcium receptor. One of the structurally important features is the intramolecular distance between the nitrogens (which carry the positive charge). Spermine is 50-fold more potent than triethylenetetramine ($EC_{50}$=8 mM) in evoking increases in $[Ca^{2+}]_i$ in bovine parathyroid cells, yet both molecules carry a net positive charge of +4. The only difference in structure between these two polyamines is the number of methylenes separating the nitrogens: in spermine it is 3-4-3 whereas in triethylenetetramine it is 2-2-2. This seemingly minor change in the spacing between nitrogens has profound implications for potency and suggests that the conformational relationships of nitrogens within the molecule are important.

Studies with hexacyclen and pentaethylenehexamine further demonstrated the importance of the conformational relationship. The former molecule is simply the cyclic analog of the latter and contains the same number of methylenes between all nitrogens, yet the presence of the ring structure increases potency 25-fold. These results indicate that positive charge per se is not the critical factor determining the activity of an organic molecule on the calcium receptor.

Another series of experiments revealed the importance of aromatic groups in determining activity on the calcium receptors. The initial results were obtained using two arylalkyl polyamines isolated from the venom of the spider Argiope lobata. These molecules, argiotoxin 636 and argiotoxin 659, have identical polycationic portions linked to different aromatic groups (FIG. 1e). Argiotoxin 659 evoked transient increases in $[Ca^{2+}]_i$ in bovine parathyroid cells when tested at concentrations of 100 to 300 μM. In contrast, argiotoxin 636 had no effect when tested at similar concentrations (FIG. 24). The only difference in structure between these two arylalkyl polyamines is in the aromatic portion of the molecules: argiotoxin 659 contains a 4-hydroxyindole moiety whereas argiotoxin 636 contains a 2,4-dihydroxyphenyl group. The net positive charge on these two arylalkyl polyamines is the same (+4), so their different potencies results from the different aromatic groups. This findings further demonstrates that net positive charge alone does not determine potency and that aromatic groups contribute significantly to the ability of molecules to activate the calcium receptor.

Substitutions on aromatic rings also effect calcium receptor-modulating activity. Agatoxin 489 (NPS 017) and Agatoxin 505 (NPS 015) both cause the mobilization of intracellular $Ca^{2+}$ in parathyroid cells with $EC_{50}$'s of 6 and 22 μM, respectively. The only difference between the structures of these molecules is a hydroxyl group on the indole moiety (FIG. 1f).

Thus, the structural features to be varied systematically from lead molecules described herein include the following: (1) net positive charge; (2) number of methylenes separating nitrogens; (3) cyclic versions of molecules, for example polyamines with and without changes in methylene spacing and net positive charge; and (4) the structure and location of aromatic groups.

A variety of arylalkyl polyamines can be isolated from the venoms of wasps and spiders. Additionally, analogous synthetic molecules can be prepared by the coupling of commercially available aromatic moieties to the argiotoxin polyamine moiety. The argiotoxin polyamine moiety can be readily coupled to any aromatic moiety containing a carboxylic acid.

One of ordinary skill in the art can readily obtain and systematically screen the hydroxy and methoxy derivatives of phenylacetic acid and benzoic acid as well as the hydroxyindoleacetic acid series using the techniques described herein. Analogues containing heteroaromatic functionalities can also be prepared and assessed for activity. Comparisons of potency and efficacy among molecules having different functional groups will reveal the optimal structure and location of the aromatic group at a constant positive charge.

(b) Testing of Natural Products

Testing of natural products and product libraries can be carried out to identify functional groups and to test molecules having particular functional groups. Screening of natural products selected on the basis of the structural information can be readily performed using the structure-function relationships established by the testing of lead molecules. For example, molecules can be selected on the basis of well-established chemotaxonomic principles using appropriate data bases, such as Napralert, to obtain pools of molecules having desired functional groups. For example, macrocyclic polyamine alkaloids derived from papilionoid legumes related to Albizia, such as Pithecolobium, and other plant-derived molecules can be screened.

The results obtained with budmunchiamine A illustrate the predictive power of the structure-activity studies and the novel structural information to be gained by testing natural products. One of the structural variations on the polyamine motif that seems to increase potency is the presence of the cyclic version of the straight-chain parent molecule. Budmunchiamine A, isolated from the plant *Albizia amara*, is a cyclic derivative of spermine (FIG. 1a). The addition of budmunchiamine A to bovine parathyroid cells caused a rapid and transient increase in $[Ca^{2+}]_i$ that persisted in the absence of extracellular $Ca^{2+}$ and was blunted by pretreatment with PMA. It therefore causes the mobilization of intracellular $Ca^{2+}$ in parathyroid cells, probably by acting on the calcium receptor. It is about equipotent with spermine ($EC_{50}$ about 200 μM), yet carries one less positive charge (+3) than does spermine.

3. Polyamines

Preferred polyamines useful as calcimimetics in this invention may be either branched or cyclic. Branched or cyclic polyamines potentially have higher calcimimetic activity than their straight-chain analogues. That is, branched or cyclic polyamines tend to have a lower $EC_{50}$ than their corresponding linear polyamines with the same effective charge at physiological pH (see Table 1).

TABLE 1

| Molecule | Net (+) Charge | EC$_{50}$($\mu$M) |
| --- | --- | --- |
| Neomycin | +6 | 20 or 40 |
| Hexacyclen | +6 | 20 |
| NPS 382 | +8 | 50 |
| NPS 381 | +10 | 100 |
| NPS 383 | +8 | 150 |
| Gentamicin | +5 | 150 |
| Spermine | +4 | 150 |
| Bekanamycin | +5 | 200 |
| Argiotoxin-659 | +4 | 300 |
| Pentaethylenehexamine (PEHA) | +6 | 500 |
| Streptomycin | +3 | 600 |
| Spermidine | +3 | 2000 |
| Tetraethylenepentamine (TEPA) | +5 | 2500 |
| 1,12-diaminododecane (DADD) | +2 | 3000 |
| Triethylenetramine (TETA) | +4 | 8000 |

"Branched polyamines" as used herein refers to a chain molecule consisting of short alkyl bridges or alkyl groups joined together by amino linkages, and also containing points at which the chain branches. These "branch points" can be located at either a carbon atom or a nitrogen atom, preferably at a nitrogen atom. A nitrogen atom branch point is typically a tertiary amine, but it may also be quaternary. A branched polyamine may have 1 to 20 branch points, preferably 1 to 10 branch points.

Generally, the alkyl bridges and alkyl branches in a branched polyamine are from 1 to 50 carbon atoms in length, preferably 1–15, more preferably from 2 to 6 carbon atoms. The alkyl branches may also be interrupted by one or more heteroatoms (nitrogen, oxygen or sulfur) or substituted with functional groups such as: halo, including fluoro, chloro, bromo, or iodo; hydroxy; nitro; acyloxy (R'COO—), acylamido (R'CONH—), or alkoxy (—OR'), where R' may contain from 1 to 4 carbon atoms. The alkyl branches may also be substituted with groups that are positively charged at physiological pH, such as amino or guanidino. These functional substituents may add or change physical properties such as solubility to increase activity, delivery or bioavailability of the molecules.

The branched polyamines may have three or more chain and branch termination points. These termination points may be methyl groups or amino groups, preferably amino groups.

A preferred group of branched polyamines have the formula:

$$H_2N\text{—}(CH_2)_j\text{—}(NR_i\text{—}(CH_2)_j)_k\text{—}NH_2$$

where k is an integer from 1 to 10;
each j is the same or different and is an integer from 2 to 20;
each R$_i$ is the same or different and is selected from the group consisting of hydrogen and —(CH$_2$)$_j$—NH$_2$, where j is as defined above; and
at least one R$_i$ is not hydrogen.

Particularly preferred branched polyamines of this invention are the molecules N$^1$,N$^1$,N$^5$,N$^{10}$,N$^{14}$,N$^{14}$-hexakis-(3-aminopropyl) spermine and N$^1$,N$^1$,N$^5$,N$^{14}$,N$^{14}$-tetrakis-(3-aminopropyl)spermine referred to as NPS 381 and NPS 382, respectively, in FIGS. 1a and 1f.

"Cyclic polyamines" refers to heterocycles containing two or more heteroatoms (nitrogen, oxygen or sulfur), at least two of which are nitrogen atoms. The heterocycles are generally from about 6 to about 20 atoms in circumference, preferably from about 10 to about 18 atoms in circumference. The nitrogen heteroatoms are separated by 2 to 10 carbon atoms. The heterocycles may also be substituted at the nitrogen sites with aminoalkyl or aminoaryl groups (NH$_2$R—), wherein R is aminoaryl or a lower alkyl of 2 to 6 carbon atoms. Particularly preferred cyclic polyamines of this invention are shown in FIGS. 1f and 1a as hexacyclen (1,4,7,10,13,16-hexaaza-cyclooctadecane) and NPS 383.

4. Polyamino Acids

"Polyamino acids" refers to polypeptides containing two or more amino acid residues which are positively charged at physiological pH. Positively charged amino acids include histidine, lysine and arginine. The polyamino acids can vary in length from 2 to 800 amino acids, more preferably from 20 to 300 amino acids and may consist of a single repeating amino acid residue or may have the variety of a naturally occurring protein or enzyme. Preferred polyamino acids are polyarginine, polylysine, and poly(argininyl-tyrosine), having 20–300 residues, and protamine or a protamine analog.

The amino acid residues present in the polyamino acids may be any of the twenty naturally occurring amino acids, or other alternative residues. Alternative residues include, for example, the $\omega$-amino acids of the formula H$_2$N(CH$_2$)$_n$COOH, where n is from 2 to 6, and other nonpolar amino acids, such as sarcosine, t-butyl alanine, t-butyl glycine, N-methyl isoleucine, norleucine, phenyl glycine, citrulline, methionine sulfoxide, cyclohexyl alanine, and hydroxyproline. Ornithine is an example of an alternative positively charged amino acid residue. The polyamino acids of this invention may also be chemically derivatized by known methods.

5. Arylalkyl Polyamines

"Arylalkyl polyamines" refers to a class of positively charged natural products derived from arthropod venoms. Preferred arylalkyl polyamines are philanthotoxin-433, argiotoxin-636, argiotoxin-659, agatoxin 505, agatoxin 489 (FIG. 1), and analogous synthetic molecules modeled after these natural products.

6. Arylalkyl Amines

Preferred molecules of the present invention are arylalkyl amines having structure I; more preferably having structure III described supra, wherein R$_2$ is an aryl group, preferably a carbocyclic aryl group such as phenyl or a bicyclic carbocyclic aryl groups such as naphthyl, preferably 1-naphthyl. Especially preferred are R-isomers.

Two examples of arylalkyl amines are NPS 467 and NPS 568. NPS 467 and NPS 568 are analogues. NPS 568 is more potent in causing increases in [Ca$^{2+}$]$_i$ in bovine and human parathyroid cells than NPS 467. The effects of NPS 568 and NPS 467 are stereospecific and it is the R-isomer that is the more potent enantiomer (see Table 6, infra). NPS R-568 is at present the lead calcimimetic compound with selective activity at the parathyroid cell calcium receptor.

NPS R-568 behaves, albeit with greater potency, similarly to NPS R-467. NPS R-568 evokes increases in [Ca$^{2+}$]$_i$ in bovine parathyroid cells in a stereospecific manner (see Table 6, infra). NPS R-568 fails to evoke increases in [Ca$^{2+}$]$_i$ in the absence of extracellular Ca2+, but it does potentiate responses to extracellular Ca$^{2+}$. NPS R-568 shifts the concentration-response curve for extracellular Ca$^{2+}$ to the left.

The oral administration of NPS R-568 to rats causes a dose-dependent decrease in the levels of serum Ca$^{2+}$ (ED$_{50}$=7 mg/kg). The hypocalcemic response elicited by the oral administration of NPS R-568 is rapid in onset and is paralleled by decreases in the levels of serum PTH. The hypocalcemic response evoked by the oral administration of NPS R-568 is only marginally affected by prior complete nephrectomy. However, NPS R-568 fails to elicit a hypocalcemic response in parathyroidectomized rats. NPS R-568 can thus target selectively the parathyroid cell calcium receptor in vivo and cause an inhibition of PTH secretion. The decreases in serum levels of PTH together with the resulting hypocalcemia are desirable therapeutic effects in cases of hyperparathyroidism.

Also preferred are arylalkyl amines having the structure:

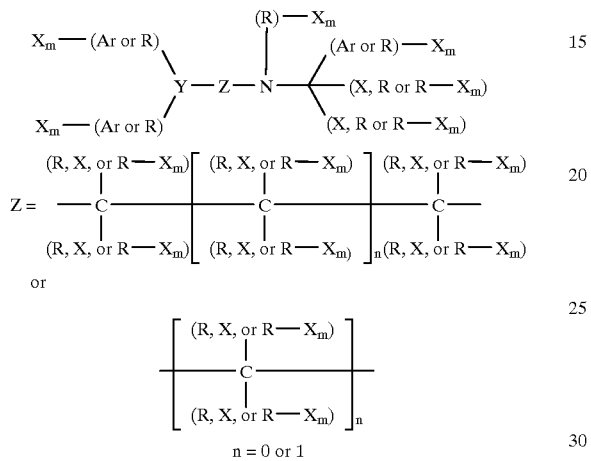

n = 0 or 1

More Preferably

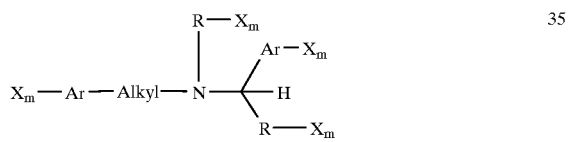

Alkyl=$C_1$–$C_6$ cyclic, preferably linear, or more preferably branched hydrocarbon (sp$^2$ or preferably sp$^3$ hybridization)
Ar=(preferably) phenyl, 1-, or 2-naphthyl More Preferably

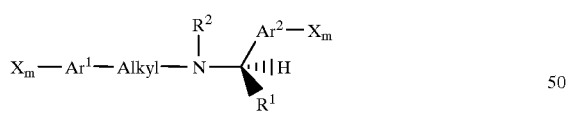

Alkyl=$C_1$–$C_6$ cyclic, preferably linear, or more preferably branched hydrocarbon (sp$^2$ or preferably sp$^3$ hybridization). Ar$^1$=(preferably) phenyl or 2-naphthyl; Ar$^2$ (preferably)= phenyl or 1-naphthyl. R$^1$=(preferably) methyl, R$^2$= (preferably) H Most Preferably

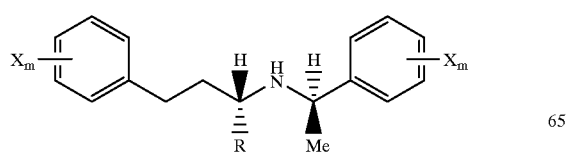

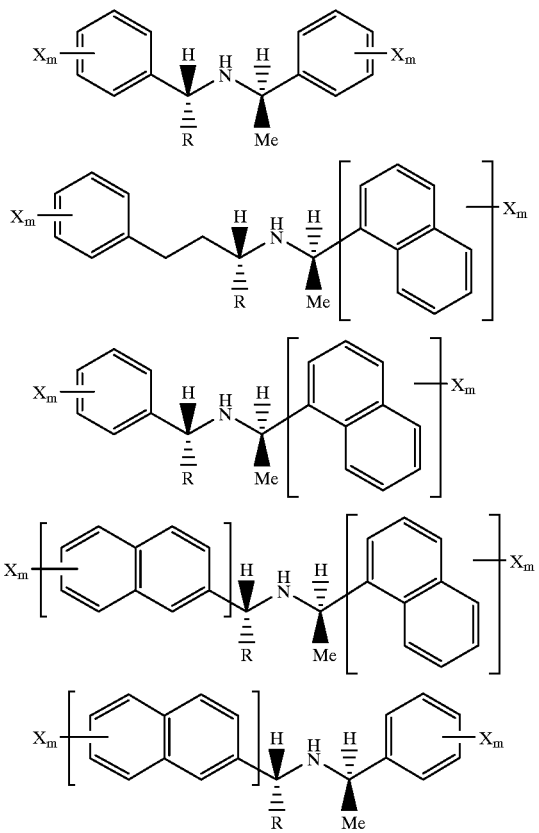

More Preferably R = $C_1$–$C_3$,
Most*Preferably R = Me

X=nothing; for example when C (Carbon, see Z=) are sp$^2$ or sp$^1$, or for example when Y=O (Oxygen). Possible combinations are not limited to these examples.

X=—H

X=—F, —Cl, —Br, or —i

X=—OR

X=—NR$_2$ (R's selected independently)

X=—SR, S(O)R, S(O)$_2$R,

X=—CN

X=—NO$_2$

X=—C(O)R —OC(O)R, —C(O)OR —NRC(O)R, C(O)NR$_2$, (R's selected independently)

R=—H, —CF$_3$, —CF$_2$H, —CFH$_2$, —CH$_2$CF$_3$, —C$_1$–C$_{10}$ (sp, sp$^2$, or sp$^3$ carbons, selected independently) alkyl (linear, branched, cyclic system, fused cyclic or bicyclic systems, selected independently) or phenyl.

Ar=any aromatic, heteroaromatic, or heterocyclic system, preferably phenyl, 1-naphthyl, 2-naphthyl, biphenyl, tetrahydronaphthyl, indanyl, indenyl, fluorenyl, 9,10-dihydranthracanyl, 9,10-dihydrophenanthrenyl, pyrrolyl, furanyl, 1,2,3-triazolyl, 1,2,4triazolyl, tetrazolyl, imidazolyl, oxazolyl, thiazolyl, pyrazolyl, thiofuranyl, isoxazolyl, pyridinyl, pyridazinyl, pyrimidinyl, pyrazinyl, 1,2,4-triazinyl, 1,3,5-triazinyl, tetrahydrofuranyl, pyrrolidinyl, imidazolinyl, thiazolidinyl, decahydroquinolinyl, decahydmisoquinolinyl, piperidinyl, piperizinyl, morpholinyl, thiomorpholinyl, benzofuranyl, dihydrobenzofuranyl, dihydrobenzopyranyl, benzimadazolyl, indazolyl, tetrahydroquinolinyl, tetrahydroisoquinoline, quinolinyl, isoquinolinyl, benzotriazolyl, carbazolyl, indolyl, indolinyl, phenoxazinyl, phenothiazinyl, α-carbolinyl, β-carbolinyl, acenaphthenyl, or acenaphthylenyl.

Y=—NR, —O, —S, —S(O), —S(O)$_2$, —C*R, —C*(O), —OC*(O), —C*(O)O, —NRC*(O), C*(O)NR, (*sp$^2$carbon), —CR$_2$, —CRX, or —CX$_2$.

m=1 through 7 inclusive (independent).

Z and N together form a pipeddinyl, piparazinyl or pyrrolinyl ring.

7. Additional Components

Calcium receptor-modulating agents may be substituted with additional components. The additional components are used to provide additional functionality to the molecules, apart from the molecules' ability to act as a calcimimetic or calcilytic. These additional components include targeting components and functionalities such as labels which enhance a molecule's ability to be used in the different applications, such as for screening for agonists or antagonists of extracellular Ca$^{2+}$ in a competitive or non-competitive assay format.

For example, an immunoglobulin or a ligand specific for parathyroid cells or a calcium receptor can be used as a target-specific component. The immunoglobulin can be a polyclonal or monoclonal antibody and may comprise whole antibodies or immunologically reactive fragments of these antibodies such as F$_{(ab')}$, F$_{(ab)}$, or (F$_{ab'}$)$_2$.

A wide variety of labeling moieties can be used, including radioisotopes, chromophores, and fluorescent labels. Radioisotope labeling in particular can be readily detected in vivo. Radioisotopes may be coupled by coordination as cations in the porphyrin system. Useful cations include technetium, gallium, and indium. In the compositions, the positively charged molecule can be linked to or associated with a label.

II. SYNTHESIS OF CALCIUM RECEPTOR-MODULATING AGENTS

Different ionomimetics and ionolytics can be synthesized by using procedures known in the art and described herein. Ionomimetics and ionolytics can also be synthesized as described by Bradford C Vanwagenen, Steven R Duff, William A. Nelson and Thomas E. D'Ambra in U.S. Patent Application, entitled "Amine Preparation" hereby incorperated by reference herein.

A. Synthesis of Polyamines

The synthetic methods used to produce polyamines described in this section are modelled after methods used to construct argiopines 636 and 659 and other arylalkyl polyamines derived from spider venoms. Polyamines can be synthesized starting with, for example, diaminoalkanes and simple polyamines such as spermidine or spermine. Strategies for the synthesis and the modification of polyamines involve using a variety of amine-protecting groups (e.g., phthalimido, BOC, CBZ, benzyl, and nitrile) which can be selectively removed to construct functionalized molecules.

Chain extensions, of the starting material, by 2–4 methylenes were typically accomplished by alkylation with the corresponding N-(bromoalkyl)phthalimide. A 1:1.2 mixture of amine to the bromoalkylphthalimide was refluxed in acetonitrile in the presence of 50% KF on Celite. Chain extensions were also accomplished by alkylation of a given amine with acrylonitrile or ethylacrylate. Reaction progress was monitored by thin-layer chromatography (TLC) and intermediates purified on silica gel using combinations of dichloromethane, methanol, and isopropylamine. Final products were purified by cation exchange (HEMA-SB) and RP-HPLC (Vydac C-18). Purity and structure verification were accomplished by $^1$H- and $^{13}$C-NMR spectroscopy and high-resolution mass spectrometry (EI, CI and/or FAB).

Amine-protecting groups, phthalimido, BOC, CBZ, benzyl, and nitrile, were added and later selectively removed to construct functionalized molecules. BOC protecting groups were added by treating a primary or secondary amine (1° or 2°) with di-tert-butyl dicarbonate in dichloromethane. Benzyl protecting groups were applied in one of two ways: (1) condensation of a 1° amine with benzaldehyde followed by sodium borohydride reduction or (2) alkylation of a 2° amine with benzylbromide in the presence of KF.

Deprotection of the different groups was carried out using different procedures. Deprotection of the phthalimido functionality was accomplished by reduction with hydrazine in refluxing methanol. Deprotection of the BOC functionality was accomplished in anhydrous TFA or concentrated HCl in acetonitrile. Deprotection of benzyl, nitrile, and CBZ protecting functionalities was accomplished by reduction in glacial acetic acid under 55 psi hydrogen in the presence of a catalytic amount of palladium hydroxide on carbon. Nitrile functionalities in the presence of benzyl and CBZ groups were selectively reduced under hydrogen in the presence of sponge Raney nickel.

Amide linkages were typically prepared by reacting an amine (1° or 2°) with an N-hydroxysuccinimide or p-nitrophenylester of a given acid. This was accomplished directly, in the case of adding cyclic groups, by treating the amine with dicyclohexylcarbodiimide under dilute conditions.

Specifically, branched polyamines are typically prepared from simple diaminoalkanes of the formula NH$_2$—(CH$_2$)$_n$—NH$_2$, or simple polyamines such as spermidine or spermine. One of the two primary (terminal) amines is protected or "masked" with a protecting group such as BOC (t-butyloxycarbonyl), phthalimido, benzyl, 2-ethylnitrile (the Michael condensation production product of an amine and acrylonitrile), or amide. A typical reaction is the addition of a BOC protecting group by treatment with di-t-butyl-dicarbonate (BOC anhydride):

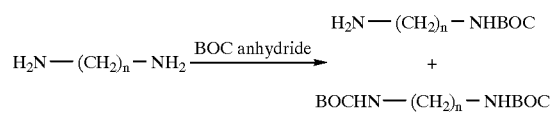

The monoprotected product is separated from the unprotected and diprotected products by simple chromatographic or distillation techniques.

The remaining free amine in the monoprotected product is then selectively alkylated (or acylated) with an alkylating (or acylating) agent. To ensure mono-alkylation, the free amine is partially protected by condensation with benzaldehyde followed by sodium borohydride reduction to form the N-benzyl derivative:

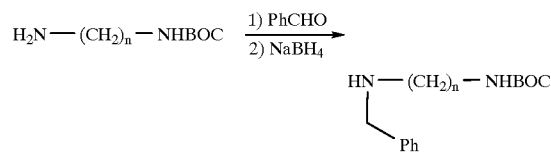

The N-benzyl derivative is then reacted with the alkylating agent. A typical alkylating agent is in an N-(bromoalkyl) phthalimide, which reacts as follows:

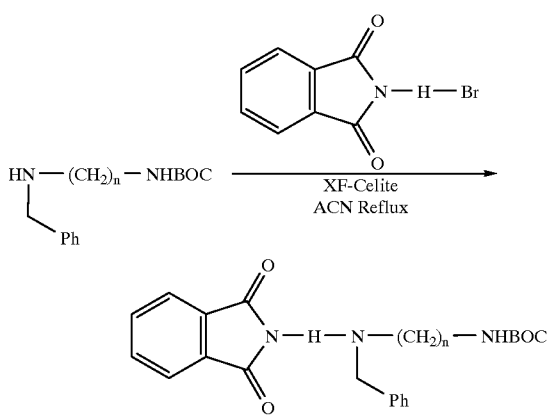

For example, N-(bromobutyl)phthalimide is used to extend or branch the chain with four methylene units. Alternatively, reaction with acrylonitrile followed by reduction of the cyano group will extend the chain by three methylenes and an amino group.

The protecting groups of the resulting chain-extended molecule can then be selectively cleaved to yield a new free amine. For example, trifluoroacetic acid is used to remove a BOC group; catalytic hydrogenation is used to reduce a nitrile functionality and remove a benzyl group; and hydrazine is used to remove phthalimido groups as follows:

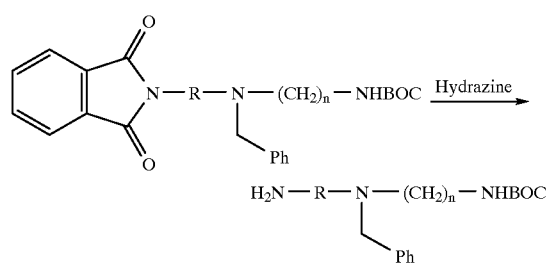

The new free amine may be alkylated (or acylated) further as above to increase the length of the polyamine. This process is repeated until the desired chain length and number of branches is obtained. In the final step, deprotection of the product results in the desired polyamine. However, further modifications may be effected at the protected end prior to deprotection. For example, prior to BOC-deprotection, the polyamine is acylated with the N-hydroxysuccinimide ester of 3,4-dimethoxyphenylacetic acid to yield a diprotected polyamine:

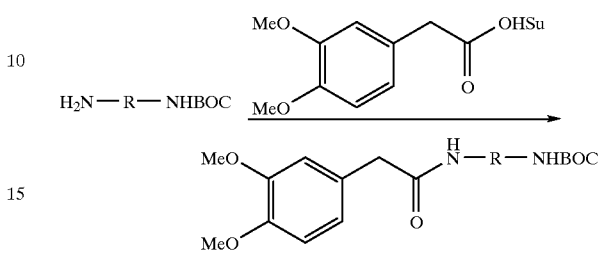

This ultimately yields an arylalkyl polyamine. The BOC group can then be selectively removed with trifluoroacetic acid to expose the other amino terminus which can be extended as above.

Certain branched polyamines may be formed by simultaneously alkylating or acylating the free primary and secondary amines in a polyamine formed as above. For example, treatment of spermine with excess acrylonitrile followed by catalytic reduction yields the following:

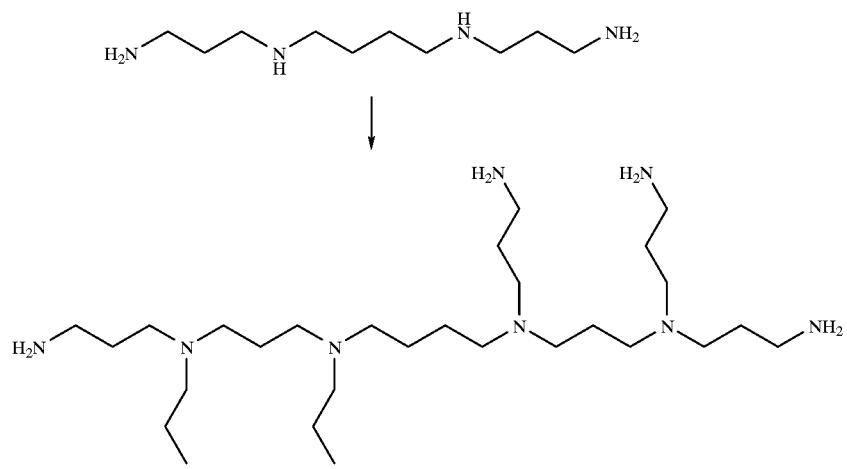

Cyclic polyamines may be prepared as above with starting materials such as hexacylen (Aldrich Chem.).

B. Polyamino Acid Synthesis

Polyamino acids can be made using standard techniques such as being translated using recombinant nucleic acid techniques or being synthesized using standard solid-phase techniques. Solid-phase synthesis is commenced from the carboxy-terminal end of the peptide using an α-amino protected amino acid. BOC protective groups can be used for all amino groups even through other protective groups are suitable. For example, BOC-lys-OH can be esterified to chloromethylated polystyrene resin supports. The polystyrene resin support is preferably a copolymer of styrene with about 0.5 to 2% divinylbenzene as a cross-linking agent which causes the polystyrene polymer to be completely insoluble in certain organic solvents. See Stewart et al., *Solid-Phase Peptide Synthesis* (1969), W. H. Freeman Co., San Francisco; and Merrifield, *J. Am. Chem. Soc.* (1963) 85:2149–2154. These and other methods of peptide synthesis are also exemplified by U.S. Pat. Nos. 3,862,925; 3,842,067; 3,972,859; and 4,105,602.

The polypeptide synthesis may use manual techniques or be automated. For example, synthesis can be carried out using an Applied Biosystems 403A Peptide Synthesizer (Foster City, Calif.) or a Biosearch SAM II automatic peptide synthesizer (Biosearch, Inc., San Rafael, Calif.), following the instructions provided in the instruction manual supplied by the manufacturer.

C. Arylalkyl Polyamines

Arylalkyl polyamines such as those shown in FIG. 1 can be obtained from natural sources isolated by known techniques, or synthesized as described in Jasys et al., *Tetrahedron Lett.* 29:6223–6226, (1988); Nason et al., *Tetrahedron Lett.* 30:2337–2340, (1989); and Schafer et al., "Polyamine Toxins from Spiders and Wasps," *The Alkaloids*, vol. 45, p. 1–125, 1994.

D. Arylalkylamines

This section describes general protocol to prepare arylalkylamines such as fendiline or fendiline analogues as shown in FIG. 36. In a 10-ml round-bottom flask equipped with a magnetic stir bar and rubber septum, 1.0 mmole 3,3'-diphenylpropylamine (or primary alkylamine such as substituted or unsubstituted phenylpropylamine) in 2 ml ethanol was treated with 1.0 mmole acetophenone (or substituted acetophenone). Two millimoles $MgSO_4$ and 1.0 mmole $NaCNBH_3$ were then added and the solution was stirred under a nitrogen atmosphere at room temperature (about 20° C.) for 24 hours. The reaction was poured into 50 ml ether and washed 3 times with 1 N NaOH and once with brine. The ether layer was dried with anhydrous $K_2CO_3$ and reduced in vacuo. The product was then purified by column chromatography or HPLC incorporating a silica stationary phase with combinations of $CH_2Cl_2$-methanol-isopropylamine (typically 3% methanol and 0.1% isopropylamine in methylene chloride).

A preferred procedure for preparing fendiline or fendiline analogues (such as those depicted in FIG. 36) uses titanium (IV) isopropoxide and was modified from methods described in *J. Org. Chem.* 55:2552 (1990). For the synthesis of Compound 2M, titanium tetrachloride (method described in *Tetrahedron Lett.* 31:5547 (1990)) was used in place of titanium(IV) isopropoxide.

A reaction scheme is depicted in FIG. 43a. In FIG. 43a, R, R' and R" depict appropriately substituted hydrocarbon and aromatic moieties groups. Referring to FIG. 43a in a 4-ml vial, 1 mmole of amine (1) (typically a primary amine) and 1 mmole ketone or aldehyde (2) (generally an appropriately substituted acetophenone) are mixed, then treated with 1.25 mmoles titanium(IV) isopropoxide (3) and allowed to stand with occasional stirring at room temperature for about 30 minutes. Alternatively, a secondary amine may be used in place of (1). Reactions giving heavy precipitates or solids can be heated to their melting point to allow for mixing during the course of the reaction.

The reaction mixture is then treated with 1 ml ethanol containing 1 mmole sodium cyanoborohydride (4) and the resulting mixture is allowed to stand at room temperature with occasional stirring for about 16 hours. After this time the reaction is quenched by the addition of about 500 µl water. The reaction mixture is then diluted to about 4 ml total volume with ethyl ether and then centrifuged. The upper organic phase is removed and reduced on a rotavapor. The resulting product (6) is partially purified by chromatography through a short silica column (or alternatively by using preparative TLC on silica) using a combination of dichloromethane-methanol-isopropylamine (typically 95:5:0.1), and then purified by HPLC (normal-phase using silica with dichloromethane-methanol-isopropylamine or reversed phase, C-18 with 0.1% TFA with acetonitrile or methanol).

Chiral resolution may be accomplished using methods such as those described in Example 22, infra.

III. INORGANIC ION RECEPTORS, DERIVATIVES, AND FRAGMENTS

The invention also relates to a superfamily of inorganic ion receptor proteins including derivatives thereof, and inorganic ion receptor fragments. Members of the superfamily are related to each other by similarity of amino acid sequence and structure. Receptor proteins, such as the calcium receptor, have intracellular domains, extracellular domains, transmembrane domains, and multiple-transmembrane domains. Preferably, the novel superfamily of inorganic ion receptors have an amino acid sequence similarity of at least 15% to the human calcium receptor (SEQ. ID. NOs. 6 and 7) and respond to inorganic ions.

Calcium receptors appear to be functionally related to a class of receptors which utilize so-called "G" proteins to couple ligand binding to intracellular signals. Such "G-coupled" receptors may elicit increases in intracellular cyclic AMP due to the stimulation of adenylyl cyclase by a receptor activated "$G_s$" protein, or else may elicit a decrease in cyclic AMP due to inhibition of adenylyl cyclase by a receptor activated "$G_i$" protein. Other receptor activated G proteins elicit changes in inositol triphosphate levels resulting in release of $Ca^{2+}$ from intracellular stores. This latter mechanism is particularly pertinent to calcium receptors.

A. Inorganic Ion Receptors

Inorganic ion receptors have an amino acid sequence encoding a functioning inorganic ion receptor. Inorganic ion receptors include proteins having the amino acid sequence of the receptor protein normally found in a cell and derivatives thereof. Inorganic ion receptors are distinguished by their ability to detect and respond to changes in the levels of inorganic ions by evoking a change in cellular function. Changes in cellular function may involve changes in secondary messenger levels such those mediated by G protein coupled to the receptor or changes in ionic transmembrane ion flux. Inorganic ions include cations such as calcium, magnesium, potassium, sodium, or hydrogen ions and anions such as phosphate or chloride ions. $Cd^{2+}$ sensing receptors are described by Herbert in U.S. application entitled "Cloned Human Cadmium(II) -Sensing Receptor and Uses thereof," hereby incorporated by reference herein.

Regardless of the nature of the physiological ligand or activator of an inorganic ion receptor, inorganic ion receptors can be "promiscuous" in that they can be activated by non-physiological stimuli. These non-physiological stimuli may be useful, for example, to identify another inorganic ion receptor or to facilitate the isolation of the gene encoding it. An example of an inorganic ion receptor responding to a non-physiological stimuli is the ability of osteoclast calcium receptor to respond not only to $Ca^{2+}$, but also to $Mn^{2+}$, $Co^{2+}$ and $Ni^{2+}$. The cations $Mn^{2+}$ and $Co^{2+}$ also serve to distinguish the osteoclast calcium receptor from the parathyroid calcium receptor.

Another example of an inorganic ion receptor responding to a non-physiological stimuli is the ability of the parathyroid calcium receptor to respond to low concentrations of $La^{3+}$ and $Gd^{3+}$ which are highly unlikely to be encountered under normal circumstances. Nevertheless, $Gd^{3+}$ has been used successfully as an activator for the calcium receptor and facilitated the cloning of this receptor by expression in *Xenopus oocytes* (see Example 25).

Additionally, receptors belonging to the superfamily of inorganic ion receptors may also be activated by stimuli other than ligand binding. For example, some members are activated by physical forces such as stretch forces acting on membranes of cells expressing inorganic ion receptors.

B. Inorganic Ion Receptor Derivatives

Derivatives of a particular receptor have similar amino acid sequences and retain, to some extent, one or more activities of the related receptor. Derivatives have at least 15% sequence similarity, preferably 70%, more preferably 90%, even more preferably 95% sequence similarity to the related receptor. "Sequence similarity" refers to "homology" observed between amino acid sequences in two different polypeptides, irrespective of polypeptide origin.

The ability of the derivative to retain some activity can be measured using techniques described herein, for example, those described in Section I supra. Derivatives include modifications occurring during or after translation, for example, by phosphorylation, glycosylation, crosslinking, acylation, proteolytic cleavage, linkage to an antibody molecule, membrane molecule or other ligand (see Ferguson et al., 1988, *Annu. Rev. Biochem.* 57:285–320).

Specific types of derivatives also include amino acid alterations such as deletions, substitutions, additions, and amino acid modifications. A "deletion" refers to the absence of one or more amino acid residue(s) in the related polypeptide. An "addition" refers to the presence of one or more amino acid residue(s) in the related polypeptide. Additions and deletions to a polypeptide may be at the amino terminus, the carboxy terminus, and/or internal. Amino acid "modification" refers to the alteration of a naturally occurring amino acid to produce a non-naturally occurring amino acid. A "substitution" refers to the replacement of one or more amino acid residue(s) by another amino acid residue(s) in the polypeptide. Derivatives can contain different combinations of alterations including more than one alteration and different types of alterations.

While the effect of an amino acid change varies depending upon factors such as phosphorylation, glycosylation, intrachain linkages, tertiary structure, and the role of the amino acid in the active site or a possible allosteric site, it is generally preferred that the substituted amino acid is from the same group as the amino acid being replaced. To some extent the following groups contain amino acids which are interchangeable: the basic amino acids lysine, arginine, and histidine; the acidic amino acids aspartic and glutamic acids; the neutral polar amino acids serine, threonine, cysteine, glutamine, asparagine and, to a lesser extent, methionine; the nonpolar aliphatic amino acids glycine, alanine, valine, isoleucine, and leucine (however, because of size, glycine and alanine are more closely related and valine, isoleucine and leucine are more closely related); and the aromatic amino acids phenylalanine, tryptophan, and tyrosine. In addition, although classified in different categories, alanine, glycine, and serine seem to be interchangeable to some extent, and cysteine additionally fits into this group, or may be classified with the polar neutral amino acids.

While proline is a nonpolar neutral amino acid, its replacement represents difficulties because of its effects on conformation. Thus, substitutions by or for proline are not preferred, except when the same or similar conformational results can be obtained. The conformation conferring properties of proline residues may be obtained if one or more of these is substituted by hydroxyproline (Hyp).

Examples of modified amino acids include the following: altered neutral nonpolar amino acids such as ω-amino acids of the formula $H_2N(CH_2)_nCOOH$ where n is 2–6, sarcosine (Sar), t-butylalanine (t-BuAla), t-butylglycine (t-BuGly), N-methyl isoleucine (N-MeIle), and norleucine (Nleu); altered neutral aromatic amino acids such as phenylglycine; altered polar, but neutral amino acids such as citrulline (Cit) and methionine sulfoxide (MSO) ; altered neutral and nonpolar amino acids such as cyclohexyl alanine (Cha); altered acidic amino acids such as cysteic acid (Cya); and altered basic amino acids such as ornithine (Orn).

Preferred derivatives have one or more amino acid alteration(s) which do not significantly affect the receptor activity of the related receptor protein. In regions of the calcium receptor protein not necessary for receptor activity amino acids may be deleted, added or substituted with less risk of affecting activity. In regions required for receptor activity, amino acid alterations are less preferred as there is a greater risk of affecting receptor activity. Such alterations should be conservative alterations. For example, one or more amino acid residues within the sequence can be substituted by another amino acid of a similar polarity which acts as a functional equivalent.

Conserved regions tend to be more important for protein activity. than non-conserved regions. Standard procedures can be used to determine the conserved and non-conserved regions important of receptor activity using in vitro mutagenesis techniques or deletion analyses and measuring receptor activity as described by the present disclosure.

Derivatives can be produced using standard chemical techniques and recombinant nucleic acid techniques. Modifications to a specific polypeptide may be deliberate, as through site-directed mutagenesis and amino acid substitution during solid-phase synthesis, or may be accidental such as through mutations in hosts which produce the polypeptide. Polypeptides including derivatives can be obtained using standard techniques such as those described herein, and by Sambrook et al., *Molecular Cloning*, Cold Spring Harbor Laboratory Press (1989). For example, Chapter 15 of Sambrook describes procedures for site-directed mutagenesis of cloned DNA.

C. Receptor Fragments

Receptor fragments are portions of inorganic ion receptors. Receptor fragments preferably bind to one or more binding agents which bind to a full-length receptor. Binding agents include ionomimetics, ionolytics, and antibodies which bind to the receptor. Fragments have different uses such as to select other molecules able to bind to a receptor.

Fragments can be generated using standard techniques such as expression of cloned partial sequences of receptor DNA and proteolytic cleavage of a receptor protein. Proteins are specifically cleaved by proteolytic enzymes, such as trypsin, chymotrypsin or pepsin. Each of these enzymes is specific for the type of peptide bond it attacks. Trypsin catalyzes the hydrolysis of peptide bonds whose carbonyl group is from a basic amino acid, usually arginine or lysine. Pepsin and chymotrypsin catalyze the hydrolysis of peptide bonds from aromatic amino acids, particularly tryptophan, tyrosine and phenylalanine.

Alternate sets of cleaved protein fragments are generated by preventing cleavage at a site which is susceptible to a proteolytic enzyme. For example, reaction of the ε-amino group of lysine with ethyltrifluorothioacetate in mildly basic solution yields a blocked amino acid residue whose adjacent peptide bond is no longer susceptible to hydrolysis by trypsin. Goldberger et al., *Biochemistry* 1:401 (1962). Treatment of such a polypeptide with trypsin thus cleaves only at the arginyl residues.

Polypeptides also can be modified to create peptide linkages that are susceptible to proteolytic enzyme-catalyzed hydrolysis. For example, alkylation of cysteine residues with β-haloethylamines yields peptide linkages that are hydrolyzed by trypsin. Lindley, Nature, 178: 647 (1956).

In addition, chemical reagents that cleave polypeptide chains at specific residues can be used. Witcop, Adv. Protein Chem. 16: 221 (1961). For example, cyanogen bromide cleaves polypeptides at methionine residues. Gross & Witkip, J. Am. Chem. Soc. 83: 1510 (1961).

Thus, by treating an inorganic ion receptor, such as, for example, a human calcium receptor or fragments thereof, with various combinations of modifiers, proteolytic enzymes and/or chemical reagents, numerous discrete overlapping peptides of varying sizes are generated. These peptide fragments can be isolated and purified from such digests by chromatographic methods. Alternatively, fragments can be synthesized using an appropriate solid-state synthetic procedure.

Fragments may be selected to have desirable biological activities. For example, a fragment may include just a ligand binding site. Such fragments are readily identified by those of ordinary skill in the art using routine methods to detect specific binding to the fragment. For example, in the case of a calcium receptor, nucleic acid encoding a receptor fragment can be expressed to produce the polypeptide fragment which is then contacted with a receptor ligand under appropriate association conditions to determine whether the ligand binds to the fragment. Such fragments are useful in screening assays for agonists and antagonists of calcium, and for therapeutic effects where it is useful to remove calcium from serum, or other bodily tissues.

Other useful fragments include those having only the external portion, membrane-spanning portion, or intracellular portion of the receptor. These portions are readily identified by comparison of the amino acid sequence of the receptor with those of known receptors, or by other standard methodology. These fragments are useful for forming chimeric receptors with fragments of other receptors to create a receptor with an intracellular portion which performs a desired function within that cell, and an extracellular portion which causes that cell to respond to the presence of ions, or those agonists or antagonists described herein. Chimeric receptor genes when appropriately formulated are useful in genetic therapies for a variety of diseases involving dysfunction of receptors or where modulation of receptor function provides a desirable effect in the patient.

Additionally, chimeric receptors can be constructed such that the intracellular domain is coupled to a desired enzymatic process which can be readily detected by calorimetric, radiometric, luminometric, spectrophotometric or fluorimetric assays and is activated by interaction of the extracellular portion with its native ligand (e.g., calcium) or agonist and/or antagonists of the invention. Cells expressing such chimeric receptors can be used to facilitate screening of inorganic ion receptor agonists and antagonists.

IV. NUCLEIC ACIDS ENCODING ION-RECEPTORS

The invention also features nucleotide sequences encoding inorganic ion receptors and receptor fragments. Nucleotide sequences encoding inorganic ion receptors may be obtained from organisms through a variety of procedures, such as through the use of hybridization probes, antibodies binding a receptor, gene walking, and/or expression assays.

A nucleic acid encoding a particular receptor provides for additional tools to obtain more receptors, for example by providing for hybridization assay probes and antibodies. Furthermore, sequence information from two or more receptors can be analyzed to determine localized sequence conservation which is useful for obtaining still additional clones encoding other members of the superfamily. Conserved sequences also may be derived from an analysis of the overall structure of BoPCaR 1, as it conventionally includes an extracellular domain, transmembrane domain and intracellular domain.

"Conserved nucleic acid regions" refers to two or more nucleic acids encoding an inorganic ion receptor, preferably a calcium receptor, to which a particular nucleic acid sequence can hybridize to under lower stringency conditions. Examples of lower stringency conditions suitable for screening for nucleic acid encoding inorganic ion receptors are provided in the examples below and in Abe et al. J. Biol. Chem., 19:13361 (1992) (hereby incorporated by reference herein). Preferably, conserved regions differ by no more than 7 out of 20 nucleotides.

In preferred embodiments the purified nucleic acid encodes an extracellular domain, but is substantially free of transmembtane and intracellular domains; the purified nucleic acid encodes an intracellular domain, but is substantially free of transmembrane and extracellular domains; the purified nucleic acid encodes a transmembrane domain, but is substantially free of an extracellular or intracellular domain; the purified nucleic acid encodes a multiple-transmembrane domain (e.g., a seven-transmembrane domain), but is substantially free of C-terminal intracellular and N-terminal extracellular regions; the purified nucleic acid encodes an extracellular domain which is transcriptionally coupled to nucleic acid encoding a transmembrane, multiple-transmembrane, and/or intracellular domain of a non-inorganic ion receptor or a different inorganic ion receptor and results in a fusion protein; the purified nucleic acid encodes an extracellular domain of a non-inorganic ion receptor or a different inorganic ion receptor which is transcriptionally coupled to nucleic acid encoding a transmembrane, multiple-transmembrane, and/or intracellular domain of an inorganic ion receptor and results in a fusion protein.

In addition, isolated nucleic acid sequences of the invention may be engineered so as to modify processing or expression of receptor sequences. For example, the coding sequence may be combined with an exogenous promoter sequence and/or a ribosome binding site. Another example, is that codons may be modified such that while they encode an identical amino acid, that codon may be a preferred codon in the chosen expression system.

Additionally, a given coding sequence can be mutated in vitro or in vivo, to create variations in coding regions and/or form new restriction endonuclease sites or destroy preexisting ones, to facilitate further in vitro modification. Standard recombinant techniques for mutagenesis such as in vitro site-directed mutagenesis (Hutchinson et al., J. Biol. Chem. 253:6551, (1978), Sambrook et al., chapter 15, supra), use of TAB® linkers (Pharmacia), and PCR-directed mutagenesis can be used to create such mutations.

Cloning the calcium receptor from different cells will allow the presence of homologous proteins in other cells to be directly assessed. A family of structurally homologous calcium receptor proteins can thus be obtained. Such receptors will allow understanding of how these cells detect extracellular $Ca^{2+}$ and enable evaluation of the mechanism (s) as a site of action for the therapeutics described herein effective in the treatment of for example, HPT, osteoporosis, and hypertension, and novel therapies for other bone and mineral-related diseases.

A. Assays To Detect Receptors

Various assays can be used to detect the presence of an inorganic ion receptor such as calcium receptor and fragments thereof. Such assays include detecting the presence of receptor protein, or receptor activity, expressed by nucleic acid encoding the receptor. Examples of assays for measuring calcium receptor activity are described below. Equivalent assays for other inorganic ion receptors such as $Na^+$, $K^+$, and phosphate are known in the art.

1. Measurement of Receptor Activity

The ability of nucleic acid to encode a functioning calcium receptor can be conveniently measured using a Xenopus expression assay to detect increases in intracellular $Ca^{2+}$ due to receptor activation. Increases in intracellular $Ca^+$ can be measured by different techniques such as by measuring current through the endogenous $Ca^{2+}$-activated $Cl^-$ channel; loading oocytes with $^{45}Ca^{2+}$ and measuring mobilization of $^{45}Ca^{2+}$ from intracellular stores; and using fluorescent $Ca^{2+}$ indicators. Expression assays can also be used to measure the calcimimetic and calcilytic activity of agents using Xenopus egg containing nucleic acid expressing a functioning calcium receptor.

Receptors are activated by using receptor ligands, such as neomycin, $Gd^{3+}$, $Ca^{2+}$, $Mg^{2+}$ or other calcimimetic compound. The ability of receptors to be activated by calcimimetics can be measured in a Xenopus expression assay. For example, molecules can be tested for their ability to elicit increases in intracellular $Ca^{2+}$ in *Xenopus oocytes* containing nucleic acid expressing a functioning calcium receptor indirectly by measuring current through the endogenous $Ca^{2+}$-activated $Cl^-$ channel. The amplification of the response afforded by this signal transduction pathway enables the detection of receptor proteins encoded by mRNA at very low levels. This allows the detection of receptor-specific cDNA clones without the need for high-affinity ligands, specific antisera, or protein or nucleic acid sequence information.

For example, for each mRNA fraction, 10–20 oocytes are injected with 50 ng of RNA at a concentration of 1 ng/nl in water. Injected oocytes are maintained at 18° C. for 48–72 hours, after which they are assessed for expression of the calcium receptor using measurements of $Cl^-$ current. For each group of injected oocytes, the number positive for expression of the receptor, as well as the magnitude of the $Ca^{2+}$-dependent $Cl^-$ current measured, is determined. As negative controls, oocytes are injected with rat liver poly $(A)^+$-enriched mRNA, yeast RNA, or water.

2. Measuring the Presence of a Receptor

The presence of a receptor protein or polypeptide fragment can be carried out using agents which bind to the receptor. The binding agent should have a group which readily indicates its presence, such as a radiolabel, or group which can be easily detected, such as an antibody.

Antibodies can be used to screen expression libraries, such as cDNA libraries in λgt11 to determine the presence of clones expressing antigenically reactive protein. Screening can be carried out using standard techniques. Sambrook et al., *Molecular Cloning*, chapter 18, Cold Spring Harbor Laboratory Press (1989. Clones testing positive can be purified and then sequenced to determine whether they encode a calcium receptor.

Similarly phage display libraries can be used to clone and analyze calcium receptors in place of monoclonal antibodies. In these libraries, antibody-variable regions or random peptides are shotgun cloned into phage expression vectors such that the antibody regions or peptides are displayed on the surface of the phage particle. Phage(s) which display antibody regions or peptides capable of high specific binding to calcium receptors will bind to cells which display these receptors (e.g., parathyroid cells, C-cells, osteoclasts, etc.). Hundreds of millions of such phage can be panned against these cell types preferentially selecting those phage which can bind to these cells (which includes those phage binding to calcium receptors). In this manner, the complexity of the library can be vastly reduced. Iterative repetition of this process results in a pool of phage which bind to the cell type used. Subsequently, screens for monoclonal antibodies can be used to isolate phage displaying a calcium receptor-binding antibody or peptide regions, and these phage can be used to isolate the calcium receptor for purposes of structural identification and cloning. Kits to prepare such phage-display libraries are commercially available (e.g., Stratacyte, or Cambridge Antibody Technology Limited).

Recombinant phage endowed with such calcium receptor-binding properties can also be used in lieu of monoclonal antibodies in the various analyses of calcium receptors. Such phage can also be used in high-throughput binding-competition screens to identify organic compounds capable of functional binding to calcium receptors which can serve as structural leads for the development of human therapeutics acting at the calcium receptor.

In another alternative, affinity cross-linking of radioligands to their receptors can be used to isolate the receptor protein as described by Pilch & Czech, 1 *Receptor Biochem. Methodol.* 161, 1984. Covalent attachment of a radioligand allows extensive washing to remove non-specific binding. For example, a high-affinity molecule, e.g., a random copolymer of arginine and tyrosine (MW=22K; argtyr ratio= 4:1) which mobilizes intracellular $Ca^{2+}$ with an $EC_{50}$ of about 100 nM or less, is iodinated with $^{125}I$, and cross-linked. Protamines, because of their much smaller size, may be preferable in cross-linking studies and can be reductively alkylated as described by Dottavio-Martin & Ravel, 87 *Analyt. Biochem.* 562, 1978.

Nonspecific labelling is kept to a minimum by cross-linking in the presence of unlabeled polycations and di- and trivalent cations. At high concentrations of these molecules, nonspecific interactions of the label with the cell surface might be reduced.

B. Expression Assay

This section describes techniques to clone bovine and human parathyroid cell calcium receptor cDNAs by functional expression in *Xenopus oocytes*. Adult female *Xenopus laevis* were obtained from *Xenopus I* (Ann Arbor, Mich.) and maintained according to standard procedures. Lobes of ovary were excised from hypothermically anesthetized toads. Clusters of oocytes were transferred into modified Barth's saline (MBS). Individual oocytes were obtained by incubation in MBS containing 2 mg/ml collagenase (Sigma, Type 1A) for 2 hours at 21° C. and stage V-VI oocytes were selected for injection.

Glass capillary tubes (1 mm diameter) were pulled to a fine tip and manually broken to achieve a tip diameter of about 15 μmeters. A droplet of mRNA (1 ng/nl in diethylpyrocarbonate (DEPC)-treated water) was placed onto PARA-FILM™ and drawn into the capillary tube by suction. The capillary tube was then connected to a picospritzer (WPI Instruments) and the volume of the air-pulsed droplets adjusted to deliver 50 ng of mRNA (typically 50 nl). A 35-mm culture dish with a patch of nylon stocking fixed to the bottom was used to secure the oocytes during injection of mRNA into the vegetal pole. The injected oocytes were placed into a 35-mm culture dish containing MBS, 100 μg/ml penicillin and 100 μg/ml streptomycin and incubated at 18° C. for 3 days.

Following incubation, an oocyte was placed into a 100-μl plastic chamber and superfused with MBS at a flow rate of 0.5 ml/min using a peristaltic pump. Test molecules or inorganic polycations were added by rapidly moving the tubing into different buffers. Recording and current-passing electrodes were constructed from thin-wall capillary tubing pulled to a resistance of 1–3 Mohms and filled with 3 M KCl. Oocytes were impaled (in the animal pole) with both electrodes under microscopic observation and connected to an Axon Instruments Axoclamp 2A voltage-clamp amplifier which was used to set the holding potential (−70 to −80 mV) and to measure the currents that were passed to maintain the holding potential. Currents were recorded directly onto a strip chart recorder.

For mRNA preparation, tissue was obtained from calves or patients with secondary HPT undergoing surgical removal of the parathyroid glands. Whole pieces of gland were used to prepare mRNA that directs the expression of the calcium receptor in *Xenopus oocytes*. Total cellular RNA was obtained by acid guanidinium thiocyanate/phenol extraction of homogenized glands. Oligo-dT cellulose chromatography was used to select poly(A)$^+$-mRNA by standard procedures.

Size fractionation of mRNA was carried out by centrifugation through glycerol gradients. The mRNA was denatured with 20 mM methylmercuric hydroxide and loaded (50–100 μg at a concentration of 1 mg/ml) onto a linear 15–30% glycerol gradient prepared in Beckman TLS55 tubes. Following centrifugation at 34,000 rpm for 16 hours, 0.3 ml gradient fractions were collected and diluted in an equal volume of water containing 5 mM beta-mercaptoethanol. The mRNA was then recovered by two cycles of ethanol precipitation.

The mRNA (50–100 μg of poly(A)$^+$) can also be separated on a 1.2% agarose/6.0 M urea preparative gel, along with a range of RNA size markers. Following visualization of the mRNA by ethidium bromide staining, gel slices containing RNA approximately 1 kb to 2 kb in size are excised. The mRNA is recovered from the agarose gel slices using RNAid binding matrix (according to the supplier's standard protocol; Stratagene, Inc.) and recovered mRNA fractions eluted into DEPC-treated water.

Amounts of recovered mRNA were quantified by UV absorbance measurement. The size range of mRNA contained within each fraction of the glycerol gradient was determined by formaldehyde/agarose gel electrophoresis using a small quantity (0.5 μg) of each sample.

The integrity of the mRNA was assessed by in vitro translation. Reticulocyte lysates (commercially available kits; BRL) were used to translate 0.05–0.5 μg of each mRNA fraction. The resulting $^{35}$S-labelled proteins were analyzed by SDS-PAGE. Intact mRNA was capable of directing the synthesis of proteins of a complete size range, corresponding roughly to the sizes of the individual mRNA fractions.

A cDNA library was then constructed in the vector λ ZAPII, using a modifications of the techniques described by Gubler and Hoffman. RNA fractions were tested for their ability to induce Cl$^-$ current. Fractions giving the best response in the oocyte assay were used as starting material for cDNA synthesis.

First-strand cDNA synthesis was primed with an oligo-dT/NotI primer-linker. Second-strand synthesis was performed using the RNase H/DNA Polymerase I self-priming method. Double-stranded cDNA was blunted with T4 DNA polymerase and EcoRI adaptors blunt-end ligated to the cDNA with T4 ligase. Following NotI digestion to cleave the linker, full-length cDNA was size-selected by exclusion chromatography on Sephacryl 500 HA. First-strand cDNA was radiolabeled with α-$^{32}$P-dATP, and all synthesis and recovery steps monitored by following the incorporation of radioactivity. Full-length cDNA recovered from the sizing column was ligated to EcoRI/NotI digested λ ZAPII arms. The ligation mix was test packaged with commercially available high-efficiency packaging extract (Stratagene, Inc.) and plated on the appropriate host strain (XL1-blue). The percentage of recombinant phage was determined by the ratio of white-to-blue plaques when the library was plated on IPTG and X-gal.

The average insert size was determined from ten randomly selected clones. Phage DNA "mini-preps" were digested with EcoRI and NotI to release the insert, and the size determined by agarose gel electrophoresis. The library consisted of >90% recombinant phage, and the insert size ranged from 1.5 to 4.2 kb. The recombinant ligation was packaged in large scale to generate 800,000 primary clones. The packaging mix was titered and plated at 50,000 plaques per 15 cm plate. Each pool of 50,000 clones was eluted in SM buffer and stored individually.

Plate lysate stocks of each of the clone pools were used for small-scale phage DNA preparation. Phage particles were concentrated by polyethylene glycol precipitation, and phage DNA purified by proteinase K digestion followed by phenol-chloroform extraction. Twenty micrograms of DNA were digested with NotI, and used as template for in vitro transcription of sense-strand RNA. In vitro transcription was carried out according to standard protocols, utilizing T7 RNA polymerase and 5' cap analog m$^7$GpppG in a 50 μl total reaction volume. Following Dnase I/Proteinase K digestion and phenol-chloroform extraction, the RNA was concentrated by ethanol precipitation and used for oocyte injection.

Oocytes were injected with synthetic mRNA (cRNA) from each of the 16 library subpools constituting 50,000 independent clones each. After incubation for 3 to 4 days, oocytes were assayed for the ability of 10 mM neomycin to elicit a Ca$^{2+}$-dependent Cl$^-$ current. A pool designated "pool 6" gave a positive signal and thus contains a cDNA clone encoding a functional calcium receptor.

Pool 6 phage was replated at about 20,000 plaques per plate and 12 plates harvested. DNA was prepared from each of these subpools and cRNA synthesized. Again, oocytes were injected with cRNA and assayed 3–4 days later for the ability of 10 mM neomycin to elicit a Ca$^{2+}$-dependent Cl$^-$ current. A subpool, pool 6-3, was positive and this pool was subjected to a further round of plating, reducing the complexity of pools to around 5,000 clones per pool. Pools were again assayed by preparation of cRNA and injection in oocytes. A subpool, pool 6-3.4, was positive.

To further purify the positive clone in pool 6-3.4, phage DNA from this pool was rescued as plasmid DNA by superinfection with the helper phage, ExAssist (Stratagene). Transfection of rescued plasmids into bacterial strain DH5alphaF' resulted in transformed bacterial colonies on ampicillin plates. These were harvested in pools of 900 clones each. Plasmid DNA was then prepared from each subpool and cRNA synthesized and assayed in the usual manner.

Subpool 6-3.4.4 was positive.

Bacteria containing the plasmid subpool 6-3.4.4 were subsequently plated in subpools of about 50 clones each. Continuation of this process is expected to result in a single clone encoding a functional calcium receptor.

C. Calcium-Trapping Assay

This section describes a "calcium-trapping assay" for the detection of COS 7 cells expressing G protein-coupled receptors. In this assay COS 7 cell monolayers are transfected with cDNA clones from a bovine parathyroid cDNA library (e.g., subfractions or pools from a library prepared in pCDNA1) and are assayed for their ability to trap radioactive $^{45}Ca^{2+}$ in response to treatment with an agonist for the calcium receptor. The monolayers undergo emulsion autoradiography and cells that have trapped $^{45}Ca^{2+}$ are identified by the presence of photographic grain clusters under darkfield microscopy. Library pools that produce a positive signal are then sequentially subdivided until a single cDNA that produces the signal is identified.

D. Hybrid-Depletion Assay

A hybrid depletion assay can be used to obtain mRNA encoding inorganic ion receptors. In this approach, clones are selected on the basis of their ability to deplete a specific mRNA species from the total mRNA population. A clone encoding a single subunit is identified by its ability to prevent the formation of the active multi-subunit complex. By exhaustive screening it is possible to identify clones encoding all of the necessary subunits.

Thus, the hybrid-depletion screening strategy can result in the isolation of clones that do not contain a complete protein coding region. Positive clones isolated by this screening strategy are sequenced to determine their protein coding capacity. Northern blot analysis of human parathyroid gland RNA permits the determination of the size of the complete mRNA corresponding to specific clones. If positive clones do not appear to be full length, the cloned cDNA will be used as a hybridization probe to screen a parathyroid gland cDNA library for complete cDNAs.

For example, human parathyroid cells express a beta-adrenergic receptor coupled to adenylate cyclase. This receptor can be expressed in oocytes, where it is capable of agonist-induced activation of the endogenous adenylate cyclase. During the hybrid-depletion screening for $Ca^{2+}$ receptor clones, oocytes injected with hybrid-depleted mRNA are assayed for isoproterenol-induced adenylate cyclase activation. A positive response in this assay serves to indicate that any observed inhibition of $Ca^{2+}$ receptor response is specific, and not due to a general inhibition of G protein receptor functions.

E. Cloning Using Hybridization Probes and Primers

The presently preferred method for isolating inorganic ion receptor nucleic acid is based upon hybridization screening. Region-specific primers or probes derived from nucleic acid encoding a calcium receptor can be used to prime DNA synthesis and PCR amplification, as well as to identify colonies containing cloned DNA encoding a member of the inorganic ion receptor family using known methods (e.g., Innis et al., PCR Protocols, Academic Press, San Diego, Calif. (1990)).

1. PCR Cloning

Primer hybridization specificity to target nucleic acid encoding an inorganic ion receptor can be adjusted by varying the hybridization conditions. When annealing at higher stringency conditions of 50–60° C., sequences which are greater than about 76% homologous to the primer will be amplified. By employing lower stringency conditions, annealing at 35–37° C., sequences which are greater than about 40–50% homologous to the primer will be amplified.

Analysis of the calcium receptor indicates that it is a G protein-coupled receptor having seven conserved transmembrane domains. One particularly useful approach is to employ degenerate primers homologous to the conserved transmembrane domain coding regions and to amplify DNA regions encoding these sequences using polymerase chain reaction (PCR). Thus, such oligonucleotide primers are mixed with genomic DNA or cDNA to RNA isolated from the tissue of choice and PCR carried out. Some experimentation may be required to specifically amplify novel G protein-coupled receptor sequences from the tissue of choice since these are not necessarily identical to already known G protein-coupled receptors, but this is well understood by those of ordinary skill in the art (see, for example, Buck, L. and Axel, R. (1991) Cell, 65:175–187).

2. Hybridization Assay Probes

Hybridization assay probes can be designed based on sequence information obtained from cloned calcium receptors and amino acid sequences encoding such receptors. Hybridization assay probes can be designed to detect the presence of a particular nucleic acid target sequence perfectly complementary to the probe and target sequences of lesser complementarity by varying the hybridization conditions and probe design.

DNA probes targeted to inorganic ion receptors can be designed and used under different hybridization conditions to control the degree of specificity needed for hybridization to a target sequence. Factors affecting probe design, such as length, G and C content, possible self-complementarity, and wash conditions, are known in the art. (See, for example, Sambrook et al., Molecular Cloning, Cold Spring Harbor Laboratory Press (1989).) Sambrook et al., Molecular Cloning, also discusses the design and use of degenerative probes based on sequence polypeptide information.

As a general guideline, high stringency conditions (hybridization at 50–65° C., 5× SSPC, 50% formamide, wash at 50–65° C., 0.5× SSPC) can be used to obtain hybridization between nucleic acid sequences having regions which are greater than about 90% complementary. Low stringency conditions (hybridization at 35–37° C., 5× SSPC, 40–45% formamide, wash at 42° C. SSPC) can be used so that sequences having regions which are greater than 35–45% complementarity will hybridize to the probe.

Any tissue encoding an inorganic ion receptor can be used as a source for genomic DNA. However, with respect to RNA, the most preferred source is tissues which express elevated levels of the desired inorganic ion receptor family member.

F. Targeting Gene Walking

Targeted gene walking (TGW) is a modification of a standard polymerase chain reaction (PCR) that allows amplification of unknown DNA sequences adjacent to short segments of known sequence. Parker et al., Nucl. Acids Res., 19: 3055 (1991). Unlike conventional PCR techniques that amplify DNA sequences between two known primer sites, TGW can amplify DNA adjacent to one such site. Thus, TGW can serve as a replacement for conventional cloning and library screening methods for isolating sequences upstream or downstream from known sequences. The procedure can be used to isolate genes from any starting DNA template for which a limited amount of sequence information is known.

For example, first, several standard PCR reactions are run in parallel using one "targeted primer" and different "walking primers." The targeted primer is a sequence-specific primer exactly complementary to a known sequence on the DNA molecule of interest, and is directed towards unknown adjacent sequences. The walking primers are non-specific sequences not complementary to DNA near the target primer. The walking primers can be any oligonucleotides unrelated to the target primer sequence.

In the first series of PCR, products are produced only when a walking primer anneals to a DNA strand contiguous with and complementary to the strand to which the targeted primer has hybridized. The PCR products of interest are preferably within the 5 kilobase size range. Amplification products are produced with as many as 60% mismatched nucleotides within the walking primer relative to DNA template. Perfect base-pairing is required only for the first two 3' nucleotides of the walking primer, but partial homology is tolerated otherwise. Annealing temperature is a key variable in determining the number of PCR products, as identified by agarose gel electrophoresis.

Second, an oligomer extension assay is performed using an "internal detection primer." This primer represents known sequences between the previous two primers, contiguous with the targeted primer. The internal detection primer is kinased with $^{32}$P-gamma-ATP, then used in a single PCR cycle with DNA from the first PCR as template. This extension identifies products in the first PCR contiguous with the targeted primer. These new products are identified by agarose gel electrophoresis and autoradiography. Any products that do not hybridize to the internal detection primer represent non-contiguous amplification products produced by any subset of the primers.

Last, bands identified in the oligomer extension assay are excised from the gel, and reamplified by standard PCR using target primer and the walking primer that produced the band initially. This new PCR band is then sequenced directly to provide previously unknown sequence information.

To extend information in the opposite direction, complements are made of the targeted and internal detection primers, and their order is reversed in the protocol. The pieces of information obtained from going in both directions are combined.

V. ANTIBODIES

Inorganic ion receptors, derivatives, and fragments thereof retaining antigenic determinants can be used to generate antibodies recognizing an inorganic ion receptor. Both polyclonal and monclonal antibodies can be generated. Because derivatives have a different amino acid sequence than the inorganic ion receptor, the derivative may not have all the antigenic determinants of the inorganic ion receptor which it is related to and may have some different antigenic determinants. Preferably, the inorganic ion receptor is a calcium receptor.

Antibodies can be produced and used to purify proteins using standard techniques such as those described by Harlow and Lane in Antibodies, *a Laboratory Manual*, Cold Spring Harbor Laboratory, 1988. Sources of immunogens for antibody production include purified inorganic ion receptors, purified inorganic ion receptor fragments, and whole cells expressing an inorganic ion receptor. Preferably, the immunogen is a purified calcium receptor, purified calcium receptor fragment, or whole cells expressing a purified calcium receptor. An example for obtaining antibodies to a calcium receptor from bovine parathyroid is described below.

For example, whole bovine parathyroid gland cells as the immunogen. Purified, dispersed cells are obtained, and live or fixed cell preparations are injected intraperitoneally into the appropriate mouse strain, according to established procedures. Standard protocols are followed for immunization schedules and for the production of hybridomas. A two-step screening procedure is used to identify hybridomas secreting monoclonal antibodies that recognize the calcium receptor.

The initial screen identifies monoclonal antibodies recognizing parathyroid cell surface antigens. Immunohistochemical techniques are then used to screen hybridoma supernatants for the presence of mouse antibodies that bind to the surface of parathyroid cells. The second screen can be performed on fixed sections of parathyroid gland tissue, or on dispersed cells in primary culture.

This procedure identifies hybridomas producing monoclonal antibodies to a variety of cell-surface determinants, and monoclonals specific for the calcium receptor would be expected to comprise only a small subset of these. To identify monoclonal antibodies that bind to the calcium receptor, hybridoma supernatants that test positive in the initial screen are assayed for their ability to block the response of cultured parathyroid cells to calcium receptor agonists. Some antibodies that bind to the extracellular domain of the receptor are expected to inhibit or activate ligand binding or to otherwise interfere with or affect receptor activation.

Monoclonal antibodies positive in both screens are characterized through western blotting, immunoprecipitation and immunohistochemistry. This permits the determination of the size of the antigen that is recognized and its tissue distribution. The appropriate monoclonal antibody is then used for purification of the calcium receptor protein by immunoaffinity chromatography, following standard techniques.

Polyclonal antibodies recognizing an ion receptor may be obtained by immunizing rabbits or other mammals with isolated ion receptor polypeptides. Polypeptides used for immunization can comprise the entire receptor polypeptide or fragments thereof.

Ion receptor polypeptides may be isolated from tissues or cells normally expressing the ion receptor of choice, or from cells constructed for the purpose of recombinant expression of such polypeptides.

VI. HIGHLIGHTED USES

This section highlights and expands on some of the uses of the ionomimetic and/or ionolytic molecules, receptor polypeptides, nucleic acids encoding receptor polypeptides and antibodies recognizing receptor polypeptides. Additional uses are discussed in other parts of the application and are apparent to one of ordinary skill in the art reading the application.

A. Treatment of Diseases

Diseases or disorders which can be treated by modulating calcium receptor activity are known in the art. For example, diseases or disorders which can be treated by modulating calcium receptor activity can be identified based on the functional responses of cells regulated by calcium receptor activity. Functional responses of cells regulated by calcium receptor are know in the art, including PTH secretion by parathyroid cells, calcitonin secretion by C-cells, and bone resorption by osteoclasts.

Such functional responses are associated with different diseases or disorders. For example, hyperparathyroidism results in elevated levels of PTH in the plasma. Decreasing the plasma levels of PTH offers an effective means of treating hyperparathyroidism. Likewise, increasing plasma levels of calcitonin is associated with an inhibition of bone resorption. Inhibiting bone resorption is an effective treatment for osteoporosis. Thus, modulation of calcium receptor activity can be used to treat diseases such as hyperparathyroidism, and osteoporosis.

Those compounds modulating inorganic ion receptor activity, preferably calcium receptor activity, can be used to confer beneficial effects to patients suffering from a variety of diseases or disorders. For example, osteoporosis is an age-related disorder characterized by loss of bone mass and increased risk of bone fracture. Compounds can be used to block osteoclastic bone resorption either directly (e.g., an osteoclast ionomimetic compound) or indirectly by increasing endogenous calcitonin levels (e.g., a C-cell calcimimetic). Alternatively, a calcilytic active on the parathyroid cell calcium receptor will increase circulating levels of parathyroid hormone, stimulating bone formation. All three of these approaches will result in beneficial effects to patients suffering from osteoporosis.

In addition, it is known that intermittent low dosing with PTH results in an anabolic effect on bone mass and appropriate bone remodeling. Thus, compounds and dosing regimens evoking transient increases in parathyroid hormone (e.g., intermittent dosing with a parathyroid cell ionolytic) can increase bone mass in patients suffering from osteoporosis.

Additional diseases or disorders can be identified by identifying additional cellular functional responses, associated with a disease or disorder, which are regulated by calcium receptor activity. Diseases or disorder which can be treated by modulating other inorganic ion receptors can be identified in an analogous manner.

Patient treatment can be carried out using different molecules described herein including: (1) inorganic ion receptor-modulating agents, preferably calcium receptor-modulation agents; (2) inorganic ion receptor proteins and fragments thereof, preferably calcium receptor proteins and fragments thereof; (3) nucleic acids encoding inorganic ion receptor proteins and fragments thereof, preferably calcium receptor proteins and fragments thereof; and (4) antibodies, and fragments thereof targeted to inorganic ion receptor proteins, preferably a calcium receptor.

1. Inorganic Ion Receptor-Modulating Agents

The inorganic ion receptor-modulating agents of the present invention can exert an affect on an inorganic ion receptor causing one or more cellular effects ultimately producing a therapeutic effect. Different types of diseases or disorders can be treated by modulating inorganic ion receptor activity, preferably calcium receptor activity, such as those having one or more of the following: (1) those characterized by abnormal inorganic ion homeostasis, preferably, calcium homeostasis; (2) those characterized by an abnormal amount of an extracellular or intracellular messenger whose production can be affected by inorganic ion receptor activity, preferably calcium receptor activity; and (3) other diseases or disorders in which modulation of inorganic ion receptor activity, preferably calcium receptor activity, will exert a beneficial effect, for example, in diseases or disorders where the production of an intracellular or extracellular messenger stimulated by receptor activity compensates for an abnormal amount of a different messenger.

Calcium receptor-modulating agents of the present invention can exert an effect on calcium receptor causing one or more cellular effects ultimately producing a therapeutic effect. Different diseases can be treated by the present invention by targeting cells having a calcium receptor. For example, primary hyperparathyroidism (HPT) is characterized by hypercalcemia and abnormal elevated levels of circulating PTH. A defect associated with the major type of HPT is a diminished sensitivity of parathyroid cells to negative feedback regulation by extracellular $Ca^{2+}$. Thus, in tissue from patients with primary HPT, the "set-point" for extracellular $Ca^{2+}$ is shifted to the right so that higher than normal concentrations of extracellular $Ca^{2+}$ are required to depress PTH secretion. Moreover, in primary HPT, even high concentrations of extracellular $Ca^{2+}$ often depress PTH secretion only partially. In secondary (uremic) HPT, a similar increase in the set-point for extracellular $Ca^{2+}$ is observed even though the degree to which $Ca^{2+}$ suppresses PTH secretion is normal. The changes in PTH secretion are paralleled by changes in $[Ca^{2+}]_i$: the set-point for extracellular $Ca^{2+}$-induced increases in $[Ca^{2+}]_i$ is shifted to the right and the magnitude of such increases is reduced.

Molecules that mimic the action of extracellular $Ca^{2+}$ are beneficial in the long-term management of both primary and secondary HPT. Such molecules provide the added impetus required to suppress PTH secretion which the hypercalcemic condition alone cannot achieve and, thereby, help to relieve the hypercalcemic condition. Molecules with greater efficacy than extracellular $Ca^{2+}$ may overcome the apparent nonsuppressible component of PTH secretion which is particularly troublesome in the major form of primary HPT caused by adenoma of the parathyroid gland. Alternatively or additionally, such molecules can depress synthesis of PTH, as prolonged hypercalcemia has been shown to depress the levels of preproPTH mRNA in bovine and human adenomatous parathyroid tissue. Prolonged hypercalcemia also depresses parathyroid cell proliferation in vitro, so calcimimetics can also be effective in limiting the parathyroid cell hyperplasia characteristic of secondary HPT.

Cells other than parathyroid cells can respond directly to physiological changes in the concentration of extracellular $Ca^{2+}$. For example, calcitonin secretion from arafollicular cells in the thyroid (C-cells) is regulated by changes in the concentration of extracellular $Ca^{2+}$.

Isolated osteoclasts respond to increases in the concentration of extracellular $Ca^{2+}$ with corresponding increases in $[Ca^{2+}]_i$ that arise partly from the mobilization of intracellular $Ca^{2+}$. Increases in $[Ca^{2+}]_i$ in osteoclasts are associated with the inhibition of bone resorption. Release of alkaline phosphatase from bone-forming osteoblasts is directly stimulated by calcium.

Renin secretion from juxtaglomerular cells in the kidney, like PTH secretion, is depressed by increased concentrations of extracellular $Ca^{2+}$. Extracellular $Ca^{2+}$ causes the mobilization of intracellular $Ca^{2+}$ in these cells. Other kidney cells respond to calcium as follows: elevated $Ca^{2+}$ inhibits formation of $1,25(OH)_2$-vitamin D by proximal tubule cells, stimulates production of calcium-binding protein in distal tubule cells, and inhibits tubular reabsorption of $Ca^{2+}$ and $Mg^{2+}$ and the action of vasopressin on the thick ascending limb of Henle's loop (MTAL), reduces vasopressin action in the cortical collecting duct cells, and affects vascular smooth muscle cells in blood vessels of the renal glomerulus.

Calcium also promotes the differentiation of intestinal goblet cells, mammary cells, and skin cells; inhibits atrial natriuretic peptide secretion from cardiac atria; reduces cAMP accumulation in platelets; alters gastrin and glucagon secretion; acts on vascular smooth muscle cells to modify cell secretion of vasoactive factors; and affects cells of the central nervous system and peripheral nervous system.

Thus, there are sufficient indications to suggest that $Ca^{2+}$, in addition to its ubiquitous role as an intracellular signal, also functions as an extracellular signal to regulate the responses of certain specialized cells. Molecules of this invention can be used in the treatment of diseases or disorders associated with disrupted $Ca^{2+}$ responses in these cells.

Specific diseases and disorders which might be treated or prevented, based upon the affected cells, also include those of the central nervous system such as seizures, stroke, head trauma, spinal cord injury, hypoxia-induced nerve cell damage such as in cardiac arrest or neonatal distress, epilepsy, neurodegenerative diseases such as Alzheimer's disease, Huntington's disease and Parkinson's disease, dementia, muscle tension, depression, anxiety, panic disorder, obsessive-compulsive disorder, post-traumatic stress disorder, schizophrenia, neuroleptic malignant syndrome, and Tourette's syndrome; diseases involving excess water reabsorption by the kidney such as syndrome of inappropriate ADH secretion (SIADH), cirrhosis, congestive heart failure, and nephrosis; hypertension; preventing and/or decreasing renal toxicity from cationic antibiotics (e.g., aminoglycoside antibiotics); gut motility disorders such as diarrhea, and spastic colon; GI ulcer diseases; GI diseases with excessive calcium absorption such as sarcoidosis; and autoimmune diseases and organ transplant rejection.

While calcium receptor-modulating agents of the present invention will typically be used in therapy for human patients, they may also be used to treat similar or identical diseases in other warm-blooded animal species such as other primates, farm animals such as swine, cattle, and poultry; and sports animals and pets such as horses, dogs and cats.

B. Toxin Binding Agents

The invention further provides receptor-binding agents includinglantibodies and/or fragments thereof which can be conjugated to a toxin moiety, or expressed along with a toxin moiety as a recombinant fusion protein. The toxin moiety will bind to and enter a target cell using the interaction of the binding agent and the corresponding target cell surface receptor. The toxin moiety results in targeted cell death. Thus, cells having calcium receptors characteristic of a disease or disorder, such as cancers, can be targeted by the present invention.

Suitable toxin moieties bound to a binding agent include proteins such as pokeweed anti-viral protein, abrin, diphtheria exotoxin, or Pseudomonas exotoxin; ricin, and a high energy-emitting radionuclide such as cobalt-60. Other examples of possible toxin moieties are known in the art. See, for example, "Conjugate Vaccines", *Contributions to Microbiology and Immunology*, J. M. Cruse and R. E. Lewis, Jr. (eds.), Carger Press, New York, (1989). The chosen toxin moiety should be pharmaceutically acceptable.

The conjugation of the binding agent to another moiety (e.g., bacterial toxin) can be accomplished by linking the two molecules using standard techniques so long as both molecules retain their respective activity. Possible linkages can be obtained by different chemical mechanisms, for example, covalent binding, affinity binding, intercalation, coordinate binding and complexation. Preferably, covalent binding is used. Covalent binding can be achieved either by direct condensation of existing side chains or by the incorporation of external bridging molecules.

Many bivalent or polyvalent linking agents are useful in coupling protein molecules, such as an antibody, to other molecules. Representative coupling agents include organic compounds such as thioesters, carbodiimides, succinimide esters, diisocyanates, glutaraldehydes, diazobenzenes and hexamethylene diamines. (See Killen and Lindstrom 1984, "Specific killing of lymphocytes that cause experimental autoimmune myasthenia gravis by toxin-acetylcholine receptor conjugates." *J. Immunol.* 133: 1335–2549; Jansen, F. K., H. E. Blythman, D. Carriere, P. Casella, O. Gros, P. Gros, J. C. Laurent, F. Paolucci, B. Pau, P. Poncelet, G. Richer, H. Vidal, and G. A. Voisin. 1982. "Immunotoxins: Hybrid molecules combining high specificity and potent cytotoxicity." *Immunological Rev.* 62: 185–216; and Vitetta et al., supra).

C. In Vitro Diagnostics

The different molecules of the present invention can be used to facilitate diagnosis of calcium-related diseases. Diagnosis can be carried in vitro or in vivo. For example, the molecules of the present invention can be used to assay for defects in calcium receptors and the ability of a cell to properly respond to extracellular calcium. Cells can be obtained from patients using standard medical techniques.

Ionomimetics and ionolytics, such as calcimimetics and calcilytics can be used to assay the responsiveness of a cell or tissue to extracellular calcium. For example, a tissue or a cell type such as an osteoclast can be obtained from a patient and treated with a calcimimetic. The cell's failure to respond to the calcimimetic indicates a defect in calcium receptor activity.

Nucleic acids encoding calcium receptors can be used to help determine whether a particular cellular defect is due to a defective calcium receptor or at a different point in calcium homeostasis. For example, after a cell defective in calcium homeostasis is identified, a nucleic acid encoding a functional calcium receptor can be inserted into the cell. The ability of the calcium receptor to return calcium homeostasis to normal indicates the defect is due to a calcium receptor.

Nucleic acid probes can be used to identify defects in calcium receptors occurring at the genetic level. For example, hybridization probes complementary to nucleic acid encoding a receptor can be used to clone the receptor. The cloned receptor can be inserted into a cell, such as an oocyte, and its responsiveness to a calcimimetic or calcilytic determined. Another example of using hybridization assay probes to detect defects involves using the probes to detect mRNA levels or the presence of nucleic acid sequences associated with a particular disease. A decreased mRNA level would be consistent with a decreased amount of expressed receptor.

Antibodies and fragments thereof able to recognize a calcium receptor antigen can be used to help determine calcium receptor number, integrity, structure, and to localize cells expressing calcium receptors in the body. For example, antibodies targeted to calcium receptors can be used to determine the number of receptors on a cell; antibodies able to distinguish defective from normal receptors can be used to determine the presence of defective receptors; antibodies targeted to a calcium receptor can be used to determine if a disease or surgical procedure results in the spread of normal or abnormal cells expressing calcium receptors; and antibodies targeted to a calcium receptor can be used to localize cells having abnormal calcium receptor number or structure to direct subsequent treatment.

D. Administration

The different molecules described by the present invention can be used to treat different diseases or disorders by modulating inorganic ion receptor activity, preferably calcium receptor activity. The molecules of the invention can be formulated for a variety of modes of administration, including systemic and topical or localized administration. Techniques and formulations generally may be found in *Remington's Pharmaceutical Sciences*, Mack Publishing Co., Easton, Pa.

Suitable dosage forms, in part, depend upon the use or the route of entry, for example oral, transdermal, or by injection. Such dosage forms should allow the agent to reach a target cell whether the target cell is present in a multicellular host or in culture. For example, pharmacological agents or compositions injected into the blood stream should be soluble. Other factors are known in the art, and include considerations such as toxicity and dosage form which retard the agent or composition from exerting its effect.

Agents can also be formulated as pharmaceutically acceptable salts (e.g., acid addition salts) and complexes thereof. Pharmaceutically acceptable salts are non-toxic salts at the concentration at which they are administered. The preparation of such salts can facilitate the pharmacological use by altering the physical characteristic of the agent without preventing it from exerting its physiological effect. Useful alterations in physical properties include lowering the melting point to facilitate transmucosal administration and increasing the volubility to facilitate administering higher concentrations of the drug.

Pharmaceutically acceptable salts include acid addition salts such as those containing sulfate, hydrochloride, phosphate, sulfamate, acetate, citrate, lactate, tartrate, methanesulfonate, ethanesulfonate, benzenesulfonate, p-toluenesulfonate, cyclohexylsulfamate and quinate. (See e.g., supra. PCT/US92/03736.) Pharmaceutically acceptable salts can be obtained from acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts can be prepared by standard techniques. For example, the free base form of a compound is dissolved in a suitable solvent, such as an aqueous or aqueous-alcohol solution, containing the appropriate acid and then isolated by evaporating the solution. In another example, a salt is prepared by reacting the free base and acid in an organic solvent.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical composition can be administered by different routes including intravenously, intraperitoneal, subcutaneous, and intramuscular, orally, topically, or transmucosally.

For systemic administration, oral administration is preferred. Alternatively, injection may be used, e.g., intramuscular, intravenous, intraperitoneal, and subcutaneous. For injection, the molecules of the invention are formulated in liquid solutions, preferably in physiologically compatible buffers such as Hank's solution or Ringer's solution. In addition, the molecules may be formulated in solid form and redissolved or suspended immediately prior to use. Lyophilized forms can also be produced.

Systemic administration can also be by transmucosal or transdermal means, or the molecules can be administered orally. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration may be through nasal sprays, for example, or using suppositories. For oral administration, the molecules are formulated into conventional oral administration dosage forms such as capsules, tablets, and liquid preparations.

For topical administration, the molecules of the invention are formulated into ointments, salves, gels, or creams, as is generally known in the art.

As shown in the examples provided herein, the amounts of various compounds of this invention to be administered can be determined by standard procedures. Generally, a therapeutically effective amount is between about 1 nmole and 3 $\mu$mole of the molecule, preferably 0.1 nmole and 1 $\mu$mole depending on its $EC_{50}$ or $IC_{50}$ and on the age and size of the patient, and the disease or disorder associated with the patient. Generally, it is an amount between about 0.1 and 50 mg/kg, preferably 0.01 and 20 mg/kg of the animal to be treated.

E. Gene and Oligonucleotide Therapy

Gene and oligonucleotide therapy include the use of nucleic acid encoding a functioning inorganic ion receptor, preferably a calcium receptor, and the use of inhibitory oligonucleotides. Inhibitory oligonucleotides include antisense nucleic acids and ribozymes. Gene and oligonucleotide therapy can be performed ex vivo on cells which are then transplanted into a patient, or can be performed by direct administration of the nucleic acid or nucleic acid-protein complex into the patient.

1. Antisense Oligonucleotides and Ribozymes

Antisense oligonucleotides and ribozymes are targeted to nucleic acid encoding an inorganic ion receptor, preferably a calcium receptor, and inhibit protein expression from the targeted nucleic acid. Numerous mechanisms have been proposed to explain the effects of antisense nucleic acids. For example, see Helene, C. and Toulme, J. *Biochimica et Biophysica Acta* 1049:99 (1990), and Uhlmann, E. and Peyman, A. *Chemical Reviews* 90:543 (1990). Proposed mechanisms include hybridization of an antisense oligonucleotide to nascent mRNA causing premature transcription termination and interfering with mRNA processing by hybridizing to a pre-mRNA intron/exon junction. These and several other proposed mechanisms for inhibiting nucleic acid activity by antisense oligonucleotides are based upon the ability of antisense nucleic acid to hybridize to a target nucleic acid sequence. Preferably, anti-sense nucleic acids are 15 to 30 bases in length.

Ribozymes are enzymatic RNA molecules capable of catalyzing the specific cleavage of RNA. Ribozyme action involves sequence specific interaction of the ribozyme to complementary target RNA, followed by a endonucleolytic cleavage. Different ribozyme cutting motifs such as hammer-head can be engineered to specifically and efficiently catalyze endonucleolytic cleavage of specific RNA sequences encoding.

Specific ribozyme cleavage sites include GUA, GUU and GUC. Once cleavage sites are identified, short RNA sequences of between 15 and 20 ribonucleotides targeted to the region of the targeted RNA containing the cleavage site may be evaluated for predicted structural features to determine ribozyme suitability. The suitability of candidate targets may also be evaluated by testing their accessibility to hybridization with complementary oligonucleotides, using ribonuclease protection assays. See, Draper PCT WO 93/23569, hereby incorporated by reference herein.

Anti-sense oligonucleotides and ribozymes may be prepared by methods known in the art for the synthesis of RNA and DNA molecules. Standard techniques for chemically synthesizing nucleic acids include solid phase phosphoramidite chemical synthesis. Specific nucleic acids can also be produced enzymatically using a host transformed with a plasmid encoding for the desired nucleic acid.

Various modifications to the nucleic acid may be introduced to increase intracellular stability and half-life. Possible modifications include modifications to the phosphodiester backbone such as the use of phosphorothioate or methylphophonate linkages.

Antisense oligonucleotides and ribozymes can be administered to a patient using different techniques such as by naked nucleic acid, nucleic acid compositions (for example, encapsulated by a liposome) and by retroviral vectors. Miller, *Nature* 357; 455–460, hereby incorporated by reference herein. Antisense oligonucleotides and ribozymes can also be introduced into a cell using nucleic acid encoding the antisense nucleic acid or ribozyme.

2. Gene Therapy

Gene therapy can be achieved by transferring a gene encoding an inorganic ion receptor, preferably a calcium receptor, into a patient in a manner allowing expression of the receptor protein. Recombinant nucleic acid molecules encoding receptor protein sequences can be introduced into a cell in vivo or ex vivo. In vivo transfection techniques include the use of liposomes and retroviral vectors. Miller, *Nature* 357; 455–460, hereby incorporated by reference herein. Ex vivo transfection increases the number of available transfection techniques, but also adds additional complications due to removal and subsequent insertion of cells into a patient.

F. Transgenic Animals

The present invention also concerns the construction and use of transgenic animals, and transformed cells encoding inorganic ion receptors, preferably human calcium receptors. Transgenic animals and transformed cells can be used to study the effects on cell function of receptor excess or depletion. Experimental model systems may be used to study the effects in cell or tissue cultures, in whole animals, or in particular cells or tissues within whole animals or tissue culture systems. The effects can be studied over specified time intervals (including during embryogenesis).

The present invention provides for experimental model systems for studying the physiological role of the receptors. Model systems can be created having varying degrees of receptor expression. For example, the nucleic acid encoding a receptor may be inserted into cells which naturally express the receptors such that the gene is expressed at much higher levels. Alternatively, a recombinant gene may be used to inactivate the endogenous gene by homologous recombination, and thereby create an inorganic ion receptor deficient cell, tissue, or animal.

Inactivation of a gene can be caused, for example, by using a recombinant gene engineered to contain an insertional mutation (e.g., the neo gene). The recombinant gene is inserted into the genome of a recipient cell, tissue or animal, and inactivates transcription of the receptor. Such a construct may be introduced into a cell, such as an embryonic stem cell, by techniques such as transfection, transduction, and injection. Stem cells lacking an intact receptor sequence may generate transgenic animals deficient in the receptor.

Preferred test models are transgenic animals. A transgenic animal has cells containing DNA which has been artificially inserted into a cell and inserted into the genome of the animal which develops from that cell. Preferred transgenic animals are primates, mice, rats, cows, pigs, horses, goats, sheep, dogs and cats.

A variety of methods are available for producing transgenic animals. For example, DNA can be injected into the pronucleus of a fertilized egg before fusion of the male and female pronuclei, or injected into the nucleus of an embryonic cell (e.g., the nucleus of a two-cell embryo) following the initiation of cell division (Brinster et al., *Proc. Nat. Acad. Sci. USA* 82: 4438–4442 (1985)). By way of another example, embryos can be infected with viruses, especially retroviruses, modified to carry inorganic ion receptor nucleotide sequences.

Pluripotent stem cells derived from the inner cell mass of the embryo and stabilized in culture can be manipulated in culture to incorporate nucleotide sequences of the invention. A transgenic animal can be produced from such stem cells through implantation into a blastocyst that is implanted into a foster mother and allowed to come to term. Animals suitable for transgenic experiments can be obtained from standard commercial sources such as Charles River (Wilmington, Mass.), Taconic (Germantown, N.Y.), and Harlan Sprague Dawley (Indianapolis, Ind.).

Methods for the culturing of embryonic stem (ES)cells and the subsequent production of transgenic animals by the introducton of DNA into ES cells using methods such as electroporation, calcium phosphate/DNA precipitation and direct injection also are well known to those of ordinary skill in the art. See, example, *teratocarcinomas and Embryonic Stem Cells, A Practical Approach*, E. J. Robertson, ed., IRL Press (1987).

Produres for embryo manipulations are well known in the art. The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, *Experienta* 47: 897–905 (1991). Other procedures for introduction of DNA into tissues of animals are described in U.S. Pat. No. 4,945,050 (Sanford et al., Jul. 30, 1990).

Transfection and isolation of desired clones can be carried out using standard techniques (e.g., E. J. Robertson, supra). For example, random gene integration can be carried out by co-transfecting the nucleic acid with a gene encoding antibiotic resistance. Alternatively, for example, the gene encoding antibiotic resistance is physically linked to a nucleic acid sequence encoding an inorganic ion receptor.

DNA molecules introduced into ES cells can also be intergrated into the chromosome through the process of homologous recombination. Capecchi, *Science* 244: 1288–1292 (1989). Methods for positive selection of the recombination event (e.g., neomycin resistance) and dual positive-negative selection (e.g., neomycin resistance and gancyclovir resistance) and the subsequent identification of the desired clones by PCR have been described by Capecchi, supra and Joyner et al., *Nature* 338:153–156 (1989), the teachings of which are incorporated herein.

The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene.

An example describing the preparation of a transgenic mouse is as follows. Female mice are induced to superovulate and placed with males. The mated females are sacrificed by $CO_2$ asphyxiation or cervical dislocation and embryos are recovered from excised oviducts. Surrounding cumulus cells are removed. Pronuclear embryos are then washed and stored until the time of injection.

Randomly cycling adult female mice paired with vasectomized males serve as recipients for implanted embryos. Recipient females are mated at the same time as donor females and embryos are transferred surgically to recipient females.

The procedure for generating transgenic rats is similar to that of mice. See Hammer et al., *Cell* 63:1099–1112 (1990). Procedures for the production of transgenic non-rodent mammals and other animals are known in art. See, for example, Houdebine and Chourrout, supra; Pursel et al., *Science* 244:1281–1288 (1989); and Simms et al., *Bio/Technology* 6:179–183 (1988).

G. Transfected Cells Lines

Nucleic acid expressing a functional inorganic ion receptor can be used to create transfected cells lines which functionally express a specific inorganic ion receptor. Such cell lines have a variety of uses such as being used for high-throughput screening for molecules able to modulate inorganic ion receptor activity, preferably calcium receptor activity; and being used to assay binding to an inorganic ion receptor, preferably a calcium receptor.

A variety of cell lines are capable of coupling exogenously expressed receptors to endogenous functional responses. A number of these cell lines (e.g., NIH-3T3, HeLa, NG115, CHO, HEK 293 and COS7) can be tested to confirm that they lack an endogenous calcium receptor. Those lines lacking a response to external $Ca^{2+}$ can be used to establish stably transfected cell lines expressing the cloned calcium receptor.

Production of these stable transfectants is accomplished by transfection of an appropriate cell line with a eukaryotic expression vector, such as pMSG, in which the coding sequence for the calcium receptor cDNA has been cloned into the multiple cloning site. These expression vectors contain a promoter region, such as the mouse mammary tumor virus promoter (MMTV), that drive high-level transcription of cDNAs in a variety of mammalian cells. In addition, these vectors contain genes for the selection of cells that stably express the cDNA of interest. The selectable marker in the pMSG vector encodes an enzyme, xanthine-guanine phosphoribosyl transferase (XGPRT), that confers resistance to a metabolic inhibitor that is added to the culture to kill the nontransfected cells. A variety of expression vectors and selection schemes are usually assessed to determine the optimal conditions for the production of calcium receptor-expressing cell lines for use in high-throughput screening assays.

The most effective method for transfection of eukaryotic cell lines with plasmid DNA varies with the given cell type. The calcium receptor expression construct will be introduced into cultured cells by the appropriate technique, either $Ca^{2+}$ phosphate precipitation, DEAE-dextran transfection, lipofection or electroporation.

Cells that have stably incorporated the transfected DNA will be identified by their resistance to selection media, as described above, and clonal cell lines will be produced by expansion of resistant colonies. The expression of the calcium receptor cDNA by these cell lines will be assessed by solution hybridization and Northern blot analysis. Functional expression of the receptor protein will be determined by measuring the mobilization of intracellular $Ca^{2+}$ in response to externally applied calcium receptor agonists.

The following examples illustrate the invention, but do not limit its scope.

EXAMPLES

In the studies described herein, a variety of organic molecules were found to mobilize intracellular $Ca^{2+}$ and depress PTH secretion in parathyroid cells. These molecules are structurally diverse, but most have a net positive charge at physiological pH. The cationic nature of the organic molecules plays an important role, but is not the sole factor determining activity.

Example 1
Screening Calcimimetic Molecules on Bovine Parathyroid cells

Dissociated bovine parathyroid cells were purified on gradients of Percoll and cultured overnight in serum-free medium. The cells were subsequently loaded with fura-2 and the concentration of free intracellular $Ca^{2+}$ measured fluorimetrically. Changes in $[Ca^{2+}]_i$ were used to screen for molecules active at the calcium receptor. To be considered a calcimimetic in this example, a molecule was required to show the normal effects caused by increasing extracellular $Ca^{2+}$ and triggered by the activation of the calcium receptor. That is, 1) The molecule must elicit an increase in $[Ca^{2+}]_i$; the increase in $[Ca^{2+}]_i$ may persist in the absence of extracellular $Ca^{2+}$ and/or the molecule may potentiate increases in $[Ca^{2+}]_i$ elicited by extracellular $Ca^{2+}$.
2) The molecule must cause a decrease in isoproterenol-stimulated cyclic AMP formation which is blocked by pertussis toxin;
3) The molecule must inhibit PTH secretion over the same 30 range of concentrations that cause the increase in $[Ca^{2+}]_i$; and
4) The concentration-response curves for increases in $[Ca^{2+}]_i$ and PTH secretion by the molecule must be shifted to the right by a PKC activator, such as phorbol myristate acetate (PMA).

Several structurally different classes of molecules were tested: polyamines, aminoglycoside antibiotics, protamine, and polymers of lysine or arginine. The structures of these molecules are depicted in FIG. 1. Included in FIG. 1 are the net positive charge of the molecules and their $EC_{50}$'s for evoking the mobilization of intracellular $Ca^{2+}$ in bovine parathyroid cells.

In general, the greater the net positive charge on the molecule, the greater its potency in causing the mobilization of intracellular $Ca^{2+}$. However, some striking exceptions to this apparent general rule have been found as discussed below.

As can be seen from the figures, spermine, neomycin B, and protamine evoked rapid and transient increases in $[Ca^{2+}]_i$ in fura-2-loaded bovine parathyroid cells (FIGS. 6, 7, 11). They did not, however, cause sustained, steady-state increases in $[Ca^{2+}]_i$ in bovine parathyroid cells (FIG. 6, 11) although they did in human parathyroid cells (FIG. 19). In this respect, they resembled the cytosolic $Ca^{2+}$ response elicited by extracellular $Mg^{2+}$, which causes the mobilization of intracellular $Ca^{2+}$ unaccompanied by an influx of extracellular $Ca^{2+}$ in bovine cells (FIG. 11b). Transient increases in $[Ca^{2+}]_i$ elicited by spermine, neomycin B, or protamine were not blocked by low concentrations (1 μM) of $La^{3+}$ or $Gd^{3+}$ (FIG. 11f,g). Cytosolic $Ca^{2+}$ transients elicited by the molecular polycations persisted in the absence of extracellular $Ca^{2+}$, but were blocked when cellular stores of $Ca^{2+}$ were depleted by pretreatment with ionomycin (FIGS. 7, 11h and 11i.). All of these molecules therefore cause the mobilization of intracellular $Ca^{2+}$ in parathyroid cells.

It was additionally shown that the molecular polycations mobilized the same pool of intracellular $Ca^{2+}$ as that used by extracellular $Ca^{2+}$. Thus, increasing the concentration of extracellular $Ca^{2+}$ progressively inhibited the transient increases in $[Ca^{2+}]_i$ evoked by spermine (FIG. 6). Conversely, a maximally effective concentration of spermine or neomycin B (FIG. 12) blocked transient, but not steady-state increases in $[Ca^{2+}]_i$ evoked by extracellular $Ca^{2+}$.

Significantly, spermine, neomycin B, and protamine inhibited PTH secretion to the same extent as extracellular $Ca^{2+}$. These inhibitory effects on secretion were obtained at concentrations that caused the mobilization of intracellular $Ca^{2+}$ (FIGS. 8, 13). These findings are relevant to understanding the mechanisms contributing to the regulation of PTH secretion by extracellular $Ca^{2+}$. Because a variety of inorganic polycations all inhibit secretion, yet only extracellular $Ca^{2+}$ causes sustained, steady-state increases in $[Ca^{2+}]_i$, such increases in $[Ca^{2+}]_i$ cannot be importantly involved in the regulation of secretion. Mobilization of intracellular $Ca^{2+}$, rather than the influx of extracellular $Ca^{2+}$, is the essential mechanism associated with the inhibition of PTH secretion. This is important because it defines the sufficient mechanism to be affected if a molecule is to affect PTH secretion; molecules stimulating selectively the influx of extracellular $Ca^{2+}$ will be relatively ineffective in suppressing PTH secretion. In contrast, molecules causing solely the mobilization of intracellular $Ca^{2+}$ should be just as efficacious as extracellular $Ca^{2+}$ in suppressing PTH secretion.

Figure 15:
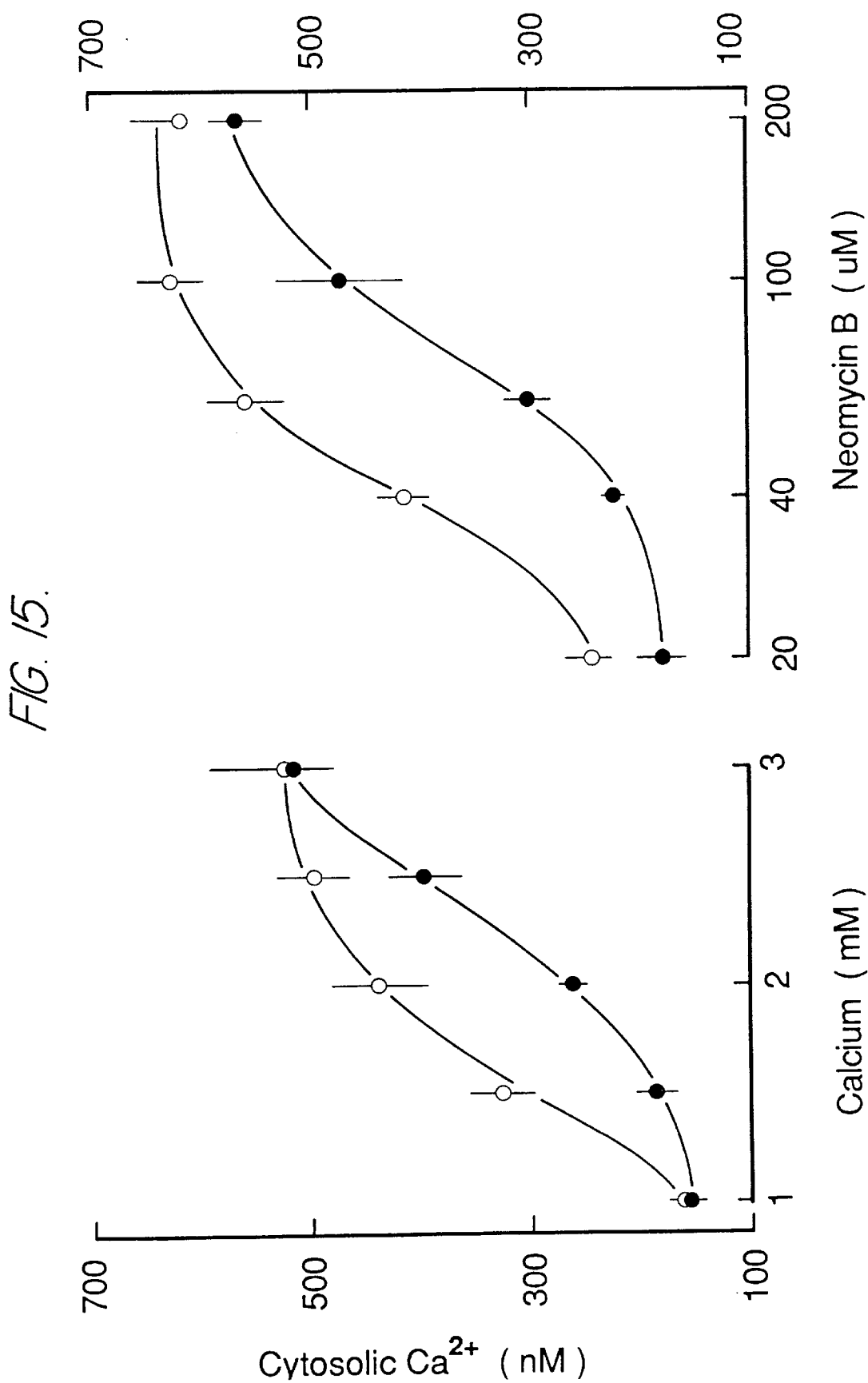

Like the mobilization of intracellular $Ca^{2+}$ elicited by extracellular $Ca^{2+}$, that elicited by molecular polycations was depressed by PMA. A representative experiment showing the preferential inhibitory effects of PMA on cytosolic $Ca^{2+}$ transients elicited by spermine is shown in FIG. 14. Cytosolic $Ca^{2+}$ transients evoked by ATP were unaffected, even when a submaximal concentration of ATP was used. The effect of PMA on cytosolic $Ca^{2+}$ transients elicited by the molecular polycations paralleled its effect on responses to extracellular $Ca^{2+}$; in both cases, there was a shift to the right in the concentration-response curve (FIG. 15). The depressive effects of PMA on $[Ca^{2+}]_i$ were accompanied by potentiating effects on secretion which were overcome at higher concentrations of the organic polycations (FIG. 16).

The mobilization of intracellular $Ca^{2+}$ elicited by molecular polycations was associated with increases in the formation of inositol phosphates. For example, protamine caused a rapid (within 30 seconds) increase in the formation of $IP_3$ which was accompanied by a rise in levels of $IP_i$. Both these affects were dependent on the concentration of extracellular protamine (FIG. 17). Moreover, pretreatment with PMA blunted the formation of inositol phosphates elicited by molecular polycations. Representative results obtained with spermine are presented in FIG. 18.

Spermine, neomycin B, and protamine depressed isoproterenol-induced increases in cyclic AMP. Like the inhibitory effects of extracellular $Ca^{2+}$ on cyclic AMP formation, those caused by molecular polycations were blocked by pretreatment with pertussis toxin (Table 2).

TABLE 2

| | cyclic AMP (% of control) | |
|---|---|---|
| | control | +PTx |
| 0.5 mM $Ca^{2+}$ | 100 | 106 ± 8 |
| 2.0 mM $Ca^{2+}$ | 19 ± 4 | 94 ± 2 |
| 0.5 mM $Ca^{2+}$, 200 μM spermine | 23 ± 5 | 93 ± 6 |
| 0.5 mM $Ca^{2+}$, 30 μM neomycin B | 28 ± 8 | 87 ± 6 |
| 0.5 mM $Ca^{2+}$, 2 μg/ml protamine | 20 ± 4 | 89 ± 9 |

Pertussis toxin (PTx) blocks the inhibitory effects of extracellular $Ca^{2+}$ and molecular polycations on cyclic AMP formation. Bovine parathyroid cells were cultured for 16 hours with or without 100 ng/ml pertussis toxin. The cells were subsequently washed and incubated for 15 min with 10 μM isoproterenol with or without the indicated concentrations of extracellular $Ca^{2+}$ or molecular polycations. Total cyclic AMP (cells+supernatant) was determined by RIA and the results are expressed as a percentage of the levels obtained in 0.5 mM $Ca^{2+}$ (112±17 pmole/$10^6$ cells). Each value is the mean±SEM of three experiments.

In human parathyroid cells, extracellular $Mg^{2+}$ elicited a sustained, steady-state increase in $[Ca^{2+}]_i$ in addition to a rapid transient increase (FIG. 10). As in bovine parathyroid cells responding to extracellular $Ca^{2+}$, the steady-state increase in $[Ca^{2+}]_i$ evoked by $Mg^{2+}$ in human parathyroid cells results from $Ca^{2+}$ influx through voltage-insensitive channels (FIG. 10a). This effect of $Mg^{2+}$ on steady-state $[Ca^{2+}]_i$ in human parathyroid cells is seen in both adenomatous and hyperplastic tissue.

Neomycin B and spermine were tested for effects on $[Ca^{2+}]_i$ in human parathyroid cells prepared from adenomatous tissue. Representative results with neomycin B are shown in FIG. 19. Neomycin B caused not only a transient, but additionally a steady-state increase in $[Ca^{2+}]_i$ in human parathyroid cells (FIG. 19a). Thus, in human cells, the pattern of change in $[Ca^{2+}]_i$ evoked by extracellular $Ca^{2+}$, $Mg^{2+}$ or neomycin B is very similar.

Cytosolic $Ca^{2+}$ transients elicited by neomycin B persisted in the presence of $La^{3+}$ (1 μM) and absence of extracellular $Ca^{2+}$. Neomycin B therefore causes the mobilization of intracellular $Ca^{2+}$ in human parathyroid cells. Neomycin B inhibited PTH secretion from human parathyroid cells at concentrations that caused the mobilization of intracellular $Ca^{2+}$ (FIG. 13). There were, however, some differences in the responses of human and bovine parathyroid cells to neomycin B. The $EC_{50}$ of neomycin B for the mobilization of intracellular $Ca^{2+}$ was 40 μM in bovine and 20 μM in human parathyroid cells (cf. FIGS. 13 and 15), whereas the potency of spermine was similar in bovine and human parathyroid cells ($EC_{50}$=150 μM). Thus, although bovine cells can be used for initial studies to screen test molecules for activity, it is important to perform follow-up studies using human parathyroid cells.

To assess the effects of molecular polycations on C-cells, a neoplastic cell line, derived from a rat medullary thyroid carcinoma (rMTC 6–23 cells) was used. Both spermine (10 mM) and neomycin B (5 mM) were without effect on basal $[Ca^{2+}]_i$ in these cells. Nor did either molecule affect the response to the subsequent addition of extracellular $Ca^{2+}$. Representative results documenting the lack of effect of neomycin B are shown in FIG. 21. Neomycin B (1 mM) or spermine (1 or 5 mM) failed to evoke any increase in $[Ca^{2+}]_i$ in osteoclasts (FIG. 23). In the trace shown, there appeared to be some potentiation of the response to a subsequent increase in the concentration of extracellular $Ca^{2+}$, although this was not a consistent finding. In two other cells, spermine (5 mM) was again without effect on basal $[Ca^{2+}]_i$ and caused a small inhibition (about 15%) of the extracellular $Ca^{2+}$-induced increase in $[Ca^{2+}]_i$. In a third cell, neomycin B (5 mM) was without effect on basal $[Ca^{2+}]_i$ and did not affect increases in $[Ca^{2+}]_i$ elicited by extracellular $Ca^{2+}$. The overall picture that develops from these studies is that spermine and neomycin B are without effect on basal or stimulated levels of cytosolic $Ca^{2+}$ in osteoclasts.

The failure of the molecular polycations to affect the $Ca^{2+}$-sensing mechanisms of C-cells or osteoclasts demonstrates the ability to discover or design novel lead molecules that act specifically on the parathyroid cell calcium receptor or otherwise modulate one or more functions of the parathyroid cell's normal response to $[Ca^{2+}]_i$.

Screening of various other molecules is described in detail below and the results summarized in Table 1.

Example 2

Polyamine Screening

Straight-chain polyamines (spermine, spermidine, TETA, TEPA, and PEHA) and two derivatives thereof (NPS 381 and NPS 382) were screened as in Example 1. These molecules were all found to mobilize intracellular $Ca^{2+}$ in bovine parathyroid cells. Their order of potency is as follows, with the net positive charge listed in parentheses:

TABLE 3

| Molecule | EC$_{50}$ (in µM) |
| --- | --- |
| NPS 382 (+8) | 50 |
| NPS 381 (+10) | 100 |
| spermine (+4) | 150 |
| PEHA (+6) | 500 |
| spermidine (+3) | 2000 |
| TEPA (+5) | 2500 |
| TETA (+4) | 8000 |

Putrescine (+2) and cadaverine (+2) were inactive at a concentration of 2 mM.

Another straight-chain polyamine, DADD, behaved somewhat differently from the other polyamines and is described in Table 1.

Example 3
Cyclic Polyamine Screening

Two cyclic polyamines, hexacyclen and NPS 383, were screened as in Example 1. Hexacyclen (+6, EC$_{50}$=20 µM) is 7-fold more potent than NPS 383 (+8, EC$_{50}$=150 µM). The converse would be expected based solely on net positive charge as the structural characteristic for calcium receptor activity.

Example 4
Aminoglycoside Antibiotic Screening

Six antibiotics were screened as in Example 1. The resulting EC$_{50}$'s for the mobilization of intracellular Ca$^{2+}$, in rank order of potency, were:

TABLE 4

| Antibiotic | EC$_{50}$ (in µM) |
| --- | --- |
| neomycin (+6) | 10 |
| gentamicin (+5) | 150 |
| bekanamycin (+5) | 200 |
| streptomycin (+3) | 600 |

Kanamycin (+4.5) and lincomycin (+1) were without effect at a concentration of 500 µM. Within the aminoglycoside series, there is a correlation between net positive charge and potency. However, neomycin is considerably more potent than various polyamines (NPS 381, NPS 382, NPS 383, PEHA) that have an equal or greater positive charge. Since aminoglycoside antibiotics of this type have renal toxicity which may be related to interaction with calcium receptors in the kidney, such screening could be used to screen for toxicity in the development of new aminoglycoside antibiotics.

Example 5
Peptide and Polyamino Acid Screening

Protamine and polymers of lysine or arginine varying in peptide length were screened for their ability to mobilize intracellular Ca$^{2+}$ as in Example 1. The resulting EC$_{50}$'s for the mobilization of intracellular Ca$^{2+}$, in rank order of potency, were:

TABLE 5

| Peptide (MW in kD) | EC$_{50}$ (in nM) |
| --- | --- |
| polyArg (100) | 4 |
| polyArg (40) | 15 |
| polyLys (27) | 30 |

TABLE 5-continued

| Peptide (MW in kD) | EC$_{50}$ (in nM) |
| --- | --- |
| protamine (4.8) | 75 |
| polyArgTyr (22) | 200 |
| polyLys (14) | 1000 |
| polyLys (3.8) | 3000 |

The net positive charge of these polymers increases as the MW increases. Thus, as for the aminoglycosides, there is a direct correlation between net charge and potency among this series of polyamino acids. Protamine is essentially polyArg with a net positive charge of +21.

Example 6
Arylalkyl Polyamine Screening

Molecules selected from the class of arylalkyl polyamines derived from the venoms of wasps and spiders were screened as in Example 1.

Philanthotoxin-433 (+3) was without effect at a concentration of 500 µM. It is similar in structure to the argiotoxins described below.

Argiotoxin-636 (400 µM) did not elicit increases in [Ca$^{2+}$], but it did potentiate cytosolic Ca$^{2+}$ responses to the subsequent addition of extracellular Ca$^{2+}$. This is a feature common to all molecules that activate the calcium receptor and is also seen with a variety of extracellular divalent cations. This is considered in more detail in Example 7.

In contrast to argiotoxin-636, argiotoxin-659 elicited increases in [Ca$^{2+}$]$_i$ with an EC$_{50}$ of 300 µM. Argiotoxin-659 differs from argiotoxin-636 in having a 4-hydroxyindole moiety rather than a 2,4-dihydroxyphenyl group. This is the only structural difference between these two molecules. Thus, the difference in potency lies in the nature of the aromatic group, not in the polyamine chain which carries the positive charge.

Example 7
Screening of Ca$^{2+}$ Channel Blockers

Ca$^{2+}$ channel blockers, i.e., those molecules which block influx of extracellular Ca$^{2+}$ through voltage-sensitive Ca$^{2+}$ channels, were screened as in Example 1. There are three structural classes of Ca$^{2+}$ channel blockers: (1) dihydropyridines, (2) phenylalkylamines, and (3) benzothiazipines.

None of the dihydropyridines tested (nifedipine, nitrendipine, BAY K 8644, and (−) 202–791 and (+) 202–791) had any effect on basal [Ca$^{2+}$]$_i$ or increases in [Ca$^{2+}$]$_i$ evoked by extracellular Ca$^{2+}$ when they were tested at 1 µM. Previous studies showed that parathyroid cells lack voltage-sensitive Ca$^{2+}$ channels, but do have voltage-insensitive Ca$^{2+}$ channels that are regulated by the calcium receptor.

The phenylalkylamines examined were verapamil, D-600 (a methoxy derivative of verapamil), TMB-8, and an analog of TMB-8, NPS 384. The first three molecules were tested at a concentration of 100 µM. The phenylalkylamines behaved differently from other molecules examined. They evoked no change in [Ca$^{2+}$]$_i$ when added to cells bathed in buffer containing a low concentration of extracellular Ca$^{2+}$ (0.5 mM). However, verapamil, D-600, and TMB-8 potentiated the mobilization of intracellular Ca$^{2+}$ elicited by extracellular divalent cations and they additionally blocked the influx of extracellular Ca$^{2+}$. At intermediate levels of extracellular Ca$^{2+}$ (1–1.5 mM), these molecules were capable of evoking a small, but robust increase in $[Ca^{2+}]_i$ that arose from the mobilization of intracellular $Ca^{2+}$.

The phenylalkylamines act differently than organic polycations like neomycin. The data suggest that verapamil, D-600 and TMB-8 are partial agonists or allosteric activators at the calcium receptor, in contrast to the other molecules examined which are full agonists.

Molecule NPS 384, at a concentration of 300 μM, did not evoke an increase in $[Ca^{2+}]_i$, but it blocked influx of extracellular $Ca^{2+}$. Testing at higher concentrations may reveal an ability of this molecule to cause the mobilization of intracellular $Ca^{2+}$.

While the ability of these molecules to block influx is intriguing and not entirely unexpected, it is the ability of these molecules to evoke transient increases in $[Ca^{2+}]_i$ (arising from intracellular $Ca^{2+}$ mobilization) that is important. Considerable experience with measurements of $[Ca^{2+}]_i$ in parathyroid cells shows that transient increases in $[Ca^{2+}]_i$ almost invariably result from the mobilization of intracellular $Ca^{2+}$ and therefore reflects activation of the calcium receptor.

The benzothiazipine examined, diltiazem, was similar in all respects to verapamil and D-600 and was also effective at 100 μM.

With the exception of the phenylalkylamines, all the active molecules tested above evoke increases in $[Ca^{2+}]_i$ having a magnitude similar to that evoked by a maximally effective concentration of extracellular $Ca^{2+}$. This shows that these molecules are equally efficacious as extracellular divalent cations. This contrasts with the activity of phenylalkylamines, which seem to act only as partial agonists.

Amongst the phenylalkylamines, some interesting structure-activity relationships emerge. Significant is the different potencies of molecules like TMB-8 and NPS 384. TMB-8 potentiated transient increases in $[Ca^{2+}]_i$ at 100 μM whereas NPS 384 fails to do so even at 300 μM, yet these molecules carry the same net positive charge. It follows that some other structural feature, unrelated to net charge, imparts greater potency to TMB-8.

Example 8
Molecule Screening on Human Parathyroid Cells

Spermine and neomycin were tested for effects on $[Ca^{2+}]_i$ in human parathyroid cells obtained from glands removed by surgery and prepared as in Example 1. In human parathyroid cells, spermine was found to cause only a small increase in $[Ca^{2+}]_i$ when tested at a concentration of 300 μM.

Neomycin, on the other hand, evoked a large increase in $[Ca^{2+}]_i$ in human parathyroid cells when tested at a concentration of 20 μM. The magnitude of the response elicited by neomycin was equal to that evoked by a maximally effective concentration of extracellular $Ca^{2+}$.

Example 9
Molecule Screening on *Xenopus* Oocytes

Oocytes injected with mRNA from human parathyroid cells express the calcium receptor and mobilize intracellular $Ca^{2+}$ in response to a variety of extracellular inorganic di- and trivalent cations. Using this screen allows one to test for an action directly on the calcium receptor. Oocytes expressing the calcium receptor also responded to several molecules active on intact parathyroid cells when screened as follows. Hexacyclen caused the mobilization of intracellular $Ca^{2+}$ at a concentration of 135 μM. Neomycin (100 μM) and NPS 382 (5 mM) were also effective. This offers rather compelling evidence showing that these molecules act on the calcium receptor or on some other protein intimately associated with its function.

For example, we have been able to detect calcium receptor expression in oocytes by measuring $^{45}Ca^{2+}$ mobilization. In these experiments, oocytes were injected with bovine parathyroid mRNA or water and, after 72 hours, exposed to serum or 10 mM neomycin. Prior to being stimulated, oocytes were loaded with $^{45}Ca^{2+}$. Stimulation with serum for 20 min resulted in intracellular $^{45}Ca^{2+}$ release representing a 45% increase compared to mock challenge with buffer. Challenge with 10 mM neomycin for 20 min resulted in a 76% increase in $^{45}Ca^{2+}$ release. The assay is sensitive enough for use in cloning the calcium receptor, and has the advantage of a higher throughput than the electrophysiological measurement of $Ca^{2+}$-activated $Cl^-$ current.

In another example, human osteoclastoma tissue was obtained from bone biopsy tissue. Oocytes injected with mRNA isolated from this tissue were challenged with 30 mM $Ca^{2+}$. Controls did not respond while 8 of 12 oocytes injected with osteoclastoma mRNA responded appropriately (FIG. 34). These experiments provide the first evidence that the $Ca^{2+}$ response of osteoclasts to extracellular $Ca^{2+}$ is in fact genetically encoded. The results also indicate that the osteoclast calcium receptor may be cloned by expression in Xenopus oocytes.

Example 10
Molecule Screening on Rat Osteoclasts

The different sensitivities of parathyroid cells and rat osteoclasts to extracellular $Ca^{2+}$ suggest that their calcium receptors are different. While parathyroid cells respond to extracellular $Ca^{2+}$ concentrations between 0.5 and 3 mM, osteoclasts respond only when the level of extracellular $Ca^{2+}$ increases beyond 5 mM. This rather high concentration of $Ca^{2+}$ is nonetheless physiological for osteoclasts; as they resorb bone, the local concentration of extracellular $Ca^{2+}$ may reach levels as high as 30 mM.

Molecule screening with rat osteoclasts was performed as follows. Osteoclasts were obtained from the long bones of neonatal rats. $[Ca^{2+}]_i$ was measured in single cells using the fluorimetric indicator indo-1. Spermine, spermidine, neomycin, and verapamil were tested, and none of these caused any large increase in $[Ca^{2+}]_i$ in osteoclasts (although small responses were detected).

At a concentration of 1 mM, spermidine caused a small increase in $[Ca^{2+}]_i$ (about 10 of that evoked by a maximal concentration of extracellular $Ca^{2+}$). Neither neomycin (10 mM) nor spermine (10 or 20 mM) caused increases in $[Ca^{2+}]_i$ in rat osteoclasts. Neomycin (10 mM) did not block the increase in $[Ca^{2+}]_i$ elicited by the subsequent addition of 25 mM extracellular $Ca^{2+}$. Pretreatment with spermine (20 mM), however, did depress the response to extracellular $Ca^{2+}$. Verapamil (100 μM) caused no detectable increase in $[Ca^{2+}]_i$, but it did block the response to extracellular $Ca^{2+}$.

Comparisons between osteoclasts and parathyroid cells show that molecules active on the latter are relatively ineffective in osteoclasts. This demonstrates that drugs that target a specific calcium receptor without affecting those receptor types present on other $Ca^{2+}$-sensing cells are readily developed. Similarly, drugs active at two or more such calcium receptors may also be developed.

Screening for Calcimimetic and Calcilytic Activity on the Osteoclast Calcium Receptor Compounds possessing activity on the osteoclast calcium receptor can be discovered by measuring $[Ca^{2+}]_i$ in single rat osteoclasts as described above. An improved assay enables moderate-to-high levels of compound throughput. This new method is based on the use of rabbit osteoclasts which can be obtained in high yield ($10^5$ per animal) and purity (95% of the cells are osteoclasts). The purity of the rabbit osteoclast preparation allows measurements of $[Ca^{2+}]_i$ to be performed on populations of cells. Because the recorded fluorescence signal is an averaged population response, intercellular variability is minimized and the precision of the assay is greatly increased. This, in turn, enables more compounds to be screened for activity.

Rabbit osteoclasts are prepared from 6-day old bunnies. The animals are sacrificed by decapitation and the long bones removed and placed into osteoclast medium (OC medium: alpha-minimum essential medium containing 5% fetal bovine serum and penicillin/streptomycin). The bones are cut into sections with a scalpel and placed in 2 ml of OC media in a 50-ml conical centrifuge tube. The bone sections are minced with scissors until a fairly homogeneous suspension of bone particles is obtained. The suspension is then diluted with 25 ml of OC media and the preparation swirled gently ("vortexed") for 30 seconds. The bone particles are allowed to settle for 2 minutes after which the supernatant is removed and added to a 50-ml centrifuge tube. The bone particles are resuspended in OC media, swirled, sedimented and harvested as just described. The supernatants from the two harvests are combined and centrifuged and the resulting cellular pellet resuspended in Percoll. The suspension is then centrifuged and the white viscous band just below the meniscus is removed and washed with OC media. The Percoll centrifugation step results in a significant improvement in purity and allows osteoclasts to be plated at high densities, suitable for measuring $[Ca^{2+}]_i$ in populations of cells. The cells are plated onto glass cover slips appropriate for measuring $[Ca^{2+}]_i$ according to one of the methods described below. If necessary, the purity of the preparation can be improved. In this case, the cells are cultured overnight and then rinsed with $Ca^{2+}$- and $Mg^{2+}$-free buffer. The cell monolayer is then immersed in $Ca^{2+}$- and $Mg^{2+}$-free buffer containing 0.02% EDTA and 0.001% pronase for 5 minutes. This buffer is then removed and replaced with OC media and the cells allowed to recover for 1 to 2 hours before loading the cells with fluorimetric indicator and measuring $[Ca^{2+}]_i$ as described below.

In one embodiment, this technique allows the measurement of $[Ca^{2+}]_i$ in populations of osteoclasts using fluorescence microscopy. The purified osteoclasts are allowed to attach to 25-mm diameter glass cover slips and then loaded with indo-1. The cover slips are secured into a superfusion chamber and placed onto the stage of a fluorescence microscope. The use of a low-power objective (×4) allows a field containing 10 to 15 osteoclasts to be visualized. In one variation, the fluorescence of each cell in the field can be recorded simultaneously and stored separately for later analysis. Changes in $[Ca^{2+}]_i$ of each cell can be estimated and the average response of all cells in the field calculated. In another variation, the fluorescence from the entire field of cells can be recorded and processed immediately. In either variation, the final data are in the form of an average response from the cells present in the microscopic field. Because of this, intercellular variability is minimized and precision of the assay greatly increased. This method enables 10–20 compounds per week to be screened for activity on the osteoclast calcium receptor.

In a more preferred embodiment, this technique allows the measurement of $[Ca^{2+}]_i$ in populations of osteoclasts using a conventional fluorimeter. The purified osteoclasts are allowed to attach to rectangular glass cover slips. In one variation, a standard quartz cuvette (1 cm$^2$) is used and the glass coverslips are 2×1.35 cm. In another variation, a microcuvette is used (0.5 cm$^2$) and the glass coverslips are 1×0.75 cm. In either case the cells are loaded with fura-2 or some other suitable fluorimetric indicator for measuring $[Ca^{2+}]_i$. The fluorescence of indicator-loaded cells is recorded as described above for bovine parathyroid cells. This method allows a higher throughput than fluorescence microscopy and enables 20–50 compounds per week to be evaluated for activity on the osteoclast calcium receptor.

In a most preferred embodiment, the technique can be used to measure $[Ca^{2+}]_i$ in osteoclasts in a 96-well plate. The purified osteoclasts are plated at high density into each well of a 96-well plate and subsequently loaded with a suitable fluorimetric indicator. The fluorescence of each well is recorded using a custom-designed fluorimeter attached to a Hamilton 220 robotic liquid handler. This method is fully automated and is capable of reading 1,000 compound per week per device.

Example 11

Calcium Receptor Selectivity

This example demonstrates that calcium receptors present on different cells exist as distinct subtypes which can be differentially affected by a particular drug. The parathyroid cell calcium receptor senses levels of extracellular $Ca^{2+}$ around 1.5 mM whereas the calcium receptor on the osteoclast responds to levels around 10 mM (FIG. 22). Neomycin or spermine, which activate the parathyroid cell calcium receptor, fail to affect the calcium receptors on C-cells or osteoclasts (FIGS. 21 and 23).

These data constitute the first evidence for pharmacologically distinct subtypes of calcium receptors and these data are being used to design and develop drugs that act selectively on a particular type of calcium receptor. Indeed, testing of lead molecules demonstrate such cell-specific effects. For example, $Mg^{2+}$, which increases $[Ca^{2+}]_i$ in bovine parathyroid cells ($EC_{50}$=5 mM), is without effect on $[Ca^{2+}]_i$ in osteoclasts even when tested at concentrations as high as 30 mM. Conversely, R-fendiline, which activates the parathyroid cell calcium receptor, is effective in activating the osteoclast calcium receptor only at concentrations 10-fold higher. Finally, agatoxin 489, although not very potent in activating the C-cell calcium receptor ($EC_{50}$=150 $\mu$M), is a quite potent activator of the parathyroid cell calcium receptor ($EC_{50}$=3 $\mu$M). The lead molecules presently under development will affect selectively the activity of a specific type of $Ca^{2+}$-sensing cell in vivo.

Drugs with less specificity might not necessarily be therapeutically undesirable. Thus, depressing osteoclast activity and stimulating calcitonin secretion are two different approaches to inhibiting bone resorption. Drugs that target the calcium receptors on both of these cells might be very effective therapies for osteoporosis. Because PTH is also involved in regulating bone metabolism, drugs acting on the parathyroid cell calcium receptor may also be useful in the treatment and/or prevention of osteoporosis.

Results of some test molecules are shown below. In Table 6, the comparative activity of calcimimetic molecules is shown. Bovine parathyroid cells and C-cells (rMTC 6–23 cells) were loaded with fura-2, and rat osteoclasts with indo-1 and the potency of the indicated molecules to mobilize intracellular $Ca^{2+}$ determined by constructing cumulative concentration-response curves. Molecules listed as "inactive" did not alter $[Ca^{2+}]_i$ when tested at a concentration of 1 mm.

TABLE 6

| COMPOUND | EC$_{50}$ ($\mu$M) | | |
|---|---|---|---|
| | PARATHYROID | OSTEOCLAST | C-CELL |
| NPS R-568 | 0.60 | 200 | 1.9 |
| NPS S-568 | 30 | — | — |
| NPS R-467 | 2 | >100 | 2.2 |
| NPS S-467 | >30 | — | — |
| NPS 017 | 6 | inactive | 150 |
| R-Fendiline | 9 | 150 | — |
| Fendiline* | 15 | 200 | >100 |
| NPS 015 | 22 | — | inactive |
| NPS 019 | 40 | >300 | 5 |
| R-Prenylamine | 7 | 150 | 6 |
| 1H* | 30 | 250 | — |
| Spermine | 150 | inactive | inactive |
| Neomycin | 40 | inactive | inactive |

*racemic mixture; "inactive" is defined as causing no increase in cytosolic Ca$^{2+}$ at a concentration of 1–5 mM.

Example 12
Lead Molecules for Parathyroid Calcium Receptor

Structure-activity studies using polyamines and arylalkyl polyamines led to the testing of molecules structurally akin to fendiline. Fendiline is a potent activator of the parathyroid cell calcium receptor. This molecule is notable because it possess only one positive charge, yet is much more potent than many polybasic molecules. Brief (2 min) pretreatment with PMA shifts the concentration-response curve for fendiline to the right. This indicates that fendiline acts through the same mechanism used by extracellular Ca$^{2+}$ to activate the calcium receptor on parathyroid cells.

Fendiline evokes the mobilization of intracellular Ca$^{2+}$ in *Xenopus oocytes* expressing the parathyroid cell calcium receptor, which demonstrates a direct action on the calcium receptor (FIG. 33). Moreover, fendiline contains a chiral carbon, and therefore exists in two isomeric forms. Both isomers have been synthesized and examined for activity. The R-isomer, R-fendiline, is 12 times more potent than the S-isomer, S-fendiline. This is the first demonstration that a calcium receptor can recognize an organic molecule in a stereospecific manner.

Because R-fendiline is a structurally simple molecule with selective and potent effects on the parathyroid cell calcium receptor, structure-activity studies around this lead molecule are simple. The aim of these studies is to generate an array of related molecules with various characteristics from which the final development candidate can be selected. This effort has already revealed some of the structural domains of R-fendiline that contribute to activity and potency. For example, the novel compound 1D is an analog of R-fendiline that is smaller (MW<240), yet nearly as potent as the parent molecule, whereas several other analogues are relatively inactive. The most interesting molecules from this analog project can be put into in vivo testing for effects on PTH secretion and serum Ca$^{2+}$ levels (see Examples 15, 16, 17, 18 and 23).

meta-Methoxyfendiline is another compound as potent as NPS 467 in causing the mobilization of intracellular Ca$^{2+}$ in parathyroid cells. meta-Methoxyfendiline is a racemic mixture and it is anticipated that the resolution of meta-methoxyfendiline into its enantiomers will result in an isomer that is more potent than the racemic mixture.

The novel compound NPS 467 is an even smaller molecule than R-fendiline, yet the former is about 3-fold more potent than the latter in causing increases in [Ca$^{2+}$]$_i$ in parathyroid cells. Like fendiline, NPS 467 is a racemic mixture. Resolution of NPS 467 into its enantiomers provides an isomer of even greater potency than the racemic mixture, i.e., NPS R-467 (see Example 17).

Further structure-activity studies on molecules related to R-fendiline, NPS 467, meta-methoxyfendiline and NPS 568 yielded pure isomers with greater potency than these molecules in their racemic forms. For example, the greater potency of NPS R-568 compared to NPS S-568 is shown in FIG. 28b using different cells lines transfected with nucleic acid encoding a human parathyroid calcium receptor (pHuPCaR4.0)

Results obtained with fendiline (NPS 456, FIG. 33) show that it elicits oscillatory increases in Cl$^-$ current at concentrations of 100 $\mu$M. The results obtained in this expression system with neomycin and fendiline demonstrate that these molecules act directly on the calcium receptor but not on control cells. NPS R-568 has subsequently been shown to be a potent molecule active on *Xenopus oocytes* expressing the parathyroid cell calcium receptor.

Results of testing some of the compounds shown in FIG. 36 are provided in Tables 7 and 8. The measured EC$_{50}$ values were determined by assaying for increases in intracellular calcium using fura-2 loaded cells (see also Example 11 and Table 6).

TABLE 7

Examples of Arylalkylamine Compounds with In Vitro EC$_{50}$ Values Greater than 5 $\mu$M at the Parathyroid Cell Calcium Receptor

| Compound Name or Code (from FIG. 36) | EC$_{50}$ ($\mu$M) |
|---|---|
| Fendiline (racemic) | 15 |
| R-Fendiline | 9 |
| S-Fendiline | >15 |
| NPS S-467 | >30 |
| NPS S-568 | 30 |
| 1A | 166 |
| 1B | 776 |
| 1C | 126 |
| 1D | 48 |
| 1E | 123 |
| 1S | 128 |
| 2A | 120 |
| 7Y | >30 |
| 7Z(R-) | >30 |
| 7Z(S-) | >100 |
| 8Y | >30 |
| 20K | >30 |
| 20V | >100 |

TABLE 8

Arylalkylamine Calcimimetics from FIG. 36 Active at the Parathyroid Cell Calcium Receptor In Vitro (EC$_{50}$ ≤ 5 $\mu$M)

| Compound Code (from FIG. 36) | EC$_{50}$ ($\mu$M) |
|---|---|
| NPS R-467 | 2.0 |
| NPS R-568 | 0.60 |
| 3U | 0.64 |
| 3V | 1.8 |
| 4A | 1.4 |
| 4B | 2.0 |
| 4C | 2.0 |
| 4D | 4.4 |
| 4G | 1.8 |
| 4H | ≧3.0 |
| 4J | 2.2 |
| 4M | 2.1 |

TABLE 8-continued

Arylalkylamine Calcimimetics from FIG. 36 Active at the
Parathyroid Cell Calcium Receptor In Vitro ($EC_{50} \leq 5 \mu M$)

| Compound Code (from FIG. 36) | $EC_{50}$ ($\mu M$) |
|---|---|
| 4N | 0.8 |
| 4P | 1.6 |
| 4R/6V | 4.2 |
| 4S | 3.3 |
| 4T/4U | 1.6 |
| 4V | 2.5 |
| 4W | 2.3 |
| 4Y | 1.3 |
| 4Z/5A | 4.4 |
| 5B/5C | 2.8 |
| 5W/5Y | 3.6 |
| 6E | 2.7 |
| 6F(R,R−) | 0.83 |
| 6R | 3.4 |
| 6T | 2.9 |
| 6X | 2.5 |
| 7W | 3.2 |
| 7X | 1.1 |
| 8D | 2.5 |
| 8J | 0.78 |
| 8K | 1.3 |
| 8R | 2.6 |
| 8S | 1.7 |
| 8T | 1.8 |
| 8U | 0.44 |
| 8X | 0.76 |
| 8Z | 0.40 |
| 9C | 0.60 |
| 9D | 1.4 |
| 9R | 0.25 |
| 9S | 4.8 |
| 10F | 0.89 |
| 11D | 1.8 |
| 11X | 0.83 |
| 11Y | 2.8 |
| 12L | 1.7 |
| 12U | 1.2 |
| 12V | 0.42 |
| 12W | 3.2 |
| 12Y | 2.0 |
| 13Q | ca. 0.8 |
| 13R | 0.25 |
| 13S | <0.13 |
| 13U | 0.19 |
| 13X | <0.75 |
| 14L | 0.26 |
| 14Q | 0.47 |
| 14U | 0.13 |
| 14V | 1.7 |
| 14Y | 0.38 |
| 15G | ca. 0.5 |
| 16Q | 0.04 |
| 16R | 0.36 |
| 16T | 0.04 |
| 16V | <0.13 |
| 16W | 0.59 |
| 16X | 0.10 |
| 17M | 0.15 |
| 17O | 0.04 |
| 17P | 0.04 |
| 17R | 0.39 |
| 17W | 0.43 |
| 17X | 0.02 |
| 20F | <1.0 |
| 20I | >1.0 |
| 20J | >3.0 |
| 20R | 2.4 |
| 20S | 4.2 |
| 21D | 3.0 |
| 21F | 0.38 |
| 21G | 1.1 |
| 21O | 0.26 |
| 21P | 0.43 |
| 21Q | 1.4 |
| 21R | 0.37 |

Example 13
Osteoclast Calcium Receptor Lead Molecules

The strategy used for elucidating the mechanism of action of extracellular $Ca^{2+}$ on the osteoclast was similar to that proven effective in parathyroid cells. The first experiments examined the effects of $La^{3+}$ on $[Ca^{2+}]_i$ in single rat osteoclasts loaded with the fluorimetric indicator indo-1. As described above, trivalent cations like $La^{3+}$ are impermeant and block $Ca^{2+}$ influx. Low micromolar concentrations of $La^{3+}$ partially depressed extracellular $Ca^{2+}$-induced increases in $[Ca^{2+}]_i$ (FIG. 29). The demonstration of a $La^{3+}$-resistant increase in $[Ca^{2+}]_i$ provides evidence for the mobilization of intracellular $Ca^{2+}$. The results of these experiments parallel those obtained in parathyroid cells and suggest that similar mechanisms are used by extracellular $Ca^{2+}$ to regulate $[Ca^{2+}]_i$ in both cell types.

Another series of experiments showed that extracellular $Mn^{2+}$ evoked transient increases in $[Ca^{2+}]_i$ (FIG. 30(b)) that persisted in the absence of extracellular $Ca^{2+}$ (FIG. 30(a)). These results are likewise indicative of the mobilization of intracellular $Ca^{2+}$. Although $Mn^{2+}$ can enter some cells, it is unlikely to do so in the osteoclast because $Mn^{2+}$ quenches the fluorescence of indo-1. Thus, if $Mn^{2+}$ penetrated the cell, a decrease, not an increase in the fluorescent signal would be observed.

The results obtained with a variety of di- and trivalent cations are all consistent with the presence of a calcium receptor on the surface of the osteoclast that is coupled to the mobilization of intracellular $Ca^{2+}$ and influx of extracellular $Ca^{2+}$ through voltage-insensitive channels. Results show evidence for genetic material in human osteoclasts that encodes a calcium receptor protein (see below). Transient increases in $[Ca^{2+}]_i$ resulting from the mobilization of intracellular $Ca^{2+}$, are sufficient to inhibit osteoclastic bone resorption in vitro. Thus, as with the parathyroid cell, activation of the calcium receptor appears to be a viable means of inhibiting the activity of osteoclasts.

Prenylamine was examined for its ability to inhibit bone resorption in vitro. This was done by morphometric analysis of pit formation on thin slices of bovine cortical bone using scanning electron microscopy. Rat osteoclasts were incubated for 24 hours in slices of bone in the presence or absence of various concentrations of prenylamine. Prenylamine caused a concentration-dependent inhibition of bone resorption with an $IC_{50}$ of 10 $\mu M$. The anticipated results provide the first demonstration that molecules acting at this novel site can inhibit osteoclastic bone resorption. More potent analogues of prenylamine will be generated using synthetic chemistry and will be tested and assayed using the methods described herein.

Example 14
C-Cell Calcium Receptor Lead Molecules

Activation of the C-cell calcium receptor stimulates the secretion of calcitonin which then acts on osteoclasts to inhibit bone resorption. Calcimimetic drugs selectively affecting C-cells are useful in the treatment of osteoporosis.

The mobilization of intracellular $Ca^{2+}$ is used as a functional index of calcium receptor activity. The screening effort in C-cells is facilitated by the availability of cultured cell lines expressing the C-cell phenotype (e.g., rat medullary thyroid carcinoma cells; rMTC 6–23 cells). Selected for initial study were three naturally occuring arylalkyl polyamines, agatoxin 489, agatoxin 505, and NPS 019. Agatoxin 505 was found to block extracellular $Ca^{2+}$-induced increases in $[Ca^{2+}]_i$ with an $IC_{50}$ of 3 $\mu$M. The inhibitory effect resulted from a block of the L-type voltage-sensitive $Ca^{2+}$ channel present in these cells. In contrast, agatoxin 489 was found to mobilize intracellular $Ca^{2+}$ in rMTC cells with an $EC_{50}$ of 150 $\mu$M. This was the first organic molecule discovered that was found to activate the C-cell calcium receptor. NPS 019 was even more potent and mobilized intracellular $Ca^{2+}$ with an $EC_{50}$ of 5 $\mu$M (FIG. 32).

It is significant that the only structural difference between NPS 019 and agatoxin 489 is the presence or absence of an hydroxyl group. The fact that such subtle differences in structure affect profoundly the potency of molecules indicates a structurally specific binding site on the calcium receptor. This, in turn, encourages the view that very potent and selective activators of calcium receptors can be developed.

NPS 019, which is a small molecule (MW<500), is a lead molecule the for development of calcimimetics of the C-cell calcium receptor and can be tested for its ability to stimulate calcitonin secretion in vitro. Subsequent in vivo testing will then determine the ability of this molecule to stimulate calcitonin secretion and inhibit bone resorption. These in vivo studies will be performed in rats. The results obtained in these studies, which are anticipated to be positive, will provide the first evidence showing that a small organic molecule acting on a novel receptor can stimulate calcitonin secretion and depress bone resorption.

Example 15
Calcilytic Activity of NPS 021 on Parathyroid Cells

For a compound to be considered a calcilytic, it must block the effects of extracellular $Ca^{2+}$ or a calcimimetic compound on an extracellular $Ca^{2+}$- sensing cell. An example of a calcilytic compound is NPS 021, the structure of which is provided in FIG. 1a. In bovine parathyroid cells loaded with fura-2, NPS 021 blocks increases in $[Ca^{2+}]_i$ elicited by extracellular $Ca^{2+}$. The $IC_{50}$ of NPS 021 for blocking this response is about 200 $\mu$M and, at concentrations around 500 $\mu$M, the increase in $[Ca^{2+}]_i$ evoked by extracellular $Ca^{2+}$ is abolished. Significantly, NPS 021 does not by itself cause any change in $[Ca^{2+}]_i$ when tested at low $[Ca^{2+}]$ (0.5 mM; FIG. 37). $Ga^{3+}$ is also calcilytic to *Xenopus oocytes* expressing the cloned calcium receptor: $Ga^{3+}$ by itself has no effect on the $Cl^-$ currents activated by $Gd^{3+}$, a calcimimetic, but pretreatment with $Ga^{3+}$ blocks the action of $Gd^{3+}$.

Example 16
NPS 467 Lowers Serum Ionized Calcium

Compounds shown to activate the bovine parathyroid cell calcium receptor in vitro were tested for hypocalcemic activity in vivo. Male Sprague-Dawley rats (200 g) were maintained on a low calcium diet for one week prior to receiving test substance or vehicle as control. Blood was collected from the tail vein three hours after the intraperitoneal administration of NPS 467. Ionized $Ca^{2+}$ in whole blood or serum was measured with a Ciba-Corning 634 Analyzer according to the instructions provided with the instrument. Serum total calcium, albumin and phosphate were measured by techniques well known in the art.

NPS-467 caused a dose-dependent reduction in serum or whole blood $Ca^{2+}$ (FIG. 38). The fall in blood $Ca^{2+}$ at this time was paralleled by a proportional fall in the levels of blood total calcium. There was no change in serum albumin or phosphate levels at any of the doses examined. In preliminary studies, NPS 467, at doses effective in lowering blood $Ca^{2+}$, caused a dose-dependent reduction in circulating levels of PTH (FIG. 39). The hypocalcemic effect of NPS 467 was maximal within three hours and returned toward control levels after 24 hours (FIG. 40).

NPS R-467 (see Example 17) was also effective in lowering serum ionized $Ca^{2+}$ in rats maintained on a normal, calcium-replete diet. A single dose of NPS R-467 (10 mg/kg i.p.) caused a rapid fall in serum levels of ionized $Ca^{2+}$ which were maximal by 1 hour (22% decrease from the control level) and remained depressed at or near this level for up to 6 hours.

Example 17
NPS 467 Lowers Serum Ionized Calcium in a Stereospecific Manner

NPS 467 is a racemic mixture. Resolution of NPS 467 into its two enantiomers was achieved by means of chiral HPLC. The R-isomer was about 100-fold more potent than the S-isomer in activating the bovine parathyroid cell calcium receptor in vitro as assessed by the ability of the enantiomers to evoke increases in $[Ca^{2+}]_i$ in parathyroid cells (FIG. 41). Likewise, similar resolution of the novel compound NPS 568 into its enantiomers showed that the R-isomer was 40-fold more potent than the S-isomer in causing the mobilization of intracellular $Ca^{2+}$ in bovine parathyroid cells (see Table 6, supra).

The isomers of NPS 467 were examined for effects on serum $Ca^{2+}$ as in Example 16. Consistent with the in vitro results, the R-isomer of NPS 467 proved to be more potent than the S-isomer in lowering serum $Ca^{2+}$ in vivo (FIG. 42; each compound was tested at a concentration of 5 mg/kg body weight).

Example 18
NPS R-467 Lowers Serum Ionized Calcium in an In Vivo Model of Secondary Hyperparathyroidism An accepted and widely used animal model of secondary hyperparathyroidism arising from chronic renal failure is the 5/6 nephrectomized rat. Animals receiving such surgery become initially hypocalcemic and, to maintain serum $Ca^{2+}$ levels, there is a compensatory hyperplasia of the parathyroid glands and elevated levels of circulating PTH. Male Sprague-Dawley rats (250 g) received a 5/6 nephrectomy and were allowed to recover for 2 weeks. At this time they were normocalcemic (due to elevated levels of serum PTH). The administration of NPS R-467 (10 mg/kg i.p.) caused a rapid (within 2 hours) fall in serum ionized $Ca^{2+}$ levels to 83% of controls in an animal model of secondary hyperparathyroidism. This suggests that compounds of this sort will effectively depress PTH secretion in patients with secondary hyperparathyroidism and hyperplastic parathyroid glands.

Example 19
NPS R-467 Fails to Lower Serum Ionized Calcium Levels in Parathyroidectomized Animals To determine the primary target tissue upon which NPS R-467 acts to cause a hypocalcemic response, the parathyroid glands in rats were surgically removed. Animals receiving a total parathyroidectomy become hypocalcemic and are largely dependent upon dietary calcium to maintain serum $Ca^{2+}$ homeostasis. Parathyroidectomized animals had serum ionized $Ca^{2+}$ levels of 0.92 mM which fell gradually to 0.76 mM after 6 hours of fasting. The administration of a single dose of NPS R-467 (10 mg/kg i.p.) did not cause any change in serum ionized $Ca^{2+}$ levels over a period of 6 hours. These results demonstrate that intact parathyroid glands are required for the hypocalcemic effects of NPS R-467. The data additionally demonstrate that NPS R-467 can target the parathyroid glands in vivo. The results are consistent with the view that NPS R-467 acts on the parathyroid cell calcium receptor in vivo to depress secretion of PTH and thereby cause serum levels of ionized $Ca^{2+}$ to fall.

Example 20
NPS R-467 and NPS S-467 Increase Intracellular Calcium in Human Parathyroid Glands Dissociated parathyroid cells were prepared from a parathyroid adenoma obtained by surgery from a patient with primary hyperparathyroidism. The cells were loaded with fura-2 and $[Ca^{2+}]_i$ measured as described above. Both NPS R-467 and NPS R-568 caused concentration-dependent increases in $[Ca^{2+}]_i$. The $EC_{50}$'s for NPS R-467 and NPS R-568 were 20 and 3 $\mu$M, respectively. Both of these compounds are thus able to increase $[Ca^{2+}]_i$ in pathological human tissue and would thus be expected to decrease serum levels of PTH and $Ca^{2+}$ in patients with primary hyperparathyroidism.

Example 21
Mechanism of Action of NPS R-467 at the Parathyroid Cell Calcium Receptor Dissociated bovine parathyroid cells were used to further explore the mechanism of action of NPS R-467 at the receptor level. In the presence of 0.5 mM extracellular $Ca^{2+}$, NPS R-467 caused a rapid and transient increase in $[Ca^{2+}]_i$ which persisted in the presence of 1 $\mu$M $La^{3+}$ and was partially depressed by pretreatment with PMA (100 nM for 2 minutes). Moreover, 30 $\mu$M of NPS R-467 caused a rapid increase in $Cl^-$ current in *Xenopus oocytes* injected with parathyroid cell mRNA. These results are consistent with an action of NPS R-467 on the calcium receptor. However, the cytosolic $Ca^{2+}$ response to NPS R-467 was abolished when parathyroid cells were suspended in $Ca^{2+}$-free buffer. This suggests that NPS R-467 cannot, by itself, cause the mobilization of intracellular $Ca^{2+}$. It does, however, elicit responses in parathyroid cells and in oocytes when a small amount of extracellular $Ca^{2+}$ is present. This suggests that partial occupancy of the $Ca^{2+}$-binding site is required for NPS R-467 to elicit a response.

To test this hypothesis, parathyroid cells were suspended in $Ca^{2+}$-free buffer and exposed to a submaximal concentration of neomycin. Neomycin was used because it mimics, in nearly all respects, the effects of extracellular $Ca^{2+}$ on parathyroid cells and on *Xenopus oocytes* expressing the parathyroid cell calcium receptor. The addition of 10 $\mu$M neomycin did not by itself cause an increase in $[Ca^{2+}]_i$ under these conditions. However, the subsequent addition of NPS R-467 (30 $\mu$M) now elicited a transient increase in $[Ca^{2+}]_i$ which, because there was no extracellular $Ca^{2+}$ present, must have come from the mobilization of intracellular $Ca^{2+}$.

When cells bathed in $Ca^{2+}$-free buffer were exposed to 30 $\mu$M NPS R-467, there was no increase in $[Ca^{2+}]_i$. This concentration of NPS R-467 is maximally effective in increasing $[Ca^{2+}]_i$ when extracellular $Ca^{2+}$ (0.5 mM) is present. However, the subsequent addition of 10 $\mu$M neomycin now evoked a transient increase in $[Ca^{2+}]_i$. Presumably, neomycin binds to the same site as extracellular $Ca^{2+}$ and can functionally substitute for it. Using a submaximal concentration, which by itself causes no response, achieves partial occupancy of the $Ca^{2+}$-binding site and allows activation of the calcium receptor by NPS R-467.

Additional studies to further define the mechanism of action of NPS R-467 were performed. The cells were once again suspended in $Ca^{2+}$-free buffer to insure that any observed increase in $[Ca^{2+}]_i$ resulted from the mobilization of intracellular $Ca^{2+}$. In these experiments, however, a maximally effective concentration (100 $\mu$M) of neomycin was used. In the absence of extracellular $Ca^{2+}$, 100 $\mu$M neomycin evoked a rapid and transient increase in $[Ca^{2+}]_i$. The subsequent addition of 30 $\mu$M NPS R-467 did not cause an increase in $[Ca^{2+}]_i$.

In the converse experiment, 30 $\mu$M NPS R-467 was added before 100 $\mu$M neomycin. As expected, NPS R-467 did not cause any increase in $[Ca^{2+}]_i$. It did not, however, affect the increase in $[Ca^{2+}]_i$ evoked by the subsequent addition of 100 $\mu$M neomycin. These results, obtained with maximally effective concentrations of NPS R-467 and neomycin, suggest that these two compounds do not act at the same site. Rather, the results can be sufficiently explained by postulating two separate sites on the calcium receptor, one to which extracellular $Ca^{2+}$ and neomycin bind, and another to which NPS R-467 and structurally related compounds (such as NPS R-568) bind.

Ligand binding to the former site can result in full activation of the calcium receptor whereas ligand binding to the latter site can only occur and/or be functionally relevant when the extracellular $Ca^{2+}$-binding site is occupied to some as yet undefined degree. It is possible that ligand binding to the extracellular $Ca^{2+}$-binding site exposes a previously occluded binding site for NPS R-467. It appears that the NPS R-467-binding site is an allosteric site that augments receptor activation in response to ligand binding at the extracellular $Ca^{2+}$ binding site.

The data demonstrate that the parathyroid cell calcium receptor possesses at least two distinct sites for organic ligands. One site binds the physiological ligand, extracellular $Ca^{2+}$, and certain organic polycations like neomycin. Binding to this site results in full activation of the calcium receptor, an increase in $[Ca^{2+}]_i$, and the inhibition of PTH secretion. NPS R-467 and NPS R-568 define a previously unrecognized binding site on the calcium receptor. Binding to this site can only occur and/or results in full activation of the calcium receptor when the extracellular $Ca^{2+}$-binding site is partially occupied. Ligands acting at either site are effective in suppressing serum $Ca^{2+}$ levels in vivo.

Allosteric Site on Parathyroid Cell Calcium Receptor

Calcimimetic compounds that activate the bovine parathyroid cell calcium receptor, such as NPS R-467 and NPS R-568, do not cause the mobilization of intracellular $Ca^{2+}$ in the absence of extracellular $Ca^{2+}$. Rather, they increase the sensitivity of the calcium receptor to activation by extracellular $Ca^{2+}$, thus causing a shift to the left in the concentration-response curve for extracellular $Ca^{2+}$. Because of this, it is unlikely that they act at the same site on the receptor as does extracellular $Ca^{2+}$. In contrast, organic and inorganic polycations do cause the mobilization of intracellular $Ca^{2+}$ in the absence of extracellular $Ca^{2+}$ and therefore probably act at the same site as does extracellular $Ca^{2+}$. Compounds like NPS R-568, presumably act in an allosteric manner and their activity is dependent on some minimal level of extracellular $Ca^{2+}$. This suggests that partial occupancy of the extracellular $Ca^{2+}$-binding site on the receptor is required for compounds like NPS R-568 to be effective. This model is consistent with the observations described in Example 21.

Other details of the mechanism of action of NPS R-568 on the parathyroid cell calcium receptor, however, are more accurately investigated by binding studies in which the specific binding of radiolabeled (using $^3$H for example) NPS R-568 is assessed. There are several molecular mechanisms that could explain the activity of NPS R-568 on the parathyroid cell calcium receptor. In one mechanism (model 1), NPS R-568 could bind to the calcium receptor at a site that, when occupied, is not sufficient to activate the receptor functionally. Activation only occurs when some level of occupancy of the extracellular $Ca^{2+}$-binding site(s) is achieved. In an alterative mechanism (model 2), the occupation of the extracellular $Ca^{2+}$-binding site could unmask latent binding sites for compounds such as NPS R-568. Occupancy of this latent site by NPS R-568 then increases the affinity and/or efficacy of binding at the extracellular $Ca^{2+}$ site. Either mechanism involves a form of allosteric activation of the calcium receptor by compounds such as NPS R-568. These are not the only possible mechanisms that could explain the effect of compounds like NPS R-568 on the parathyroid cell calcium receptor. Other mechanisms of action may be suggested by the results of the binding studies described below.

To further investigate the mechanism of action of compounds like NPS R-568 on the parathyroid cell calcium receptor, binding studies using $^3$H-NPS R-568 can be performed. The specific binding of $^3$H-NPS R-568 to intact parathyroid cells or to membranes prepared from parathyroid cells is initially investigated by techniques well known in the art. The kinetic parameters of binding will then be measured as a function of extracellular $Ca^{2+}$ concentrations. Specifically, Scatchard analysis of the data will reveal the number of binding sites and the apparent affinity of the receptor site for $^3$H-NPS R-568. These parameters will then be investigated as a function of changes in the level of extracellular $Ca^{2+}$ in the buffer used for the assay. If model 1 is correct, then a significant level of specific binding should occur in the absence of extracellular $Ca^{2+}$. Large changes in the kinetic parameters of binding as a function of the level of extracellular $Ca^{2+}$ would favor model 2. It is expected that various other inorganic and organic polycations described above in other examples will cause similar changes in the binding parameters of $^3$H-NPS R-568 as does extracellular $Ca^{2+}$. This would support the view that these polycations act at the extracellular $Ca^{2+}$-binding site, which is distinct from that to which compounds like NPS R-568 bind.

Example 22
Synthesis and Chiral Resolution of NPS 467

This example describes a protocol used to synthesis NPS 467 and its resolution into individual enantiomers. In a 250-ml round-bottom flask, 10.0 g (100 mmoles) 3'-methoxyacetophenone and 13.5 g (100 mmoles) 3-phenylpropylamine were mixed and treated with 125 mmoles (35.5 g) titanium(IV) isopropoxide. The reaction mixture was stirred 30 minutes at room temperature under a nitrogen atmosphere. After this time 6.3 g (100 mmoles) sodium cyanoborohydride in 100 ml ethanol was added dropwise over the course of 2 minutes. The reaction was stirred at room temperature under nitrogen for 16 hours. After this time the reaction mixture was transferred to a 2-L separatory funnel with 1.5 L of diethyl ether and 0.5 L of water. The phases were equilibrated and the ether layer removed. The remaining aqueous phase was thoroughly extracted with four 1-L portions of diethylether. The washes were combined, dried over anhydrous potassium carbonate and reduced to a clear, light amber oil.

TLC analysis of this material on silica gel using chloroform-methanol-isopropylamine (100:5:1) showed product at $R_f$ 0.65 with traces of the two starting materials at $R_f$ 0.99 (3'-methoxy acetophenone) and $R_f$ 0.0 (3-phenylpropylamine).

The reaction mixture was chromatographed through silica gel (48×4.6 cm) using a gradient of chloroform-methanol-isopropylamine (99:1:0.1) to (90:10:0.1) which yielded 13.66 g of purified NPS 467. This material was dissolved in hexane-isopropanol (99:1) containing 0.1% diethylamine to yield a solution with a concentration of 50 mg/ml. Chiral resolution was accomplished by chromatography of 4 ml of this solution (200 mg, maximum to achieve separation) through ChiralCel OD (25×2 cm) using 0.7%. isopropanol, 0.07% diethylamine in hexane at 10 ml/min, monitoring optical density at 260 nm.

Under these conditions (with injections of 100 mg material) the early-eluting isomer (NPS R-467; (R)-(+)-N-(3-phenylpropyl)-α-methyl-3-methoxybenzylamine) began to emerge from the column at about 26 minutes, the late-eluting isomer (NPS S-467) began to emerge at about 34 minutes. Baseline resolution was accomplished under these conditions. Each optical isomer (free base) was converted to the corresponding hydrochloride salt by dissolving 3 g of the free base in 100 ml ethanol and treating it with 100 ml water containing 10 molar equivalents HCl. Lyophilization of these solutions yielded white solids.

Example 23
Synthesis of NPS R-568

NPS R-568, (R)-(+)-N-[3-(2-chlorophenyl)propyl]-α-methyl-3-methoxybenzylamine, was synthesized using the methods described in Example 22 substituting an equivalent amount of 3-(2-chlorophenyl)propylamine for 3-phenylpropylamine. It was found that allowing the mixture of 3'-methoxyacetophenone, 3-(2-chlorophenyl)propylamine and titanium(IV) isopropoxide to stir for 5 hours prior to treatment with NaCNBH$_3$/EtOH resulted in significantly greater yield (98%).

Example 24
NPS R-467 Lowers Serum Ionized Calcium When Administered Orally

Rats (male, Sprague-Dawley, 250–300 g) were fed standard rat chow and fasted overnight prior to the experiment. NPS R-467 was suspended in corn oil and administered as a single oral dose through a gavage needle. Three hours later a sample of blood was taken from the tail vein and assessed for ionized $Ca^{2+}$ levels. FIG. 44 shows that NPS R-467 caused a dose-dependent reduction in serum levels of ionized $Ca^{2+}$ when administered orally.

Example 25
BoPCaR 1 Cloning Method

This example describes the cloning of a bovine parathyroid calcium receptor using an expression cloning strategy. The expression cloning strategy involved assaying the ability of nucleic acid to express a polypeptide which activates Cl$^-$ currents in *Xenopus laevis* oocytes. *X. laevis* oocytes were chosen as hosts, to express nucleic acid encoding the bovine parathyroid calcium receptor, based on the following factors: (i) they exhibit a high level of maturity (i.e., Stage V, VI); (ii) they exhibit a high activity of Cl$^-$ currents activated by $Ca^{2+}$ ionophores like A23187; and (iii) they exhibit a high level of functional expression of $Gd^{3+}$-induced Cl$^-$ current when injected with 25 ng/oocyte of total poly(A)$^+$-mRNA isolated from bovine parathyroid.

The techniques used to clone the parathyroid calcium receptor are briefly described in this example; a more complete description of the techniques is provided in preceding sections, which describe techniques which may be used to clone additional forms of the $Ca^{2+}$-receptor from other cell types. Poly($A^+$)-enriched mRNA was initially prepared from bovine parathyroid glands by extracting with guanidinium thiocyanate, centrifugation through CsCl and oligo(dT) cellulose chromatography. Injection of the resultant poly($A^+$)-enriched mRNA into oocytes (25–50 ng/oocyte) conferred sensitivity to elevated extracellular concentrations of $Ca^{2+}$ and the trivalent cation (1–100 $\mu$M) $Gd^{3+}$ as described herein, such that the two cations elicited calcium-activated chloride currents. No such currents were elicited in control eggs injected with water.

The mRNA was then subjected to size fractionation, utilizing preparative, continuous flow agarose gel electrophoresis (Hediger, M. A., Anal. Biochem. 159: 280–286 (1986) ) to obtain fractions of poly($A^+$)-mRNA further enriched in transcripts coding for the $Ca^{2+}$ receptor. Oocytes injected with size-fractionated mRNA of about 4–5.5 Kb showed enhanced expression of $Gd^{3+}$-activated $Cl^-$ currents.

Size-fractionated mRNA of about 4–5.5 Kb in size were used to prepare a size-selected, directional cDNA library in the plasmid pSPORT1 that was enriched in full-length transcripts. Sense complementary RNA (cRNA) was then synthesized from the DNA inserts pooled from 350–500 independent clones from this library and injected into oocytes. $Gd^{3+}$-activated $Cl^-$ currents were observed following injection of RNA from a single filter containing 350 colonies. Preparation and injection of cRNA from successively smaller pools of clones led to isolation of a single clone (BoPCaR 1) with a cDNA insert of 5.3 kb which expressed greatly enhanced $Ca^{2+}$-receptor activity following injection of its cRNA into oocytes. A plasmid containing the BoPCaR 1 cDNA (See restriction map, FIG. 45; plasmid, FIG. 46; and nucleotide sequence (SEQ. ID. NO. 1), FIG. 47) has been deposited in the ATCC under deposit number 75416.

The BoPCaR 1 cDNA is outside the size range of the size-selected RNA found to express neomycin elicited $Cl^-$ channel activity in Xenopus oocytes. This is consistent with the possibilities that different isoforms of the calcium receptor exist or that multiple genes encode other members of the calcium receptor gene family.

Several pharmacological and biochemical criteria were used to identify this clone as encoding a bona fide bovine parathyroid $Ca^{2+}$ receptor. Oocytes expressing the cloned receptor, but not water-injected oocytes, responded to increasing concentrations of extracellular $Ca^{2+}$ (1.5–5 mM) or $Gd^{3+}$(20–600 $\mu$M) with large increases in $Cl^-$ currents (up to at least 1.8 microamperes) that were several-fold larger than those observed in poly($A^+$)-injected oocytes. These responses increased markedly over a period of one to four days after injection of the eggs with cRNA prepared from the BoPCaR 1 cDNA. Furthermore, the ranges of the concentrations of the two cations eliciting this response were very similar to those shown previously to act on bovine parathyroid cells in vitro. Neomycin (20–100 $\mu$M), which is known to closely mimic the effects of $Ca^{2+}$ on parathyroid cells, produced changes in $Cl^-$ current in oocytes essentially identical to those produced by $Ca^{2+}$ or $Gd^{3+}$, and these occurred over the same range of concentrations over which this antibiotic modulates parathyroid function in vitro.

Finally, in vitro translation of RNA prepared from the clone resulted in a single major protein on polyacrylamide gels with a molecular weight of about 120 kd, whose synthesis was enhanced by inclusion of dog pancreatic microsomes, concomitant with an increase in apparent molecular weight of 10–15%. The latter suggests that the cloned receptor interacts strongly with membranes, as might be expected of an integral membrane protein receptor, and is glycosylated in its native form. Studies with the lectin concanavalin A indicate that the $Ca^{2+}$ receptor is likely a glycoprotein. Thus, the pharmacological properties of the cloned receptor, which is expressed at high levels in oocytes, as well as the biochemical studies carried out to date are completely consistent with its identity as the bovine parathyroid $Ca^{2+}$ receptor.

Oocytes injected with cRNA (50 nl of 0.125 $\mu$g/ml) prepared from BoPCaR1 show large inward currents in response to elevated extracellular concentrations of $Ca^{2+}$ (5 mM), $Mg^{2+}$ (10–20 mM), $Gd^{3+}$ (600 $\mu$M), or neomycin (200 $\mu$M), resulting from activation of the $Ca^{2+}$-activated chloride currents. These responses are mediated by the following series of biochemical events:

(1) Activation of phospholipase C by a pertussis toxin-sensitive guanine nucleotide regulatory (G) protein resulting in 4–7 fold increases in the levels of inositol 1,4,5-triphosphate ($IP_3$). Preincubation with 10 $\mu$g/ml of pertussis toxin for 48 hours inhibits the increase by 75%;

(2) Release of $Ca^{2+}$ from intracellular stores. The several-fold increase in the $[Ca^{2+}]_i$ measured in oocytes loaded with the $Ca^{2+}$-sensitive fluorescent dye, fluo-3, persists even when the oocytes are exposed to $Gd^{3+}$ or neomycin in the absence of extracellular $Ca^{2+}$. Furthermore, the inward currents elicited by $Gd^{3+}$ or neomycin also persist despite removal of extracellular $Ca^{2+}$.

(3) The polyvalent cation-induced increases in $[Ca^{2+}]_i$ are necessary for the associated electrophysiological responses. The $Ca^{2+}$ chelator, EGTA (100 $\mu$M), prevents oocytes expressing the calcium receptor from responding with inward currents to 600 $\mu$M $Gd^{3+}$.

(4) The activated currents appear to be $Ca^{2+}$-activated chloride currents. The currents are activated by the divalent cation ionophore, A23187, which raises $[Ca^{2+}]_i$. The chloride channel-blocker 9AC blocks the currents.

Example 26

Use of NPS R-568, and Other Compounds, as a Diagnostic Tool

NPS R-568 or other compounds active on a calcium receptor can be used as a diagnostic tool. Specifically, a pharmaceutical preparation of such compounds is useful as a diagnostic tool. In one example, a pharmaceutical preparation containing a parathyroid cell calcimimetic compound such as NPS R-568 can be given by oral or another route of administration to hypercalcemic patients with symptoms of mental depression. If these symptoms arise from an underlying hyperparathyroid state, such as primary hyperparathyroidism, then administration of NPS R-568 or a compound that acts similarly will alleviate those symptoms. If the symptoms do not abate, then the mental depression results from some pathological state that is not hyperparathyroidism. Thus, parathyroid cell calcimimetic compounds can be used in the differential diagnosis of mental depression.

Symptoms and signs common to hyperparathyroidism and other disorders can also be differentially diagnosed in the manner described above. Such shared signs and symptoms include, but are not limited to, hypertension, muscular weakness, and a general feeling of malaise. Alleviation of these symptoms following treatment with a parathyroid cell calcium receptor calcimimetic compound would indicate that the problems result from the underlying hyperparathyroidism.

In another example, a compound acting as an antagonist (calcilytic) at the C-cell calcium receptor can be administered as described above to diagnose medullary thyroid carcinoma. In this case, administration of the C-cell calcium receptor calcilytic compound will depress serum levels of calcitonin which can be readily measured by radioimmunoassay. Certain symptoms associated with medullary thyroid carcinoma, such as diarrhea, may also be monitored to determine if they are abated or lessened following administration of the calcilytic compound.

In a third example, a compound acting as a calcimimetic at the juxtaglomerular cell calcium receptor can be used in the differential diagnosis of hypertension. In this case, administration of the juxtaglomerular cell calcium receptor calcimimetic compound can be carried out as described above. A decrease in blood pressure to normal levels will occur if the hypertension results mostly or exclusively from elevated levels of renin rather than from an alternative pathological state.

In another example, a compound acting as a specific calcimimetic on the osteoclast calcium receptor can be used in the differential diagnosis of high- and low-turnover forms of osteoporosis. In this case, such a compound can be administered in a suitable pharmaceutical preparation and the levels of serum alkaline phosphatase, osteocalcin, pyridinoline and/or deoxypyridinoline crosslinks, and/or some other predictive marker of bone resorption and/or formation measured by techniques well known in the art. A large decrease in one or more of these parameters would be predictive of high-turnover osteoporosis, whereas a small or no decrease in these parameters would be predictive of low-turnover osteoporosis. Such information would dictate the appropriate treatment. Antiresorptive drugs would not be the appropriate sole therapy for low-turnover osteoporosis.

These examples are not exhaustive but serve to illustrate that specific calcium receptors can be targeted with pharmaceutical preparations and that the observed effects of such preparations on bodily functions and/or chemical constituents can be used diagnostically. In general, calcimimetic and calcilytic compounds that act on calcium receptors of the various cells described above can be used in the diagnosis of the various diseases associated with the particular cell type. These diseases include, but are not limited to, bone and mineral-related disorders (as described in Coe and Favus, *Disorders of Bone and Mineral Metabolism*, Raven Press, 1990), kidney diseases, endocrine diseases, cancer, cardiovascular diseases, neurological diseases, gastrointestinal diseases, and diseases associated with gestation. Examples of human diseases or disorders in which such molecules may be therapeutically effective are as follows:

(1) A calcimimetic is expected to ameliorate psoriasis by reducing the proliferation of the abnormal skin cells.

(2) Since $Ca^{2+}$ blocks the effect of vasopressin on MTAL and cortical collecting duck cells, a calcimimetic is expected to reduce water retention in states of vasopressin excess, such as the syndrome of inappropriate vasopressin (ADH) secretion. Conversely, calcium receptor antagonists used in states of ADH deficiency are expected to potentiate the action of any ADH present, such as in partial central diabetes insipidus.

(3) Calcimimetics may be used to treat hypertension by: (a) reducing renin secretion and/or (b) by stimulating production of vasodilators such as PTHrP (PTH-related peptide) by vascular smooth muscle.

(4) Calcimimetics are expected to increase platelet aggregability, which may be useful when platelet counts are low. Conversely, calcilytics are expected to inhibit platelet function in states where there is hypercoagulability.

(5) Calcium promotes differentiation of colon and mammary cells. A calcimimetic is expected to reduce the risk of colon or breast cancer.

(6) Calcium promotes urinary calcium excretion in the MTAL. A calcimimetic is expected to have a useful hypocalcemic action in the therapy of hypercalcemic disorders. The inhibitory effect of calcimimetics on osteoclasts and their stimulation of the secretion of the hypocalcemic peptide calcitonin make them expected to be useful in the therapy of hypercalcemia and its symptoms. A calcimimetic may also improve hypocalcemic symptoms by activating calcium receptors. Conversely, a calcilytic is expected to reduce urinary calcium excretion and be useful in the treatment of kidney stones. In addition, calcium suppresses the formation of 1,25-dihydroxyvitamin D in the proximal renal tubule, and this vitamin D metabolite is frequently overproduced in renal stone patients and contributes to their hypercalciuria. Suppression of 1,25-dihydroxyvitamin D formation by a calcimimetic is expected to be useful in treating renal calcium stone disease.

(7) Endogenous amines could reproduce the symptoms in uremic patients by calcimimetic or calcilytic actions. Calcimimetic and/or calcilytic agents are expected to improve these symptoms.

(8) Some of the renal toxicity of aminoglycoside antibiotics may be mediated by interaction of these drugs with renal calcium receptors. Having the calcium receptor is expected to make it possible to carry out drug screening easily when designing new drugs of these classes to minimize renal toxicity. In addition, a renal calcium receptor antagonist would prevent or treat this renal toxicity if it is related to this mechanism.

(9) Some of the genetic components of calcium-related disorders, such as osteoporosis, renal stones, and hypertension are expected to be related to inherited problems with certain forms of the receptor. These now can be studied and genetic screening/testing carried out using receptor-based reagents. The human disease, familial hypocalciuric hypercalcemia, may be due to a calcium receptor defect. Definitive diagnostic separation from cases of primary hyperparathyroidism could be carried out with receptor-based technology.

(10) Calcium receptors are present in the placenta and are expected to impact on disorders of placental function and transfer of nutrients to the growing fetus.

Example 27

Cloning of Human Parathyroid Calcium Receptor From a Human Parathyroid Gland Adenoma Tumor This example describes the cloning of a human parathyroid calcium receptor from a human parathyroid gland adenoma tumor using pBoPCaR1 as a hybridization probe. The probe was used to identify nucleic acid encoding human parathyroid gland calcium receptor by cross-hybridization at reduced stringency.

Messenger RNA was prepared from a human parathyroid gland adenoma tumor removed from a 39-year-old Caucasian male diagnosed with primary hyperparathyroidism. Northern blot analysis of this mRNA using pBoPCaR1 as a hybridization probe identified calcium receptor transcripts of about 5 Kb and about 4 Kb. A cDNA library was constructed from the mRNA. Double-stranded cDNA larger than 3 Kbp were size-selected on an agarose gel and ligated into the cloning vector lambda ZapII. Five hundred thousand primary recombinant phage were screened with the 5.2 Kbp cDNA insert of pBoPCaR1 as a hybridization probe. The pBoPCaR1 insert was labeled by random-primed synthesis using [$^{32}$p]-dCTP to a specific activity of $1\times10^9$ cpm/μg.

Library screening was performed at a hybridization stringency of 400 mM Na$^+$, 50% formamide at a temperature of 38° C. Plaque lift filters were hybridized at a probe concentration of 500,000 cpm/ml for 20 hours. Following hybridization, filters were washed in 1× SSC at 40° C. for 1 hr.

The primary screen identified about 250 positive clones identified by hybridization to pBoPCaR1. Seven of these clones were taken through secondary and tertiary screens to isolate single clones that hybridized to the pBoPCaR1 probe. These seven clones were analyzed by restriction enzyme mapping and Southern blot analysis. Three of the clones contained cDNA inserts of about 5 Kbp and appear to be full-length clones corresponding to the 5 Kb mRNA. Two of the clones contain cDNA inserts of about 4 Kbp and appear to be full-length clones corresponding to the 4 Kb mRNA.

Restriction enzyme mapping of the two different sized inserts indicate that they share regions of sequence similarity in their 5' ends, but diverge in their 3' end sequences. DNA sequence analyses indicate that the smaller insert may result from alternative polyadenylation upstream of the polyadenylation site used in the larger insert.

Representative cDNA inserts for both size classes were subcloned into the plasmid vector pBluescript SK. Linearization followed by in vitro transcription using T7 RNA polymerase produced cRNA transcripts. The cRNA transcripts were injected into Xenopus oocytes (150 ng/μl RNA; 50 nl/oocyte) for functional analysis. Following incubation periods of 2–4 days, the oocytes were assayed for the presence of functional calcium receptors. Both clone types gave rise to functional calcium receptors as assessed by the stimulation of calcium-activated chloride currents upon addition of appropriate calcium receptor agonists. Known calcium receptor agonists, including NPS R-467 and NPS R-568, activated the oocyte-expressed receptor at about the same concentrations known to be effective for the native parathyroid cell receptor. Thus, both clones encode a functional, human parathyroid cell calcium receptor.

Plasmids were prepared by subcloning each size class of insert into pBluescript thereby producing pHuPCaR 5.2 and pHuCaR 4.0. The nucleic acid sequence, and amino acid sequence, of the inserts are shown in FIGS. 48 (pHuPCaR 5.2, SEQ. ID. NO. 2) and 49 (pHuPCaR 4.0, SEQ. ID. NO. 3).

Several differences were observed between the nucleic acid sequences of the two cDNA inserts. Sequence analyses of the two cDNA inserts indicate the existence of at least two sequence variants differing in the 3' untranslated region and which may result from alternative polyadenylation (see SEQ. ID. NOs. 2 and 3). In addition, sequence variation exists at the 5' end of the inserts (see SEQ. ID. NOs. 2 and 3). These distinct sequences correspond to untranslated regions and may have arisen due to alternative transcriptional initiation and/or splicing.

Three additional sites of sequence variation are observed within the coding regions of cDNA clones pHuPCaR4.0 and pHuPCaR5.2 (see SEQ. ID. NOs. 2 and 3) demonstrating that these cDNA clones encode distinct proteins. Sequence analysis of the human CaR gene (obtained from overlapping clones as described in Example 29) indicates that the additional 30 base pairs of DNA in cDNA clone pHuPCaR5.2, as compared to the pHuPCaR 4.0 cDNA clone, results from alternative mRNA splicing. The alternative mRNA splicing is predicted to insert 10 additional amino acids into the CaR polypeptide encoded by the pHuPCaR5.2 cDNA at a site between aa#536 and aa#537 in polypeptide encoded by pHuPCaR4.0 cDNA. In addition, pHuPCaR4.0 encodes glutamine (Gln) at aa#925 and glycine (Gly) at position 990 whereas pHuPCaR5.2 encodes arg (Arg) at both equivalent positions. The human CaR gene encodes for Gln and Arg, respectively, at these positions. The difference between the pHuPCaR4.0 cDNA compared to human DNA appears to represent a true sequence polymorphism within the human population while the single base change in pHuPCaR5.2 probably reflects a mutation which occurred during its cloning. Both cDNAs encode functional calcium receptors as demonstrated by the ability of Xenopus oocytes injected with cRNA prepared from these cDNA clones to respond to 10 mM extracellular calcium as ascertained by Cl– conductance. However, it is possible that these two receptor isoforms are functionally and/or pharmacologically distinct.

Example 28

Cloning a Calcium Receptor From Normal Human Parathyroid Tissue

This example describes the cloning of a calcium receptor from normal human parathyroid tissue. Experimental evidence has shown that parathyroid cells from adenomatous tissue are less responsive to increases in extracellular calcium (they have an elevated calcium "set-point"). It has been postulated that this change may arise from an alteration of the calcium receptor itself. One of the uses of the cloned receptor found in normal parathyroid tissue is to compare its primary nucleic acid sequence with that of the calcium receptor found in adenomatous tissue to determine if there are any differences in the nucleic acid sequences. Such differences may account for the alteration in the calcium receptor and may be used to further characterize regions of the calcium receptor associated with responsiveness to calcium.

Parathyroid glands (150 mg) were removed at autopsy from a 69-year-old Caucasian female with no history of parathyroid disease. Messenger RNA was prepared from this tissue and used in the construction of a cDNA library. cDNA inserts from this library were not size-selected. Six-hundred-thousand primary recombinants were screened with probe made from the 5.2 Kbp cDNA insert from the human calcium receptor clone, pHtPCaR-5.2. Hybridization was carried out at 42° C. and filters were washed at a stringency of 1× SSC, at 52° C. The primary screen identified about 30 positive clones, twelve of which were isolated and characterized. Partial sequence analysis indicated that these clones are essentially identical to cDNA sequences obtained from ademonous parathyroid (see Example 27).

Example 29

Isolation of Human Genomic Clones With Homology to the Calcium Receptor

Human calcium receptor genomic clones were isolated using the pBoPCaR1 cDNA insert as a hybridization probe. In particular, a human genomic DNA library, obtained from Stratagene, was screened using the pBoPCaR1 cDNA insert as hybridization probe.

A portion of the library (500,000 clones) was screened with the pBoPCaR1 cDNA insert by hybridizing in 400 mM Na$^+$, 50% formamide, at 37° C., and washing with 1× SSC at 40° C. Twenty-four clones were identified. The nucleic acid from these clones were analyzed by restriction mapping and Southern blot analysis using distinct regions of the pHuPCaR-5.2 cDNA insert as hybridization probes. Nine of the 13 clones encoded portions of the human parathyroid calcium receptor gene as evinced by hybridization to pHuPCaR-5.2 cDNA. The complete gene is represented on overlapping clones pHuCaR-#4, #5, #6, #7 and #9. DNA sequence analysis of these clones indicates that the receptor is encoded by seven coding exons. The majority of the receptor mRNA (3' end) appears to be encoded by a single exon. The receptor encoded by these genomic clones is essentially identical to those encoded by cDNA clones pHuPCaR4.0 and pHuPCaR5.2 (Seq. ID. Nos. 2 and 3) (see Example 27, supra, which describes the differences between the human nucleic acid sequence obtained from overlapping clones pHuCaR-#4, #5, #6, #7 and #9, pHuPCaR4.0 and pHuPCaR5.2). Equivalent clones can be isolated as described herein, as can other clones encoding members of this receptor family.

Example 30
Cloning Ion Receptors From the Kidney

This example describes the cloning of ion receptors from rat kidney cells using pBoPCaR1 as a hybridization probe. A cDNA library was prepared from rat kidney outer medulla mRNA size-fractionated to contain transcripts between 3 and 7 Kb. About seventy-five-thousand clones were screened using pBoPCaR1 as a hybridization probe at 42° C. overnight followed by washing in 0.5× SSCP at 42° C. Three positive clones were identified.

Clone 3A (pRakCaR 3A) contained an insert of about 4.0 Kbp. The nucleic acid and amino acid sequence of the 3A insert is shown in FIG. 50 (SEQ. ID. NO. 8). Northern analysis indicated that pRakCaR 3A hybridized to both 7.5 Kb and 4.0 Kb transcripts. DNA sequence analysis of clone 3A (SEQ. ID. No. 4) indicates that it is highly homologous to other calcium receptor sequences. Xenopus oocyte analysis of in vitro transcripts of the clone confirmed that clone pRakCaR 3A encodes a functional calcium receptor.

Example 31
Cloning of C-cell Calcium Receptor

This example describes the cloning of human thyroid C-cell calcium receptor using pHuPCaR 5.2 as a hybridization probe. Functional evidence indicates that the calcitonin-secreting C-cells of the thyroid gland express a calcium receptor. Pharmacological evidence indicates that this receptor is functionally distinct from the parathyroid calcium receptor. Northern blot analysis of human, bovine and rat thyroid gland mRNA identifies a faintly hybridizing transcript when pHuPCaR-5.2 is used as hybridization probe. The diminished intensity of the identified transcript may be due either to low abundance (C-cells represent 0.01% to 1% of thyroid cells) or may indicate structural differences between parathyroid and C-cell calcium receptors.

Northern blot analysis of a rat C-cell line (44-2) using a rat calcium receptor genomic clone as hybridization probe identifies a single, moderately abundant transcript about 8.0 Kb. This is similar to the size of the rat parathyroid calcium receptor transcript and provides evidence that C-cells express a calcium receptor. DNA sequence analysis of products from polymerase chain reaction amplification of selected regions of the rat C-Cell calcium receptor showed it to be essentially identical to the calcium receptor encoded by the rat kidney cDNA clone of Example 30 (FIG. 50).

A human C-cell calcium receptor was cloned from a thyroid cDNA library obtained from Clonetech. The library was prepared from tissue obtained at autopsy from normal Caucasian males (trauma victims; no history of thyroid disease). About five-hundred-thousand recombinant phage were screened at a stringency of 400 mM $Na^+$, 50% formamide at a temperature of 40° C., and filters were washed at 1× SSC, 42° C. Four cDNA clones hybridizing with pHuPCaR-5.2 were obtained. Insert sizes ranged from 0.8 to 2 Kbp. Initial sequence analysis indicates that this calcium receptor sequence is highly homologous to the human parathyroid calcium receptor. Equivalent clones can be readily isolated as described herein.

Example 32
Cloning Inorganic ion Receptors by Use of Degenerate Sequence PCR Analysis of the calcium receptor sequences (bovine, rat and human) by sequence database comparison indicates that the calcium receptor sequence is unique. No significant homology is obvious to any known protein or nucleic acid sequence with one exception. The parathyroid calcium receptor exhibits weak, but significant homology (20–30% amino acid identity) with the metabotropic glutamate receptors (mGluRs). This surprising and unexpected result indicates that calcium receptors are structurally related to mGluRs and probably evolved from a common ancestral gene several hundred million years ago. However, calcium receptors are functionally distinct from mGluRs and in experiments on bovine parathyroid cells, or on Xenopus oocytes ectopically expressing calcium receptors, did not respond to the mGluR agonists glutamate, trans-ACPD and quisqualate.

The discovery of the calcium receptor sequence makes it possible to determine regions of extremely high sequence conservation. Such regions are useful for guiding the preparation of hybridization and PCR probes which can be used to detect and isolate cDNA and genomic sequences encoding additional related receptors such as inorganic ion receptors.

Analysis of the amino acid sequences of calcium receptors and mGluRs indicates that the homology is highest in several limited regions including portions of both N-terminal putative extracellular domains and the seven-transmembrane domain regions. Based on the later, four degenerate oligonucleotides have been synthesized for use in PCR. These are:

TM2: SEQ. ID. NO:17 CCTGCTCGAGACIA(A,G)(C,T)CGGGA(A,G)CT(C,T)T(C,G)CTA(C,T) (C,A)T;

TM5: SEQ. ID. NO:18 CGGAATTCCGTTCGGG(A,T)(C,T)TTGAA(C,G)GC(A,G)(A,T)A(G,C);

CL1: SEQ. ID. NO:19 CCTGCTCGAGTCAAGGCTACG(A,G)(A,G)I(C,A)G(G,A,C,T)GA(G,A)(C,T)T;

and, CL3: SEQ. ID. NO:20 CGGAATTCCATTTGGCTTCGTTGAAI(T,G)T(A,G,C,T)(G,T)C(G,A,T,C)GG.

These oligonucleotides contain XhoI or EcoR1 restriction sites within "PCR anchors" at their 5' ends to facilitate subcloning of the amplification products. The sequences were selected based on conservation of sequences within transmembrane domains 2 and 5 and cytoplasmic loops 1 and 3.

Four different primer combinations can be used to obtain ion receptor clones: TM2+TM5, TM2+CL3, CL1+TM5, and CL1+CL3. PCR reactions were carried out using standard conditions (see, e.g., Abe et al. J. Biol. Chem., 19:13361 (1992)) using annealing temperatures between 37° C. and 55° C. Each combination gave rise to products approximately 500 bp when used to amplify cDNAs or genomic DNAs containing ion receptors and/or mGluRs. Libraries of such PCR products have been prepared after amplification of such sequences from cDNAs prepared from a variety of tissues, and from genomic DNA. Analysis of the products resulted in the detection of parathyroid calcium receptor sequences, 5 mGluR sequences and additional sequences which are being characterized. The additional new sequences may encode other inorganic ion receptors.

This example, like the other examples described herein, is not meant to be limiting. Various other highly conserved sequence regions can be identified and utilized in a similar fashion. Such advances are made possible by the discovery of the parathyroid calcium receptor sequence, as will be recognized by those of ordinary skill in the art. The cloning of such PCR products enables the isolation of complete genomic clones and of full-length cDNA clones from the tissue sources identified by, for example, Northern analysis using the cloned PCR product. As additional members of this family are discovered and their sequences determined, refinement of this approach will be possible. Thus, the invention herein enables the discovery of more and more members of this receptor family via an iterative process.

Example 33
Antibodies Against Calcium Receptors

Cloned human and bovine calcium receptors can be used to produce antibodies which recognize various regions of the receptor including extracellular domains, cytoplasmic domains, extracellular loops and cytoplasmic loops. Recombinant expression of three regions of the N-terminal extracellular domain has been achieved. In particular, GST fusion products have been produced containing amino acids 9–258 and 259–334, respectively, of the bovine parathyroid calcium receptor and amino acids 340–620 from the human parathyroid calcium receptor. These fusion products were isolated by preparative SDS-PAGE and injected into rabbits resulting in polyclonal antibodies against the putative extracellular domain.

In addition, the following synthetic peptides have been produced by Multiple Peptide Systems, Inc:
SEQ. ID. NO. 9: YKDQDLKSRPESVEC,
SEQ. ID. NO. 10: ADDDYGRPGIEKFREEAEERDIC,
SEQ. ID. NO. 11: CIDFSELISQYSDEEKIQQ,
SEQ. ID. NO. 12: YHNGFAKEFWEETFNC,
SEQ. ID. NO. 13: DGEYSDETDASAC,
SEQ. ID. NO. 14: NTPIVKATNRELSYC,
SEQ. ID. NO. 15: YRNHELEDEIIFITC, and
SEQ. ID. NO. 16: RKLPENFNEAKYC.
These amino acid sequence are based upon regions of the bovine parathyroid calcium receptor.

These peptides were conjugated to KLH and injected into rabbits to produce polyclonal antibodies or injected into mice to produce monoclonal antibodies. Such antibodies are capable of recognizing specific regions of the bovine parathyroid calcium receptor and most would be expected to recognize calcium receptors from other species including human calcium receptors. Highly acidic peptides (e.g., SEQ. ID. NOs. 9–12 and 15), derived from acid-rich regions of the calcium receptor may be involved in binding to calcium ion. It is expected, therefore, that such antibodies will be capable, alone or in combination, of neutralizing the calcium receptor by preventing the binding or action of calcium.

Example 34
Recombinant Expression of Parathyroid Calcium Receptors in Vertebrate Cells Recombinant expression of calcium receptors in vertebrate cells can be achieved by inserting cDNA encoding these receptors into appropriate expression vectors. To assess the best cell line for functional expression, the following seven plasmid vectors were constructed using bovine and human cDNAs encoding parathyroid calcium receptors:

(1) The plasmid pSV-BoPCaR was constructed by subcloning the 5.3 Kbp XbaI-SalI fragment from the bovine parathyroid calcium receptor cDNA into XbaI-XhoI cut PSVL. The expression vector pSVL was purchased from Pharmacia. The vector pSVL contains the SV40 late promoter and VP1 processing signals, and is designed to give high levels of expression in a variety,of cell lines.

(2) The plasmid CMV-BoPCaR was constructed by subcloning the 5.3 Kbp XbaI-SalI fragment from bovine parathyroid calcium receptor into XbaI-XhoI cut pcDNAI/Amp. The vector pcDNAI/Amp was purchased from Invitrogen. This vector utilizes the promoter/enhancer sequences from the immediate early gene of the human cytomegalovirus to drive high-level expression in a variety of cell lines.

(3) The plasmid-471 SportsCaRB, having 471 bp of noncoding sequence removed from the 5' end of BoPCaR cDNA, was constructed by subcloning a 4.8 Kbp blunt-ended SauI-XbaI fragment of BPoCaR cDNA into SmaI cut PSV-SPORT. The vector pSV-SPORT was purchased from Gibco-BRL. This vector utilizes the SV40 early promoter to drive transient expression in a ariety of cell lines.

(4) The plasmid CMVHuPCaR4.0 was constructed by subcloning the HindIII-NotI 4.0 Kbp fragment from human calcium receptor cDNA into HindIII-NotI cut pcDNAI/Amp.

(5) The plasmid CMVHuPCaR5.2 was constructed by subcloning the HindIII-NotI 5.2 Kbp fragment from human calcium receptor cDNA into HindIII-NotI cut pcDNAI/Amp.

(6) The plasmid pSV-HuPCaR4.0 was constructed by subcloning the SalI-NotI 4.0 Kbp fragment from human calcium receptor cDNA into SalI-NotI cut pcDNAI/Amp.

(7) The plasmid pSV-HuPCaR5.2 was constructed by subcloning the SalI-NotI 5.2 Kbp fragment from human calcium receptor cDNA into SalI-NotI cut pcDNAI/Amp.

The above expression vectors were first validated for correct construction by in vitro transcription and injection into *Xenopus oocytes*. All were found to elicit expression of functional calcium receptors.

Next, these vectors were transfected into a variety of vertebrate cells including: COS7, CHO, DHFR-CHO, HEK293, JEG, Rat2 fibroblasts, MDBK, CV1, UMR, AtT20, Y1, OK, LLC-20 PK1. Several different transfection techniques were used including calcium phosphate precipitation, DEAE-dextran, electroporation and lipofection. All the transfected cell lines gave rise to substantial levels of calcium receptor transcript.

Functional calcium receptor expression was assessed by loading cells with fura-2 and measuring changes in intracellular calcium levels after addition of calcium receptor agonists. Control constructs were prepared by cloning the substance K receptor and the M1 muscarinic receptor cDNAs into similar commercial vectors as described above. Control constructs were transfected into the various cell lines described above, and the response of the cells containing the control constructs to substance K or to carbachol, respectively, was measured. Classical responses (i.e., a rapid and transient increase in internal calcium followed by a lower, sustained increase in internal calcium) were generally observed for cells containing control receptor constructs when treated with the ligand appropriate for the receptor being expressed, but not when treated with an inappropriate ligand. Neither control responded to increases in extracellular calcium. Similarly, HEK293, CHO and JEG-3 cells transfected with the calcium receptor constructs did not respond to substance K or to carbachol. However, a weak, but significant, response was observed in these cells only when extracellular calcium was increased from 1 mM to 10 mM.

Example 35
Selection of Stable Recombinant Cells Expressing the Calcium Receptor Clonal cell lines that stably express the two human and the bovine calcium receptors have been isolated. Calcium receptor cDNAs were subcloned in two different, commercially available expression vectors; pMSG (obtained from Pharmacia) and Cep4B (obtained from Invitrogen). The first vector contains the selectable marker gene for xanthine-guanine phosphoribosyltransferase (gpt) allowing stably transfected cells to overcome the blockade of the purine biosynthetic pathway imposed by addition of 2 $\mu$g/ml aminopterin and 25 $\mu$g/ml mycophenolic acid. The second vector encodes a gene conferring resistance to the antibiotic hygromycin (used at 200 $\mu$g/ml). HuPCaR 5.2 and HuPCaR 4.0 cDNAs (SEQ. ID. NOs. 2 and 3, respectively) were removed from the parent bluescript plasmid with Not I and Hind III restriction enzymes and then either ligated directly into Not I+Hind III digested Cep4B or treated with the klenow fragment of DNA polymerase prior to blunt-end ligation into Sma I digested PMSG.

The pMSG subclone containing the HuPCaR 5.2 insert was transfected into CHO cells as discussed above. Selection has resulted in 20 resistant clones which are being characterized. The Cep4B subclone containing the HuPCaR 5.2 insert was transfected into HEK293 cells as described above. Selection with hygromycin resulted in a pool of stable clones. Clones expressing the HuPCaR 4.0 receptor isoform were prepared similarly.

Cells obtained from the pool of hygromycin selected HEK293 cells transfected with Cep4B containing the HuPCaR 5.2 insert were plated on collagen coated Aklar squares which had been placed into individual wells of 12-well tissue culture plates. Two to six days later, medium was removed and the cells washed with balanced salt solution and 1 ml of buffer containing 1 $\mu$M fura2-AM, 1 mM $CaCl_2$ and 0.1% BSA and 1 mM $CaCl_2$. Measurements of fluorescence in response to calcium receptor agonists were performed at 37° C. in a spectrofluorimeter using excitation and emission wavelengths of 340 and 510 nm, respectively. For signal calibration, Fmax was determined after addition of ionomycin (40 $\mu$M) and the apparent Fmin was determined by addition of 0.3 M EGTA, 2.5 M Tris-HCl; pH 10. Robust increases in intracellular calcium were observed in response to the addition of the following calcium receptor agonists: $Ca^{2+}$ (10 mM), $Mg^{2+}$ (20 mM) and NPS R-467. Control cells expressing functional substance K receptors did not respond to these calcimimetic compounds.

Additional clonal isolates of HEK 293 cells transfected with pHuPCaR4.0 sequence were obtained. These were tested for responsiveness to calcimimetics as described above except that the cells were tested while in suspension. Similar positive results were obtained (FIG. 28b).

Example 36
Activity of NPS R-568 in *Xenopus Oocytes* Expressing a Bovine Parathyroid Cell Calcium Receptor

*Xenopus oocytes* were injected with BoPCaR 1, the 5.3 Kb cDNA encoding a bovine parathyroid cell calcium receptor as described in Example 25. After two to three days, Cl⁻ currents were examined in the oocytes using a two-electrode voltage clamp. In the presence of 0.3 or 1 mM extracellular $Ca^{2+}$, exposure of BoPCaR 1-injected oocytes to NPS R-568 caused increases in the Cl⁻ current. The $EC_{50}$ for NPS R-568 in this assay was about 3 $\mu$M. NPS R-568 failed to evoke responses in uninjected oocytes or in oocytes injected with water or rat liver mRNA. NPS S-568 elicited responses in BoPCaR 1-injected oocytes only at much higher concentrations (100 $\mu$M). The results of these experiments demonstrate that NPS R-568 acts in a stereoselective manner in oocytes expressing a bovine parathyroid cell calcium receptor. The data are consistent with a direct action of NPS R-568 on the calcium receptor.

The Cl⁻ current response to NPS R-568 in oocytes expressing BoPCaR 1 was abolished in the absence of extracellular $Ca^{2+}$. Increasing the concentration of extracellular $Mg^{2+}$ to 4 mM (in the absence of extracellular $Ca^{2+}$) restored responsiveness to NPS R-568. NPS R-568 potentiated the responses to submaximal concentrations of extracellular $Ca^{2+}$ and shifted the extracellular $Ca^{2+}$ concentration-response curve to the left without greatly affecting the maximal response (FIG. 51). These effects obtained in oocytes expressing a parathyroid cell calcium receptor mirror those obtained in intact bovine parathyroid cells and offer compelling evidence for a direct effect of NPS R-568 on a parathyroid cell calcium receptor.

The data are also consistent with NPS R-568 increasing the sensitivity of the receptor through an allosteric mechanism by binding to a domain on the calcium receptor distinct from that which binds extracellular $Ca^{2+}$. Alternatively, NPS R-568, although binding at the extracellular $Ca^{2+}$ domain, may lack intrinsic efficacy unless the domain is partially occupied by extracellular $Ca^{2+}$. The more likely hypothesis is the former, in which NPS R-568 acts through an allosteric mechanism to increase the sensitivity of the receptor to activation by extracellular $Ca^{2+}$.

The failure of NPS R-568 to elicit responses in the absence of extracellular $Ca^{2+}$ demonstrates that partial occupancy of the calcium receptor by extracellular $Ca^{2+}$ is necessary for NPS R-568 to activate the receptor. It is not presently known if NPS R-568 binds to the calcium receptor in the absence of extracellular $Ca^{2+}$ or if binding of extracellular $Ca^{2+}$ to the calcium receptor unmasks a cryptic binding site for NPS R-568. These alternative hypotheses can be readily resolved by direct binding studies using $^3$H-NPS R-568 as described above under the heading of "Allosteric Site on Parathyroid Cell Calcium Receptor."

Example 37
Activity of Arylalkyl Polyamines in *Xenopus Oocytes* Expressing a Bovine Parathyroid Cell Calcium Receptor

*Xenopus oocytes* were injected with BoPCaR 1 as described in Example 25. After two to three days, Cl⁻ currents were examined in the oocytes using two electrode voltage clamp. In the presence of 1 mM extracellular $Ca^{2+}$, exposure of BoPCaR 1-injected oocytes to the arylalkyl polyamine compounds NPS 017 (shown as AGA 489 in FIG. 1f) or NPS 019 caused oscillatory increases in the Cl⁻ current. Increases in Cl⁻ current evoked by NPS 019 persisted in the absence of extracellular $Ca^{2+}$. Neither NPS 017 nor NPS 019 elicited changes in Cl⁻ current in uninjected oocytes or in oocytes injected with water or rat liver mRNA.

The results provide compelling evidence for a direct action of arylalkyl polyamine compounds on a parathyroid cell calcium receptor. In authentic bovine parathyroid cells, arylalkyl polyamine compounds mobilize intracellular $Ca^{2+}$ in the absence. Of extracellular $Ca^{2+}$; they have identical effects in oocytes expressing a bovine parathyroid cell calcium receptor. Also, like the inorganic di- and trivalent cations, the arylalkyl polyamines are positively charged. In the aggregate, the results suggest that the arylalkyl polyamines act at the same site on the calcium receptor as does extracellular $Ca^{2+}$.

These data also distinguish the action of arylalkyl polyamines like NPS 019 from arylalkylamines like NPS R-568 (see Example 36). These two classes of compounds have different mechanisms of action on the parathyroid cell calcium receptor and probably bind at different domains on the receptor. For example, while arylalkyl polyamines can stimulate the parathyroid calcium receptor in the absence of extracellular $Ca^{2+}$, NPS R-568 requires the presence of extracellular $Ca^{2+}$ or an appropriate agonist, such as an arylalkyl polyamine, to stimulate the receptor. Arylalkyl polyamines can completely restore responses to NPS R-568 in the absence of extracellular $Ca^{2+}$. Moreover, NPS R-568 shifts the concentration-response curve of NPS 019 to the left.

Arylalkyl polyamines mimic, in all respects tested, the actions of extracellular divalent cations and are true calcimimetic compounds. Arylalkyl polyamines therefore define a new structural class of calcimimetic compounds that act through a different mechanism than compounds like NPS R-568, probably by binding to a different domain on the calcium receptor. Arylalkyl polyamines can be used as structural templates for drugs useful in the treatment of various bone and mineral-related disorders.

Example 38
Analogs of Arylalkyl Polyamines and Polyamines Useful as Antagonists of Calcium Influx in Parathyroid Cells Arylalkyl polyamines such as NPS 019 and polyamines such as spermine act as calcimimetics at the parathyroid cell calcium receptor presumably by binding to the extracellular $Ca^{2+}$-binding domain on the receptor (Examples 2, 6 and 36). Certain structural analogs of the arylalkyl polyamines or polyamines, in which the secondary amines are replaced by methylenes, act as blockers of $Ca^{2+}$ influx in parathyroid cells. NPS 384 and NPS 472 (1,12-diaminododecane, see FIG. 1a) are arylalkyl polyamine and polyamine analogs, respectively, lacking secondary amines. When tested at high micromolar concentrations (100 to 1000 $\mu$M), either of these compounds causes a prompt fall in $[Ca^{2+}]_i$ in bovine parathyroid cells bathed in buffer containing 2 mM $CaCl_2$. Pretreatment of parathyroid cells with either of these compounds depresses steady-state, but not transient increases in $[Ca^{2+}]_i$ elicited by increasing the concentration of extracellular $Ca^{2+}$. In both these respects, the effects of NPS 384 and NPS 472 are similar to low concentrations of $La^{3+}$ or $Gd^{3+}$ which block $Ca^{2+}$ influx.

Structural analogs of NPS 384 and NPS 472 with greater potency for blocking $Ca^{2+}$ influx in parathyroid cells can be synthesized by modification of the aromatic moiety or alkyl chain. Compounds that block the influx of extracellular $Ca^{2+}$ in parathyroid cells may find therapeutic utility in the treatment of various bone and mineral-related disorders. For example, it is known that the level of extracellular $Ca^{2+}$ can regulate the mRNA levels for PTH. Thus, blocking the influx of extracellular $Ca^{2+}$ may increase mRNA levels for PTH. Such an increase in mRNA transcripts would be expected to increase PTH synthesis, resulting in a larger reserve of PTH for secretion. Calcilytic compounds might therefore cause an augmented release of PTH when administered after a drug that blocks influx of extracellular $Ca^{2+}$ in parathyroid cells.

Example 39
Activity of NPS R-568 and Arylalkyl Polyamines in Xenopus Oocytes Expressing a Human Parathyroid Cell Calcium Receptor Xenopus oocytes were injected with pHuPCaR 5.2, the 5.2 Kb cDNA encoding a parathyroid cell calcium receptor derived from a human parathyroid cell adenoma. (See Example 27.) After two to three days, Cl⁻ currents were measured in the oocytes using a two-electrode voltage clamp. In the presence of 0.3 mM extracellular $Ca^{2+}$, both NPS R-568 or NPS 019 (3 to 30 $\mu$M) evoked increases in the Cl⁻ current indicating activation of the expressed calcium receptor. In the absence of extracellular $Ca^{2+}$, the response to NPS 019 persisted whereas that to NPS R-568 was abolished. In Xenopus oocytes expressing a human parathyroid cell calcium receptor, NPS R-568 shifted the concentration-response curve to the left without greatly altering the maximal response. Thus, a human parathyroid cell calcium receptor responds to NPS R-568 and to NPS 019 similarly to bovine parathyroid cells.

Example 40
Activity of NPS R-467 and NPS R-568 on C-Cells

C-cells appear to express a calcium receptor that is structurally similar to that present on parathyroid cells (see Example 31). The effects of NPS R-467 and NPS R-568 on $[Ca^{2+}]_i$ in a rat medullary thyroid carcinoma C-cell line (44-2 cells) were examined. In the presence of extracellular $Ca^{2+}$ (1 mM), either compound evoked a concentration-dependent increase in $[Ca^{2+}]_i$. Both compounds were less potent on C-cells than bovine parathyroid cells. The $EC_{50}$'s for NPS R-467 and NPS R-568 were 1.9 and 2.2 $\mu$M, respectively. Thus, compounds in this structural series appear to activate the C-cell calcium receptor.

Arylalkyl polyamines likewise elicit increases in $[Ca^{2+}]_i$ in C-cells as they do in parathyroid cells (see Examples 6 and 13). Some arylalkyl polyamines are more potent on C-cells than on parathyroid cells. Thus, compounds structurally related to NPS R-568, but with greater potency on C-cells compared to parathyroid cells, may reside in the compound library illustrated in FIG. 36. Compounds more potent on C-cells than parathyroid cells could be used to selectively increase calcitonin secretion while having little or no effect on PTH secretion.

Example 41
NPS R-568 Increases Calcitonin Secretion In Vivo

Normal adult Sprague-Dawley rats were administered various doses of NPS R-568 p.o. At various times following the administration of NPS R-568, blood samples were withdrawn and measured for PTH, ionized $Ca^{2+}$, and calcitonin. NPS R-568 caused a rapid, dose-dependent decrease in the plasma levels of PTH and $Ca^{2+}$ and an increase in calcitonin. The $ED_{50}$ values for the depression of PTH and $Ca^{2+}$ and stimulation of calcitonin were 1, 8 and 40 mg/kg p.o. Thus, the oral administration of NPS R-568 suppresses plasma levels of PTH at doses lower than those which increase plasma levels of calcitonin.

In subsequent studies, rats received a thyroidectomy (parathyroid glands intact). This surgical procedure effectively removed the C-cells secreting calcitonin and therefore enabled the relative contributions of PTH and calcitonin to the hypocalcemic effect of this compound to be determined. In thyroidectomized animals, the administration of NPS R-568 (3 to 100 mg/kg p.o.) caused a hypocalcemic response equal in magnitude to that produced in sham-operated animals. The only difference was that the rate of onset of the hypqcalcemic response was somewhat delayed in thyroidectomized animals. Thus, the major action of NPS R-568 causing the hypocalcemic response is an inhibition of PTH secretion. Stimulatory effects of this compound on calcitonin secretion increases the rate of onset, but not the extent, of hypocalcemia.

Example 42
Effectiveness of NPS R-568 in Humans

NPS R-568 was studied in a placebo-controlled, single-dose, dose-escalation format in a healthy, post-menopausal woman. A range of single oral doses was used to assess safety, tolerance, and changes in primary hyperparathyroidism markers (e.g., plasma concentrations of parathyroid hormone and ionized serum calcium) and of serum calcitonin. The data are shown in Tables 9–11.

TABLE 9

Effect of NPS R-568 on Serum Parathyroid Hormone in a Human

| DOSE | TIME (hours) | | | | | | | |
|---|---|---|---|---|---|---|---|---|
| | 0 | 0.5 | 1 | 2 | 4 | 8 | 12 | 24 |
| | Serum PTH (pg/ml) | | | | | | | |
| Placebo | 34 | 32 | 32 | 34 | 32 | 36 | 44 | 32 |
| 20 mg | 31 | 23 | 18 | 24 | 34 | 34 | 48 | 32 |
| 240 mg | 29 | 18 | 6 | 6 | 10 | 27 | 35 | 34 |
| 400 mg | 33 | 13 | 9 | 8 | 11 | 20 | 31 | 31 |

TABLE 10

Effect of NPS R-568 on Serum Ionized Calcium in a Human

| DOSE | TIME (hours) | | | | | | | |
|---|---|---|---|---|---|---|---|---|
| | 0 | 0.5 | 1 | 2 | 4 | 8 | 12 | 24 |
| | Serum Ionized Calcium (mg/dl) | | | | | | | |
| Placebo | 1.24 | 1.23 | 1.24 | 1.24 | 1.25 | 1.23 | 1.23 | 1.23 |
| 20 mg | 1.26 | 1.26 | 1.26 | 1.26 | 1.26 | 1.26 | 1.23 | 1.29 |
| 240 mg | 1.26 | 1.26 | 1.25 | 1.23 | 1.19 | 1.16 | 1.18 | 1.23 |
| 400 mg | 1.24 | 1.26 | 1.25 | 1.22 | 1.19 | 1.13 | 1.15 | 1.22 |

TABLE 11

Effect of NPS R-568 on Serum Calcitonin in a Human

| DOSE | TIME (hours) | | | | | | | |
|---|---|---|---|---|---|---|---|---|
| | 0 | 0.5 | 1 | 2 | 4 | 8 | 12 | 24 |
| | Serum Calcitonin (pg/ml) | | | | | | | |
| Placebo | 3.5 | 4.0 | 3.8 | 4.2 | 3.9 | 3.6 | 3.4 | 3.4 |
| 20 mg | 3.2 | 3.8 | 3.2 | 4.5 | 4.2 | 3.9 | 3.2 | 3.6 |
| 240 mg | 5.8 | 4.8 | 6.5 | 7.5 | 6.1 | 4.7 | 5.3 | 8.3 |
| 400 mg | 3.4 | 4.0 | 6.0 | 7.1 | 5.2 | 3.8 | 3.7 | 3.0 |

The data illustrated in Tables 9–11 indicate that NPS R-568 causes a transient dose-dependent decrease in plasma PTH concentration (Table 9), and, at higher doses, a decrease in serum ionized calcium concentration (Table 10) in the human subject. There was no apparent change in serum calcitonin at the doses studied (Table 11). Higher doses are expected to affect calcitonin levels as observed in rats (see Example 41).

Examples 43–54

Examples 43 to 54 describing the syntheses of compounds 4L, 8J, 8U, 9R, 11X, 12U, 12V, 12Z, 14U, 17M and 17P, are provided below. Compounds 4L, 8J, 8U, 11X and 17M were prepared from the condensation of a primary amine with an aldehyde or ketone in the presence of titanium(IV) isopropoxide. The resulting intermediate imines were then reduced in situ by the action of sodium cyanoborohydride, sodium borohydride, or sodium triacetoxyborohydride. The intermediate enamine for the synthesis of compound 8U was catalytically reduced using palladium hydroxide.

Compounds 9R, 14U, and 17P were synthesized by reductive amination of a commercially available aldehyde or ketone with a primary amine in the presence of sodium cyanoborohydride or sodium triacetoxyborohydride. It was found for the syntheses of these three compounds (9R, 14U, and 17P) that sodium triacetoxyborohydride afforded the desired diastereomers with greater diastereoselectivity than using sodium cyanoborohydride. The enriched mixtures were further purified to a single diastereomer by normal-phase HPLC or by recystallization.

Compounds 12U, 12V and 12Z were prepared by a diisobutylaluminum hydride (DIBAL-H)-mediated condensation of an amine with a nitrile. The resulting intermediate imine is reduced in situ by the action of sodium cyanoborohydride or sodium borohydride. The intermediate alkenes (compounds 12U and 12V) were reduced by catalytic hydrogenation in EtOH using palladium on carbon. Compounds which were converted to their corresponding hydrochlorides were done so by treatment of the free base with ethereal HCl to afford white solids.

The starting materials for these syntheses were: (1) purchased from Aldrich Chemical Co., Milwaukee, Wis., (2) purchased from Celgene Corp., Warren, N.J., or (3) prepared synthetically using standard techniques known in the art. All other reagent chemicals were purchased from Aldrich Chemical Co.

Example 43
Synthesis of Compound 4L
N-3-Phenyl-1-propyl-1-(1-naphthyl)ethylamine A mixture of 3-phenyl-1-propylamine (135 mg, 1 mmol), 1'-acetonaphthone (170 mg, 1 mmol), and titanium (IV) isopropoxide (355 mg, 1.3 mmol) was stirred at room temperature for 1 hour. The reaction was treated with 1 M ethanolic sodium cyanoborohydride (1 mL) and stirred at room temperature for 16 hours. The reaction was diluted with ether and treated with water (0.1 mL). The reaction was centrifuged and the ether layer removed and concentrated to a milky oil. A small portion of this material (10 mg) was purified by HPLC (Phenomenex, 1.0×25 cm, 5-$\mu$M silica) using a gradient of dichloromethane to 10% methanol in dichloromethane containing 0.1% isopropylamine. This afforded the product (free base) as a single component by GC/EI-MS ($R_f$=10.48 min) m/z (rel. int.) 289 ($M^+$, 11), 274 (63), 184 (5), 162 (5), 155 (100), 141 (18), 115 (8), 91 (45), and 77(5).

Example 44
Synthesis of Compound 8J
N-(3-Phenylpropyl)-1-(3-thiomethylphenyl)ethylamine hydrochloride 3'-Aminoacetophenone (2.7 g, 20 mmol) was dissolved in 4 mL of concentrated HCl, 4 g of ice and 8 mL of water. The solution was cooled to 0° C., and sodium nitrite (1.45 g, 21 mmol) dissolved in 3–5 mL of water was added over 5 minutes while maintaining the temperature below 6° C. Sodium thiomethoxide (1.75 g, 25 mmol) was dissolved in 5 mL of water and cooled to 0° C. To this solution was added the diazonium salt over 10 minutes while maintaining the temperature below 10° C. The reaction was stirred for an additional hour while allowing the temperature to rise to ambient. The reaction mixture was partitioned between ether and water. The ether layer was separated and washed with sodium bicarbonate and sodium chloride, and dried over sodium sulfate. The ether was evaporated to give a 74% yield of 3'-thiomethylacetophenone. The crude material was purified by distillation at reduced pressure.

3-Phenylpropylamine (0.13 g, 1 mmol), 3'-thiomethylacetophenone (0.17 g, 1 mmol), and titanium (IV) isopropoxide (0.36 g, 1.25 mmol) were mixed together and allowed to stand for 4 hours. Ethanol (1 mL) and sodium cyanoborohydride (0.063 g, 1 mmol) were added and the reaction was stirred overnight. The reaction was worked up by the addition of 4 mL of ether and 200 μL of water. The mixture was vortexed and then spun in a centrifuge to separate the solids. The ether layer was separated from the precipitate, and the solvent removed in vacuo. The oil was redissolved in dichloromethane and the compound purified by preparative TLC on silica gel eluted with 3% methanol-dichloromethane to yield the title compound as a pure oil: GC/EI-MS($R_f$=7.64 min) m/z (rel. int.)285 ($M^+$, 18), 270 (90), 180(17), 151(100), 136(32), 104(17), 91(54), and 77(13).

Example 45
Synthesis of Compound 8U
(R)-(+)-N-3-(2-Methoxyphenyl)-1-propyl-3-methoxy-α-methylbenzylamine hydrochloride A mixture of (R)-(+)-3-methoxy-α-methylbenzylamine (3.02 g, 20 mmol), 2-methoxycinnamaldehyde (3.24 g, 20 mmol), and titanium (IV) isopropoxide (8.53 g, 30 mmol, 1.5 eq.) was stirred for 2 hours at room temperature and treated with 1 M (20 mL) ethanolic sodium cyanoborohydride. The reaction was stirred overnight (16 hours), diluted with diethyl ether, and treated with water (1.44 mL, 80 mmol, 4 eq.). After mixing for 1 hour, the reaction mixture was centrifuged and the ether layer removed and concentrated to an oil. This material was dissolved in glacial acetic acid, hydrogenated at 60 p.s.i. hydrogen in the presence of palladium hydroxide for 2 hours at room temperature. The catalyst was removed by filtration and the resulting solution concentrated to a thick oil. This material was dissolved in dichloromethane and neutralized with 1 N NaOH. The dichloromethane solution was separated from the aqueous phase, dried over anhydrous potassium carbonate and concentrated to an oil. This material was dissolved in ether and treated with 1 M HCl in diethylether. The resulting precipitate (white solid) was collected, washed with diethyl ether, and air dried. GC/EI-MS ($R_f$=9.69 min) of this material (free base) showed a single component: m/z (rel. int.) 299 (M+, 21), 284 (100), 164 (17), 150 (8), 135 (81), 121 (40), 102 (17), 91 (43), and 77 (18).

Example 46
Synthesis of Compound 9R
(R,R)-N-(1-(2-Naphthyl)ethyl)-1-(1-naphthyl)ethylamine hydrochloride A mixture of (R)-(+)-1-(1-naphthyl)ethylamine (10.0 g, 58 mmol), 2'-acetonaphthone (9.4 g, 56 mmol), titanium (IV) isopropoxide (20.7 g, 73.0 mmol), and EtOH (abs.) (100 mL) was heated to 60° C. for 3 hours. Sodium cyanoborohydride ($NaCNBH_3$) (3.67 g, 58.4 mmol) was then added. The reaction mixture was stirred at room temperature for 18 hours. Ether (1 L) and $H_2O$ (10 mL) were added to the reaction mixture and the resulting precipitate was removed by centrifugation. The supernatant was evaporated under vacuum and the crude product was recrystallized four times from hot hexane, to provide 1.5 g of pure (98+%) diastereomer. The free base was dissolved in hexane, filtered, and then ethereal HCl was added to precipitate the product as a white solid (1.1 g, 6% yield), m.p.: softens 200–240° C. (dec.).

Example 47
Synthesis of Compound 11X
(R)-N-(4-Isopropylbenzyl)-1-(1-naphthyl)ethylamine hydrochloride A mixture of (R)-(+)-1-(1-naphthyl)ethylamine (1.06 g, 6.2 mmol), 4-isopropylbenzaldehyde (0.92 g, 6.2 mmol), and titanium (IV) isopropoxide (2.2 g, 7.7 mmol) was heated to 100° C. for 5 min then allowed to stir at room temperature for 4 hours. Sodium cyanoborohydride ($NaCNBH_3$) (0.39 g, 6.2 mmol) was then added followed by EtOH (1 mL). The reaction mixture was stirred at room temperature for 18 hours. Ether (100 mL) and $H_2O$ (1 mL) were added to the reaction mixture and the resulting precipitate was then removed by centrifugation. The supernatant was evaporated under vacuum and the crude product was chromatographed on silica gel (50 mm×30 cm column) (elution with 1% MeOH/$CHCl_3$). The chromatographed material was then dissolved in hexane and ethereal HCl was added to precipitate the product as a white solid (0.67 g, 35% yield); m.p. 257–259° C.

Example 48
Synthesis of Compound 12U
(R)-N-3-(2-Methylphenyl)-1-propyl-3-methoxy-α-methylbenzylamine hydrochloride A solution of 2-methylcinnamonitrile (1.43 g, 10 mmol) in dichloromethane (10 mL) was cooled to 0° C. and treated dropwise (15 minutes) with 1 M diisobutylaluminum hydride (10 mL, dichloromethane). The reaction was stirred at 0° C. for 15 minutes and treated dropwise (15 minutes) with a 1 M solution of (R)-(+)-3-methoxy-α-methylbenzylamine (1.51 g, 10 mmol) in dichloromethane (10 mL). The reaction was stirred for 1 hour at 0° C. and poured into a solution of ethanol (100 mL) containing sodium cyanoborohydride (1 g, 16 mmol). The reaction mixture was stirred 48 hours at room temperature. The reaction was diluted with diethyl ether and neutralized with 1 N NaOH. The diethyl ether layer was removed, dried over anhydrous potassium carbonate and concentrated to an oil. This material was chromatographed through silica using a gradient of dichloromethane to 5% methanol in dichloromethane to afford the unsaturated intermediate, a single component by GC/EI-MS ($R_f$=10.06 min) m/z (rel. int.) 281 ($M^+$, 17), 266 (59), 176 (19), 146 (65), 135(73), 131 (100), 91 (21), and 77 (13).

The unsaturated intermediate in ethanol was hydrogenated (1 atm $H_2$) in the presence of palladium on carbon for 16 hours at room temperature. The product from this reaction was converted to the hydrochloride salt by treatment with 1 M HCl in diethyl ether. GC/EI-MS ($R_f$=9.31 min) of this material (free base) showed a single component: m/z (rel. int.) 283 (M+, 21), 268 (100), 164 (12), 148 (8), 135 (85), 121 (12), 105 (49), 91 (23), and 77 (21).

Example 49
Synthesis of Compound 12V
(R)-N-3-(3-Methylphenyl)-1-propyl-3-methoxy-α-methylbenzylamine hydrochloride The compound was prepared following the procedure described in Example 48, but using 2-methylcinnamonitrile.

The unsaturated intermediate was a single component by GC/EI-MS ($R_f$=10.21 min) m/z (rel. int.) 281 ($M^+$, 57), 266 (86), 146 (98), 135 (88), 131 (100), 115 (43), 102 (26), 91 (43), and 77 (18). Reduction of this material and hydrochloride formation using the procedure described in Example 48 afforded the product. GC/EI-MS ($R_f$=9.18 min) of this material (free base) showed a single component; m/z (rel. int.) 283 ($M^+$, 19), 268 (100), 164 (11), 148 (8), 135 (76), 121 (16), 105 (45), 91 (23), and 77 (21).

Example 50
Synthesis of Compound 12Z
(R)-N-3-(2-Chlorophenyl)-1-propyl-1-(1-naphthyl) ethylamine hydrochloride The compound was prepared following the procedures described in Example 48, but using 2-chlorohydrocinnamonitrile and (R)-(+)-1-(1-naphthyl) ethylamine on a 10-mmol scale. Chromatography through silica gel using a gradient of dichloromethane to 5% methanol in dichloromethane afforded the product as a single component by silic gel TLC analysis (5% methanol in dichloromethane). The hydrochloride was prepared by treatment with 1 M HCl in diethyl ether.

Example 51
Synthesis of Compound 14U
(R,R)-N-(1-(4-Methoxyphenyl)ethyl)-1-(1-naphthyl) ethylamine hydrochloride A mixture of (R)-(+)-1-(1-naphthyl) ethylamine (1.1 g, 6.2 mmol), 4'-methoxyacetophenone (0.93 g, 6.2 mmol), titanium (IV) isopropoxide (2.2 g, 7.7 mmol), and EtOH (abs.) (1 mL) was heated to 60° C. for 3 hours. Sodium cyanoborohydride ($NaCNBH_3$) (0.39 g, 6.2 mmol) was then added, and the reaction mixture was stirred at room temperature for 18 hours. Ether (200 mL) and $H_2O$ (2 mL) were added to the reaction mixture and the resulting precipitate was then removed by centrifugation. The supernatant was evaporated under vacuum and the crude product was chromatographed on silica gel (25 mm×25 cm column) (elution with 1% MeOH-$CHCl_3$). A portion of this material was HPLC chromatographed [Selectosil, 5-$\mu$M silica gel; 25 cm×10.0 mm (Phenomenex, Torrance, Calif.), 4 mL per minute; UV det. 275 nm; 12% ethyl acetate-88% hexane (elution time, 12.0 min)]. The HPLC purified diastereomer was then dissolved in hexane and ethereal HCl was added to precipitate the product as a white solid (20 mg), m.p. 209–210° C. (dec.).

Example 52
Synthesis of Compound 17M
(R)-N-(3-Chloro-4-methoxybenzyl)-1-(1-naphthyl) ethylamine hydrochloride A mixture of (R)-(+)-1-(1-naphthyl)ethylamine (6.6 g, 39 mmol), 3'-chloro-4'-methoxybenzaldehyde (6.6 g, 39 mmol), titanium (IV) isopropoxide (13.8 g, 48.8 mmol), and EtOH (abs.) (30 mL) was heated to 80° C. for 30 minutes and then stirred at room temperature for 3 hours. Sodium cyanoborohydride ($NaCNBH_3$) (2.45 g, 39 mmol) was then added and the reaction mixture was stirred at room temperature for an additional 18 hours. Diethyl ether (100 mL) and $H_2O$ (2 mL) were then added to the reaction mixture and the resulting precipitate was removed by centrifugation. The supernatant was evaporated under vacuum and the crude product was chromatographed on silica gel (50 mm×30 cm column) (elution with $CH_2Cl_2$). The chromatographed material was then dissolved in hexane (500 mL), decolorized with Norit®, filtered (0.2 $\mu$M), and then ethereal HCl was added to precipitate the product as a while solid (10.2 g, 56% yield), m.p. 241–242° C. (dec.).

Example 53
Synthesis of Compound 17P
4-Methoxy-3-methylacetophenone [17P Precursor]

A mixture of 4'-hydroxy-3'-methylacetophenone (5.0 g, 33.3 mmol), iodomethane (5.7 g, 40.0 mmol), $K_2CO_3$ (granular, anhydrous) (23.0 g, 167 mmol), and acetone (250 mL) was refluxed for 3 hours. The reaction mixture was then cooled to room temperature, filtered to remove the inorganic salts, and evaporated under vacuum. The crude product was dissolved in ether (100 mL) and washed with $H_2O$ (2×20 mL) The organic layer was dried ($Na_2SO_4$) and evaporated to yield 4.5 g, 82.4% yield. The ketone was used in the following reaction without further purification.
(R,R)-N-(1-(4-Methoxy-3-methylphenyl)ethyl)-1-(1-naphthyl)ethylamine hydrochloride [Compound 17P]

A mixture of (R)-(+)-1-(1-naphthyl)ethylamine (4.24 g, 24.8 mmol), 4'-methoxy-3'-methylacetophenone (4.06 g, 24.8 mmol), titanium (IV) isopropoxide (8.8 g, 30.9 mmol), and EtOH (abs.) (1 mL) was heated to 100° C. for 2 hours. Isopropanol (45 mL) was added and the reaction was cooled to 10° C. in an ice bath. Sodium triacetoxyborohydride $NaHB(O_2CCH_3)_3$, 10.5 g, 49.5 mmol was then added in portions over 15 minutes. The reaction mixture was then heated to 70° C. for 18 hours. The mixture was cooled to room temperature and poured into ether (400 mL). The suspension was centrifuged, the supernatant was collected and the pellet was washed with ether (400 mL). The combined organic washings were evaporated under vacuum. The residue was dissolved in ether (400 mL) and washed with 1 N NaOH (4×50 mL) and $H_2O$ (2×50 mL). The organic layer was dried ($Na_2SO_4$), filtered and evaporated under vacuum. EtOH (abs.) was added to the wet residue, which was then dried thoroughly on a rotary evaporator to provide an oil. The mixture was then chromatographed on silica gel (50 mm×30 cm) [elution with (1% MeOH-1% isopropylamine-$CHCl_3$) to give 4.8 g of an oil].

The desired diastereomer was further purified by HPLC chromatography [SUPELCOSIL™ PLC-Si, 18-$\mu$M silica gel; 25 cm×21.2 mm (Supelco, Inc., Bellefonte, Pa.), 7 mL per minute; UV det. 275 nm: 20% EtOAc-80% hexane (elution time 9.5–11.0 min)]. Injections (800-$\mu$L aliquots) of the mixture (100 mg/mL solution in eluent) provided 65 mg of the desired isomer. Multiple HPLC injections provided 1.0 g of purified material. The HPLC-chromatographed material was dissolved in hexane (50 mL) and the hydrochloride salt was precipitated with ethereal HCl. The salt was collected on fritted glass and washed with hexane to provide 1.0 g of a white solid, mp 204–205° C.

Example 54
Synthesis of Compound 17X
3-Chloro-4-methoxybenzal dehyde

A mixture of 3-chloro-4-hydroxybenzaldehyde (25 g, 160 mmol), iodomethane (27.25 g, 192 mmol), $K_2CO_3$ (granular, anhydrous) (110.6 g, 800 mmol), and acetone (300 mL) was refluxed for 3 hours. The reaction mixture was then cooled to room temperature. Diethyl ether (500 mL) was added and the mixture was filtered through paper to remove the inorganic solids. The filtrate was evaporated under reduced pressure, dissolved in diethyl ether (800 mL), and washed with 0.1 N NaOH (3×100 mL). The organic layer was dried ($Na_2SO_4$) and evaporated under vacuum to yield 24 g, 92% yield of crude product. This material was further purified by chromatography on silica gel (50 mm×30 cm) (elution with hexane-EtOAc, 5:1) to give 15.02 g, 56% yield of a white solid: TLC (hexane-EtOAc, 5:1) $R_f$=0.24; GC $R_f$=4.75 min; MS (EI) m/z 170($M^+$), 172(M+2).
1-Methyl-(3'-chloro-4'-methoxybenzyl) alcohol A mixture of 3-chloro-4-methoxybenzaldehyde (13 g, 76.5 mmol), methylmagnesium chloride (52 g, 153 mmol), and THF (300 mL) was refluxed for 3 hours. The reaction mixture was cooled to room temperature. $NH_4Cl$ (satd. soln., 6 mL) was added dropwise followed by diethyl ether (500 mL) and the mixture was filtered through paper to remove the inorganic solids. The filtrate was evaporated under reduced pressure and the resulting solid was dissolved in diethyl ether (300 mL) and washed with water (4×25 mL). The organic layer was dried ($Na_2SO_4$) and evaporated under vacuum to yield 11.3 g, 80% yield of crude product. This material was further purified by chromatography on silica gel (50 mm×30 cm) (elution with $CH_2Cl_2$) to yield 11.3 g, 63% yield of an oil; TLC ($CH_2Cl_2$) $R_f$=0.25; GC $R_t$=5.30 min; MS (EI) m/z 186($M^+$), 188(M+2).

3'-Chloro-4'-methoxyacetophenone

A mixture of 1-methyl-(3'-Chloro-4'-methoxybenzyl) alcohol (7.6 g, 41 mmol), pyridinium chlorochromate (PCC) (13.16 g, 61.5 mmol), and $CH_2Cl_2$ (300 mL) was allowed to stir at room temperature for 2 hours. Diethyl ether (1000 mL) was added and the resulting mixture was placed on a chromatography column of silica gel (50 mm×30 cm) (elution with diethyl ether) to yield 7.3 g, 97% yield of crude solid product. GC analysis of this material showed it to be 99% pure and it was used in the following reaction without further purification. TLC (diethyl ether) $R_f$=1.0; GC $R_t$=5.3 min; MS (EI) m/z 184 ($M^+$), 184(M+2).

(R,R)-N-(1-Ethyl-4'-methoxy-3'-chlorophenyl)-1-(1-naphthylethyl)amine

A mixture of 3'-chloro-4'-methoxyacetophenone (5.3 g, 29 mmol), (R)-(+)-1-(1-naphthyl)ethylamine (4.98 g, 29 mmol), titanium (IV) isopropoxide (10.2 g, 36 mmol), and isopropanol (20 mL) was heated to 100° C. for 3 hours. Sodium triacetoxy-borohydride. ($NaB(O_2CCH_3)_3$; 12.29 g, 58 mmol) was added in portions over 10 minutes. The reaction mixture was heated to reflux for 30 minutes and was then allowed to stir at room temperature for 18 hours. The mixture was then poured into diethyl ether (500 mL); $H_2O$ (2 mL) was added and the suspension was centrifuged to remove the fine precipitate of titanium salts. The supernatant was collected and the pellet was washed with ether (500 mL). The combined organic layers were dried ($Na_2SO_4$) and evaporated under vacuum to yield 6.81 g, 70% of crude product.

This material was further purified by chromatography on silica gel (50 mm×30 cm) (elution with 3% MeOH-97% $CH_2Cl_2$) to give 2.01 g of an oil. The diastereomer was further purified by recrystallization. The free base (1.98 g) was converted to its HCl salt with ethereal HCl. This salt was dissolved in hot isopropanol (65 mL) and the solution was filtered through paper. The filtrate was evaporated under vacuum and the resulting solid dissolved in isopropanol (30 mL). After standing at room temperature for 18 hours, the crystalline solid was collected, washed with cold isopropanol (20 mL), and dried to yield 0.87 g, 40% (from free base) of the diastereomerically pure hydrochloride salt: mp 236–237° C. (dec); TLC (MeOH—$CH_2Cl_2$ [99:1]) $R_f$=0.25; GC $R_t$=11.06 min; FTIR (KBr pellet, $cm^{-1}$) 3433, 2950, 2931, 2853, 2803, 2659, 2608, 2497, 1604, 1595, 1504, 1461, 1444, 1268, 1260, 1067, 1021, 802, 781, 733; MS (EI) m/z 339($M^+$), 341(M+2).

Other embodiments are within the following claims.

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
      (A) LENGTH:         5275 base pairs
      (B) TYPE:           nucleic acid
      (C) STRANDEDNESS:   single
      (D) TOPOLOGY:      linear (ii) MOLECULE TYPE:     cDNA to mRNA (iii) FEATURE:
      (A) NAME/KEY:      CDS
      (B) LOCATION:      515..3769
      (C) OTHER INFORMATION:

(ix) SEQUENCE DESCRIPTION: SEQ ID NO: 1:

```
CGGAAAAAAA AAAAAAGTTC CCCACTCTAG TACAGAGAAG GTTGGCAGAG TCGTAAGCCC        60

CCAACCTCTT AAACTTCTCT GCATCTCCAA GGAGAAGGAG GGAAGAGGGG TTCTTTCCGA       120

CCTGAGGAGC TGGATCTGGG GTCCGAGAAC CCCAAGGTAG CACCGGAAAG AACAGCACAG       180

GAGGCGAGAG CGTGGCCGGT GGCCGGGAGA ACCAGACCCG ACGCGCGGTC CTCGGCGCCG       240

GGGTCCCGGG GACTCAGCTC AGCACGACTG GGAAGCCGAA AGTACTACAC ACGGTCTCTG       300

CATGATGTGA CTTCTGAAGA CTCAAGAGCC ACCCACTTCA CTAGTCTGCA ATGGAGAAGG       360

CAGAAATGGA AAGTCAAACC CCACGGTTCC ATTCTATTAA TTCTGTAGAC ATGTGCCCCC       420

ACTGCAGGGA GTGAGTCGCA CCAAGGGGGA AAGTCCTCAG GGGCCCCCAG ACCACCAGCG       480

CTTGAGTCCC TCTTCCTGGA GAGAAAGCAG AACT ATG GCA CTT TAT AGC TGC           532
                                  Met Ala Leu Tyr Ser Cys
                                    1               5
```

| | |
|---|---|
| TGT TGG ATC CTC TTG GCT TTT TCT ACC TGG TGC ACT TCC GCC TAT GGG<br>Cys Trp Ile Leu Leu Ala Phe Ser Thr Trp Cys Thr Ser Ala Tyr Gly<br>               10                      15                  20 | 580 |
| CCT GAC CAG CGA GCC CAA AAG AAA GGG GAC ATT ATC CTC GGG GGG CTC<br>Pro Asp Gln Arg Ala Gln Lys Lys Gly Asp Ile Ile Leu Gly Gly Leu<br>               25                      30                  35 | 628 |
| TTT CCT ATT CAT TTT GGG GTT GCA GTG AAA GAT CAG GAT CTA AAG TCG<br>Phe Pro Ile His Phe Gly Val Ala Val Lys Asp Gln Asp Leu Lys Ser<br>    40                      45                      50 | 676 |
| AGG CCG GAG TCC GTG GAG TGT ATC AGG TAT AAT TTC CGA GGA TTT CGC<br>Arg Pro Glu Ser Val Glu Cys Ile Arg Tyr Asn Phe Arg Gly Phe Arg<br>55                    60                      65                  70 | 724 |
| TGG TTA CAA GCT ATG ATA TTT GCC ATA GAG GAA ATA AAC AGC AGT CCA<br>Trp Leu Gln Ala Met Ile Phe Ala Ile Glu Glu Ile Asn Ser Ser Pro<br>               75                      80                  85 | 772 |
| GCC CTT CTT CCC AAC ATG ACC CTG GGA TAC AGG ATA TTC GAC ACT TGT<br>Ala Leu Leu Pro Asn Met Thr Leu Gly Tyr Arg Ile Phe Asp Thr Cys<br>               90                      95                  100 | 820 |
| AAC ACC GTC TCT AAA GCC TTG GAG GCC ACC CTG AGT TTT GTG GCC CAG<br>Asn Thr Val Ser Lys Ala Leu Glu Ala Thr Leu Ser Phe Val Ala Gln<br>             105                    110                115 | 868 |
| AAC AAA ATT GAC TCT TTG AAC CTT GAT GAG TTC TGC AAC TGC TCA GAG<br>Asn Lys Ile Asp Ser Leu Asn Leu Asp Glu Phe Cys Asn Cys Ser Glu<br>120                    125                  130 | 916 |
| CAC ATC CCC TCT ACC ATC GCA GTG GTG GGA GCT ACT GGC TCG GGC ATC<br>His Ile Pro Ser Thr Ile Ala Val Val Gly Ala Thr Gly Ser Gly Ile<br>135                    140                  145                150 | 964 |
| TCC ACA GCA GTG GCC AAC CTG CTG GGG CTC TTC TAC ATC CCC CAG GTC<br>Ser Thr Ala Val Ala Asn Leu Leu Gly Leu Phe Tyr Ile Pro Gln Val<br>               155                    160                165 | 1012 |
| AGC TAT GCC TCC TCC AGC AGA CTC CTC AGC AAC AAG AAT CAA TTC AAG<br>Ser Tyr Ala Ser Ser Ser Arg Leu Leu Ser Asn Lys Asn Gln Phe Lys<br>             170                    175                180 | 1060 |
| TCC TTC CTC CGC ACC ATA CCC AAT GAT GAA CAC CAG GCC ACG GCC ATG<br>Ser Phe Leu Arg Thr Ile Pro Asn Asp Glu His Gln Ala Thr Ala Met<br>               185                    190                195 | 1108 |
| GCT GAC ATC ATC GAG TAC TTC CGC TGG AAC TGG GTG GGC ACA ATT GCA<br>Ala Asp Ile Ile Glu Tyr Phe Arg Trp Asn Trp Val Gly Thr Ile Ala<br>200                    205                  210 | 1156 |
| GCT GAC GAT GAC TAT GGC CGG CCA GGG ATC GAG AAG TTT CGA GAG GAA<br>Ala Asp Asp Asp Tyr Gly Arg Pro Gly Ile Glu Lys Phe Arg Glu Glu<br>215                    220                  225                230 | 1204 |
| GCT GAG GAG AGG GAC ATC TGC ATC GAC TTC AGC GAG CTC ATC TCC CAA<br>Ala Glu Glu Arg Asp Ile Cys Ile Asp Phe Ser Glu Leu Ile Ser Gln<br>             235                    240                245 | 1252 |
| TAC TCT GAT GAG GAA AAG ATC CAG CAG GTG GTG GAG GTG ATC CAG AAT<br>Tyr Ser Asp Glu Glu Lys Ile Gln Gln Val Val Glu Val Ile Gln Asn<br>               250                    255                260 | 1300 |
| TCC ACC GCC AAA GTC ATT GTC GTC TTC TCC AGC GGC CCA GAC CTG GAA<br>Ser Thr Ala Lys Val Ile Val Val Phe Ser Ser Gly Pro Asp Leu Glu<br>             265                    270                275 | 1348 |
| CCC CTC ATC AAA GAG ATC GTC CGG CGC AAT ATC ACA GGC AGG ATC TGG<br>Pro Leu Ile Lys Glu Ile Val Arg Arg Asn Ile Thr Gly Arg Ile Trp<br>280                    285                  290 | 1396 |
| CTG GCC AGC GAG GCC TGG GCC AGC TCT TCC CTG ATT GCT ATG CCC GAG<br>Leu Ala Ser Glu Ala Trp Ala Ser Ser Ser Leu Ile Ala Met Pro Glu<br>295                    300                  305                310 | 1444 |
| TAT TTC CAT GTG GTC GGA GGC ACC ATT GGG TTT GGT TTG AAA GCT GGG<br>Tyr Phe His Val Val Gly Gly Thr Ile Gly Phe Gly Leu Lys Ala Gly<br>             315                    320                325 | 1492 |

```
CAG ATC CCA GGC TTC CGG GAA TTC CTG CAG AAA GTC CAC CCC AGG AAG   1540
Gln Ile Pro Gly Phe Arg Glu Phe Leu Gln Lys Val His Pro Arg Lys
        330                 335                 340

TCT GTC CAC AAT GGT TTT GCC AAG GAG TTT TGG GAA GAA ACA TTT AAC   1588
Ser Val His Asn Gly Phe Ala Lys Glu Phe Trp Glu Glu Thr Phe Asn
            345                 350                 355

TGC CAC CTG CAA GAG GGT GCT AAA GGC CCA TTA CCG GTG GAC ACC TTC   1636
Cys His Leu Gln Glu Gly Ala Lys Gly Pro Leu Pro Val Asp Thr Phe
    360                 365                 370

CTG AGA GGT CAC GAA GAA GGA GGT GCC AGG TTA AGC AAC AGT CCC ACT   1684
Leu Arg Gly His Glu Glu Gly Gly Ala Arg Leu Ser Asn Ser Pro Thr
375                 380                 385                 390

GCC TTC CGA CCT CTG TGC ACT GGG GAG GAG AAC ATC AGC AGT GTC GAG   1732
Ala Phe Arg Pro Leu Cys Thr Gly Glu Glu Asn Ile Ser Ser Val Glu
                395                 400                 405

ACT CCT TAC ATG GAT TAT ACA CAT TTA CGG ATA TCC TAC AAC GTC TAC   1780
Thr Pro Tyr Met Asp Tyr Thr His Leu Arg Ile Ser Tyr Asn Val Tyr
            410                 415                 420

TTA GCC GTC TAC TCC ATT GCT CAT GCC CTA CAA GAT ATA TAC ACC TGC   1828
Leu Ala Val Tyr Ser Ile Ala His Ala Leu Gln Asp Ile Tyr Thr Cys
        425                 430                 435

ATA CCT GGG AGA GGG CTC TTC ACC AAC GGT TCC TGC GCA GAT ATC AAG   1876
Ile Pro Gly Arg Gly Leu Phe Thr Asn Gly Ser Cys Ala Asp Ile Lys
    440                 445                 450

AAG GTT GAA GCT TGG CAG GTC CTG AAA CAC CTG CGG CAC CTA AAT TTT   1924
Lys Val Glu Ala Trp Gln Val Leu Lys His Leu Arg His Leu Asn Phe
455                 460                 465                 470

ACC AGC AAT ATG GGG GAG CAA GTA ACT TTC GAT GAA TGT GGA GAC CTG   1972
Thr Ser Asn Met Gly Glu Gln Val Thr Phe Asp Glu Cys Gly Asp Leu
                475                 480                 485

GCA GGG AAC TAT TCC ATC ATC AAC TGG CAC CTC TCC CCA GAG GAC GGC   2020
Ala Gly Asn Tyr Ser Ile Ile Asn Trp His Leu Ser Pro Glu Asp Gly
            490                 495                 500

TCC ATA GTG TTT AAG GAA GTT GGA TAT TAC AAT GTC TAT GCC AAG AAA   2068
Ser Ile Val Phe Lys Glu Val Gly Tyr Tyr Asn Val Tyr Ala Lys Lys
        505                 510                 515

GGA GAG AGA CTC TTC ATC AAT GAT GAA AAA ATT CTG TGG AGT GGA TTC   2116
Gly Glu Arg Leu Phe Ile Asn Asp Glu Lys Ile Leu Trp Ser Gly Phe
    520                 525                 530

TCA AGG GAG GTG CCT TTC TCC AAC TGC AGT CGA GAC TGC CTG GCA GGG   2164
Ser Arg Glu Val Pro Phe Ser Asn Cys Ser Arg Asp Cys Leu Ala Gly
535                 540                 545                 550

ACC AGG AAA GGA ATC ATT GAG GGG GAG CCC ACC TGC TGC TTT GAG TGT   2212
Thr Arg Lys Gly Ile Ile Glu Gly Glu Pro Thr Cys Cys Phe Glu Cys
                555                 560                 565

GTG GAA TGT CCT GAT GGG GAG TAC AGC GAC GAG ACA GAT GCA AGT GCC   2260
Val Glu Cys Pro Asp Gly Glu Tyr Ser Asp Glu Thr Asp Ala Ser Ala
            570                 575                 580

TGT GAT AAG TGC CCT GAT GAC TTC TGG TCC AAT GAG AAC CAC ACT TCC   2308
Cys Asp Lys Cys Pro Asp Asp Phe Trp Ser Asn Glu Asn His Thr Ser
        585                 590                 595

TGC ATC GCC AAG GAG ATC GAG TTT CTG TCG TGG ACC GAG CCC TTC GGG   2356
Cys Ile Ala Lys Glu Ile Glu Phe Leu Ser Trp Thr Glu Pro Phe Gly
    600                 605                 610

ATC GCA CTC ACG CTC TTT GCT GTG CTG GGC ATT TTC CTC ACA GCC TTC   2404
Ile Ala Leu Thr Leu Phe Ala Val Leu Gly Ile Phe Leu Thr Ala Phe
615                 620                 625                 630

GTG CTG GGC GTC TTC ATC AAG TTC CGC AAC ACG CCC ATC GTC AAG GCC   2452
Val Leu Gly Val Phe Ile Lys Phe Arg Asn Thr Pro Ile Val Lys Ala
                635                 640                 645
```

```
ACC AAC CGG GAG CTC TCC TAT CTC CTT CTC TTC TCC CTG CTC TGC TGC    2500
Thr Asn Arg Glu Leu Ser Tyr Leu Leu Leu Phe Ser Leu Leu Cys Cys
        650                 655                 660

TTC TCC AGC TCC CTG TTC TTC ATC GGG GAG CCC CAG GAC TGG ACG TGC    2548
Phe Ser Ser Ser Leu Phe Phe Ile Gly Glu Pro Gln Asp Trp Thr Cys
            665                 670                 675

CGC CTG CGC CAG CCG GCC TTT GGC ATC AGC TTC GTG CTC TGC ATC TCG    2596
Arg Leu Arg Gln Pro Ala Phe Gly Ile Ser Phe Val Leu Cys Ile Ser
                680                 685                 690

TGC ATC CTG GTG AAA ACC AAT CGG GTC CTC CTG GTG TTT GAG GCC AAG    2644
Cys Ile Leu Val Lys Thr Asn Arg Val Leu Leu Val Phe Glu Ala Lys
695                 700                 705                 710

ATT CCC ACC AGC TTC CAC CGG AAG TGG TGG GGG CTC AAC CTG CAG TTC    2692
Ile Pro Thr Ser Phe His Arg Lys Trp Trp Gly Leu Asn Leu Gln Phe
                715                 720                 725

CTG CTG GTC TTC CTC TGC ACC TTC ATG CAG ATT GTC ATC TGT GCC ATT    2740
Leu Leu Val Phe Leu Cys Thr Phe Met Gln Ile Val Ile Cys Ala Ile
                    730                 735                 740

TGG CTC AAT ACA GCG CCC CCC TCG AGC TAC CGC AAC CAC GAG CTG GAG    2788
Trp Leu Asn Thr Ala Pro Pro Ser Ser Tyr Arg Asn His Glu Leu Glu
            745                 750                 755

GAC GAG ATC ATC TTC ATC ACC TGC CAC GAG GGC TCG CTC ATG GCG CTG    2836
Asp Glu Ile Ile Phe Ile Thr Cys His Glu Gly Ser Leu Met Ala Leu
760                 765                 770

GGC TTC CTG ATC GGC TAC ACC TGC TTG CTG GCC GCC ATC TGC TTC TTC    2884
Gly Phe Leu Ile Gly Tyr Thr Cys Leu Leu Ala Ala Ile Cys Phe Phe
775                 780                 785                 790

TTC GCC TTC AAG TCC CGG AAG CTG CCA GAG AAC TTC AAT GAA GCC AAG    2932
Phe Ala Phe Lys Ser Arg Lys Leu Pro Glu Asn Phe Asn Glu Ala Lys
                795                 800                 805

TTC ATC ACC TTC AGC ATG CTC ATC TTC TTC ATC GTC TGG ATC TCT TTC    2980
Phe Ile Thr Phe Ser Met Leu Ile Phe Phe Ile Val Trp Ile Ser Phe
                810                 815                 820

ATC CCC GCC TAC GCC AGC ACT TAC GGC AAG TTC GTC TCT GCC GTG GAG    3028
Ile Pro Ala Tyr Ala Ser Thr Tyr Gly Lys Phe Val Ser Ala Val Glu
            825                 830                 835

GTG ATC GCC ATC CTG GCG GCC AGC TTT GGC TTG CTG GCC TGT ATC TTC    3076
Val Ile Ala Ile Leu Ala Ala Ser Phe Gly Leu Leu Ala Cys Ile Phe
840                 845                 850

TTC AAC AAG GTC TAC ATC ATC CTC TTC AAG CCT TCC CGG AAC ACC ATC    3124
Phe Asn Lys Val Tyr Ile Ile Leu Phe Lys Pro Ser Arg Asn Thr Ile
855                 860                 865                 870

GAG GAG GTG CGC TGC AGC ACC GCG GCA CAC GCC TTC AAG GTG GCC GCC    3172
Glu Glu Val Arg Cys Ser Thr Ala Ala His Ala Phe Lys Val Ala Ala
                875                 880                 885

CGA GCC ACG CTG CGC CGC AGC AAC GTC TCC CGC CAG CGG TCC AGC AGC    3220
Arg Ala Thr Leu Arg Arg Ser Asn Val Ser Arg Gln Arg Ser Ser Ser
            890                 895                 900

CTA GGG GGC TCC ACG GGA TCC ACC CCC TCC TCC TCC ATC AGC AGC AAG    3268
Leu Gly Gly Ser Thr Gly Ser Thr Pro Ser Ser Ser Ile Ser Ser Lys
        905                 910                 915

AGC AAC AGC GAG GAC CCG TTC CCT CAG CAG CAG CCG AAG AGG CAG AAG    3316
Ser Asn Ser Glu Asp Pro Phe Pro Gln Gln Gln Pro Lys Arg Gln Lys
920                 925                 930

CAG CCG CAG CCG CTG GCC CTG AGC CCG CAC AAC GCG CAG CAG CCA CAG    3364
Gln Pro Gln Pro Leu Ala Leu Ser Pro His Asn Ala Gln Gln Pro Gln
935                 940                 945                 950

CCG CGG CCA CCC TCG ACC CCA CAG CCG CAG CCA CAG TCG CAG CAG CCG    3412
Pro Arg Pro Pro Ser Thr Pro Gln Pro Gln Pro Gln Ser Gln Gln Pro
            955                 960                 965
```

| | |
|---|---|
| CCC CGA TGC AAG CAG AAG GTC ATC TTC GGC AGC GGC ACC GTC ACC TTC<br>Pro Arg Cys Lys Gln Lys Val Ile Phe Gly Ser Gly Thr Val Thr Phe<br>970                        975                      980 | 3460 |
| TCG CTG AGC TTT GAC GAG CCT CAG AAG ACC GCC GTG GCT CAC AGG AAT<br>Ser Leu Ser Phe Asp Glu Pro Gln Lys Thr Ala Val Ala His Arg Asn<br>985                        990                      995 | 3508 |
| TCC ACG CAC CAG ACC TCC CTG GAG GCC CAG AAA AAC AAT GAC GCC CTG<br>Ser Thr His Gln Thr Ser Leu Glu Ala Gln Lys Asn Asn Asp Ala Leu<br>1000                      1005                  1010 | 3556 |
| ACC AAA CAC CAG GCG TTG CTC CCG CTG CAG TGC GGA GAG ACG GAC TCA<br>Thr Lys His Gln Ala Leu Leu Pro Leu Gln Cys Gly Glu Thr Asp Ser<br>1015                    1020                  1025              1030 | 3604 |
| GAA TTG ACC TCC CAG GAG ACA GGC CTG CAG GGC CCT GTG GGT GAG GAC<br>Glu Leu Thr Ser Gln Glu Thr Gly Leu Gln Gly Pro Val Gly Glu Asp<br>                  1035                  1040                  1045 | 3652 |
| CAC CAG CTA GAG ATG GAG GAC CCC GAA GAG ATG TCC CCG GCA CTT GTA<br>His Gln Leu Glu Met Glu Asp Pro Glu Glu Met Ser Pro Ala Leu Val<br>                  1050                  1055                  1060 | 3700 |
| GTG TCT AAT TCC CGG AGC TTT GTC ATC AGT GGC GGA GGC AGC ACT GTT<br>Val Ser Asn Ser Arg Ser Phe Val Ile Ser Gly Gly Gly Ser Thr Val<br>          1065                    1070                  1075 | 3748 |
| ACG GAA AAC ATG CTG CGT TCT TAAAAGGGAA GGAGAAAGCC AGTTCAGGGG<br>Thr Glu Asn Met Leu Arg Ser<br>          1080                    1085 | 3799 |
| GAATCCAGGC AGTTTCCCCG GGATGACCTT CTCCAAAGGG ATGAGGAACT GCCCCCCCAC | 3859 |
| CCCCACCCCC TTCCTCCAGG AAGGAGGGAT AAGACCCACC AAATGCTTGG AACTTAGTTG | 3919 |
| CACTGCTATA AACGACAGTG AATGAAATAA TGTCCCCCTT AAAATTAAAA AGAGGGGAGC | 3979 |
| GGTGTGCTTC TGTGGTTAGG TTTATCAGAG TGCTGAGATC CCTATAGTCA GGTTCGCCTT | 4039 |
| TCCTATCCCT GCTTCCATTC TCCTCTTCTG TTCTATCCCA TCCAACAGTC CAGAGATAAA | 4099 |
| ACCATGGCTT TAAGATACCC ACCTATTCCC CCTAGGGTCT TATTTGTTGT TTTTGTTGCT | 4159 |
| GTTGTTTTGG TTTGATTTTT GTTTTTAATG TTGAAACGTC TGCCCTGAAC TTTGCAGACA | 4219 |
| GCCTGGTCCA AAAACAAACC TGTGCAGAGT GACAGGACCT CCTATGGGCA CCACTAGAGT | 4279 |
| TGAGTGCGAA AGACAGAATG TCGCCAGCGC TGCCCAACAC CTTGACAGTG GAAGAACTT | 4339 |
| GAAATGTCCA GAGCTGTAAG ATGAATGTGT CCCCTCCTAT TTATGAAAAA TGTTAAATAT | 4399 |
| GTGGTTTCCT ACTTGCTGCT GCTGTCACGT GACATGGAGA AGGTTAGCAT CCATCCTCCA | 4459 |
| GCAGTATGTC TGATCTTGTC CAGAGTGTGA TGGTGATGCC ACGTTAGAT TCCAATATCT | 4519 |
| CAGGAATCAC CTCAGCCTGC ATGAATCCAA TGAGCTGTAT CTGTAATTAA TATTGTCATA | 4579 |
| TGTAGCTTTA TCCTTAAGAA AATGTGTTTG TTTTAATAGT CCGTGGAAAA TATAAGCTGG | 4639 |
| AAAAAATGTC CCAGTCTGGT TGATATAAGG CAGTATTATT GAGTCCCGTT TTCTTTGCCC | 4699 |
| GCCCCACCAC CCACACCCCA ATGAGCTAAG CCCTAAATGA GCCCTTTCAG GGCCCAGGGA | 4759 |
| TCCAGAAGCT CCCTCTTTCT CCACCCCAAA CGCTTCCTGA AGTCAGATCC ATGCCTTTCC | 4819 |
| CTGTGAAGAA TAAGCTCCCA GTCTCTGACC TCCTACCAGT TTCTGGGGTA AGAACACGTG | 4879 |
| GTTCCAAGAG AGCTCTCATG GGATATTACT CTTGGCACCC CCCAATGCCA TACTTAGGTT | 4939 |
| CCCTCCAGCA GTGGGATCTG CCCATGGGTA GTTACAAGAT TGAACGTTGA ATGGCATACT | 4999 |
| GCTGAACAGT CAGTTCTGGA GCTAGAGAGG CCTGGGGTCA AGTGCTGGGT TGTCACTCA | 5059 |
| CAAGTTGGGT GACCACAGGC AGGGAACCTT GACCTCACTC AGCCCAGCT TCTTTGTGTC | 5119 |
| TAAAATGGAG GTAATAATCA TCCTTTTCCC GCAGAGCTCT TATGTGGGTT AAATGAGATA | 5179 |
| AATGTATGTA AAGTATTTTA GCATGGTGCC TAGCCCATAG TAAGCACGCA ATAAATATTA | 5239 |

```
GTTAATATTA AAAAAAAAAA AAAAAAAAAA AAAAA                                    5275

(2) INFORMATION FOR SEQ ID NO: 2:

(i) SEQUENCE CHARACTERISTICS:
        (A) LENGTH:          5006 base pairs
        (B) TYPE:            nucleic acid
        (C) STRANDEDNESS:    single
        (D) TOPOLOGY:        linear (ii) MOLECULE TYPE:      cDNA to mRNA (ix) FEATURE:
         (A) NAME/KEY:       CDS
         (B) LOCATION:       436..3699
         (D) OTHER INFORMATION:

(xi) SEQUENCE DESCRIPTION: SEQ ID NO: 2:

GCTGCTGTGG CCGGACCCGA AGGCGGGCGC CGGGAGCGCA GCGAGCCAGA CGCGCCTCTC            60

CAAGACCGTG ACCTTGGCAT AGGGAGCGGG GCTGCGCGCA GTCCTGAGAT CAGACCAGAG           120

CTCATCCTCG TGGAGACCCA CGGCCGAGGG GCCGAGCTG  CCTCTGTGCG AGGGAGCCCT           180

GGCCGCGGCG CAGAAGGCAT CACAGGAGGC CTCTGCATGA TGTGGCTTCC AAAGACTCAA           240

GGACCACCCA CATTACAAGT CTGGATTGAG GAAGGCAGAA ATGGAGATTC AAACACCACG           300

TCTTCTATTA TTTTATTAAT CAATCTGTAG ACATGTGTCC CCACTGCAGG GAGTGAACTG           360

CTCCAAGGGA GAAACTTCTG GGAGCCTCCA AACTCCTAGC TGTCTCATCC CTTGCCCTGG           420

AGAGACGGCA GAACC ATG GCA TTT TAT AGC TGC TGC TGG GTC CTC TTG GCA           471
              Met Ala Phe Tyr Ser Cys Cys Trp Val Leu Leu Ala
                 1               5                  10

CTC ACC TGG CAC ACC TCT GCC TAC GGG CCA GAC CAG CGA GCC CAA AAG           519
Leu Thr Trp His Thr Ser Ala Tyr Gly Pro Asp Gln Arg Ala Gln Lys
            15                  20                  25

AAG GGG GAC ATT ATC CTT GGG GGG CTC TTT CCT ATT CAT TTT GGA GTA           567
Lys Gly Asp Ile Ile Leu Gly Gly Leu Phe Pro Ile His Phe Gly Val
     30                  35                  40

GCA GCT AAA GAT CAA GAT CTC AAA TCA AGG CCG GAG TCT GTG GAA TGT           615
Ala Ala Lys Asp Gln Asp Leu Lys Ser Arg Pro Glu Ser Val Glu Cys
 45                  50                  55                  60

ATC AGG TAT AAT TTC CGT GGG TTT CGC TGG TTA CAG GCT ATG ATA TTT           663
Ile Arg Tyr Asn Phe Arg Gly Phe Arg Trp Leu Gln Ala Met Ile Phe
                 65                  70                  75

GCC ATA GAG GAG ATA AAC AGC AGC CCA GCC CTT CTT CCC AAC TTG ACG           711
Ala Ile Glu Glu Ile Asn Ser Ser Pro Ala Leu Leu Pro Asn Leu Thr
             80                  85                  90

CTG GGA TAC AGG ATA TTT GAC ACT TGC AAC ACC GTT TCT AAG GCC TTG           759
Leu Gly Tyr Arg Ile Phe Asp Thr Cys Asn Thr Val Ser Lys Ala Leu
         95                 100                 105

GAA GCC ACC CTG AGT TTT GTT GCT CAA AAC AAA ATT GAT TCT TTG AAC           807
Glu Ala Thr Leu Ser Phe Val Ala Gln Asn Lys Ile Asp Ser Leu Asn
    110                 115                 120

CTT GAT GAG TTC TGC AAC TGC TCA GAG CAC ATT CCC TCT ACG ATT GCT           855
Leu Asp Glu Phe Cys Asn Cys Ser Glu His Ile Pro Ser Thr Ile Ala
125                 130                 135                 140

GTG GTG GGA GCA ACT GGC TCA GGC GTC TCC ACG GCA GTG GCA AAT CTG           903
Val Val Gly Ala Thr Gly Ser Gly Val Ser Thr Ala Val Ala Asn Leu
                145                 150                 155

CTG GGG CTC TTC TAC ATT CCC CAG GTC AGT TAT GCC TCC TCC AGC AGA           951
Leu Gly Leu Phe Tyr Ile Pro Gln Val Ser Tyr Ala Ser Ser Ser Arg
            160                 165                 170

CTC CTC AGC AAC AAG AAT CAA TTC AAG TCT TTC CTC CGA ACC ATC CCC           999
```

```
            Leu Leu Ser Asn Lys Asn Gln Phe Lys Ser Phe Leu Arg Thr Ile Pro
                    175                 180                 185

AAT GAT GAG CAC CAG GCC ACT GCC ATG GCA GAC ATC ATC GAG TAT TTC           1047
Asn Asp Glu His Gln Ala Thr Ala Met Ala Asp Ile Ile Glu Tyr Phe
            190                 195                 200

CGC TGG AAC TGG GTG GGC ACA ATT GCA GCT GAT GAC GAC TAT GGG CGG           1095
Arg Trp Asn Trp Val Gly Thr Ile Ala Ala Asp Asp Asp Tyr Gly Arg
205                 210                 215                 220

CCG GGG ATT GAG AAA TTC CGA GAG GAA GCT GAG GAA AGG GAT ATC TGC           1143
Pro Gly Ile Glu Lys Phe Arg Glu Glu Ala Glu Glu Arg Asp Ile Cys
                    225                 230                 235

ATC GAC TTC AGT GAA CTC ATC TCC CAG TAC TCT GAT GAG GAA GAG ATC           1191
Ile Asp Phe Ser Glu Leu Ile Ser Gln Tyr Ser Asp Glu Glu Glu Ile
            240                 245                 250

CAG CAT GTG GTA GAG GTG ATT CAA AAT TCC ACG GCC AAA GTC ATC GTG           1239
Gln His Val Val Glu Val Ile Gln Asn Ser Thr Ala Lys Val Ile Val
            255                 260                 265

GTT TTC TCC AGT GGC CCA GAT CTT GAG CCC CTC ATC AAG GAG ATT GTC           1287
Val Phe Ser Ser Gly Pro Asp Leu Glu Pro Leu Ile Lys Glu Ile Val
270                 275                 280

CGG CGC AAT ATC ACG GGC AAG ATC TGG CTG GCC AGC GAG GCC TGG GCC           1335
Arg Arg Asn Ile Thr Gly Lys Ile Trp Leu Ala Ser Glu Ala Trp Ala
285                 290                 295                 300

AGC TCC TCC CTG ATC GCC ATG CCT CAG TAC TTC CAC GTG GTT GGC GGC           1383
Ser Ser Ser Leu Ile Ala Met Pro Gln Tyr Phe His Val Val Gly Gly
                305                 310                 315

ACC ATT GGA TTC GCT CTG AAG GCT GGG CAG ATC CCA GGC TTC CGG GAA           1431
Thr Ile Gly Phe Ala Leu Lys Ala Gly Gln Ile Pro Gly Phe Arg Glu
            320                 325                 330

TTC CTG AAG AAG GTC CAT CCC AGG AAG TCT GTC CAC AAT GGT TTT GCC           1479
Phe Leu Lys Lys Val His Pro Arg Lys Ser Val His Asn Gly Phe Ala
        335                 340                 345

AAG GAG TTT TGG GAA GAA ACA TTT AAC TGC CAC CTC CAA GAA GGT GCA           1527
Lys Glu Phe Trp Glu Glu Thr Phe Asn Cys His Leu Gln Glu Gly Ala
        350                 355                 360

AAA GGA CCT TTA CCT GTG GAC ACC TTT CTG AGA GGT CAC GAA GAA AGT           1575
Lys Gly Pro Leu Pro Val Asp Thr Phe Leu Arg Gly His Glu Glu Ser
365                 370                 375                 380

GGC GAC AGG TTT AGC AAC AGC TCG ACA GCC TTC CGA CCC CTC TGT ACA           1623
Gly Asp Arg Phe Ser Asn Ser Ser Thr Ala Phe Arg Pro Leu Cys Thr
                385                 390                 395

GGG GAT GAG AAC ATC AGC AGT GTC GAG ACC CCT TAC ATA GAT TAC ACG           1671
Gly Asp Glu Asn Ile Ser Ser Val Glu Thr Pro Tyr Ile Asp Tyr Thr
            400                 405                 410

CAT TTA CGG ATA TCC TAC AAT GTG TAC TTA GCA GTC TAC TCC ATT GCC           1719
His Leu Arg Ile Ser Tyr Asn Val Tyr Leu Ala Val Tyr Ser Ile Ala
            415                 420                 425

CAC GCC TTG CAA GAT ATA TAT ACC TGC TTA CCT GGG AGA GGG CTC TTC           1767
His Ala Leu Gln Asp Ile Tyr Thr Cys Leu Pro Gly Arg Gly Leu Phe
            430                 435                 440

ACC AAT GGC TCC TGT GCA GAC ATC AAG AAA GTT GAG GCG TGG CAG GTC           1815
Thr Asn Gly Ser Cys Ala Asp Ile Lys Lys Val Glu Ala Trp Gln Val
445                 450                 455                 460

CTG AAG CAC CTA CGG CAT CTA AAC TTT ACA AAC AAT ATG GGG GAG CAG           1863
Leu Lys His Leu Arg His Leu Asn Phe Thr Asn Asn Met Gly Glu Gln
                465                 470                 475

GTG ACC TTT GAT GAG TGT GGT GAC CTG GTG GGG AAC TAT TCC ATC ATC           1911
Val Thr Phe Asp Glu Cys Gly Asp Leu Val Gly Asn Tyr Ser Ile Ile
            480                 485                 490

AAC TGG CAC CTC TCC CCA GAG GAT GGC TCC ATC GTG TTT AAG GAA GTC           1959
```

```
Asn Trp His Leu Ser Pro Glu Asp Gly Ser Ile Val Phe Lys Glu Val
        495                 500                 505

GGG TAT TAC AAC GTC TAT GCC AAG AAG GGA GAA AGA CTC TTC ATC AAC          2007
Gly Tyr Tyr Asn Val Tyr Ala Lys Lys Gly Glu Arg Leu Phe Ile Asn
        510                 515                 520

GAG GAG AAA ATC CTG TGG AGT GGG TTC TCC AGG GAG CCA CTC ACC TTT          2055
Glu Glu Lys Ile Leu Trp Ser Gly Phe Ser Arg Glu Pro Leu Thr Phe
525                 530                 535                 540

GTG CTG TCT GTC CTC CAG GTG CCC TTC TCC AAC TGC AGC CGA GAC TGC          2103
Val Leu Ser Val Leu Gln Val Pro Phe Ser Asn Cys Ser Arg Asp Cys
                545                 550                 555

CTG GCA GGG ACC AGG AAA GGG ATC ATT GAG GGG GAG CCC ACC TGC TGC          2151
Leu Ala Gly Thr Arg Lys Gly Ile Ile Glu Gly Glu Pro Thr Cys Cys
            560                 565                 570

TTT GAG TGT GTG GAG TGT CCT GAT GGG GAG TAT AGT GAT GAG ACA GAT          2199
Phe Glu Cys Val Glu Cys Pro Asp Gly Glu Tyr Ser Asp Glu Thr Asp
        575                 580                 585

GCC AGT GCC TGT AAC AAG TGC CCA GAT GAC TTC TGG TCC AAT GAG AAC          2247
Ala Ser Ala Cys Asn Lys Cys Pro Asp Asp Phe Trp Ser Asn Glu Asn
        590                 595                 600

CAC ACC TCC TGC ATT GCC AAG GAG ATC GAG TTT CTG TCG TGG ACG GAG          2295
His Thr Ser Cys Ile Ala Lys Glu Ile Glu Phe Leu Ser Trp Thr Glu
605                 610                 615                 620

CCC TTT GGG ATC GCA CTC ACC CTC TTT GCC GTG CTG GGC ATT TTC CTG          2343
Pro Phe Gly Ile Ala Leu Thr Leu Phe Ala Val Leu Gly Ile Phe Leu
                625                 630                 635

ACA GCC TTT GTG CTG GGT GTG TTT ATC AAG TTC CGC AAC ACA CCC ATT          2391
Thr Ala Phe Val Leu Gly Val Phe Ile Lys Phe Arg Asn Thr Pro Ile
            640                 645                 650

GTC AAG GCC ACC AAC CGA GAG CTC TCC TAC CTC CTC CTC TTC TCC CTG          2439
Val Lys Ala Thr Asn Arg Glu Leu Ser Tyr Leu Leu Leu Phe Ser Leu
        655                 660                 665

CTC TGC TGC TTC TCC AGC TCC CTG TTC TTC ATC GGG GAG CCC CAG GAC          2487
Leu Cys Cys Phe Ser Ser Ser Leu Phe Phe Ile Gly Glu Pro Gln Asp
        670                 675                 680

TGG ACG TGC CGC CTG CGC CAG CCG GCC TTT GGC ATC AGC TTC GTG CTC          2535
Trp Thr Cys Arg Leu Arg Gln Pro Ala Phe Gly Ile Ser Phe Val Leu
685                 690                 695                 700

TGC ATC TCA TGC ATC CTG GTG AAA ACC AAC CGT GTC CTC CTG GTG TTT          2583
Cys Ile Ser Cys Ile Leu Val Lys Thr Asn Arg Val Leu Leu Val Phe
                705                 710                 715

GAG GCC AAG ATC CCC ACC AGC TTC CAC CGC AAG TGG TGG GGG CTC AAC          2631
Glu Ala Lys Ile Pro Thr Ser Phe His Arg Lys Trp Trp Gly Leu Asn
            720                 725                 730

CTG CAG TTC CTG CTG GTT TTC CTC TGC ACC TTC ATG CAG ATT GTC ATC          2679
Leu Gln Phe Leu Leu Val Phe Leu Cys Thr Phe Met Gln Ile Val Ile
        735                 740                 745

TGT GTG ATC TGG CTC TAC ACC GCG CCC CCC TCA AGC TAC CGC AAC CAG          2727
Cys Val Ile Trp Leu Tyr Thr Ala Pro Pro Ser Ser Tyr Arg Asn Gln
        750                 755                 760

GAG CTG GAG GAT GAG ATC ATC TTC ATC ACG TGC CAC GAG GGC TCC CTC          2775
Glu Leu Glu Asp Glu Ile Ile Phe Ile Thr Cys His Glu Gly Ser Leu
765                 770                 775                 780

ATG GCC CTG GGC TTC CTG ATC GGC TAC ACC TGC CTG CTG GCT GCC ATC          2823
Met Ala Leu Gly Phe Leu Ile Gly Tyr Thr Cys Leu Leu Ala Ala Ile
                785                 790                 795

TGC TTC TTC TTT GCC TTC AAG TCC CGG AAG CTG CCG GAG AAC TTC AAT          2871
Cys Phe Phe Phe Ala Phe Lys Ser Arg Lys Leu Pro Glu Asn Phe Asn
            800                 805                 810

GAA GCC AAG TTC ATC ACC TTC AGC ATG CTC ATC TTC TTC ATC GTC TGG          2919
```

```
                Glu Ala Lys Phe Ile Thr Phe Ser Met Leu Ile Phe Phe Ile Val Trp
                        815                 820                 825

ATC TCC TTC ATT CCA GCC TAT GCC AGC ACC TAT GGC AAG TTT GTC TCT                 2967
Ile Ser Phe Ile Pro Ala Tyr Ala Ser Thr Tyr Gly Lys Phe Val Ser
        830                 835                 840

GCC GTA GAG GTG ATT GCC ATC CTG GCA GCC AGC TTT GGC TTG CTG GCG                 3015
Ala Val Glu Val Ile Ala Ile Leu Ala Ala Ser Phe Gly Leu Leu Ala
845                 850                 855                 860

TGC ATC TTC TTC AAC AAG ATC TAC ATC ATT CTC TTC AAG CCA TCC CGC                 3063
Cys Ile Phe Phe Asn Lys Ile Tyr Ile Ile Leu Phe Lys Pro Ser Arg
                865                 870                 875

AAC ACC ATC GAG GAG GTG CGT TGC AGC ACC GCA GCT CAC GCT TTC AAG                 3111
Asn Thr Ile Glu Glu Val Arg Cys Ser Thr Ala Ala His Ala Phe Lys
        880                 885                 890

GTG GCT GCC CGG GCC ACG CTG CGC CGC AGC AAC GTC TCC CGC AAG CGG                 3159
Val Ala Ala Arg Ala Thr Leu Arg Arg Ser Asn Val Ser Arg Lys Arg
895                 900                 905

TCC AGC AGC CTT GGA GGC TCC ACG GGA TCC ACC CCC TCC TCC TCC ATC                 3207
Ser Ser Ser Leu Gly Gly Ser Thr Gly Ser Thr Pro Ser Ser Ser Ile
        910                 915                 920

AGC AGC AAG AGC AAC AGC GAA GAC CCA TTC CCA CGG CCC GAG AGG CAG                 3255
Ser Ser Lys Ser Asn Ser Glu Asp Pro Phe Pro Arg Pro Glu Arg Gln
925                 930                 935                 940

AAG CAG CAG CAG CCG CTG GCC CTA ACC CAG CAA GAG CAG CAG CAG CAG                 3303
Lys Gln Gln Gln Pro Leu Ala Leu Thr Gln Gln Glu Gln Gln Gln Gln
                945                 950                 955

CCC CTG ACC CTC CCA CAG CAG CAA CGA TCT CAG CAG CAG CCC AGA TGC                 3351
Pro Leu Thr Leu Pro Gln Gln Gln Arg Ser Gln Gln Gln Pro Arg Cys
        960                 965                 970

AAG CAG AAG GTC ATC TTT GGC AGC GGC ACG GTC ACC TTC TCA CTG AGC                 3399
Lys Gln Lys Val Ile Phe Gly Ser Gly Thr Val Thr Phe Ser Leu Ser
            975                 980                 985

TTT GAT GAG CCT CAG AAG AAC GCC ATG GCC CAC AGG AAT TCT ACG CAC                 3447
Phe Asp Glu Pro Gln Lys Asn Ala Met Ala His Arg Asn Ser Thr His
        990                 995                 1000

CAG AAC TCC CTG GAG GCC CAG AAA AGC AGC GAT ACG CTG ACC CGA CAC                 3495
Gln Asn Ser Leu Glu Ala Gln Lys Ser Ser Asp Thr Leu Thr Arg His
1005                1010                1015                1020

CAG CCA TTA CTC CCG CTG CAG TGC GGG GAA ACG GAC TTA GAT CTG ACC                 3543
Gln Pro Leu Leu Pro Leu Gln Cys Gly Glu Thr Asp Leu Asp Leu Thr
                1025                1030                1035

GTC CAG GAA ACA GGT CTG CAA GGA CCT GTG GGT GGA GAC CAG CGG CCA                 3591
Val Gln Glu Thr Gly Leu Gln Gly Pro Val Gly Gly Asp Gln Arg Pro
        1040                1045                1050

GAG GTG GAG GAC CCT GAA GAG TTG TCC CCA GCA CTT GTA GTG TCC AGT                 3639
Glu Val Glu Asp Pro Glu Glu Leu Ser Pro Ala Leu Val Val Ser Ser
            1055                1060                1065

TCA CAG AGC TTT GTC ATC AGT GGT GGA GGC AGC ACT GTT ACA GAA AAC                 3687
Ser Gln Ser Phe Val Ile Ser Gly Gly Gly Ser Thr Val Thr Glu Asn
        1070                1075                1080

GTA GTG AAT TCA TAAAATGGAA GGAGAAGACT GGGCTAGGGA GAATGCAGAG                     3739
Val Val Asn Ser
1085

AGGTTTCTTG GGGTCCCAGG GATGAGGAAT CGCCCCAGAC TCCTTTCCTC TGAGGAAGAA               3799

GGGATAATAG ACACATCAAA TGCCCCGAAT TTAGTCACAC CATCTTAAAT GACAGTGAAT               3859

TGACCCATGT TCCCTTTAAA ATTAAAAAAA AGAAGAGCCT TGTGTTTCTG TGGTTGCATT               3919

TGTCAAAGCA TTGAGATCTC CACGGTCAGA TTTGCTGTTC ACCCACATCT AATGTCTCTT               3979

CCTCTGTTCT ATCCCACCCA ACAGCTCAGA GATGAAACTA TGGCTTTAAA CTACCCTCCA               4039
```

```
GAGTGTGCAG ACTGATGGGA CATCAAATTT GCCACCACTA GAGCTGAGAG TCTGAAAGAC    4099

AGAATGTCAC CAGTCCTGCC CAATGCCTTG ACAACAGACT GAATTTTAAA TGTTCACAAC    4159

ATAAGGAGAA TGTATCTCCT CCTATTTATG AAAACCATAT GATATTTTGT CTCCTACCTG    4219

CTGCTGCTAT TATGTAACAT CCAGAAGGTT TGCACCCCTC CTATACCATA TGTCTGGTTC    4279

TGTCCAGGAC ATGATACTGA TGCCATGTTT AGATTCCAGG ATCACAAGAA TCACCTCAAA    4339

TTGTTAGGAA GGGACTGCAT AAACCAATGA GCTGTATCTG TAATTAATAT TCCTATATGT    4399

AGCTTTATCC TTAGGAAAAT GCTTCTGTTG TAATAGTCCA TGGACAATAT AAACTGAAAA    4459

ATGTCAGTCT GGTTTATATA AGGCAGTATT ATTGAGCTCT ATTTCCCCAC CCCACTATCC    4519

TCACTCCCAT AAGCTAAGCC TTATGTGAGC CCCTTCAGGG ACTCAAGGGT CCAGAAGTCC    4579

CTCCCATCTC TACCCCAAAG AATTCCTGAA GCCAGATCCA CCCTATCCCT GTACAGAGTA    4639

AGTTCTCAAT TATTGGCCTG CTAATAGCTG CTAGGGTAGG AAAGCGTGGT TCCAAGAAAG    4699

ATCCACCCTC AAATGTCGGA GCTATGTTCC CTCCAGCAGT GGTATTAATA CTGCCGGTCA    4759

CCCAGGCTCT GGAGCCAGAG AGACAGACCG GGGTTCAAGC CATGGCTTCG TCATTTGCAA    4819

GCTGAGTGAC TGTAGGCAGG GAACCTTAAC CTCTCTAAGC CACAGCTTCT TCATCTTTAA    4879

AATAAGGATA ATAATCATTC CTTCCCCTCA GAGCTCTTAT GTGGATTAAA CGAGATAATG    4939

TATATAAAGT ACTTTAGCCT GGTACCTAGC ACACAATAAG CATTCAATAA ATATTAGTTA    4999

ATATTAT                                                             5006

(2) INFORMATION FOR SEQ ID NO: 3:

(i) SEQUENCE CHARACTERISTICS:
           (A) LENGTH:            3809 base pairs
           (B) TYPE:              nucleic acid
           (C) STRANDEDNESS:      single
           (D) TOPOLOGY:          linear (ii) MOLECULE TYPE:          cDNA to mRNA (ix) FEATURE:
           (A) NAME/KEY:          CDS
           (B) LOCATION:          373..3606
           (D) OTHER INFORMATION:

(xi) SEQUENCE DESCRIPTION: SEQ ID NO: 3:

CAACAGGCAC CTGGCTGCAG CCAGGAAGGA CCGCACGCCC TTTCGCGCAG GAGAGTGGAA     60

GGAGGGAGCT GTTTGCCAGC ACCGAGGTCT TGCGGCACAG GCAACGCTTG ACCTGAGTCT    120

TGCAGAATGA AAGGCATCAC AGGAGGCCTC TGCATGATGT GGCTTCCAAA GACTCAAGGA    180

CCACCCACAT TACAAGTCTG GATTGAGGAA GGCAGAAATG GAGATTCAAA CACCACGTCT    240

TCTATTATTT TATTAATCAA TCTGTAGACA TGTGTCCCCA CTGCAGGGAG TGAACTGCTC    300

CAAGGGAGAA ACTTCTGGGA GCCTCCAAAC TCCTAGCTGT CTCATCCCTT GCCCTGGAGA    360

GACGGCAGAA CC ATG GCA TTT TAT AGC TGC TGC TGG GTC CTC TTG GCA        408
              Met Ala Phe Tyr Ser Cys Cys Trp Val Leu Leu Ala
                1               5                  10

CTC ACC TGG CAC ACC TCT GCC TAC GGG CCA GAC CAG CGA GCC CAA AAG      456
Leu Thr Trp His Thr Ser Ala Tyr Gly Pro Asp Gln Arg Ala Gln Lys
        15                  20                  25

AAG GGG GAC ATT ATC CTT GGG GGG CTC TTT CCT ATT CAT TTT GGA GTA      504
Lys Gly Asp Ile Ile Leu Gly Gly Leu Phe Pro Ile His Phe Gly Val
    30                  35                  40

GCA GCT AAA GAT CAA GAT CTC AAA TCA AGG CCG GAG TCT GTG GAA TGT      552
Ala Ala Lys Asp Gln Asp Leu Lys Ser Arg Pro Glu Ser Val Glu Cys
45                  50                  55                  60
```

```
ATC AGG TAT AAT TTC CGT GGG TTT CGC TGG TTA CAG GCT ATG ATA TTT      600
Ile Arg Tyr Asn Phe Arg Gly Phe Arg Trp Leu Gln Ala Met Ile Phe
             65                  70                  75

GCC ATA GAG GAG ATA AAC AGC AGC CCA GCC CTT CTT CCC AAC TTG ACG      648
Ala Ile Glu Glu Ile Asn Ser Ser Pro Ala Leu Leu Pro Asn Leu Thr
         80                  85                  90

CTG GGA TAC AGG ATA TTT GAC ACT TGC AAC ACC GTT TCT AAG GCC TTG      696
Leu Gly Tyr Arg Ile Phe Asp Thr Cys Asn Thr Val Ser Lys Ala Leu
             95                 100                 105

GAA GCC ACC CTG AGT TTT GTT GCT CAA AAC AAA ATT GAT TCT TTG AAC      744
Glu Ala Thr Leu Ser Phe Val Ala Gln Asn Lys Ile Asp Ser Leu Asn
        110                 115                 120

CTT GAT GAG TTC TGC AAC TGC TCA GAG CAC ATT CCC TCT ACG ATT GCT      792
Leu Asp Glu Phe Cys Asn Cys Ser Glu His Ile Pro Ser Thr Ile Ala
125                 130                 135                 140

GTG GTG GGA GCA ACT GGC TCA GGC GTC TCC ACG GCA GTG GCA AAT CTG      840
Val Val Gly Ala Thr Gly Ser Gly Val Ser Thr Ala Val Ala Asn Leu
                145                 150                 155

CTG GGG CTC TTC TAC ATT CCC CAG GTC AGT TAT GCC TCC TCC AGC AGA      888
Leu Gly Leu Phe Tyr Ile Pro Gln Val Ser Tyr Ala Ser Ser Ser Arg
                160                 165                 170

CTC CTC AGC AAC AAG AAT CAA TTC AAG TCT TTC CTC CGA ACC ATC CCC      936
Leu Leu Ser Asn Lys Asn Gln Phe Lys Ser Phe Leu Arg Thr Ile Pro
        175                 180                 185

AAT GAT GAG CAC CAG GCC ACT GCC ATG GCA GAC ATC ATC GAG TAT TTC      984
Asn Asp Glu His Gln Ala Thr Ala Met Ala Asp Ile Ile Glu Tyr Phe
190                 195                 200

CGC TGG AAC TGG GTG GGC ACA ATT GCA GCT GAT GAC GAC TAT GGG CGG     1032
Arg Trp Asn Trp Val Gly Thr Ile Ala Ala Asp Asp Asp Tyr Gly Arg
205                 210                 215                 220

CCG GGG ATT GAG AAA TTC CGA GAG GAA GCT GAG GAA AGG GAT ATC TGC     1080
Pro Gly Ile Glu Lys Phe Arg Glu Glu Ala Glu Glu Arg Asp Ile Cys
                225                 230                 235

ATC GAC TTC AGT GAA CTC ATC TCC CAG TAC TCT GAT GAG GAA GAG ATC     1128
Ile Asp Phe Ser Glu Leu Ile Ser Gln Tyr Ser Asp Glu Glu Glu Ile
                240                 245                 250

CAG CAT GTG GTA GAG GTG ATT CAA AAT TCC ACG GCC AAA GTC ATC GTG     1176
Gln His Val Val Glu Val Ile Gln Asn Ser Thr Ala Lys Val Ile Val
            255                 260                 265

GTT TTC TCC AGT GGC CCA GAT CTT GAG CCC CTC ATC AAG GAG ATT GTC     1224
Val Phe Ser Ser Gly Pro Asp Leu Glu Pro Leu Ile Lys Glu Ile Val
270                 275                 280

CGG CGC AAT ATC ACG GGC AAG ATC TGG CTG GCC AGC GAG GCC TGG GCC     1272
Arg Arg Asn Ile Thr Gly Lys Ile Trp Leu Ala Ser Glu Ala Trp Ala
285                 290                 295                 300

AGC TCC TCC CTG ATC GCC ATG CCT CAG TAC TTC CAC GTG GTT GGC GGC     1320
Ser Ser Ser Leu Ile Ala Met Pro Gln Tyr Phe His Val Val Gly Gly
                305                 310                 315

ACC ATT GGA TTC GCT CTG AAG GCT GGG CAG ATC CCA GGC TTC CGG GAA     1368
Thr Ile Gly Phe Ala Leu Lys Ala Gly Gln Ile Pro Gly Phe Arg Glu
                320                 325                 330

TTC CTG AAG AAG GTC CAT CCC AGG AAG TCT GTC CAC AAT GGT TTT GCC     1416
Phe Leu Lys Lys Val His Pro Arg Lys Ser Val His Asn Gly Phe Ala
            335                 340                 345

AAG GAG TTT TGG GAA GAA ACA TTT AAC TGC CAC CTC CAA GAA GGT GCA     1464
Lys Glu Phe Trp Glu Glu Thr Phe Asn Cys His Leu Gln Glu Gly Ala
350                 355                 360

AAA GGA CCT TTA CCT GTG GAC ACC TTT CTG AGA GGT CAC GAA GAA AGT     1512
Lys Gly Pro Leu Pro Val Asp Thr Phe Leu Arg Gly His Glu Glu Ser
365                 370                 375                 380
```

```
GGC GAC AGG TTT AGC AAC AGC TCG ACA GCC TTC CGA CCC CTC TGT ACA    1560
Gly Asp Arg Phe Ser Asn Ser Ser Thr Ala Phe Arg Pro Leu Cys Thr
            385                     390                 395

GGG GAT GAG AAC ATC AGC AGT GTC GAG ACC CCT TAC ATA GAT TAC ACG    1608
Gly Asp Glu Asn Ile Ser Ser Val Glu Thr Pro Tyr Ile Asp Tyr Thr
            400                 405                 410

CAT TTA CGG ATA TCC TAC AAT GTG TAC TTA GCA GTC TAC TCC ATT GCC    1656
His Leu Arg Ile Ser Tyr Asn Val Tyr Leu Ala Val Tyr Ser Ile Ala
            415                 420                 425

CAC GCC TTG CAA GAT ATA TAT ACC TGC TTA CCT GGG AGA GGG CTC TTC    1704
His Ala Leu Gln Asp Ile Tyr Thr Cys Leu Pro Gly Arg Gly Leu Phe
            430                 435                 440

ACC AAT GGC TCC TGT GCA GAC ATC AAG AAA GTT GAG GCG TGG CAG GTC    1752
Thr Asn Gly Ser Cys Ala Asp Ile Lys Lys Val Glu Ala Trp Gln Val
445                 450                 455                 460

CTG AAG CAC CTA CGG CAT CTA AAC TTT ACA AAC AAT ATG GGG GAG CAG    1800
Leu Lys His Leu Arg His Leu Asn Phe Thr Asn Asn Met Gly Glu Gln
            465                 470                 475

GTG ACC TTT GAT GAG TGT GGT GAC CTG GTG GGG AAC TAT TCC ATC ATC    1848
Val Thr Phe Asp Glu Cys Gly Asp Leu Val Gly Asn Tyr Ser Ile Ile
            480                 485                 490

AAC TGG CAC CTC TCC CCA GAG GAT GGC TCC ATC GTG TTT AAG GAA GTC    1896
Asn Trp His Leu Ser Pro Glu Asp Gly Ser Ile Val Phe Lys Glu Val
            495                 500                 505

GGG TAT TAC AAC GTC TAT GCC AAG AAG GGA GAA AGA CTC TTC ATC AAC    1944
Gly Tyr Tyr Asn Val Tyr Ala Lys Lys Gly Glu Arg Leu Phe Ile Asn
            510                 515                 520

GAG GAG AAA ATC CTG TGG AGT GGG TTC TCC AGG GAG GTG CCC TTC TCC    1992
Glu Glu Lys Ile Leu Trp Ser Gly Phe Ser Arg Glu Val Pro Phe Ser
525                 530                 535                 540

AAC TGC AGC CGA GAC TGC CTG GCA GGG ACC AGG AAA GGG ATC ATT GAG    2040
Asn Cys Ser Arg Asp Cys Leu Ala Gly Thr Arg Lys Gly Ile Ile Glu
            545                 550                 555

GGG GAG CCC ACC TGC TGC TTT GAG TGT GTG GAG TGT CCT GAT GGG GAG    2088
Gly Glu Pro Thr Cys Cys Phe Glu Cys Val Glu Cys Pro Asp Gly Glu
            560                 565                 570

TAT AGT GAT GAG ACA GAT GCC AGT GCC TGT AAC AAG TGC CCA GAT GAC    2136
Tyr Ser Asp Glu Thr Asp Ala Ser Ala Cys Asn Lys Cys Pro Asp Asp
            575                 580                 585

TTC TGG TCC AAT GAG AAC CAC ACC TCC TGC ATT GCC AAG GAG ATC GAG    2184
Phe Trp Ser Asn Glu Asn His Thr Ser Cys Ile Ala Lys Glu Ile Glu
            590                 595                 600

TTT CTG TCG TGG ACG GAG CCC TTT GGG ATC GCA CTC ACC CTC TTT GCC    2232
Phe Leu Ser Trp Thr Glu Pro Phe Gly Ile Ala Leu Thr Leu Phe Ala
605                 610                 615                 620

GTG CTG GGC ATT TTC CTG ACA GCC TTT GTG CTG GGT GTG TTT ATC AAG    2280
Val Leu Gly Ile Phe Leu Thr Ala Phe Val Leu Gly Val Phe Ile Lys
            625                 630                 635

TTC CGC AAC ACA CCC ATT GTC AAG GCC ACC AAC CGA GAG CTC TCC TAC    2328
Phe Arg Asn Thr Pro Ile Val Lys Ala Thr Asn Arg Glu Leu Ser Tyr
            640                 645                 650

CTC CTC CTC TTC TCC CTG CTC TGC TGC TTC TCC AGC TCC CTG TTC TTC    2376
Leu Leu Leu Phe Ser Leu Leu Cys Cys Phe Ser Ser Ser Leu Phe Phe
            655                 660                 665

ATC GGG GAG CCC CAG GAC TGG ACG TGC CGC CTG CGC CAG CCG GCC TTT    2424
Ile Gly Glu Pro Gln Asp Trp Thr Cys Arg Leu Arg Gln Pro Ala Phe
            670                 675                 680

GGC ATC AGC TTC GTG CTC TGC ATC TCA TGC ATC CTG GTG AAA ACC AAC    2472
Gly Ile Ser Phe Val Leu Cys Ile Ser Cys Ile Leu Val Lys Thr Asn
685                 690                 695                 700
```

```
CGT GTC CTC CTG GTG TTT GAG GCC AAG ATC CCC ACC AGC TTC CAC CGC      2520
Arg Val Leu Leu Val Phe Glu Ala Lys Ile Pro Thr Ser Phe His Arg
                705                 710                 715

AAG TGG TGG GGG CTC AAC CTG CAG TTC CTG CTG GTT TTC CTC TGC ACC      2568
Lys Trp Trp Gly Leu Asn Leu Gln Phe Leu Leu Val Phe Leu Cys Thr
                720                 725                 730

TTC ATG CAG ATT GTC ATC TGT GTG ATC TGG CTC TAC ACC GCG CCC CCC      2616
Phe Met Gln Ile Val Ile Cys Val Ile Trp Leu Tyr Thr Ala Pro Pro
                735                 740                 745

TCA AGC TAC CGC AAC CAG GAG CTG GAG GAT GAG ATC ATC TTC ATC ACG      2664
Ser Ser Tyr Arg Asn Gln Glu Leu Glu Asp Glu Ile Ile Phe Ile Thr
        750                 755                 760

TGC CAC GAG GGC TCC CTC ATG GCC CTG GGC TTC CTG ATC GGC TAC ACC      2712
Cys His Glu Gly Ser Leu Met Ala Leu Gly Phe Leu Ile Gly Tyr Thr
765                 770                 775                 780

TGC CTG CTG GCT GCC ATC TGC TTC TTC TTT GCC TTC AAG TCC CGG AAG      2760
Cys Leu Leu Ala Ala Ile Cys Phe Phe Phe Ala Phe Lys Ser Arg Lys
                785                 790                 795

CTG CCG GAG AAC TTC AAT GAA GCC AAG TTC ATC ACC TTC AGC ATG CTC      2808
Leu Pro Glu Asn Phe Asn Glu Ala Lys Phe Ile Thr Phe Ser Met Leu
                800                 805                 810

ATC TTC TTC ATC GTC TGG ATC TCC TTC ATT CCA GCC TAT GCC AGC ACC      2856
Ile Phe Phe Ile Val Trp Ile Ser Phe Ile Pro Ala Tyr Ala Ser Thr
                815                 820                 825

TAT GGC AAG TTT GTC TCT GCC GTA GAG GTG ATT GCC ATC CTG GCA GCC      2904
Tyr Gly Lys Phe Val Ser Ala Val Glu Val Ile Ala Ile Leu Ala Ala
        830                 835                 840

AGC TTT GGC TTG CTG GCG TGC ATC TTC TTC AAC AAG ATC TAC ATC ATT      2952
Ser Phe Gly Leu Leu Ala Cys Ile Phe Phe Asn Lys Ile Tyr Ile Ile
845                 850                 855                 860

CTC TTC AAG CCA TCC CGC AAC ACC ATC GAG GAG GTG CGT TGC AGC ACC      3000
Leu Phe Lys Pro Ser Arg Asn Thr Ile Glu Glu Val Arg Cys Ser Thr
                865                 870                 875

GCA GCT CAC GCT TTC AAG GTG GCT GCC CGG GCC ACG CTG CGC CGC AGC      3048
Ala Ala His Ala Phe Lys Val Ala Ala Arg Ala Thr Leu Arg Arg Ser
                880                 885                 890

AAC GTC TCC CGC AAG CGG TCC AGC AGC CTT GGA GGC TCC ACG GGA TCC      3096
Asn Val Ser Arg Lys Arg Ser Ser Ser Leu Gly Gly Ser Thr Gly Ser
                895                 900                 905

ACC CCC TCC TCC TCC ATC AGC AGC AAG AGC AAC AGC GAA GAC CCA TTC      3144
Thr Pro Ser Ser Ser Ile Ser Ser Lys Ser Asn Ser Glu Asp Pro Phe
910                 915                 920

CCA CAG CCC GAG AGG CAG AAG CAG CAG CAG CCG CTG GCC CTA ACC CAG      3192
Pro Gln Pro Glu Arg Gln Lys Gln Gln Gln Pro Leu Ala Leu Thr Gln
925                 930                 935                 940

CAA GAG CAG CAG CAG CAG CCC CTG ACC CTC CCA CAG CAG CAA CGA TCT      3240
Gln Glu Gln Gln Gln Gln Pro Leu Thr Leu Pro Gln Gln Gln Arg Ser
                945                 950                 955

CAG CAG CAG CCC AGA TGC AAG CAG AAG GTC ATC TTT GGC AGC GGC ACG      3288
Gln Gln Gln Pro Arg Cys Lys Gln Lys Val Ile Phe Gly Ser Gly Thr
                960                 965                 970

GTC ACC TTC TCA CTG AGC TTT GAT GAG CCT CAG AAG AAC GCC ATG GCC      3336
Val Thr Phe Ser Leu Ser Phe Asp Glu Pro Gln Lys Asn Ala Met Ala
                975                 980                 985

CAC GGG AAT TCT ACG CAC CAG AAC TCC CTG GAG GCC CAG AAA AGC AGC      3384
His Gly Asn Ser Thr His Gln Asn Ser Leu Glu Ala Gln Lys Ser Ser
        990                 995                 1000

GAT ACG CTG ACC CGA CAC CAG CCA TTA CTC CCG CTG CAG TGC GGG GAA      3432
Asp Thr Leu Thr Arg His Gln Pro Leu Leu Pro Leu Gln Cys Gly Glu
1005                1010                1015                1020
```

```
ACG GAC TTA GAT CTG ACC GTC CAG GAA ACA GGT CTG CAA GGA CCT GTG          3480
Thr Asp Leu Asp Leu Thr Val Gln Glu Thr Gly Leu Gln Gly Pro Val
            1025                1030                1035

GGT GGA GAC CAG CGG CCA GAG GTG GAG GAC CCT GAA GAG TTG TCC CCA          3528
Gly Gly Asp Gln Arg Pro Glu Val Glu Asp Pro Glu Glu Leu Ser Pro
            1040                1045                1050

GCA CTT GTA GTG TCC AGT TCA CAG AGC TTT GTC ATC AGT GGT GGA GGC          3576
Ala Leu Val Val Ser Ser Ser Gln Ser Phe Val Ile Ser Gly Gly Gly
            1055                1060                1065

AGC ACT GTT ACA GAA AAC GTA GTG AAT TCA TAAAATGGAA GGAGAAGACT            3626
Ser Thr Val Thr Glu Asn Val Val Asn Ser
            1070                1075

GGGCTAGGGA GAATGCAGAG AGGTTTCTTG GGGTCCCAGG GATGAGGAAT CGCCCCAGAC        3686

TCCTTTCCTC TGAGGAAGAA GGGATAATAG ACACATCAAA TGCCCCGAAT TTAGTCACAC        3746

CATCTTAAAT GACAGTGAAT TGACCCATGT TCCCTTTAAA AAAAAAAAAA AAAAAGCGGC        3806

CGC                                                                      3809

(2) INFORMATION FOR SEQ ID NO: 4:

(i) SEQUENCE CHARACTERISTICS:
        (A) LENGTH:           4131 base pairs
        (B) TYPE:             nucleic acid
        (C) STRANDEDNESS:     single
        (D) TOPOLOGY:         linear (ii) MOLECULE TYPE:       cDNA to mRNA (ix) FEATURE:
        (A) NAME/KEY:         CDS
        (B) LOCATION:         574..3810
        (D) OTHER INFORMATION:

(xi) SEQUENCE DESCRIPTION: SEQ ID NO: 4:

CGGGACTCTC CAGGCCGGCT CAGGCACCGG ACTGTAGGTG TATTTGGAGG GATTTGGAGG         60

CTGGAGACCC CAGGAAGCAC GCAGGCGGGA GCAGGCAAGG GGCGGAGCCC CGGGCCCGGC        120

CAAGGTGGCC GTCAGAGGGT CTGCGGGGAG GCAGTAGCTT GACCCAAGGC GACCAGGGAA        180

CTTCAGACGG TAGCACGCCA CTCAAACAAA TTAACTTGAC ATCGCAAGCT GGGCGGGCTG        240

GTACGACATC CTGACTTCAG CATCCAGCTG TTCCTGGGCA GACAGAGGGC CAACAGGTGT        300

TCCTGTGGAA GAAGCCAGGA CAAGGACTCC AGAAAACATC TCGGGCAGCC TCTACATGAT        360

GTCACTTCTC AGGACTCGAG GACCAGCCAC CCTACACCTC TACTACAGAG AAGGCAGAAA        420

TGGAGACCCA AAGGCCATCA CTCCTGCTCT GTCACTAACC ACTCTGTAAT CATGTCTCCC        480

CACCAGAAGG TGTGAACCGC ACCAGGGCCG TGGAGTTCTC GGGCTCCCAA TCCACTGACA        540

CCTTTACCTG TCCCCTGAAG AGAAGGCAAC GCT ATG GCA TCG TAC AGC TGC TGT        594
                                   Met Ala Ser Tyr Ser Cys Cys
                                    1               5

TTG GCC CTA TTG GCT CTT GCC TGG CAC TCC TCT GCC TAT GGG CCT GAC          642
Leu Ala Leu Leu Ala Leu Ala Trp His Ser Ser Ala Tyr Gly Pro Asp
        10                  15                  20

CAG CGA GCC CAA AAG AAG GGG GAC ATT ATC CTA GGA GGT CTC TTT CCT          690
Gln Arg Ala Gln Lys Lys Gly Asp Ile Ile Leu Gly Gly Leu Phe Pro
    25                  30                  35

ATC CAT TTT GGA GTA GCA GCC AAA GAT CAA GAT CTG AAG TCA AGA CCA          738
Ile His Phe Gly Val Ala Ala Lys Asp Gln Asp Leu Lys Ser Arg Pro
40                  45                  50                  55

GAG TCT GTG GAG TGC ATT AGG TAT AAC TTC CGT GGA TTC CGA TGG TTA          786
Glu Ser Val Glu Cys Ile Arg Tyr Asn Phe Arg Gly Phe Arg Trp Leu
            60                  65                  70
```

```
CAA GCC ATG ATA TTC GCC ATA GAG GAG ATA AAC AGC AGC CCC TCC CTT         834
Gln Ala Met Ile Phe Ala Ile Glu Glu Ile Asn Ser Ser Pro Ser Leu
            75                  80                  85

CTT CCC AAC ATG ACA CTG GGA TAT AGG ATA TTT GAC ACC TGT AAC ACC         882
Leu Pro Asn Met Thr Leu Gly Tyr Arg Ile Phe Asp Thr Cys Asn Thr
        90                  95                 100

GTC TCC AAG GCG CTG GAA GCC ACC TTG AGT TTT GTT GCC CAG AAC AAA         930
Val Ser Lys Ala Leu Glu Ala Thr Leu Ser Phe Val Ala Gln Asn Lys
    105                 110                 115

ATC GAT TCT TTG AAC CTG GAC GAG TTC TGC AAC TGC TCT GAG CAC ATC         978
Ile Asp Ser Leu Asn Leu Asp Glu Phe Cys Asn Cys Ser Glu His Ile
120                 125                 130                 135

CCT TCG ACC ATT GCC GTG GTG GGA GCC ACC GGC TCC GGT GTC TCC ACG        1026
Pro Ser Thr Ile Ala Val Val Gly Ala Thr Gly Ser Gly Val Ser Thr
            140                 145                 150

GCG GTA GCC AAC CTG CTG GGA CTT TTC TAC ATC CCC CAG GTG AGC TAC        1074
Ala Val Ala Asn Leu Leu Gly Leu Phe Tyr Ile Pro Gln Val Ser Tyr
        155                 160                 165

GCC TCC TCC AGC AGG CTC CTC AGC AAT AAG AAC CAG TAC AAA TCC TTC        1122
Ala Ser Ser Ser Arg Leu Leu Ser Asn Lys Asn Gln Tyr Lys Ser Phe
    170                 175                 180

CTC CGC ACC ATT CCC AAT GAC GAA CAC CAG GCA ACC GCG ATG GCC GAC        1170
Leu Arg Thr Ile Pro Asn Asp Glu His Gln Ala Thr Ala Met Ala Asp
185                 190                 195

ATC ATC GAG TAC TTC CGC TGG AAC TGG GTG GGC ACA ATT GCA GCT GAT        1218
Ile Ile Glu Tyr Phe Arg Trp Asn Trp Val Gly Thr Ile Ala Ala Asp
200                 205                 210                 215

GAC GAC TAT GGC AGA CCT GGC ATT GAG AAG TTC CGA GAG GAA GCC GAA        1266
Asp Asp Tyr Gly Arg Pro Gly Ile Glu Lys Phe Arg Glu Glu Ala Glu
            220                 225                 230

GAG AGG GAT ATC TGC ATT GAT TTT AGC GAG CTC ATC TCC CAG TAC TCT        1314
Glu Arg Asp Ile Cys Ile Asp Phe Ser Glu Leu Ile Ser Gln Tyr Ser
        235                 240                 245

GAC GAG GAA GAG ATC CAG CAG GTG GTC GAA GTG ATC CAA AAC TCT ACG        1362
Asp Glu Glu Glu Ile Gln Gln Val Val Glu Val Ile Gln Asn Ser Thr
    250                 255                 260

GCC AAG GTC ATT GTC GTT TTC TCC AGC GGC CCG GAC CTA GAA CCT CTC        1410
Ala Lys Val Ile Val Val Phe Ser Ser Gly Pro Asp Leu Glu Pro Leu
265                 270                 275

ATC AAG GAG ATT GTG CGG CGT AAC ATC ACA GGC AGG ATC TGG CTG GCT        1458
Ile Lys Glu Ile Val Arg Arg Asn Ile Thr Gly Arg Ile Trp Leu Ala
280                 285                 290                 295

AGC GAG GCC TGG GCC AGT TCC TCG CTG ATT GCT ATG CCT GAG TAT TTC        1506
Ser Glu Ala Trp Ala Ser Ser Ser Leu Ile Ala Met Pro Glu Tyr Phe
            300                 305                 310

CAT GTA GTC GGG GGC ACC ATT GGG TTC GGT CTG AAG GCT GGG CAG ATT        1554
His Val Val Gly Gly Thr Ile Gly Phe Gly Leu Lys Ala Gly Gln Ile
        315                 320                 325

CCA GGC TTC AGA GAA TTC CTA CAG AAA GTT CAT CCT AGG AAG TCT GTC        1602
Pro Gly Phe Arg Glu Phe Leu Gln Lys Val His Pro Arg Lys Ser Val
    330                 335                 340

CAC AAT GGT TTT GCC AAA GAG TTT TGG GAA GAA ACT TTT AAT TGC CAC        1650
His Asn Gly Phe Ala Lys Glu Phe Trp Glu Glu Thr Phe Asn Cys His
345                 350                 355

CTC CAA GAA GGC GCA AAA GGA CCT TTA CCT GTG GAC ACC TTC GTG AGA        1698
Leu Gln Glu Gly Ala Lys Gly Pro Leu Pro Val Asp Thr Phe Val Arg
360                 365                 370                 375

AGT CAC GAA GAA GGT GGC AAC AGG TTA CTC AAT AGC TCT ACT GCC TTC        1746
Ser His Glu Glu Gly Gly Asn Arg Leu Leu Asn Ser Ser Thr Ala Phe
            380                 385                 390
```

-continued

| | |
|---|---|
| CGA CCC CTC TGC ACA GGG GAT GAG AAC ATC AAC AGT GTG GAG ACC CCT<br>Arg Pro Leu Cys Thr Gly Asp Glu Asn Ile Asn Ser Val Glu Thr Pro<br>                395                          400                        405 | 1794 |
| TAC ATG GAT TAC GAA CAT TTA CGG ATA TCC TAC AAT GTG TAC TTA GCC<br>Tyr Met Asp Tyr Glu His Leu Arg Ile Ser Tyr Asn Val Tyr Leu Ala<br>                410                          415                        420 | 1842 |
| GTC TAC TCC ATT GCG CAT GCC CTA CAA GAT ATA TAC ACC TGC TTA CCC<br>Val Tyr Ser Ile Ala His Ala Leu Gln Asp Ile Tyr Thr Cys Leu Pro<br>       425                           430                        435 | 1890 |
| GGA AGA GGG CTT TTC ACC AAC GGG TCC TGT GCA GAC ATC AAG AAG GTT<br>Gly Arg Gly Leu Phe Thr Asn Gly Ser Cys Ala Asp Ile Lys Lys Val<br>440                          445                        450                        455 | 1938 |
| GAG GCC TGG CAG GTC TTG AAG CAC CTA CGG CAC CTG AAC TTC ACC AAC<br>Glu Ala Trp Gln Val Leu Lys His Leu Arg His Leu Asn Phe Thr Asn<br>                      460                          465                        470 | 1986 |
| AAC ATG GGG GAG CAG GTG ACC TTC GAT GAG TGT GGT GAT CTG GTG GGG<br>Asn Met Gly Glu Gln Val Thr Phe Asp Glu Cys Gly Asp Leu Val Gly<br>                475                          480                        485 | 2034 |
| AAC TAT TCT ATC ATC AAC TGG CAC CTC TCC CCA GAG GAC GGC TCC ATT<br>Asn Tyr Ser Ile Ile Asn Trp His Leu Ser Pro Glu Asp Gly Ser Ile<br>       490                           495                        500 | 2082 |
| GTG TTC AAG GAA GTT GGG TAC TAC AAT GTG TAT GCC AAG AAG GGA GAA<br>Val Phe Lys Glu Val Gly Tyr Tyr Asn Val Tyr Ala Lys Lys Gly Glu<br>505                          510                        515 | 2130 |
| AGA CTC TTC ATC AAT GAG GAG AAG ATC TTG TGG AGT GGG TTC TCC AGA<br>Arg Leu Phe Ile Asn Glu Glu Lys Ile Leu Trp Ser Gly Phe Ser Arg<br>520                          525                        530                        535 | 2178 |
| GAG GTG CCT TTC TCC AAT TGC AGC CGG GAC TGT CAG GCA GGG ACC AGG<br>Glu Val Pro Phe Ser Asn Cys Ser Arg Asp Cys Gln Ala Gly Thr Arg<br>                      540                          545                        550 | 2226 |
| AAG GGG ATC ATC GAG GGA GAG CCC ACC TGC TGC TTT GAG TGT GTG GAG<br>Lys Gly Ile Ile Glu Gly Glu Pro Thr Cys Cys Phe Glu Cys Val Glu<br>                555                          560                        565 | 2274 |
| TGT CCT GAT GGA GAG TAC AGT GGA GAG ACA GAT GCG AGT GCC TGT GAC<br>Cys Pro Asp Gly Glu Tyr Ser Gly Glu Thr Asp Ala Ser Ala Cys Asp<br>       570                           575                        580 | 2322 |
| AAG TGC CCG GAT GAC TTC TGG TCC AAT GAG AAC CAC ACT TCT TGC ATT<br>Lys Cys Pro Asp Asp Phe Trp Ser Asn Glu Asn His Thr Ser Cys Ile<br>585                          590                        595 | 2370 |
| GCC AAG GAG ATT GAG TTT CTG GCG TGG ACC GAG CCC TTT GGA ATC GCT<br>Ala Lys Glu Ile Glu Phe Leu Ala Trp Thr Glu Pro Phe Gly Ile Ala<br>600                          605                        610                        615 | 2418 |
| CTC ACT CTC TTT GCG GTG CTG GGC ATT TTC CTG ACC GCC TTT GTG CTG<br>Leu Thr Leu Phe Ala Val Leu Gly Ile Phe Leu Thr Ala Phe Val Leu<br>                    620                          625                        630 | 2466 |
| GGT GTC TTC ATC AAG TTC CGA AAC ACA CCT ATC GTC AAG GCC ACC AAC<br>Gly Val Phe Ile Lys Phe Arg Asn Thr Pro Ile Val Lys Ala Thr Asn<br>                635                          640                        645 | 2514 |
| CGA GAA CTG TCC TAC CTC CTG CTC TTC TCC CTA CTC TGC TGC TTC TCC<br>Arg Glu Leu Ser Tyr Leu Leu Leu Phe Ser Leu Leu Cys Cys Phe Ser<br>       650                           655                        660 | 2562 |
| AGC TCC TTG TTC TTC ATT GGG GAG CCC CAG GAC TGG ACG TGC CGC CTG<br>Ser Ser Leu Phe Phe Ile Gly Glu Pro Gln Asp Trp Thr Cys Arg Leu<br>                665                          670                        675 | 2610 |
| CGA CAG CCT GCT TTC GGC ATC AGC TTT GTG CTC TGT ATC TCG TGC ATC<br>Arg Gln Pro Ala Phe Gly Ile Ser Phe Val Leu Cys Ile Ser Cys Ile<br>680                          685                        690                        695 | 2658 |
| TTG GTG AAG ACC AAT CGC GTC CTC CTG GTA TTT GAA GCC AAG ATA CCC<br>Leu Val Lys Thr Asn Arg Val Leu Leu Val Phe Glu Ala Lys Ile Pro<br>                700                          705                        710 | 2706 |

```
ACC AGC TTC CAC CGG AAG TGG TGG GGG CTC AAC CTG CAG TTC CTG CTG        2754
Thr Ser Phe His Arg Lys Trp Trp Gly Leu Asn Leu Gln Phe Leu Leu
            715                 720                 725

GTT TTC CTC TGC ACC TTC ATG CAG ATC CTC ATC TGC ATC ATC TGG CTC        2802
Val Phe Leu Cys Thr Phe Met Gln Ile Leu Ile Cys Ile Ile Trp Leu
            730                 735                 740

TAC ACG GCG CCC CCC TCT AGC TAC CGC AAC CAT GAG CTG GAA GAC GAA        2850
Tyr Thr Ala Pro Pro Ser Ser Tyr Arg Asn His Glu Leu Glu Asp Glu
745                 750                 755

ATC ATC TTC ATC ACG TGC CAT GAG GGC TCA CTC ATG GCA CTT GGC TCC        2898
Ile Ile Phe Ile Thr Cys His Glu Gly Ser Leu Met Ala Leu Gly Ser
760                 765                 770                 775

CTG ATC GGC TAT ACC TGC CTG CTG GCT GCC ATC TGC TTC TTC TTT GCC        2946
Leu Ile Gly Tyr Thr Cys Leu Leu Ala Ala Ile Cys Phe Phe Phe Ala
                780                 785                 790

TTC AAG TCC AGG AAG TTA CCA GAG AAC TTC AAC GAA GCC AAG TTC ATT        2994
Phe Lys Ser Arg Lys Leu Pro Glu Asn Phe Asn Glu Ala Lys Phe Ile
            795                 800                 805

ACC TTC AGC ATG CTC ATC TTC TTC ATC GTC TGG ATC TCC TTC ATT CCA        3042
Thr Phe Ser Met Leu Ile Phe Phe Ile Val Trp Ile Ser Phe Ile Pro
            810                 815                 820

GCC TAT GCC AGC ACC TAC GGC AAG TTT GTC TCT GCC GTA GAG GTG ATC        3090
Ala Tyr Ala Ser Thr Tyr Gly Lys Phe Val Ser Ala Val Glu Val Ile
825                 830                 835

GCC ATT TTG GCA GCC AGC TTT GGC TTA CTA GCC TGC ATC TTC TTC AAC        3138
Ala Ile Leu Ala Ala Ser Phe Gly Leu Leu Ala Cys Ile Phe Phe Asn
840                 845                 850                 855

AAG GTC TAC ATT ATC CTC TTC AAG CCT TCC CGG AAC ACC ATT GAG GAA        3186
Lys Val Tyr Ile Ile Leu Phe Lys Pro Ser Arg Asn Thr Ile Glu Glu
                860                 865                 870

GTC CGC TCC AGC ACC GCA GCA CAT GCT TTC AAA GTA GCA GCC CGC GCC        3234
Val Arg Ser Ser Thr Ala Ala His Ala Phe Lys Val Ala Ala Arg Ala
                875                 880                 885

ACT CTA CGC CGT CCC AAC ATC TCC CGG AAG CGG TCC AGC AGC CTT GGA        3282
Thr Leu Arg Arg Pro Asn Ile Ser Arg Lys Arg Ser Ser Ser Leu Gly
            890                 895                 900

GGC TCC ACC GGC TCC ATT CCC TCC TCC TCC ATC AGC AGC AAA AGC AAC        3330
Gly Ser Thr Gly Ser Ile Pro Ser Ser Ser Ile Ser Ser Lys Ser Asn
905                 910                 915

AGC GAA GAC CGG TTC CCG CAG CCA GAG AGG CAG AAG CAA CAG CAA CCG        3378
Ser Glu Asp Arg Phe Pro Gln Pro Glu Arg Gln Lys Gln Gln Gln Pro
920                 925                 930                 935

CTG TCC CTG ACC CAG CAA GAA CAG CAG CAG CCC CTG ACC CTC CAC            3426
Leu Ser Leu Thr Gln Gln Glu Gln Gln Gln Pro Leu Thr Leu His
                940                 945                 950

CCA CAG CAA CAG CAG CAG CCA CAG CAG CCG AGA TGC AAA CAG AAG GTC        3474
Pro Gln Gln Gln Gln Gln Pro Gln Gln Pro Arg Cys Lys Gln Lys Val
            955                 960                 965

ATC TTC GGC AGT GGT ACG GTC ACC TTC TCT CTG AGT TTT GAC GAG CCT        3522
Ile Phe Gly Ser Gly Thr Val Thr Phe Ser Leu Ser Phe Asp Glu Pro
            970                 975                 980

CAG AAG AAT GCC ATG GCC CAC AGG AAC TCC ATG CGT CAG AAC TCC CTG        3570
Gln Lys Asn Ala Met Ala His Arg Asn Ser Met Arg Gln Asn Ser Leu
985                 990                 995

GAG GCC CAG AGG AGC AAC GAC ACC TTG GGC AGA CAC CAG GCC CTG CTT        3618
Glu Ala Gln Arg Ser Asn Asp Thr Leu Gly Arg His Gln Ala Leu Leu
1000                1005                1010                1015

CCC CTA CAG TGT GCA GAT GCG GAC TCA GAA ATG ACC ATT CAG GAA ACG        3666
Pro Leu Gln Cys Ala Asp Ala Asp Ser Glu Met Thr Ile Gln Glu Thr
            1020                1025                1030
```

```
GGC CTG CAA GGG CCC ATG GTG GGG GAC CAC CAG CCA GAA ATG GAA AGC         3714
Gly Leu Gln Gly Pro Met Val Gly Asp His Gln Pro Glu Met Glu Ser
        1035                1040                1045

TCA GAT GAA ATG TCC CCA GCG CTG GTC ATG TCC ACC TCT CGG AGC TTC         3762
Ser Asp Glu Met Ser Pro Ala Leu Val Met Ser Thr Ser Arg Ser Phe
        1050                1055                1060

GTC ATT AGT GGT GGA GGT AGC TCT GTG ACG GAA AAC GTA TTA CAC TCC         3810
Val Ile Ser Gly Gly Gly Ser Ser Val Thr Glu Asn Val Leu His Ser
        1065                1070                1075

TAATGGAGGG AAAGGCTATC CAGTTGAGAG GTTTTTCTTA GAGCCCTGAG CAAAAGGATG       3870

GGTCCTTCCT TTCTTCCCAG GAAGCCAGGG AGAGTAGGTA CGTCAAAGCC TGTACTCAGT       3930

TGCACTGCTT TGAATGACAG TGAACTGACT GGTGTGCTCT TTAGAGTTAA AAGAAGAGCC       3990

ATGTTTTGGG GTCGTTTTCC AGAGCTCAGT ATCACACCTG GGTTTGCTGA AGTCTTTTCC       4050

TCTGCTCTAT CCACCATCAG TTCAGACGAA AGCAAGGCTC TAAGCTACCC ATCTGCTTCC       4110

CTCAAAAAAA AAAAAAAAA A                                                  4131

(2) INFORMATION FOR SEQ ID NO: 5:

(i) SEQUENCE CHARACTERISTICS:
        (A) LENGTH:          1085 amino acids
        (B) TYPE:            amino acid
        (D) TOPOLOGY:        linear (ii) MOLECULE TYPE:           protein (xi) SEQUENCE DESCRIPTION: SEQ ID NO: 5:

Met Ala Leu Tyr Ser Cys Cys Trp Ile Leu Leu Ala Phe Ser Thr Trp
 1               5                  10                  15

Cys Thr Ser Ala Tyr Gly Pro Asp Gln Arg Ala Gln Lys Lys Gly Asp
                20                  25                  30

Ile Ile Leu Gly Gly Leu Phe Pro Ile His Phe Gly Val Ala Val Lys
            35                  40                  45

Asp Gln Asp Leu Lys Ser Arg Pro Glu Ser Val Glu Cys Ile Arg Tyr
        50                  55                  60

Asn Phe Arg Gly Phe Arg Trp Leu Gln Ala Met Ile Phe Ala Ile Glu
65                  70                  75                  80

Glu Ile Asn Ser Ser Pro Ala Leu Leu Pro Asn Met Thr Leu Gly Tyr
                85                  90                  95

Arg Ile Phe Asp Thr Cys Asn Thr Val Ser Lys Ala Leu Glu Ala Thr
            100                 105                 110

Leu Ser Phe Val Ala Gln Asn Lys Ile Asp Ser Leu Asn Leu Asp Glu
        115                 120                 125

Phe Cys Asn Cys Ser Glu His Ile Pro Ser Thr Ile Ala Val Val Gly
    130                 135                 140

Ala Thr Gly Ser Gly Ile Ser Thr Ala Val Ala Asn Leu Leu Gly Leu
145                 150                 155                 160

Phe Tyr Ile Pro Gln Val Ser Tyr Ala Ser Ser Arg Leu Leu Ser
                165                 170                 175

Asn Lys Asn Gln Phe Lys Ser Phe Leu Arg Thr Ile Pro Asn Asp Glu
            180                 185                 190

His Gln Ala Thr Ala Met Ala Asp Ile Ile Glu Tyr Phe Arg Trp Asn
        195                 200                 205

Trp Val Gly Thr Ile Ala Ala Asp Asp Asp Tyr Gly Arg Pro Gly Ile
    210                 215                 220

Glu Lys Phe Arg Glu Glu Ala Glu Glu Arg Asp Ile Cys Ile Asp Phe
```

```
         225                 230                 235                 240
Ser Glu Leu Ile Ser Gln Tyr Ser Asp Glu Glu Lys Ile Gln Gln Val
                245                 250                 255
Val Glu Val Ile Gln Asn Ser Thr Ala Lys Val Ile Val Phe Ser
                260                 265                 270         Ser
Ser Gly Pro Asp Leu Glu Pro Leu Ile Lys Glu Ile Val Arg Arg Asn
            275                 280                 285
Ile Thr Gly Arg Ile Trp Leu Ala Ser Glu Ala Trp Ala Ser Ser Ser
        290                 295                 300
Leu Ile Ala Met Pro Glu Tyr Phe His Val Gly Gly Thr Ile Gly
305                 310                 315                 320
Phe Gly Leu Lys Ala Gly Gln Ile Pro Gly Phe Arg Glu Phe Leu Gln
                325                 330                 335
Lys Val His Pro Arg Lys Ser Val His Asn Gly Phe Ala Lys Glu Phe
                340                 345                 350
Trp Glu Glu Thr Phe Asn Cys His Leu Gln Glu Gly Ala Lys Gly Pro
                355                 360                 365
Leu Pro Val Asp Thr Phe Leu Arg Gly His Glu Gly Gly Ala Arg
370                 375                 380
Leu Ser Asn Ser Pro Thr Ala Phe Arg Pro Leu Cys Thr Gly Glu Glu
385                 390                 395                 400
Asn Ile Ser Ser Val Glu Thr Pro Tyr Met Asp Tyr Thr His Leu Arg
                405                 410                 415
Ile Ser Tyr Asn Val Tyr Leu Ala Val Tyr Ser Ile Ala His Ala Leu
                420                 425                 430
Gln Asp Ile Tyr Thr Cys Ile Pro Gly Arg Gly Leu Phe Thr Asn Gly
                435                 440                 445
Ser Cys Ala Asp Ile Lys Lys Val Glu Ala Trp Gln Val Leu Lys His
450                 455                 460
Leu Arg His Leu Asn Phe Thr Ser Asn Met Gly Glu Gln Val Thr Phe
465                 470                 475                 480
Asp Glu Cys Gly Asp Leu Ala Gly Asn Tyr Ser Ile Ile Asn Trp His
                485                 490                 495
Leu Ser Pro Glu Asp Gly Ser Ile Val Phe Lys Glu Val Gly Tyr Tyr
                500                 505                 510
Asn Val Tyr Ala Lys Lys Gly Glu Arg Leu Phe Ile Asn Asp Glu Lys
                515                 520                 525
Ile Leu Trp Ser Gly Phe Ser Arg Glu Val Pro Phe Ser Asn Cys Ser
            530                 535                 540
Arg Asp Cys Leu Ala Gly Thr Arg Lys Gly Ile Ile Glu Gly Glu Pro
545                 550                 555                 560
Thr Cys Cys Phe Glu Cys Val Glu Cys Pro Asp Gly Glu Tyr Ser Asp
                565                 570                 575
Glu Thr Asp Ala Ser Ala Cys Asp Lys Cys Pro Asp Asp Phe Trp Ser
                580                 585                 590
Asn Glu Asn His Thr Ser Cys Ile Ala Lys Glu Ile Glu Phe Leu Ser
                595                 600                 605
Trp Thr Glu Pro Phe Gly Ile Ala Leu Thr Leu Phe Ala Val Leu Gly
                610                 615                 620
Ile Phe Leu Thr Ala Phe Val Leu Gly Val Phe Ile Lys Phe Arg Asn
625                 630                 635                 640
Thr Pro Ile Val Lys Ala Thr Asn Arg Glu Leu Ser Tyr Leu Leu Leu
                645                 650                 655
```

-continued

```
Phe Ser Leu Leu Cys Cys Phe Ser Ser Leu Phe Ile Gly Glu
        660                 665                 670

Pro Gln Asp Trp Thr Cys Arg Leu Arg Gln Pro Ala Phe Gly Ile Ser
        675                 680                 685

Phe Val Leu Cys Ile Ser Cys Ile Leu Val Lys Thr Asn Arg Val Leu
690                 695                 700

Leu Val Phe Glu Ala Lys Ile Pro Thr Ser Phe His Arg Lys Trp Trp
705                 710                 715                 720

Gly Leu Asn Leu Gln Phe Leu Val Phe Leu Cys Thr Phe Met Gln
                725                 730                 735

Ile Val Ile Cys Ala Ile Trp Leu Asn Thr Ala Pro Pro Ser Ser Tyr
                740                 745                 750

Arg Asn His Glu Leu Glu Asp Glu Ile Phe Ile Thr Cys His Glu
            755                 760                 765

Gly Ser Leu Met Ala Leu Gly Phe Leu Ile Gly Tyr Thr Cys Leu Leu
770                 775                 780

Ala Ala Ile Cys Phe Phe Ala Phe Lys Ser Arg Lys Leu Pro Glu
785                 790                 795                 800

Asn Phe Asn Glu Ala Lys Phe Ile Thr Phe Ser Met Leu Ile Phe Phe
                805                 810                 815

Ile Val Trp Ile Ser Phe Ile Pro Ala Tyr Ala Ser Thr Tyr Gly Lys
            820                 825                 830

Phe Val Ser Ala Val Glu Val Ile Ala Ile Leu Ala Ala Ser Phe Gly
            835                 840                 845

Leu Leu Ala Cys Ile Phe Phe Asn Lys Val Tyr Ile Ile Leu Phe Lys
850                 855                 860

Pro Ser Arg Asn Thr Ile Glu Glu Val Arg Cys Ser Thr Ala Ala His
865                 870                 875                 880

Ala Phe Lys Val Ala Arg Ala Thr Leu Arg Arg Ser Asn Val Ser
                885                 890                 895

Arg Gln Arg Ser Ser Ser Leu Gly Gly Ser Thr Gly Ser Thr Pro Ser
            900                 905                 910

Ser Ser Ile Ser Ser Lys Ser Asn Ser Glu Asp Pro Phe Pro Gln Gln
            915                 920                 925

Gln Pro Lys Arg Gln Lys Gln Pro Gln Pro Leu Ala Leu Ser Pro His
930                 935                 940

Asn Ala Gln Gln Pro Gln Pro Arg Pro Pro Ser Thr Pro Gln Pro Gln
945                 950                 955                 960

Pro Gln Ser Gln Gln Pro Pro Arg Cys Lys Gln Lys Val Ile Phe Gly
                965                 970                 975

Ser Gly Thr Val Thr Phe Ser Leu Ser Phe Asp Glu Pro Gln Lys Thr
            980                 985                 990

Ala Val Ala His Arg Asn Ser Thr His Gln Thr Ser Leu Glu Ala Gln
            995                 1000                1005

Lys Asn Asn Asp Ala Leu Thr Lys His Gln Ala Leu Leu Pro Leu Gln
1010                1015                1020

Cys Gly Glu Thr Asp Ser Glu Leu Thr Ser Gln Glu Thr Gly Leu Gln
1025                1030                1035                1040

Gly Pro Val Gly Glu Asp His Gln Leu Glu Met Glu Asp Pro Glu Glu
                1045                1050                1055

Met Ser Pro Ala Leu Val Val Ser Asn Ser Arg Ser Phe Val Ile Ser
                1060                1065                1070

Gly Gly Gly Ser Thr Val Thr Glu Asn Met Leu Arg Ser
            1075                1080                1085
```

(2) INFORMATION FOR SEQ ID NO: 6:

(i) SEQUENCE CHARACTERISTICS:
        (A) LENGTH:           1088 amino acids
        (B) TYPE:             amino acid
        (D) TOPOLOGY:         linear (ii) MOLECULE TYPE:       protein (xi) SEQUENCE DESCRIPTION: SEQ ID NO: 6:

```
Met Ala Phe Tyr Ser Cys Cys Trp Val Leu Leu Ala Leu Thr Trp His
  1               5                  10                  15

Thr Ser Ala Tyr Gly Pro Asp Gln Arg Ala Gln Lys Lys Gly Asp Ile
             20                  25                  30

Ile Leu Gly Gly Leu Phe Pro Ile His Phe Gly Val Ala Ala Lys Asp
         35                  40                  45

Gln Asp Leu Lys Ser Arg Pro Glu Ser Val Glu Cys Ile Arg Tyr Asn
 50                  55                  60

Phe Arg Gly Phe Arg Trp Leu Gln Ala Met Ile Phe Ala Ile Glu Glu
 65                  70                  75                  80

Ile Asn Ser Ser Pro Ala Leu Leu Pro Asn Leu Thr Leu Gly Tyr Arg
                 85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
            165                 170                 175

Lys Asn Gln Phe Lys Ser Phe Leu Arg Thr Ile Pro Asn Asp Glu His
        180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Tyr Gly Arg Pro Gly Ile Glu
210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Glu Ile Gln His Val Val
            245                 250                 255

Glu Val Ile Gln Asn Ser Thr Ala Lys Val Ile Val Phe Ser Ser
        260                 265                 270

Gly Pro Asp Leu Glu Pro Leu Ile Lys Glu Ile Val Arg Arg Asn Ile
        275                 280                 285

Thr Gly Lys Ile Trp Leu Ala Ser Glu Ala Trp Ala Ser Ser Ser Leu
290                 295                 300

Ile Ala Met Pro Gln Tyr Phe His Val Val Gly Gly Thr Ile Gly Phe
305                 310                 315                 320

Ala Leu Lys Ala Gly Gln Ile Pro Gly Phe Arg Glu Phe Leu Lys Lys
            325                 330                 335

Val His Pro Arg Lys Ser Val Asn Gly Phe Ala Lys Glu Phe Trp
        340                 345                 350

Glu Glu Thr Phe Asn Cys His Leu Gln Glu Gly Ala Lys Gly Pro Leu
```

-continued

```
                355                 360                 365
Pro Val Asp Thr Phe Leu Arg Gly His Glu Glu Ser Gly Asp Arg Phe
    370                 375                 380
Ser Asn Ser Ser Thr Ala Phe Arg Pro Leu Cys Thr Gly Asp Glu Asn
385                 390                 395                 400
Ile Ser Ser Val Glu Thr Pro Tyr Ile Asp Tyr Thr His Leu Arg Ile
                405                 410                 415
Ser Tyr Asn Val Tyr Leu Ala Val Tyr Ser Ile Ala His Ala Leu Gln
                420                 425                 430
Asp Ile Tyr Thr Cys Leu Pro Gly Arg Gly Leu Phe Thr Asn Gly Ser
            435                 440                 445
Cys Ala Asp Ile Lys Lys Val Glu Ala Trp Gln Val Leu Lys His Leu
450                 455                 460
Arg His Leu Asn Phe Thr Asn Asn Met Gly Glu Gln Val Thr Phe Asp
465                 470                 475                 480
Glu Cys Gly Asp Leu Val Gly Asn Tyr Ser Ile Ile Asn Trp His Leu
                485                 490                 495
Ser Pro Glu Asp Gly Ser Ile Val Phe Lys Glu Val Gly Tyr Tyr Asn
                500                 505                 510
Val Tyr Ala Lys Lys Gly Glu Arg Leu Phe Ile Asn Glu Glu Lys Ile
                515                 520                 525
Leu Trp Ser Gly Phe Ser Arg Glu Pro Leu Thr Phe Val Leu Ser Val
    530                 535                 540
Leu Gln Val Pro Phe Ser Asn Cys Ser Arg Asp Cys Leu Ala Gly Thr
545                 550                 555                 560
Arg Lys Gly Ile Ile Glu Gly Glu Pro Thr Cys Cys Phe Glu Cys Val
                565                 570                 575
Glu Cys Pro Asp Gly Glu Tyr Ser Asp Glu Thr Asp Ala Ser Ala Cys
                580                 585                 590
Asn Lys Cys Pro Asp Asp Phe Trp Ser Asn Glu Asn His Thr Ser Cys
                595                 600                 605
Ile Ala Lys Glu Ile Glu Phe Leu Ser Trp Thr Glu Pro Phe Gly Ile
    610                 615                 620
Ala Leu Thr Leu Phe Ala Val Leu Gly Ile Phe Leu Thr Ala Phe Val
625                 630                 635                 640
Leu Gly Val Phe Ile Lys Phe Arg Asn Thr Pro Ile Val Lys Ala Thr
                645                 650                 655
Asn Arg Glu Leu Ser Tyr Leu Leu Leu Phe Ser Leu Leu Cys Cys Phe
                660                 665                 670
Ser Ser Ser Leu Phe Phe Ile Gly Glu Pro Gln Asp Trp Thr Cys Arg
            675                 680                 685
Leu Arg Gln Pro Ala Phe Gly Ile Ser Phe Val Leu Cys Ile Ser Cys
    690                 695                 700
Ile Leu Val Lys Thr Asn Arg Val Leu Leu Val Phe Glu Ala Lys Ile
705                 710                 715                 720
Pro Thr Ser Phe His Arg Lys Trp Trp Gly Leu Asn Leu Gln Phe Leu
                725                 730                 735
Leu Val Phe Leu Cys Thr Phe Met Gln Ile Val Ile Cys Val Ile Trp
                740                 745                 750
Leu Tyr Thr Ala Pro Pro Ser Ser Tyr Arg Asn Gln Glu Leu Glu Asp
            755                 760                 765
Glu Ile Ile Phe Ile Thr Cys His Glu Gly Ser Leu Met Ala Leu Gly
    770                 775                 780
```

```
Phe Leu Ile Gly Tyr Thr Cys Leu Leu Ala Ala Ile Cys Phe Phe Phe
785                 790                 795                 800

Ala Phe Lys Ser Arg Lys Leu Pro Glu Asn Phe Asn Glu Ala Lys Phe
            805                 810                 815

Ile Thr Phe Ser Met Leu Ile Phe Phe Ile Val Trp Ile Ser Phe Ile
                820                 825                 830

Pro Ala Tyr Ala Ser Thr Tyr Gly Lys Phe Val Ser Ala Val Glu Val
            835                 840                 845

Ile Ala Ile Leu Ala Ala Ser Phe Gly Leu Leu Ala Cys Ile Phe Phe
            850                 855                 860

Asn Lys Ile Tyr Ile Ile Leu Phe Lys Pro Ser Arg Asn Thr Ile Glu
865                 870                 875                 880

Glu Val Arg Cys Ser Thr Ala Ala His Ala Phe Lys Val Ala Ala Arg
                885                 890                 895

Ala Thr Leu Arg Arg Ser Asn Val Ser Arg Lys Arg Ser Ser Ser Leu
            900                 905                 910

Gly Gly Ser Thr Gly Ser Thr Pro Ser Ser Ile Ser Ser Lys Ser
            915                 920                 925

Asn Ser Glu Asp Pro Phe Pro Arg Pro Glu Arg Gln Lys Gln Gln Gln
            930                 935                 940

Pro Leu Ala Leu Thr Gln Gln Glu Gln Gln Gln Pro Leu Thr Leu
945                 950                 955                 960

Pro Gln Gln Gln Arg Ser Gln Gln Pro Arg Cys Lys Gln Lys Val
                965                 970                 975

Ile Phe Gly Ser Gly Thr Val Thr Phe Ser Leu Ser Phe Asp Glu Pro
            980                 985                 990

Gln Lys Asn Ala Met Ala His Arg Asn Ser Thr His Gln Asn Ser Leu
            995                 1000                1005

Glu Ala Gln Lys Ser Ser Asp Thr Leu Thr Arg His Gln Pro Leu Leu
1010                1015                1020

Pro Leu Gln Cys Gly Glu Thr Asp Leu Asp Leu Thr Val Gln Glu Thr
1025                1030                1035                1040

Gly Leu Gln Gly Pro Val Gly Gly Asp Gln Arg Pro Glu Val Glu Asp
                1045                1050                1055

Pro Glu Glu Leu Ser Pro Ala Leu Val Val Ser Ser Ser Gln Ser Phe
            1060                1065                1070

Val Ile Ser Gly Gly Gly Ser Thr Val Thr Glu Asn Val Val Asn Ser
            1075                1080                1085
```

(2) INFORMATION FOR SEQ ID NO: 7:

(i) SEQUENCE CHARACTERISTICS:
        (A) LENGTH:       1078 amino acids
        (B) TYPE:         amino acid
        (D) TOPOLOGY:     linear (ii) MOLECULE TYPE:       protein (xi) SEQUENCE DESCRIPTION: SEQ ID NO: 7:

```
Met Ala Phe Tyr Ser Cys Cys Trp Val Leu Leu Ala Leu Thr Trp His
1               5                   10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
            35                  40                  45

Gln Asp Leu Lys Ser Arg Pro Glu Ser Val Glu Cys Ile Arg Tyr Asn
50                  55                  60
```

```
Phe Arg Gly Phe Arg Trp Leu Gln Ala Met Ile Phe Ala Ile Glu Glu
 65                  70                  75                  80

Ile Asn Ser Ser Pro Ala Leu Leu Pro Asn Leu Thr Leu Gly Tyr Arg
             85                  90                  95

Ile Phe Asp Thr Cys Asn Thr Val Ser Lys Ala Leu Glu Ala Thr Leu
                100                 105                 110

Ser Phe Val Ala Gln Asn Lys Ile Asp Ser Leu Asn Leu Asp Glu Phe
         115                 120                 125

Cys Asn Cys Ser Glu His Ile Pro Ser Thr Ile Ala Val Val Gly Ala
         130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                 165                 170                 175

Lys Asn Gln Phe Lys Ser Phe Leu Arg Thr Ile Pro Asn Asp Glu His
             180                 185                 190

Gln Ala Thr Ala Met Ala Asp Ile Ile Glu Tyr Phe Arg Trp Asn Trp
             195                 200                 205

Val Gly Thr Ile Ala Ala Asp Asp Tyr Gly Arg Pro Gly Ile Glu
210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln His Val Val
                 245                 250                 255

Glu Val Ile Gln Asn Ser Thr Ala Lys Val Ile Val Phe Ser Ser
                 260                 265                 270

Gly Pro Asp Leu Glu Pro Leu Ile Lys Glu Ile Val Arg Arg Asn Ile
             275                 280                 285

Thr Gly Lys Ile Trp Leu Ala Ser Glu Ala Trp Ala Ser Ser Ser Leu
290                 295                 300

Ile Ala Met Pro Gln Tyr Phe His Val Val Gly Gly Thr Ile Gly Phe
305                 310                 315                 320

Ala Leu Lys Ala Gly Gln Ile Pro Gly Phe Arg Glu Phe Leu Lys Lys
                 325                 330                 335

Val His Pro Arg Lys Ser Val His Asn Gly Phe Ala Lys Glu Phe Trp
             340                 345                 350

Glu Glu Thr Phe Asn Cys His Leu Gln Glu Gly Ala Lys Gly Pro Leu
             355                 360                 365

Pro Val Asp Thr Phe Leu Arg Gly His Glu Glu Ser Gly Asp Arg Phe
370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Ile Asp Tyr Thr His Leu Arg Ile
                 405                 410                 415

Ser Tyr Asn Val Tyr Leu Ala Val Tyr Ser Ile Ala His Ala Leu Gln
             420                 425                 430

Asp Ile Tyr Thr Cys Leu Pro Gly Arg Gly Leu Phe Thr Asn Gly Ser
             435                 440                 445

Cys Ala Asp Ile Lys Lys Val Glu Ala Trp Gln Val Leu Lys His Leu
         450                 455                 460

Arg His Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
```

-continued

```
                485                 490                 495
Ser Pro Glu Asp Gly Ser Ile Val Phe Lys Glu Val Gly Tyr Tyr Asn
                500                 505                 510

Val Tyr Ala Lys Lys Gly Glu Arg Leu Phe Ile Asn Glu Glu Lys Ile
                515                 520                 525

Leu Trp Ser Gly Phe Ser Arg Glu Val Pro Phe Ser Asn Cys Ser Arg
            530                 535                 540

Asp Cys Leu Ala Gly Thr Arg Lys Gly Ile Ile Glu Gly Glu Pro Thr
545                 550                 555                 560

Cys Cys Phe Glu Cys Val Glu Cys Pro Asp Gly Glu Tyr Ser Asp Glu
                565                 570                 575

Thr Asp Ala Ser Ala Cys Asn Lys Cys Pro Asp Asp Phe Trp Ser Asn
            580                 585                 590

Glu Asn His Thr Ser Cys Ile Ala Lys Glu Ile Glu Phe Leu Ser Trp
            595                 600                 605

Thr Glu Pro Phe Gly Ile Ala Leu Thr Leu Phe Ala Val Leu Gly Ile
        610                 615                 620

Phe Leu Thr Ala Phe Val Leu Gly Val Phe Ile Lys Phe Arg Asn Thr
625                 630                 635                 640

Pro Ile Val Lys Ala Thr Asn Arg Glu Leu Ser Tyr Leu Leu Leu Phe
                645                 650                 655

Ser Leu Leu Cys Cys Phe Ser Ser Ser Leu Phe Phe Ile Gly Glu Pro
                660                 665                 670

Gln Asp Trp Thr Cys Arg Leu Arg Gln Pro Ala Phe Gly Ile Ser Phe
            675                 680                 685

Val Leu Cys Ile Ser Cys Ile Leu Val Lys Thr Asn Arg Val Leu Leu
        690                 695                 700

Val Phe Glu Ala Lys Ile Pro Thr Ser Phe His Arg Lys Trp Trp Gly
705                 710                 715                 720

Leu Asn Leu Gln Phe Leu Leu Val Phe Leu Cys Thr Phe Met Gln Ile
                725                 730                 735

Val Ile Cys Val Ile Trp Leu Tyr Thr Ala Pro Pro Ser Ser Tyr Arg
            740                 745                 750

Asn Gln Glu Leu Glu Asp Glu Ile Ile Phe Ile Thr Cys His Glu Gly
            755                 760                 765

Ser Leu Met Ala Leu Gly Phe Leu Ile Gly Tyr Thr Cys Leu Leu Ala
        770                 775                 780

Ala Ile Cys Phe Phe Phe Ala Phe Lys Ser Arg Lys Leu Pro Glu Asn
785                 790                 795                 800

Phe Asn Glu Ala Lys Phe Ile Thr Phe Ser Met Leu Ile Phe Phe Ile
                805                 810                 815

Val Trp Ile Ser Phe Ile Pro Ala Tyr Ala Ser Thr Tyr Gly Lys Phe
            820                 825                 830

Val Ser Ala Val Glu Val Ile Ala Ile Leu Ala Ala Ser Phe Gly Leu
        835                 840                 845

Leu Ala Cys Ile Phe Phe Asn Lys Ile Tyr Ile Ile Leu Phe Lys Pro
            850                 855                 860

Ser Arg Asn Thr Ile Glu Glu Val Arg Cys Ser Thr Ala Ala His Ala
865                 870                 875                 880

Phe Lys Val Ala Ala Arg Ala Thr Leu Arg Arg Ser Asn Val Ser Arg
                885                 890                 895

Lys Arg Ser Ser Ser Leu Gly Gly Ser Thr Gly Ser Thr Pro Ser Ser
                900                 905                 910
```

-continued

```
Ser Ile Ser Ser Lys Ser Asn Ser Glu Asp Pro Phe Pro Gln Pro Glu
            915                 920                 925

Arg Gln Lys Gln Gln Pro Leu Ala Leu Thr Gln Gln Glu Gln Gln
        930                 935                 940

Gln Gln Pro Leu Thr Leu Pro Gln Gln Gln Arg Ser Gln Gln Pro
945                 950                 955                 960

Arg Cys Lys Gln Lys Val Ile Phe Gly Ser Gly Thr Val Thr Phe Ser
                965                 970                 975

Leu Ser Phe Asp Glu Pro Gln Lys Asn Ala Met Ala His Gly Asn Ser
            980                 985                 990

Thr His Gln Asn Ser Leu Glu Ala Gln Lys Ser Ser Asp Thr Leu Thr
            995                 1000                1005

Arg His Gln Pro Leu Leu Pro Leu Gln Cys Gly Glu Thr Asp Leu Asp
        1010                1015                1020

Leu Thr Val Gln Glu Thr Gly Leu Gln Gly Pro Val Gly Gly Asp Gln
1025                1030                1035                1040

Arg Pro Glu Val Glu Asp Pro Glu Leu Ser Pro Ala Leu Val Val
                1045                1050                1055

Ser Ser Ser Gln Ser Phe Val Ile Ser Gly Gly Ser Thr Val Thr
            1060                1065                1070

Glu Asn Val Val Asn Ser
        1075

(2) INFORMATION FOR SEQ ID NO: 8:

(i) SEQUENCE CHARACTERISTICS:
        (A) LENGTH:         1079 amino acids
        (B) TYPE:           amino acid
        (D) TOPOLOGY:       linear (ii) MOLECULE TYPE:         protein (xi) SEQUENCE DESCRIPTION: SEQ ID NO: 8:

Met Ala Ser Tyr Ser Cys Cys Leu Ala Leu Leu Ala Leu Ala Trp His
1               5                   10                  15

Ser Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
50                  55                  60

Phe Arg Gly Phe Arg Trp Leu Gln Ala Met Ile Phe Ala Ile Glu Glu
65                  70                  75                  80

Ile Asn Ser Ser Pro Ser Leu Leu Pro Asn Met Thr Leu Gly Tyr Arg
            85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
        130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175

Lys Asn Gln Tyr Lys Ser Phe Leu Arg Thr Ile Pro Asn Asp Glu His
            180                 185                 190
```

```
Gln Ala Thr Ala Met Ala Asp Ile Ile Glu Tyr Phe Arg Trp Asn Trp
        195                 200                 205
Val Gly Thr Ile Ala Ala Asp Asp Tyr Gly Arg Pro Gly Ile Glu
    210                 215                 220
Lys Phe Arg Glu Glu Ala Glu Arg Asp Ile Cys Ile Asp Phe Ser
225                 230                 235                 240
Glu Leu Ile Ser Gln Tyr Ser Asp Glu Glu Ile Gln Gln Val Val
            245                 250                 255
Glu Val Ile Gln Asn Ser Thr Ala Lys Val Ile Val Phe Ser Ser
            260                 265                 270
Gly Pro Asp Leu Glu Pro Leu Ile Lys Glu Ile Val Arg Arg Asn Ile
    275                 280                 285
Thr Gly Arg Ile Trp Leu Ala Ser Glu Ala Trp Ala Ser Ser Ser Leu
    290                 295                 300
Ile Ala Met Pro Glu Tyr Phe His Val Val Gly Gly Thr Ile Gly Phe
305                 310                 315                 320
Gly Leu Lys Ala Gly Gln Ile Pro Gly Phe Arg Glu Phe Leu Gln Lys
            325                 330                 335
Val His Pro Arg Lys Ser Val His Asn Gly Phe Ala Lys Glu Phe Trp
            340                 345                 350
Glu Glu Thr Phe Asn Cys His Leu Gln Gly Ala Lys Gly Pro Leu
            355                 360                 365
Pro Val Asp Thr Phe Val Arg Ser His Glu Glu Gly Gly Asn Arg Leu
    370                 375                 380
Leu Asn Ser Ser Thr Ala Phe Arg Pro Leu Cys Thr Gly Asp Glu Asn
385                 390                 395                 400
Ile Asn Ser Val Glu Thr Pro Tyr Met Asp Tyr Glu His Leu Arg Ile
            405                 410                 415
Ser Tyr Asn Val Tyr Leu Ala Val Tyr Ser Ile Ala His Ala Leu Gln
            420                 425                 430
Asp Ile Tyr Thr Cys Leu Pro Gly Arg Gly Leu Phe Thr Asn Gly Ser
        435                 440                 445
Cys Ala Asp Ile Lys Lys Val Glu Ala Trp Gln Val Leu Lys His Leu
    450                 455                 460
Arg His Leu Asn Phe Thr Asn Asn Met Gly Glu Gln Val Thr Phe Asp
465                 470                 475                 480
Glu Cys Gly Asp Leu Val Gly Asn Tyr Ser Ile Ile Asn Trp His Leu
            485                 490                 495
Ser Pro Glu Asp Gly Ser Ile Val Phe Lys Glu Val Gly Tyr Tyr Asn
            500                 505                 510
Val Tyr Ala Lys Lys Gly Glu Arg Leu Phe Ile Asn Glu Glu Lys Ile
    515                 520                 525
Leu Trp Ser Gly Phe Ser Arg Glu Val Pro Phe Ser Asn Cys Ser Arg
    530                 535                 540
Asp Cys Gln Ala Gly Thr Arg Lys Gly Ile Ile Glu Gly Glu Pro Thr
545                 550                 555                 560
Cys Cys Phe Glu Cys Val Glu Cys Pro Asp Gly Glu Tyr Ser Gly Glu
            565                 570                 575
Thr Asp Ala Ser Ala Cys Asp Lys Cys Pro Asp Asp Phe Trp Ser Asn
            580                 585                 590
Glu Asn His Thr Ser Cys Ile Ala Lys Glu Ile Glu Phe Leu Ala Trp
            595                 600                 605
Thr Glu Pro Phe Gly Ile Ala Leu Thr Leu Phe Ala Val Leu Gly Ile
```

```
            610                 615                 620
Phe Leu Thr Ala Phe Val Leu Gly Val Phe Ile Lys Phe Arg Asn Thr
625                 630                 635                 640

Pro Ile Val Lys Ala Thr Asn Arg Glu Leu Ser Tyr Leu Leu Leu Phe
                    645                 650                 655

Ser Leu Leu Cys Cys Phe Ser Ser Leu Phe Phe Ile Gly Glu Pro
                660                 665                 670

Gln Asp Trp Thr Cys Arg Leu Arg Gln Pro Ala Phe Gly Ile Ser Phe
                675                 680                 685

Val Leu Cys Ile Ser Cys Ile Leu Val Lys Thr Asn Arg Val Leu Leu
690                 695                 700

Val Phe Glu Ala Lys Ile Pro Thr Ser Phe His Arg Lys Trp Trp Gly
705                 710                 715                 720

Leu Asn Leu Gln Phe Leu Leu Val Phe Leu Cys Thr Phe Met Gln Ile
                    725                 730                 735

Leu Ile Cys Ile Ile Trp Leu Tyr Thr Ala Pro Pro Ser Ser Tyr Arg
                740                 745                 750

Asn His Glu Leu Glu Asp Glu Ile Ile Phe Ile Thr Cys His Glu Gly
                755                 760                 765

Ser Leu Met Ala Leu Gly Ser Leu Ile Gly Tyr Thr Cys Leu Leu Ala
                770                 775                 780

Ala Ile Cys Phe Phe Ala Phe Lys Ser Arg Lys Leu Pro Glu Asn
785                 790                 795                 800

Phe Asn Glu Ala Lys Phe Ile Thr Phe Ser Met Leu Ile Phe Phe Ile
                    805                 810                 815

Val Trp Ile Ser Phe Ile Pro Ala Tyr Ala Ser Thr Tyr Gly Lys Phe
                820                 825                 830

Val Ser Ala Val Glu Val Ile Ala Ile Leu Ala Ala Ser Phe Gly Leu
                835                 840                 845

Leu Ala Cys Ile Phe Phe Asn Lys Val Tyr Ile Ile Leu Phe Lys Pro
850                 855                 860

Ser Arg Asn Thr Ile Glu Glu Val Arg Ser Ser Thr Ala Ala His Ala
865                 870                 875                 880

Phe Lys Val Ala Ala Arg Ala Thr Leu Arg Arg Pro Asn Ile Ser Arg
                    885                 890                 895

Lys Arg Ser Ser Ser Leu Gly Gly Ser Thr Gly Ser Ile Pro Ser Ser
                900                 905                 910

Ser Ile Ser Ser Lys Ser Asn Ser Glu Asp Arg Phe Pro Gln Pro Glu
                915                 920                 925

Arg Gln Lys Gln Gln Gln Pro Leu Ser Leu Thr Gln Gln Glu Gln Gln
930                 935                 940

Gln Gln Pro Leu Thr Leu His Pro Gln Gln Gln Gln Pro Gln Gln
945                 950                 955                 960

Pro Arg Cys Lys Gln Lys Val Ile Phe Gly Ser Gly Thr Val Thr Phe
                965                 970                 975

Ser Leu Ser Phe Asp Glu Pro Gln Lys Asn Ala Met Ala His Arg Asn
                980                 985                 990

Ser Met Arg Gln Asn Ser Leu Glu Ala Gln Arg Ser Asn Asp Thr Leu
                995                 1000                1005

Gly Arg His Gln Ala Leu Leu Pro Leu Gln Cys Ala Asp Ala Asp Ser
        1010                1015                1020

Glu Met Thr Ile Gln Glu Thr Gly Leu Gln Gly Pro Met Val Gly Asp
1025                1030                1035                1040
```

```
His Gln Pro Glu Met Glu Ser Ser Asp Glu Met Ser Pro Ala Leu Val
             1045                1050                1055

Met Ser Thr Ser Arg Ser Phe Val Ile Ser Gly Gly Gly Ser Ser Val
             1060                1065                1070

Thr Glu Asn Val Leu His Ser
             1075

(2) INFORMATION FOR SEQ ID NO:9:

(i) SEQUENCE CHARACTERISTICS:
        (A) LENGTH:         15 amino acids
        (B) TYPE:           amino acids
        (C) STRANDEDNESS:   single
        (D) TOPOLOGY:       linear (ii) MOLECULE TYPE:     peptide (xi) SEQUENCE DESCRIPTION: SEQ ID NO:9:

Tyr Lys Asp Gln Asp Leu Lys Ser Arg Pro Glu Ser Val Glu Cys
 1               5                  10                  15

(2) INFORMATION FOR SEQ ID NO:10:

(i) SEQUENCE CHARACTERISTICS:
        (A) LENGTH:         23 amino acids
        (B) TYPE:           amino acids
        (C) STRANDEDNESS:   single
        (D) TOPOLOGY:       linear (ii) MOLECULE TYPE:     peptide (xi) SEQUENCE DESCRIPTION: SEQ ID NO:10:

Ala Asp Asp Asp Tyr Gly Arg Pro Gly Ile Glu Lys Phe Arg Glu Glu
 1               5                  10                  15

Ala Glu Glu Arg Asp Ile Cys
                 20

(2) INFORMATION FOR SEQ ID NO:11:

(i) SEQUENCE CHARACTERISTICS:
        (A) LENGTH:         19 amino acids
        (B) TYPE:           amino acids
        (C) STRANDEDNESS:   single
        (D) TOPOLOGY:       linear (ii) MOLECULE TYPE:     peptide (xi) SEQUENCE DESCRIPTION: SEQ ID NO:11:

Cys Ile Asp Phe Ser Glu Leu Ile Ser Gln Tyr Ser Asp Glu Glu Lys
 1               5                  10                  15

Ile Gln Gln (2) INFORMATION FOR SEQ ID NO:12:

(i) SEQUENCE CHARACTERISTICS:
        (A) LENGTH:         16 amino acids
        (B) TYPE:           amino acids
        (C) STRANDEDNESS:   single
        (D) TOPOLOGY:       linear (xi) SEQUENCE DESCRIPTION: SEQ ID NO:12:

Tyr His Asn Gly Phe Ala Lys Glu Phe Trp Glu Glu Thr Phe Asn Cys
 1               5                  10                  15

(2) INFORMATION FOR SEQ ID NO:13:

(i) SEQUENCE CHARACTERISTICS:
```

```
            (A) LENGTH:              13 amino acids
            (B) TYPE:                amino acids
            (C) STRANDEDNESS:        single
            (D) TOPOLOGY:            linear (ii) MOLECULE TYPE:        peptide (xi) SEQUENCE DESCRIPTION: SEQ ID NO:13:

Asp Gly Glu Tyr Ser Asp Glu Thr Asp Ala Ser Ala Cys
 1               5                  10

(2) INFORMATION FOR SEQ ID NO:14:

(i) SEQUENCE CHARACTERISTICS:
            (A) LENGTH:              15 amino acids
            (B) TYPE:                amino acids
            (C) STRANDEDNESS:        single
            (D) TOPOLOGY:            linear (ii) MOLECULE TYPE:        peptide (xi) SEQUENCE DESCRIPTION: SEQ ID NO:14:

Asn Thr Pro Ile Val Lys Ala Thr Asn Arg Glu Leu Ser Tyr Cys
 1               5                  10                  15

(2) INFORMATION FOR SEQ ID NO:15:

(i) SEQUENCE CHARACTERISTICS:
            (A) LENGTH:              15 amino acids
            (B) TYPE:                amino acids
            (C) STRANDEDNESS:        single
            (D) TOPOLOGY:            linear (ii) MOLECULE TYPE:        peptide (xi) SEQUENCE DESCRIPTION: SEQ ID NO:15:

Tyr Arg Asn His Glu Leu Glu Asp Glu Ile Ile Phe Ile Thr Cys
 1               5                  10                  15

(2) INFORMATION FOR SEQ ID NO:16:

(i) SEQUENCE CHARACTERISTICS:
            (A) LENGTH:              13 amino acids
            (B) TYPE:                amino acids
            (C) STRANDEDNESS:        single
            (D) TOPOLOGY:            linear (ii) MOLECULE TYPE:        peptide (xi) SEQUENCE DESCRIPTION: SEQ ID NO:16:

Arg Lys Leu Pro Glu Asn Phe Asn Glu Ala Lys Tyr Cys
 1               5                  10

(2) INFORMATION FOR SEQ ID NO:17:

(i) SEQUENCE CHARACTERISTICS:
            (A) LENGTH:              33 base pairs
            (B) TYPE:                nucleic
            (C) STRANDEDNESS:        single
            (D) TOPOLOGY:            linear (ii) MOLECULE TYPE:        nucleic acid (iii) FEATURE:
            (A) NAME/KEY: Modified Base
            (B) LOCATION: 13...13
            (C) OTHER INFORMATION: Inosine (iv) SEQUENCE DESCRIPTION: SEQ ID NO:17:

CCTGCTCGAG ACNARYCGGG ARCTYTSCTA YMT                             33
```

(2) INFORMATION FOR SEQ ID NO:18:

(i) SEQUENCE CHARACTERISTICS:
        (A) LENGTH:        31 base pairs
        (B) TYPE:          nucleic
        (C) STRANDEDNESS:  single
        (D) TOPOLOGY:      linear (ii) MOLECULE TYPE:      nucleic acid (iii) FEATURE:
        (A) NAME/KEY: Modified Base
        (B) LOCATION: 13...13
        (C) OTHER INFORMATION: Inosine (xi) SEQUENCE DESCRIPTION: SEQ ID NO:18:

CGGAATTCCG TTNCGGGWYT TGAASGCRWA S                  31

(2) INFORMATION FOR SEQ ID NO:19:

(i) SEQUENCE CHARACTERISTICS:
        (A) LENGTH:        32 base pairs
        (B) TYPE:          nucleic
        (C) STRANDEDNESS:  single
        (D) TOPOLOGY:      linear (ii) MOLECULE TYPE:      nucleic acid (iii) FEATURE:
        (A) NAME/KEY: Modified Base
        (B) LOCATION: 24...24
        (C) OTHER INFORMATION: Inosine (xi) SEQUENCE DESCRIPTION: SEQ ID NO:19:

CCTGCTCGAG TCAAGGCTAC GRRNMGNGAR YT                32

(2) INFORMATION FOR SEQ ID NO:20:

(i) SEQUENCE CHARACTERISTICS:
        (A) LENGTH:        34 base pairs
        (B) TYPE:          nucleic
        (C) STRANDEDNESS:  single
        (D) TOPOLOGY:      linear (ii) MOLECULE TYPE:      nucleic acid (iii) FEATURE:
        (A) NAME/KEY: Modified Base
        (B) LOCATION: 26...26
        (C) OTHER INFORMATION: Inosine (xi) SEQUENCE DESCRIPTION: SEQ ID NO:20:

CGGAATTCCA TTTGGCTTCG TTGAANKTNK CNGG              34

We claim:

1. An expression vector comprising at least 20 contiguous nucleotides of a nucleic acid sequence from nucleotide 515 to 3769 of SEQ ID NO: 1.

2. An expression vector comprising at least 27 contiguous nucleotides of a nucleic acid sequence from nucleotide 515 to 3769 of SEQ ID NO: 1.

3. An expression vector comprising at least 45 contiguous nucleotides of a nucleic acid sequence from nucleotide 515 to 3769 of SEQ ID NO: 1.

4. An expression vector comprising a nucleic acid sequence selected from the group consisting of: nucleotides 515 to 3769 of SEQ ID NO: 1, nucleotides 436 to 3699 of SEQ ID NO: 2, nucleotides 373 to 3606 of SEQ ID NO: 3 and nucleotides 574 to 3810 of SEQ ID NO: 4.

5. The expression vector of claim 4, wherein said nucleic acid sequence is SEQ ID NO: 1.

6. The expression vector of claim 4, wherein said nucleic acid sequence is SEQ ID NO: 2.

7. The expression vector of claim 4, wherein said nucleic acid sequence is SEQ ID NO: 3.

8. The expression vector of claim 4, wherein said nucleic acid sequence is SEQ ID NO: 4.

9. An expression vector comprising a nucleic acid sequence encoding at least 12 contiguous amino acids of an amino acid sequence provided in SEQ ID NO: 5.

10. An expression vector comprising a nucleic acid sequence encoding at least 18 contiguous amino acids of an amino acid sequence provided in SEQ ID NO: 5.

11. An expression vector comprising a nucleic acid sequence encoding at least 54 contiguous amino acids of an amino acid sequence provided in SEQ ID NO: 5.

12. An expression vector comprising a nucleic acid sequence encoding an amino acid sequence selected from the group consisting of SEQ ID NO: 5, SEQ ID NO: 6, SEQ ID NO: 7 and SEQ ID NO: 8.

13. The expression vector of claim 12, wherein said amino acid sequence is SEQ ID NO: 5.

14. The expression vector of claim 12, wherein said amino acid sequence is SEQ ID NO: 6.

15. The expression vector of claim 12, wherein said amino acid sequence is SEQ ID NO: 7.

16. The expression vector of claim 12, wherein said amino acid sequence is SEQ ID NO: 8.

17. A recombinant cell comprising the expression vector of any one of claims 1–16.

18. A recombinant cell made by a process comprising the step of introducing the expression vector of any one of claims 1–16 into the cell.

19. A recombinant nucleic acid comprising at least 20 contiguous nucleotides of a sequence from nucleotide 515 to 3769 of SEQ ID NO: 1, transcriptionally coupled to an exogenous promoter.

20. A recombinant nucleic acid comprising at least 27 contiguous nucleotides of a sequence from nucleotide 515 to 3769 of SEQ ID NO: 1, transcriptionally coupled to an exogenous promoter.

21. A recombinant nucleic acid comprising at least 45 contiguous nucleotides of a sequence from nucleotide 515 to 3769 of SEQ ID NO: 1, transcriptionally coupled to an exogenous promoter.

22. A recombinant nucleic acid comprising a nucleic acid sequence selected from the group consisting of: nucleotides 515 to 3769 of SEQ ID NO: 1, nucleotides 436 to 3699 of SEQ ID NO: 2, nucleotides 373 to 3606 of SEQ ID NO: 3 and nucleotides 574 to 3810 of SEQ ID NO: 4, wherein said nucleic acid sequence is transcriptionally coupled to an exogenous promoter.

23. The recombinant nucleic acid of claim 22, wherein said nucleic acid sequence is SEQ ID NO: 1.

24. The recombinant nucleic acid of claim 22, wherein said nucleic acid sequence is SEQ ID NO: 2.

25. The recombinant nucleic acid of claim 22, wherein said nucleic acid sequence is SEQ ID NO: 3.

26. The recombinant nucleic acid of claim 22, wherein said nucleic acid sequence is SEQ ID NO: 4.

27. A recombinant nucleic acid comprising a nucleic acid sequence encoding at least 12 contiguous amino acids of an amino acid sequence provided in SEQ ID NO: 5, wherein said nucleic acid sequence is trancriptionally coupled to an exogenous promoter.

28. A recombinant nucleic acid comprising a nucleic acid sequence encoding at least 18 contiguous amino acids of an amino acid sequence provided in SEQ ID NO: 5, wherein said nucleic acid sequence is transcriptionally coupled to an exogenous promoter.

29. A recombinant nucleic acid comprising a nucleic acid sequence encoding at least 54 contiguous amino acids of an amino acid sequence provided in SEQ ID NO: 5, wherein said nucleic acid sequence is transcriptionally coupled to an exogenous promoter.

30. A recombinant nucleic acid comprising a nucleic acid sequence encoding an amino acid sequence selected from the group consisting of SEQ ID NO: 5, SEQ ID NO: 6, SEQ ID NO: 7 and SEQ ID NO: 8, wherein said nucleic acid sequence is transcriptionally coupled to an exogenous promoter.

31. The recombinant nucleic acid of claim 30, wherein said amino acid sequence is SEQ ID NO: 5.

32. The recombinant nucleic acid of claim 30, wherein said amino acid sequence is SEQ ID NO: 6.

33. The recombinant nucleic acid of claim 30, wherein said amino acid sequence is SEQ ID NO: 7.

34. The recombinant nucleic acid of claim 3, wherein said amino acid sequence is SEQ ID NO: 8.

35. A recombinant cell comprising the recombinant nucleic acid of any one of claims 19–34.

36. A recombinant cell made by a process comprising the step of introducing the recombinant nucleic acid of any one of claims 19–34 into the cell.

* * * * *